(12) United States Patent
Griffith et al.

(10) Patent No.: US 8,540,999 B2
(45) Date of Patent: Sep. 24, 2013

(54) ALLERGENIC PROTEINS AND PEPTIDES FROM JAPANESE CEDAR POLLEN

(75) Inventors: Irwin J. Griffith, North Reading, MA (US); Joanne Pollock, Arlington, MA (US); Julian F. Bond, Weymouth, MA (US); Richard D. Garman, Arlington, MA (US); Mei-Chang Kuo, Winchester, MA (US); Stephen P. Powers, Waltham, MA (US); Mark A. Exley, Brookline, MA (US); Xian Chen, North Chelmsford, MA (US); Ze'ev Shaked, Berkeley, CA (US)

(73) Assignee: Merck Patent GmbH, Darmstadt (DE)

( * ) Notice: Subject to any disclaimer, the term of this patent is extended or adjusted under 35 U.S.C. 154(b) by 1296 days.

(21) Appl. No.: 10/931,260

(22) Filed: Aug. 30, 2004

(65) Prior Publication Data
US 2005/0152927 A1 Jul. 14, 2005

Related U.S. Application Data

(60) Continuation of application No. 09/240,203, filed on Jan. 29, 1999, now Pat. No. 6,982,326, which is a continuation of application No. 08/467,023, filed on Jun. 6, 1995, now Pat. No. 6,090,386, which is a division of application No. 08/350,225, filed on Dec. 6, 1994, now abandoned, which is a continuation-in-part of application No. 08/226,248, filed on Apr. 8, 1994, now abandoned, which is a continuation-in-part of application No. 07/975,179, filed on Nov. 12, 1992, now abandoned, and a continuation-in-part of application No. PCT/US93/00139, filed on Jan. 15, 1993, which is a continuation-in-part of application No. 07/938,990, filed on Sep. 1, 1992, now abandoned, which is a continuation-in-part of application No. 07/730,452, filed on Jul. 15, 1991, now abandoned, which is a continuation-in-part of application No. 07/729,134, filed on Jul. 12, 1991.

(51) Int. Cl.
| | |
|---|---|
| A61K 39/00 | (2006.01) |
| A61K 39/35 | (2006.01) |
| A61K 39/36 | (2006.01) |
| A61K 39/38 | (2006.01) |
| C07K 1/00 | (2006.01) |
| C07K 14/00 | (2006.01) |
| C07K 17/00 | (2006.01) |

(52) U.S. Cl.
USPC .................. 424/184.1; 424/185.1; 424/275.1; 530/350

(58) Field of Classification Search
None
See application file for complete search history.

(56) References Cited

U.S. PATENT DOCUMENTS
4,939,239 A 7/1990 Matsuhashi et al.
5,547,669 A 8/1996 Rogers et al.

FOREIGN PATENT DOCUMENTS
| EP | 0308147 B1 | 3/1989 |
|---|---|---|
| EP | 0416816 B1 | 11/1994 |
| JP | 62 205 794 A | 9/1987 |
| JP | 11 56 926 A | 6/1989 |
| WO | WO-92/03551 A1 | 3/1992 |
| WO | WO-93/01213 A1 | 1/1993 |

OTHER PUBLICATIONS

Blumenthal et al. 'Definition of an Allergen.' Allergens and Allergen Immunotherapy. Ed. R Lockey, S. Bukantz and J. Bousquet. New York: Marcel Decker, 2004.37-50.*
Lerner et al. 'Tapping the immunological repertoire to produce antibodies of predetermined specificity.' Nature 299:592-596, 1982.*
Maleki et al. 'The effects of roasting on the allergenic properties of peanut proteins.' Journal of Allergy and Clinical Immunology. 763-768, 2000.*
Howlett et al. 'Role of carbohydrates as an antigenic determinant of a glycoprotein from rye-grass (*Lolium perenne*) pollen.' Biochem. J. 197:707-714, 1981.*
Sone et al. 'T Cell Epitopes in Japanese Cedar (*Cryptomeria japonica*) Pollen Allergens: Choice of Major T Cell Epitopes in Cry j 1 and Cry j 2 Toward Design of the Peptide-Based Immunotherapeutics for the Management of Japanese Cedar Pollinosis.' J. Immunol. 161:448-457, 1998.*
Alberts, et al., "Molecular Biology of the Cell," 2nd Edition, pp. 174, 262-263.

(Continued)

*Primary Examiner* — Nora Rooney
(74) *Attorney, Agent, or Firm* — Perkins Coie LLP

(57) ABSTRACT

The present invention provides nucleic acid sequences coding for the *Cryptomeria japonica* major pollen allergen Cry j I, Cry j II, Jun s I and Jun v I and fragments or peptides thereof. The present invention also provides purified Cry j I, Cry j II, Jun s I and Jun v I and at least one fragment thereof produced in a host cell transformed with a nucleic acid sequence coding for Cry j I, Cry j II, Jun s I and Jun v I or at least one fragment thereof, and fragments of Cry j I, Cry j II, Jun s I or Jun v I or at least one fragment thereof, and fragments of Cry j I, Cry j II, Jun s I or Jun v I prepared synthetically. Cry j I, Cry j II, Jun s I and Jun v I and fragments thereof are useful for diagnosing, treating, and preventing Japanese cedar pollinosis. The present invention also provides isolated peptides of Cry j I and Cry j II. Peptides within the scope of the invention comprise at least one T cell epitope, or preferably at least two T cell epitopes of Cry j I or Cry j II. The invention also pertains to modified peptides having similar or enhanced therapeutic properties as the corresponding naturally-occurring allergen or portion thereof but having reduced side effects. Methods of treatment or of diagnosis of sensitivity to Japanese cedar pollens in an individual and therapeutic compositions, and multipeptide formulations comprising one or more peptides of the invention are also provided.

2 Claims, 59 Drawing Sheets

(56) References Cited

OTHER PUBLICATIONS

Chiba, et al., "Experimental Cedar Pollinosis in Rhesus Monkeys," *Int. Arch. Allergy Appl. Immunol.*, vol. 93:83-88 (1990).

Colina, et al., "The Identification of an Onchocerca-Specific Recombinant Antigen Containing a T Cell Epitope," *The Amer. Assoc. of Immunol.*, pp. 1551-1553 (1990).

Eynon, et al., "Small B Cells as Antigen-presenting Cells in the Induction of Tolerance to Soluble Protein Antigens," *J. Exp. Med.*, vol. 175:131-138 (1992).

Frick, "Immediate Hypersensitivity," in Basic & Clinical Immunology, 6th Ed., Appleton & Lange, pp. 197, 223 (1987).

Ishizaki, et al., "Studies of Prevalence of Japanese Cedar Pollinoisis Among the Residents in a Densely Cultivated Area," *Annals of Allergy*, vol. 58:265-270 (1987).

Ito, et al., "Analysis by Electrophoretic Transfer Blotting of Japanese Cedar Pollen Allergens Which React with IgG and IgE Antibodies in the Serum of Patients," *Int. Archs Allergy Appl. Immun.*, vol. 81:174-179 (1986).

King, et al., "Chemical and Biological Properties of Some Atopic Allergens," *Advances in Immunology*, vol. 23:77-105 (1976).

Kumar, et al., "Amino Acid Variations at a Single Residue in an Autoimmune Peptide Profoundly Affect its Properties: T-cell Activation . . . " *Proc. Natl. Acad. Sci. USA*, vol. 87:1337-1341 (1990).

Larsen, et al., "PCR Based Cloning and Sequencing of Isogenes Encoding the Tree Pollen . . . " *Molecular Immunology*, vol. 40:703-711 (1992).

Matsushita, et al., "HLA-Linked Nonresponsiveness to *Cryptomeria japonica* Pollen Allergen," *Journal of Immunol.*, vol. 138(1):109-115 (1987).

Miyazawa, et al., "A Reverse-Sandwich ELISA for IgG Antibody to a Pollen Allergen," *J. Allergy Clin. Immunol.*, vol. 82:407-413 (1989).

Panzani, et al., "Cross-reactivity Between the Pollens of *Cupressus sumpervirens* (Common Cypress) and of *Crytomeria japonica* (Japanese Cedar)," *Annals of Allergy*, vol. 57:26-30 (1986).

Rieger, et al., "Glossary of Genetics," 5th Edition, Springer-Verlag, pp. 16-17 (1991).

Roitt, et al., "Immunology," Gower Medical Publishing, New York, pp. 192 (1985).

Sakaguchi, et al., "Identification of the Second Major Allergen of Japanese Cedar Pollen," *Allergy*, vol. 45:309-312 (1990).

Schad, et al., "The Potential Use of T Cell Epitopes to Alter the Immune Response," *Immunology*, vol. 3:217-224 (1991).

Tamura, et al., "IgE Antibody Responses Against Japanese Cedar Pollen in the Mouse," *Microbiol Immunol.*, vol. 30(9):883-891 (1986).

Tanai, et al., "N-terminal Amino Acid Sequence of a Major Allergen of Japanese Cedar Pollen (*Cry j I*)," *FEBS Letters*, vol. 239(2):329-332 (1988).

Yasueda, H., et al., "Isolation and partial characterization of the major allergen from Japanese cedar (*Cryptomeria japonica*) pollen," *J. Allergy Clin Immunol.*, vol. 71(1 Pt. 1):77-86 (1983).

Burgess, Wilson H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology*, vol. 111:2129-2138 (1990).

Lazar, Eliane, et al., "Transforming Growth Factor α: Mutation of Aspartic Acid 47 and Leucine 48 Results in Different Biological Activities," *Molecular and Cellular Biology*, vol. 8(3):1247-1252 (1988).

Sone, Toshio, et al., "Cloning and Sequencing of cDNA Coding for *Cry j 1*, A Major Allergen of Japanese Cedar Pollen," *Biochemical and Biophysical Research Communications*, vol. 199(2):619-625 (1994).

Ukai, K., et al., "The evaluation of hyposensitization with sugi pollen extracts in patients with nasal allergy to Japanese sugi pollen," *Arerugi*, vol. 43(2 pt. 1):101-105 (1994).

Yeo, Ava, et al., "Manipulating the immune response in allergic disease: targeting CD4+ T cells," *Tibtech*, vol. 13:186-190 (1995).

Molecular Biology of the Cell, $2^{nd}$ Edition, Alberts et al. p. 174, 262-263.

\* cited by examiner

```
5'-AGTCAATCTG CTCATAATCA TAGCATAGCC GTATAGAAAG AAATTCTACA CTCTGCTACC      60

AAAAA ATG GAT TCC CCT TGC TTA GTA GCA TTA CTG GTT TTC TCT TTT           107
      Met Asp Ser Pro Cys Leu Val Ala Leu Leu Val Phe Ser Phe
      -21 -20                                  -15

GTA ATT GGA TCT TGC TTT TCT GAT AAT CCC ATA GAC AGC TGC TGG AGA         155
Val Ile Gly Ser Cys Phe Ser Asp Asn Pro Ile Asp Ser Cys Trp Arg
 -5                                   1                       5

GGA GAC TCA AAC TGG GCC CAA AAT AGA ATG AAG CTC GCA GAT TGT GCA         203
Gly Asp Ser Asn Trp Ala Gln Asn Arg Met Lys Leu Ala Asp Cys Ala
 10                              15                            20                       25

GTG GGC TTC GGA AGC TCC ACC ATG GGA AAG GGA GGA GAT CTT TAT             251
Val Gly Phe Gly Ser Ser Thr Met Gly Lys Gly Gly Asp Leu Tyr
            30                              35                       40

ACG GTC ACG AAC TCA GAT GAC GAC CCT GCA CCT GTG AAT CCT GCA CCA GGA ACT 299
Thr Val Thr Asn Ser Asp Asp Asp Pro Val Asn Pro Ala Pro Gly Thr
        45                              50                       55

CTG CGC TAT GGA GCA ACC CGA GAT AGG CCC CTG TGG ATA ATT TTC AGT         347
Leu Arg Tyr Gly Ala Thr Arg Asp Arg Pro Leu Trp Ile Ile Phe Ser
 60                              65                            70
```

FIG. 4A

```
GGG AAT ATG AAT ATA AAG CTC AAA ATG CCT ATG TAC ATT GCT GGG TAT    395
Gly Asn Met Asn Ile Lys Leu Lys Met Pro Met Tyr Ile Ala Gly Tyr
          75                  80                  85

AAG ACT TTT GAT GGC AGG GGA GCA CAA GTT TAT ATT GGC AAT GGC GGT    443
Lys Thr Phe Asp Gly Arg Gly Ala Gln Val Tyr Ile Gly Asn Gly Gly
      90                  95                 100                105

CCC TGT GTG TTT ATC AAG AGA GTT AGC AAT GTT ATC ATA CAC GGT TTG    491
Pro Cys Val Phe Ile Lys Arg Val Ser Asn Val Ile Ile His Gly Leu
              110                 115                 120

TAT CTG TAC GGC TGT AGT ACT AGT GTT TTG GGG AAT GTT TTG ATA AAC    539
Tyr Leu Tyr Gly Cys Ser Thr Ser Val Leu Gly Asn Val Leu Ile Asn
          125                 130                 135

GAG AGT TTT GGG GTG GAG CCT GTT CAT CCT CAG GAT GGC GAT GCT CTT    587
Glu Ser Phe Gly Val Glu Pro Val His Pro Gln Asp Gly Asp Ala Leu
      140                 145                 150

ACT CTG CGC ACT GCT ACA AAT ATT TGG ATT GAT CAT AAT TCT TTC TCC    635
Thr Leu Arg Thr Ala Thr Asn Ile Trp Ile Asp His Asn Ser Phe Ser
  155                 160                 165
```

FIG. 4B

```
AAT TCT TCT GAT GGT CTG GTC GAT GTC ACT CTT ACT TCG ACT GGA GTT        683
Asn Ser Ser Asp Gly Leu Val Asp Val Thr Leu Thr Ser Thr Gly Val
170                 175                 180                 185

ACT ATT TCA AAC AAT CTT TTT TTC AAC CAT AAA GTG ATG TTG TTA            731
Thr Ile Ser Asn Asn Leu Phe Phe Asn His Lys Val Met Leu Leu
            190                 195                 200

GGG CAT GAT GAT GCA TAT AGT GAT GAC AAA TCC ATG AAG GTG ACA GTG        779
Gly His Asp Asp Ala Tyr Ser Asp Asp Lys Ser Met Lys Val Thr Val
                205                 210                 215

GCG TTC AAT CAA TTT GGA CCT AAC TGT GGA CAA AGA ATG CCC AGG GCA        827
Ala Phe Asn Gln Phe Gly Pro Asn Cys Gly Gln Arg Met Pro Arg Ala
220                 225                 230

CGA TAT GGA CTT GTA CAT GTT GCA AAC AAT AAT TAT GAC CCA TGG ACT        875
Arg Tyr Gly Leu Val His Val Ala Asn Asn Asn Tyr Asp Pro Trp Thr
235                 240                 245

ATA TAT GCA ATT GGT GGG AGT TCA AAT CCA ACC ATT CTA AGT GAA GGG        923
Ile Tyr Ala Ile Gly Gly Ser Ser Asn Pro Thr Ile Leu Ser Glu Gly
250                 255                 260                 265
```

FIG. 4C

```
AAT AGT TTC ACT GCA CCA AAT GAG AGC TAC AAG AAG CAA GTA ACC ATA        971
Asn Ser Phe Thr Ala Pro Asn Glu Ser Tyr Lys Lys Gln Val Thr Ile
                270                     275                 280

CGT ATT GGA TGC AAA ACA TCA TCT TGT TCA AAT TGG GTG TGG CAA           1019
Arg Ile Gly Cys Lys Thr Ser Ser Cys Ser Asn Trp Val Trp Gln
            285                     290                 295

TCT ACA CAA GAT GTT TAT GGA GCT TAT TTT GTA TCA TCA GGG               1067
Ser Thr Gln Asp Val Phe Tyr Asn Gly Ala Tyr Phe Val Ser Ser Gly
            300                     305                 310

AAA TAT GAA GGG GGT AAT ATA TAC ACA AAG AAA GAA GCT TTC AAT GTT       1115
Lys Tyr Glu Gly Gly Asn Ile Tyr Thr Lys Lys Glu Ala Phe Asn Val
        315                     320                 325

GAG AAT GGG AAT GCA ACT CCT CAA TTG ACA AAA AAT GCT GGG GTT TTA       1163
Glu Asn Gly Asn Ala Thr Pro Gln Leu Thr Lys Asn Ala Gly Val Leu
        330                     335                 340             345

ACA TGC TCT CTC TCT AAA CGT TGT TGA TGA TGC A TATATTCTAG CATGTTGTAC    1217
Thr Cys Ser Leu Ser Lys Arg Cys
                350

TATCTAAATT AACACAACA AGAAAATATA TCATGATGTA TATTGTTGTA TTGATGTCAA       1277

AATAAAAATG TATCTTTTAC TATTAAAAAA AAAAATGATC GATCGGACGG TACCTCTAGA-3'   1337
```

FIG. 4D

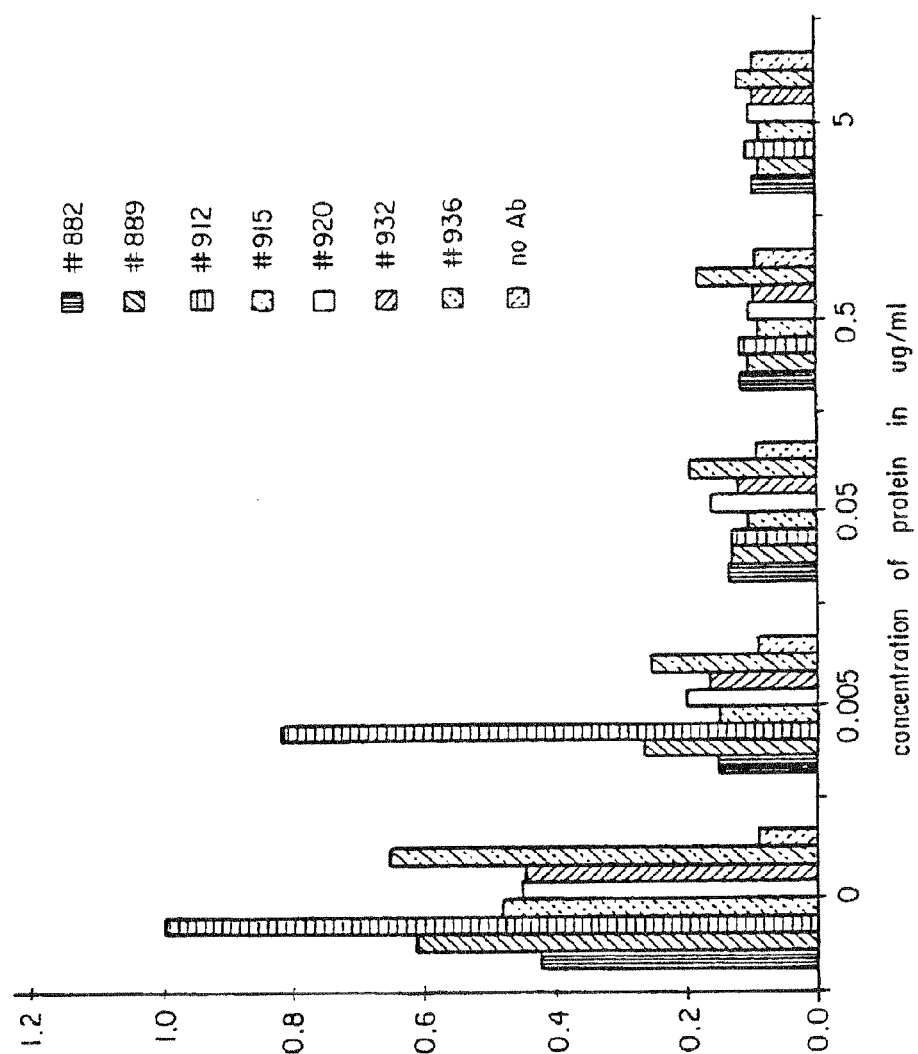

| PEPTIDE NAME | |
|---|---|
| CJI-1 (1-20) | DNPIDSCWRGDSNWAQNRMK |
| CJI-2 (11-30) | DSNWAQNRMKLADCAVGFGS |
| CJI-3 (21-40) | LADCAVGFGSSTMGGKGGDL |
| CJI-4 (31-50) | STMGGKGGDLYTVTNSDDDP |
| CJI-5 (41-60) | YTVTNSDDDPVNPAPGTLRY |
| CJI-6 (51-70) | VNPAPGTLRYGATRDRPLWI |
| CJI-7 (61-80) | GATRDRPLWIIFSGNMNIKL |
| CJI-8 (71-90) | IFSGNMNIKLKMPMYIAGYK |
| CJI-9 (81-100) | KMPMYIAGYKTFDGRGAQVY |
| CJI-10 (91-110) | TFDGPGAQVYIGNGGPCVFI |
| CJI-11 (101-120) | IGNGGPCVFIKRVSNVIIHG |
| CJI-12 (111-130) | KRVSNVIIHGLYLYGCSTSV |
| CJI-13 (121-140) | LYLYGCSTSVLGNVLINESF |
| CJI-14 (131-150) | LGNVLINESFGVEPVHPQDG |
| CJI-15 (141-160) | GVEPVHPQDGDALTLRTATN |
| CJI-16 (151-170) | DALTLRTATNIWIDHNSFSN |
| CJI-17 (161-180) | IWIDHNSFSNSSDGLVDVTL |
| CJI-18 (171-190) | SSDGLVDVTLTSTGVTISNN |
| CJI-19 (181-200) | TSTGVTISNNLFFNHHKVML |
| CJI-20 (191-210) | LFFNHHKVMLLGHDDAYSDD |
| CJI-21 (201-220) | LGHDDAYSDDKSMKVTVAFN |
| CJI-22 (211-230) | KSMKVTVAFNQFGPNCGQRM |
| CJI-23 (221-240) | QFGPNCGQRMPRARYGLVHV |
| CJI-24 (231-250) | PRARYGLVHVANNNYDPWTI |
| CJI-25 (241-260) | ANNNYDPWTIYAIGGSSNPT |
| CJI-26 (251-270) | YAIGGSSNPTILSEGNSFTA |
| CJI-27 (261-280) | ILSEGNSFTAPNESYKKQVT |
| CJI-28 (271-290) | PNESYKKQVTIRIGCKTSSS |
| CJI-29 (281-300) | IRIGCKTSSSCSNWVWQSTQ |
| CJI-30 (291-310) | CSNWVWQSTQDVFYNGAYFV |
| CJI-31 (301-320) | DVFYNGAYFVSSGKYEGGNI |
| CJI-32 (311-330) | SSGKYEGGNIYTKKEAFNVE |
| CJI-33 (321-340) | YTKKEAFNVENGNATPQLTK |
| CJI-34 (331-350) | NGNATPQLTKNAGVLTCSLS |
| CJI-35 (341-353) | NAGVLTCSLSKRC |

FIG. 13

```
5'--AAATTCTATATTCTGAACCCTAAAAATGGCTTCCCCATGCTTAATAGCAGTCCTTGTTT        60
                         M  A  S  P  C  L  I  A  V  L  V  F
                        -21 -20              -15              -10

CCTTTGTGCAATTGTATCTTGTTACTCTGATAATCCCATCGACAGCTGCTGGAGAGGAGA       120
 L  C  A  I  V  S  C  Y  S  D  N  P  I  D  S  C  W  R  G  D
       -5                        +1                 5              10

TTCGAACTGGGATCAAAACAGAATGAAGCTCGCAGACTGTGCTGTGGGATTTGGAAGCTC       180
 S  N  W  D  Q  N  R  M  K  L  A  D  C  A  V  G  F  G  S  S
             15                       20                 25              30

CACCATGGGAGGAGGCAAAGGAGGAGATTTTTACACCGTCACAAGCACAGATGATAATCCTGT    240
 T  M  G  G  G  K  G  G  D  F  Y  T  V  T  S  T  D  D  N  P  V
       35                       40                 45              50

GAATCCCTACACCAGGAACTTTGCGCTATGGAGCAACAAGAGAAAAAGCACTTTGGATCAT    300
 N  P  T  P  G  T  L  R  Y  G  A  T  R  E  K  A  L  W  I  I
       55                       60                 65              70

TTTCTCTCAGAATATGAATATAAAGCTCAAGATGCCTTTGTATGTGCTGGACATAAGAC       360
 F  S  Q  N  M  N  I  K  L  K  M  P  L  Y  V  A  G  H  K  T
             75                       80                 85              90

TATTGACGGCAGGCAGGGAGCAGATGTTCATCTTGGCAACGGCGGTCCCTGTCTGTTTATGAG   420
 I  D  G  R  Q  G  A  D  V  H  L  G  N  G  G  P  C  L  F  M  R
             95                      100                 105              110
```

FIG. 16A

```
GAAAGTGAGCCATGTTATTCTCCATAGTTTGCATATACACGGTTGTAATACGAGTGTTTT    480
 K  V  S  H  V  I  L  H  S  L  H  H  G  C  N  T  S  V  L
              115              120              125              130

GGGGGATGTGTTTGGTAAGTGAGTCTATTGGGGGTCGAGCCTGTTCATGCTCAGGAGGGGA    540
 G  D  V  L  V  S  E  S  I  G  V  E  P  V  H  A  Q  D  G  D
              135              140              145              150

CGCCATTACTATGCGCCATGTTACAAATGCTTGGATTGATCATAATTCTCTCTCCGATTG    600
 A  I  T  M  R  H  V  T  N  A  W  I  D  H  N  S  L  S  D  C
              155              160              165              170

TTCTGATGGTCTTATCGATGTTACGCTTGGCCTCCACTGGAATTACTATCTCCAACAATCA    660
 S  D  G  L  I  D  V  T  L  G  S  T  G  I  T  I  S  N  N  H
              175              180              185              190

CTTCTTCAACCATCATAAAGTGATGTTATTAGGACATGATGATACATATGACGATGACAA    720
 F  F  N  H  H  K  V  M  L  L  G  H  D  D  T  Y  D  D  D  K
              195              200              205              210

ATCTATGAAAGTGACAGTGGCGTTCAATCAATTTGGACCTAATGCTGGGCAAAGAATGCC    780
 S  M  K  V  T  V  A  F  N  Q  F  G  P  N  A  G  Q  R  M  P
              215              220              225              230
```

FIG. 16B

```
AAGGGCACGATATGGACTTGTACATGTTGCAAACAATAATTATGATCCATGGAATATATA  840
 R  A  R  Y  G  L  V  H  Y  A  N  N  N  Y  D  P  W  N  I  Y
      235                 240                 245                 250

TGCTATTGGTGGGAGTTCAAATCCAACCATTCTGAGTGAAGGAATAGTTTCACTGCCCC   900
 A  I  G  G  S  S  N  P  T  I  L  S  E  G  N  S  F  T  A  P
      255                 260                 265                 270

AAGTGAGAGTTACAAGAAGCAAGTAACAAAGCGTATAGGGTGTGAATCACCATCAGCTTG  960
 S  E  S  Y  K  K  Q  V  T  K  R  I  G  C  E  S  P  S  A  C
      275                 280                 285                 290

TGCCGAACTGGGTGTGGAGATCTACACGAGATGCTTTTATTAATGGAGCTTATTTTGTATC 1020
 A  N  W  V  W  R  S  T  R  D  A  F  I  N  G  A  Y  F  V  S
      295                 300                 305                 310

ATCGGGGAAAACTGAAGAGACCAATATATACAATAGTAATGAAGCTTTCAAAGTTGAGAA 1080
 S  G  K  T  E  E  T  N  I  Y  N  S  N  E  A  F  K  V  E  N
      315                 320                 325                 330

TGGGAATGCAGCTCCTCAATTAACCAAAAATGCTGGAGTTGTAACCTAAGCTCTCTCTAA 1140
 G  N  A  A  P  Q  L  T  K  N  A  G  V  V  T  -
      335                 340                 345

ATCTTGCTTATGAAACGAAAAAATATATAG-3'                             1170
```

FIG. 16C

```
5'-CGGTATAGATAGATTCTATATTCTGAGCCCTAAAAATGGCTTCCCCATGCTTAATAGCAT       60
                                     M  A  S  P  C  L  I  A
                                    -21 -20              -15

TCCTTGTTTTCCTTTGTGCAATTGTATCTTGTGCTCTGATAATCCCATAGACAGCTGCT        120
 F  L  V  F  L  C  A  I  V  S  C  C  S  D  N  P  I  D  S  C
        -10                       -5                       +1  5

GGAGAGGAGATTCGAACTGGGGTCAAAACAGAATGAAGCTCGCAGATTGCGCTGTGGGAT       180
 W  R  G  D  S  N  W  G  Q  N  R  M  K  L  A  D  C  A  V  G
         10                      15                      20      25

TTGGAAGCTCCACCATGGGAGGCAAAGGAGGAGATTTTACACCGTCACAAGGCGCAGATG       240
 F  G  S  T  M  G  G  K  G  G  D  F  Y  T  V  T  S  A  D
         30                      35                      40      45

ATAATCCTGTGAATCCTACACCAGGAACTTTGCGCTATGGAGCAACAAGAGAAAAAGCAC       300
 D  N  P  V  N  P  T  P  G  T  L  R  Y  G  A  T  R  E  K  A
         50                      55                      60      65

TTTGGATCATTTTCTCTCAGAATATGAATATAAAGCTCAAGATGCCTTTGTATGTTGCTG       360
 L  W  I  I  F  S  Q  N  M  N  I  K  L  K  M  P  L  Y  V  A
         70                      75                      80      85

GACATAAGACTATTGACGGCAGGGGAGCAGATGTTCATCTTGGCAACGGCGGTCCCTGTC       420
 G  H  K  T  I  D  G  R  G  A  D  V  H  L  G  N  G  G  P  C
         90                      95                     100     105
```

FIG. 17A

```
TGTTTATGAGGAAAGTGAGCCATGTTATTCTCCATGGTTTGCATATACACGGTTGTAATA      480
 L  F  M  R  K  V  S  H  V  I  L  H  G  L  H  I  H  G  C  N
    110             115             120             125

CTAGTGTTTGGGGATGTTTTGTTGGTAAGTGAGTCTATTGGGGTGGTGCCTGTACACCCCC      540
 T  S  V  L  G  D  V  L  V  S  E  S  I  G  V  V  P  V  H  P
    130             135             140             145

AGGACGGAGATGCGTTTACTGTGAGGACCCTCTGACACATATTGGGTCGACCATAATACTC      600
 Q  D  G  D  A  F  T  V  R  T  S  E  H  I  W  V  D  H  N  T
    150             155             160             165

TCTCCAATGGCACCGACGCGTTACTCTGCTTCCACTGCTGTGTACTATTT      660
 L  S  N  G  T  D  G  L  V  D  V  T  L  A  S  T  A  V  T  I
    170             175             180             185

CCAATAACCACTTCTTCGACCATGATGAAGTGATGTTGTAGGACATAGTGATTCATTCT      720
 S  N  N  H  F  F  D  H  D  E  V  M  L  G  H  S  D  S  F
    190             195             200             205

CAGATGATAAAGTGATGAAAGTCACAGTTGCATTTAACCACTTTGGACCTAATTGTGTGC      780
 S  D  D  K  V  M  K  V  T  V  A  F  N  H  F  G  P  N  C  V
    210             215             220             225

AACGATTGCCAAGGGCTAGATATGGACACTTTCATGTTGTTAATAATAATTATGAGCCAT      840
 Q  R  L  P  R  A  R  Y  G  H  F  H  V  V  N  N  Y  E  P
    230             235             240             245
```

FIG. 17B

```
GGGGAAAATATGCCATTGGAGGAAGTTCTGATCCAACAATTATAAGTGAAGGGAATAGAT    900
 W  G  K  Y  A  I  G  G  S  S  D  P  T  I  I  S  E  G  N  R
          250                255                260                265

TTCTTGCACCAAATGAATCTTATAAAAGGAGGTGACAATACGTGTAGGTTGTAAATCTA    960
 F  L  A  P  N  E  S  Y  K  K  E  V  T  I  R  V  G  C  K  S
          270                275                280                285

CAAGTTGTGATGCATGGGAGTGGAGATCAAAAGATGATGCCTTCCTTAATGGTGCCTATT    1020
 T  S  C  D  A  W  E  W  R  S  K  D  D  A  F  L  N  G  A  Y
          290                295                300                305

TTGTACAATCAGGCAAGGGGTATAATGGTGGAGAGGCATTCAAGGTTGAAAGTGCAAATG    1080
 F  V  Q  S  G  K  G  Y  N  G  G  E  A  F  K  V  E  S  A  N
          310                315                320                325

AGGTGCCAACATTGACTAAACATGCTGGAGCATTAAAATGTATACCTACCAAACAATGTG    1140
 E  V  P  T  L  T  K  H  A  G  A  L  K  C  I  P  T  K  Q  C
          330                335                340                345

TGATATGAAAAGTCAATCGATATAATAATGTGTTATTTGTAAATATTTCAGCTTTGAATAT    1200
 V  I  -

GTATAGAAAAGAATTTCAACAAAATGACACTATTATATAAATAAATTCTTAGTTTATTA    1260

GTTGGTATTAAAAAAAAA-3'    1278
```

FIG. 17C

| | |
|---|---|
| CJI-41 | KMPMYIAGYKTFDGRGAQVYIGNGGPCVFI |
| CJI-41.1 | PMYIAGYKTFDGRGAQVYIGNGGP |
| CJI-41.2 | YIAGYKTFDGRGAQVYIGNGGP |
| CJI-41.3 | KKYIAGYKTFDGRGAQVYIGNGGP |
| | |
| CJI-42 | DALTLRTATNIWIDHNSFSNSSDGLVDVTL |
| CJI-42.1 | RTATNIWIDHNSFSNSSDGLVD |
| CJI-42.2 | KRTATNIWIDHNSFSNSSDGLVDK |
| | |
| CJI-43 | KSMKVTVAFNQFGPNCGQRMPRARYGLVHVANNNYD |
| CJI-43.1 | KSMKVTVAFNQFGPNCGQRMPRARYGLVHV |
| CJI-43.6 | KSMKVTVAFNQFGPNSGQRMPRARYGLVHV |
| CJI-43.7 | KSMKVTVAFNQFGPNCGQRMPRARYGLV |
| CJI-43.8 | KSMKVTVAFNQFGPNSGQRMPRARYGLV |
| CJI-43.9 | KSMKVTVAFNQFGPNCGQRMPRARYG |
| CJI-43.10 | KSMKVTVAFNQFGPNSGQRMPRARYG |
| CJI-43.11 | KSMKVTVAFNQFGPNSGQRMPRARYGKK |
| CJI-43.12 | KSMKVTVAFNQFGPNCGQRMPRARYG |
| | |
| CJI-45 | PRARYGLVHVANNNYDPWTIYAIGGSSNPT |
| CJI-45.1 | RARYGLVHVANNNYDPWTIYAIGGSSNP |
| CJI-45.2 | RARYGLVHVANNNYDPWTIYAIGGSS |
| | |
| CJI-44 | DVFYNGAYFVSSGKYEGGNIYTKKEAFNVE |
| CJI-44.1 | NGAYFVSSGKYEGGNIYTKKEAFNVE |
| CJI-44.2 | NGAYFVSSGKYEGGNIYTKKEAFN |
| CJI-44.3 | KKNGAYFVSSGKYEGGNIYTKKEAFN |

Fig. 18

| | |
|---|---|
| CJI-42.5 | DERTATNIWIDHNSFSNSSDD |
| CJI-42.8 | DERTATNIWIDHNSFSNSSDGLAD |
| | |
| CJI-43.26 | DEKSMKATVAFNQFGPNDE |
| CJI-43.27 | DEKSMKVTAAFNQFGPNDE |
| CJI-43.30 | DEEKSMKATVAFNEFGPNDEE |
| CJI-43.31 | DEEKSMKVTVAANQFGPNDEE |
| CJI-43.32 | DEEKSMKVTVAFNQAGPNDEE |
| CJI-43.35 | DEKSMKATAAFNQFGPNDE |
| CJI-43.36 | DEEKSMKATAAFNQFGPNDEE |
| CJI-43.39 | DDAYSDDKSMKVTVAFNQFGDE |
| | |
| CJI-24.5 | DKEPRARYGLVHVANNNYDPWTIEEE |
| | |
| CJI-44.5 | DENGAYFVSSGKYEGGNIYTKKEAFNAE |
| CJI-44.6 | DEENGAYFVSSGKYEGGNIYTKKEAFNVE |
| CJI-44.8 | DEEGAYFVSSGKYEGGNIYTKKEAFNVE |

Fig. 20

```
TGAGTTCGAGACAAGTATAGAAAGAATTTCTTTTATTAAAATGGCCATGAAATTAATTG
                                      M  A  M  K  L  I
 10        20        30        40        50        60

CTCCAATGGCCTTTCTGGCCATGCAATTGATTATAATGGCGGCAGCAGAAGATCAATCTG
 A  P  M  A  F  L  A  M  Q  L  I  M  A  A  A  E  D  Q  S
                     10                    20
 70        80        90       100       110       120

CCCAAATTATGTTGGACAGTGTTGTCGAAAAATATCTTAGATCGAATCGGAGTTTAAGAA
 A  Q  I  M  L  D  S  V  V  E  K  Y  L  R  S  N  R  S  L  R
              30                    40
130       140       150       160       170       180

AAGTTGAGCATTCCCGTCATGATGCTATCAACATTCTTCAATGTGGAAAAGTATGGCGCAG
 K  V  E  H  S  R  H  D  A  I  N  I  F  N  V  E  K  Y  G  A
              50                    60
190       200       210       220       230       240
```

FIG. 28A

```
250         260         270         280         290         300
TAGGCGATGGAAAGCATGATTGCACTGAGGCATTTCAACAGCATGGCAAGCTGCATGCA
 V  G  D  G  K  H  D  C  T  E  A  F  S  T  A  W  Q  A  A  C
          70                        80

310         320         330         340         350         360
AAACCCATCAGCAATGTTGCTTGTGCCAGGCAGCAAGAAATTTGTTAAACAATCTGT
 K  N  P  S  A  M  L  L  V  P  G  S  K  K  F  V  V  N  N  L
          90                       100

370         380         390         400         410         420
TCTTCAATGGGCCATGTCAACCTCACTTTACTTTTAAGGTAGATGGGATAATAGCTGCGT
 F  F  N  G  P  C  Q  P  H  F  T  F  K  V  D  G  I  I  A  A
         110                       120

430         440         450         460         470         480
ACCAAAATCCAGCGAGCTGGAAGAATAATAGAATATGGTTGCAGTTTGCTAAACTTACAG
 Y  Q  N  P  A  S  W  K  N  N  R  I  W  L  Q  F  A  K  L  T
         130                       140
```

FIG. 28B

```
490        500        510        520        530        540
GTTTACTCTAATGGGTAAAGGTGTAATTGATGGGCAAGGAAAACAATGGTGGGCTGGCC
 G  F  T  L  M  G  K  G  V  I  D  G  Q  G  K  Q  W  W  A  G
          150                           160

550        560        570        580        590        600
AATGTAAATGGTCAATGGAAAGTTGTAACGATCGTGATAGACCAACAGCCATTA
 Q  C  K  W  V  N  G  R  E  I  C  N  D  R  D  R  P  T  A  I
          170                           180

610        620        630        640        650        660
AATTCGATTTTTCCACGGGTCTGATAATCCAAGGACTGAAACTAATGAACAGTCCCGAAT
 K  F  D  F  S  T  G  L  I  I  Q  G  L  K  L  M  N  S  P  E
          190                           200

670        680        690        700        710        720
TTCATTAGTTTTTGGGAATTGTGAGGGAGTAAAAATCATCGGCATTAGTATTACGGCAC
 F  H  L  V  F  G  N  C  E  G  V  K  I  I  G  I  S  I  T  A
          210                           220
```

FIG. 28C

```
      730         740         750         760         770         780
       |           |           |           |           |           |
CGAGAGACAGTCCTAACACTGATGGAATTGATATCTTTGCATCTAAAAACTTTCACTTAC
 P  R  D  S  P  N  T  D  G  I  D  I  F  A  S  K  N  F  H  L
230                                     240

790         800         810         820         830         840
       |           |           |           |           |           |
AAAAGAACACGATAGGAACAGGGGATGACTGCGTCGCTATAGGCACAGGTCTTCTAATA
 Q  K  N  T  I  G  T  G  D  D  C  V  A  I  G  T  G  S  S  N
        250                                     260

850         860         870         880         890         900
       |           |           |           |           |           |
TTGTGATTGAGGATCTGATTTGCGGTCCAGGCCATGGAATAAGTATAGGAAGTCTTGGGA
 I  V  I  E  D  L  I  C  G  P  G  H  G  I  S  I  G  S  L  G
           270                                     280

910         920         930         940         950         960
       |           |           |           |           |           |
GGGAAACTCTAGAGCAGAGGTTTCATACGTGCACGTAAATGGGGCTAAAATTCATAGACA
 R  E  N  S  R  A  E  V  S  Y  V  H  V  N  G  A  K  F  I  D
              290                                     300
```

FIG.28D

```
       970         980         990        1000        1010        1020
        |           |           |           |           |           |
CACAAAATGGATTAAGAATCAAAACATGGCAGGGTGTTCAGGCATGGCAAGCCATATAA
 T  Q  N  G  L  R  I  K  T  W  Q  G  G  S  G  M  A  S  H  I
            310                 320

1030        1040        1050        1060        1070        1080
        |           |           |           |           |           |
TTTATGAGAATGTTGAAATGATAAATTCGGAGAACCCCATATTAATAAATCAATTCTACT
 I  Y  E  N  V  E  M  I  N  S  E  N  P  I  L  I  N  Q  F  Y
            330                 340

1090        1100        1110        1120        1130        1140
        |           |           |           |           |           |
GCACTTCAGCTTCTGCTTGCCAAAACCAGAGGTCTGCGGTTCAAATCCAAGATGTGACAT
 C  T  S  A  S  A  C  Q  N  Q  R  S  A  V  Q  I  Q  D  V  T
            350                 360

1150        1160        1170        1180        1190        1200
        |           |           |           |           |           |
ACAAGAACATACGTGGGACATCAGCAACAGCAGCAATTCAACTTAAGTGCAGTGACA
 Y  K  N  I  R  G  T  S  A  T  A  A  A  I  Q  L  K  C  S  D
            370                 380
```

FIG. 28E

```
1210          1220          1230          1240          1250          1260
GTATGCCCTGCAAAGATATAAAGCTAAGTGATATATCTTTGAAGCTTACCTTCAGGGAAAA
 S  M  P  C  K  D  I  K  L  S  D  I  S  L  K  L  T  S  G  K
              390                         400

1270          1280          1290          1300          1310          1320
TTGCTTCCTGCCTTAATGATAATGCAAATGGATATTTCAGTGGACACGTCATCCCTGCAT
 I  A  S  C  L  N  D  N  A  N  G  Y  F  S  G  H  V  I  P  A
              410                         420

1330          1340          1350          1360          1370          1380
GCAAGAATTTAAGTCCAAGTGCTAAGCGAAAAGAATCTAAATCCCATAAACACCCAAAAA
 C  K  N  L  S  P  S  A  K  R  K  E  S  K  S  H  K  H  P  K
              430                         440

1390          1400          1410          1420          1430          1440
CTGTAATGGTTGAAAATATGCGAGCATATGACAAGGGTAACAGAACACGCATATTGTTGG
 T  V  M  V  E  N  M  R  A  Y  D  K  G  N  R  T  R  I  L  L
              450                         460
```

FIG. 28F

```
                1450         1460         1470         1480         1490         1500
                 |            |            |            |            |            |
         GGTCGAGGCCTCCGAATTGTACAAACAATGTCATGGTTGCAGTCCATGTAAGGCCAAGT
          G  S  R  P  P  N  C  T  N  K  C  H  G  C  S  P  C  K  A  K
                                               480

1510         1520         1530         1540         1550         1560
                 |            |            |            |            |            |
         TAGTTATTGTTCATCGTATTATGCCCGCAGGAGTATTATCCTCAGAGGTGGATATGCAGCT
          L  V  I  V  H  R  I  M  P  Q  E  Y  Y  P  Q  R  W  I  C  S
                    490                              500

1570         1580         1590         1600         1610         1620
                 |            |            |            |            |            |
         GTCATGGCAAAATCTACCATCCATAATGAGATACATTGAAACTGTATGTGCTAGTGAATA
          C  H  G  K  I  Y  H  P  -
                    510       514

1630         1640         1650         1660         1670         1680
                 |            |            |            |            |            |
         TTCTTTGTTGTACAATATTATTAGAACTGATATTGAAAATAAATCATCAATGTTTCTAAGGCAT 1690         1700         1710         1720
                 |            |            |            |
         TTATAATAGATTATATTAATGGTTCAGCCTGGTGCAAAAAAAAAA

FIG. 28G
```

```
        10         20         30         40         50
         |          |          |          |          |
MAMKLIAPMAFLAMQLITMAAAEDQSAQIMLDSVVEKYLRSNRSLRKVEH 60         70         80         90        100
         |          |          |          |          |
SRHDAINIFNVEKYGAVGDGKHDCTEAFSTAWQAACKNPSAMLLVPGSKK 110        120        130    N   140        150
         |          |          |          |          |
FVVNNLFFNGPCQPHFTFKVDGIIAAYQNPASWKNNRIWLQFAKLTGFTL 160        170        180        190        200
         |          |          |          |          |
MGKGVIDGQGKQWWAGQCKWVNGREICNDRDRPTAIKFDFSTGLIIQGLR 210        220        230        240        250
         |          |          |          |          |
LMNSPEFHLVFGNCEGVKIIGISITAPRDSPNTDGIDIFASKNFHLQKNT 260        270        280        290        300
         |          |          |          |          |
IGTGDDCVAIGTGSSNIVIEDLICGPGHGISIGSLGRENSRAEVSYVHVN 310        320        330        340        350
         |          |          |          |          |
GAKFIDTQNGLRIKTWQGGSGMASHIIYENVEMINSENPILINQFYCTSA 360        370        380        390        400
         |          |          |          |          |
SACQNQRSAVQIQDVTYKNIRGTSATAAAIQLKCSDSMPCKDIRLSDISL 410        420        430        440        450
         |          |          |          |          |
KLTSGKIASCLNDNANGYFSGHVIPACRNLSPSAKRKESKSHKHPKTVMV 460        470        480        490        500
         |          |          |          |          |
ENMRAYDKGNRTRILLGSRPPNCTNKCHGCSPCKAKLVIVHRIMPQEYYP 510 514
         |   |
QRWICSCHGKIYHP
```

FIG. 29

```
                        50                60
Cry j II    R K V E H S R H D A I N F N V E K Y G A
LONG        R K V E H S R H D A I N F N V E K Y G A
SHORT                   S R H D A I N F N V E K Y G A
SAKAGUCHI                       A I N F N V E K Y 70                80                90
Cry j II    V G D G K H D C T E A F S T A W Q A A C K N P S
LONG        V G D G K H D C T E A F S T A W(Q       )K N P( )
SHORT       V G D G K H D C T E A F S T A W(Q       )K N P( )
```

Fig. 30

| PATIENT # | MAST | PURIFIED NATIVE Cry j I | PURIFIED NATIVE Cry j II | RECOMBINANT Cry j II (rCry j II) |
|---|---|---|---|---|
| 1034 | 2 | - | + | - |
| 1142 | 2 | + | - | - |
| 1143 | 0 | + | + | + |
| 1144 | 1 | + | + | - |
| 1145 | 0 | - | - | + |
| 1146 | 3 | + | - | - |
| 1147 | 3 | + | - | - |
| 1148 | 3 | + | + | + |
| 1151 | 3 | + | + | - |
| 1153 | 1 | + | - | - |
| 1154 | 3 | + | + | - |
| 1158 | 2 | + | + | - |
| 1159 | 2 | + | + | + |
| 1165 | 1 | + | - | + |
| 1167 | 1/0 | - | + | - |
| 1170 | 1/0 | + | - | - |
| 1171 | 2 | + | - | - |
| 1178 | 1 | + | - | - |
| 1181 | 1/0 | + | − | - |
| 1182 | 1 | + | + | - |
| 1183 | 1 | + | + | + |
| 1185 | 1/0 | + | + | - |
| 1186 | 1/0 | + | + | + |
| POSITIVE | 21 | 20 | 13 | 5 |

Fig. 40

Cry j IIA       FTFKVDGIIAAYQ

Cry j IIB       NGYFSGHVIPACKN

Cry j IIC:

```
1         10        20        30        40        50        60
|         |         |         |         |         |         |
MGHHHHHHEFRKVEHSRHDAINIFNVEKYGAVGDGKHDCTEAFSTAWQAACKNPSAMLLV 70        80        90        100       110       120
          |         |         |         |         |         |
PGSKKFVVNNLFFNGPCQPHFTPKVDGIIAAYQNPASWKNNRIWLQFAKLTGFTLMGKGV

128
     |
IDGQGKQW
```

Cry j IID:

```
1         10        20        30        40        50        60
|         |         |         |         |         |         |
MGHHHHHHEFWAGQCKWVNGREICNDRDRPTAIKFDFSTGLIIQGLKLMNSPEFHLVFGN 70        80        90        100       110       120
          |         |         |         |         |         |
CEGVKIIGISITAPRDSPNTDGIDIFASKNFHLQKNTIGTGDDCVAIGTGSSNIVIEDLI

127
     |
CGPGHG

Cry j IIE:

```
1         10        20        30        40        50        60
|         |         |         |         |         |         |
MGHHHHHHEFSIGSLGRENSRAEVSYVXVNGAKFIDTQNGLRIKTWQGGSGMASHIIYEN 70        80        90        100       110       120
          |         |         |         |         |         |
VEMINSENPILINQFYCTSASACQNQRSAVQIQDVTYKNIRGTSATAAAIQLKCSDSMPC

127
       |
KDIKLSD
```

Cry j IIF:

```
1         10        20        30        40        50        60
|         |         |         |         |         |         |
MGHHHHHHEFISLKLTSGKIASCLNDNANGYFSGHVIPACKNLSPSAKRKESKSHKHPKT 70        80        90        100       110       120
          |         |         |         |         |         |
VMVENMRAYDKGNRTRILLGSRPPNCTNKCHGCSPCKAKLVIVHRIMPQEYYPQRWICSC
            I K   S S
       127
       |
HGKIYHP
```

Cry j IIG (J1 )    GKGVIDGQGKQWWAGQCKWVNGRE

Cry j-IIH (J3 )    DSMPCKDIKSDISLKLTSGKIAS

Cry j-IIQ (J2 )    EDLICGPGHGISIGSLGRENSRA

FIG. 41B

| | |
|---|---|
| CJI-42.3 | KDDRTATNIWIDHNSFSNSSDGLVDK |
| CJI-42.4 | DRTATNIWIDHNSFSNSSDD |
| CJI-42.6 | DKERTATNIWIDHNSFSNSSDDE |
| CJI-42.7 | DERTATNIWIDHNSFSNSSDGLVDD |
| CJI-42.9 | DEDRTATNIWIDHNSFSNSSDED |
| CJI-42.10 | DKERTATNIWIDHNSFSNSSDKE |
| CJI-42.11 | DEDRTATNIWIDHNSFSNDED |
| CJI-42.12 | DKERTATNIWIDHNSFSNDKE |
| CJI-42.13 | DEDRTATNIWIDHNSDED |
| CJI-42.14 | DKERTATNIWIDHNSDKE |
| CJI-42.15 | KRTATNIWIDHNSKRK |
| | |
| CJI-43.2 | KVTVAFNQFGPNCGQRMPRARYGLVHVANNNYD |
| CJI-43.3 | TVAFNQFGPNCGQRMPRARYGLVHVANNNYD |
| CJI-43.4 | KKAFNQFGPNCGQRMPRARYGLVHVANNNYD |
| CJI-43.5 | AFNQFGPNCGQRMPRARYGLVHVANNNYD |
| CJI-43.12 | KSMKVTVAFNQFGPNCGQRMPRARYGDK |
| CJI-43.13 | DSMKVTVAFNQFGPNSGQRMPRARYGDE |
| CJI-43.14 | KSMKVTVAFNQFGPNSGQRMPRARYGDE |
| CJI-43.15 | DKSMKVTVAFNQFGPNSGQRMPRARYGDE |
| CJI-43.16 | DEKSMKVTVAFNQFGPNSGQRMPRARYGDE |
| CJI-43.17 | KKSMKVTVAFNQFGPNSGQRMPRARYGKK |
| CJI-43.18 | KSMKVTVAFNQFGPNSGQRMPRARYGKK |
| CJI-43.19 | DEKSMKVTVAFNQFGPNSGQRMDE |
| CJI-43.20 | DESMKVTVAFNQFGPNSGQRMDE |
| CJI-43.21 | DEKSMKVTVAFNQFGPNSGQRDE |
| CJI-43.22 | DEKSMKVTVAFNQFGPNDE |
| CJI-43.23 | RSMKVTVAFNQFGPNSGQRMPRARYG |
| CJI-43.24 | RSMKVTVAFNQFGPNSGQRMPRARAG |
| CJI-43.25 | DEEKSMKVTVAFNQFGPNDE |
| CJI-43.28 | DEEKSMKVTVAFNQFGPNDEE |
| CJI-43.29 | KSMKVTVAFNQFGPNSGERAPRARAG |
| CJI-43.33 | DEEKSMKVTVAFNQFGPNSGDKE |
| CJI-43.34 | DDAYSDDKSMKVTVAFNQFG |
| CJI-43.36 | DEEKSMKATAAFNQFGPNDEE |
| CJI-43.37 | KSMKVTVAFNQFG |
| CJI-43.38 | KKKSMKVTVAFNQFGPNKK |
| CJI-43.40 | DDAYSDDKSMKVTVAFNQFGDKE |
| CJI-43.41 | DKDAYSDDKSMKVTVAFNQFGDKE |
| CJI-43.42 | DDDKSMKVTVAFNQFGDED |
| CJI-43.43 | DDDKSMKVTVAFNQDED |
| CJI-43.44 | DEDKSMKVTVAFNQDED |
| CJI-43.45 | DEDKSMKVTVAFNQAED |
| CJI-43.46 | KRKSMKVTVAFNQKRK |
| CJI-43.47 | KRKSMKVTVAFNQARK |
| CJI-43.48 | KRKSMKVTVAFNQRK |
| CJI-43.49 | DEDEDKSMKVTVAFNQ |
| CJI-43.50 | KSMKVTVAFNQARK |
| CJI-43.51 | KSMKVTVAFNQFGKRK |
| CJI-43.52 | DSMKVTVAFNQFGEDE |
| CJI-43.53 | KSMKVTVAFNQFGRKR |

FIG. 44A

```
CJI-43.54    KSMKVTVAFNQFGDEDE
CJI-43.55    KRKSMKVTVAFNQFGKRK
CJI-43.56    DEKSMKVTVAFNQFGDEDE
CJI-43.57    KSMKVTVAFNQAGKRK
CJI-43.58    HKSMKVTVAFNQFGH
CJI-43.59    NKSMKVTVAFNQFGN
CJI-43.60    NNKSMKVTVAFNQFGNN
CJI-24.2     RARYGLVHVANNNYDPWTI

CJI-44.5     DENGAYFVSSGKYEGGNIYTKKEAFNAE
CJI-44.7     DEGAYFVSSGKYEGGNIYTEKEAFNAE
CJI-44.9     DEEGAYFVSSGKYEGGNIYTKKEAFNVEDE
CJI-44.10    DKEGAYFVSSGKYEGGNIYTKKEAFNVEKD
```

FIG. 44B

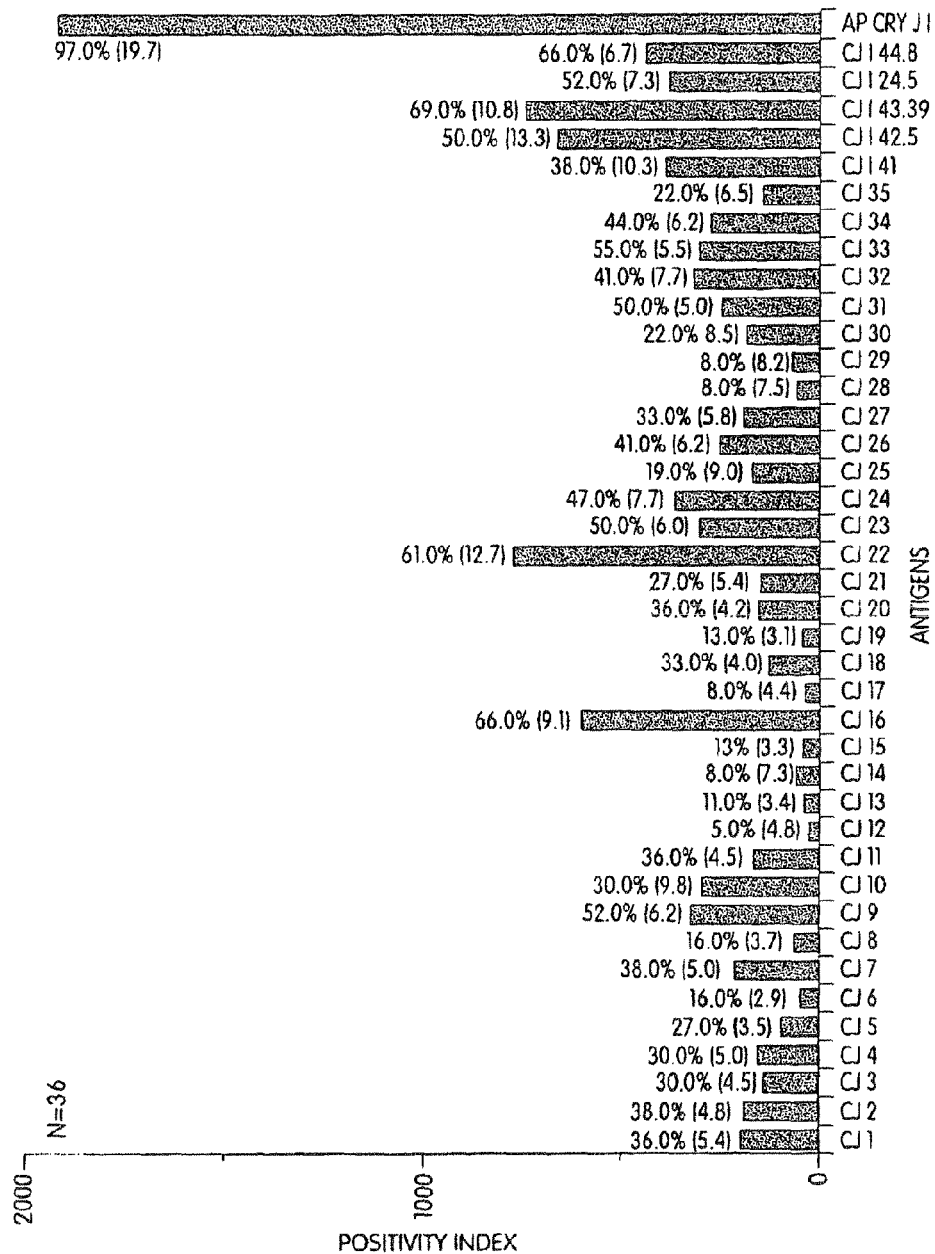

ALLERGENIC PROTEINS AND PEPTIDES FROM JAPANESE CEDAR POLLEN

RELATED CASES

This application is a continuation of U.S. Ser. No. 09/240,203, filed Jan. 29. 1999 (patented)which is a continuation of U.S. Ser. No. 08/487,023, filed Jun. 6, 1995 (patented), which is a divisional of U.S. Ser. No. 08/350,225, filed Dec. 6, 1994 (abandoned), which is a continuation-in-part of U.S. Ser. No. 08/226,248 filed Apr. 8, 1994 (abandoned), which is a continuation-in-part of PCT/US93/00139 (designating the U.S.) filed Jan. 15, 1993 which is a continuation-in-part of U.S. Ser. No. 07/938,990 filed Sep. 1. 1992 (abandoned) which is a continuation-in-part of U.S. Ser. No. 07/730,452 filed Jul. 15, 1991 (abandoned) which is a continuation-in-part of U.S. Ser. No. 07/729,134 filed Jul. 12, 1981 (abandoned). U.S. Ser. No. 08/226,248 filed Apr. 8, 1994 (abandoned) is also a continuation-in-part of U.S. Ser. No. 07/975,179 filed Nov. 12, 1992 (abandoned). All of the above-mentioned cases are hereby incorporated herein by Reference.

BACKGROUND OF THE INVENTION

Genetically predisposed individuals, who make up about 10% of the population, become hypersensitized (allergic) to antigens from a variety of environmental sources to which they are exposed. Those antigens that can induce immediate and/or delayed types of hypersensitivity are known as allergens. (King, T. P., *Adv. Immunol.* 23: 77-105, (1976)). Anaphylaxis or atopy, which includes the symptoms of hay fever, asthma, and hives, is one form of immediate allergy. It can be caused by a variety of atopic allergens, such as products of grasses, trees, weeds, animal dander, insects, food, drugs, and chemicals.

The antibodies involved in atopic allergy belong primarily to the IgE class of immunoglobulins. IgE binds to mast cells and basophils. Upon combination of a specific allergen with IgE bound to mast cells or basophils, the IgE may be cross-linked on the cell surface, resulting in the physiological effects of IgE-antigen interaction. These physiological effects include the release of, among other substances, histamine, serotonin, heparin, a chemotactic factor for eosinophilic leukocytes and/or the leukotrienes, C4, D4, and E4, which cause prolonged constriction of bronchial smooth muscle cells (Hood, L. E. et al. *Immunology* (2nd ed.), The Benjamin/Cumming Publishing Co., Inc. (1984)). These released substances are the mediators which result in allergic symptoms caused by a combination of IgE with a specific allergen. Through them, the effects of an allergen are manifested. Such effects may be systemic or local in nature, depending on the route by which the antigen entered the body and the pattern of deposition of IgE on mast cells or basophils. Local manifestations generally occur on epithelial surfaces at the location to at which the allergen entered the body. Systemic effects can include anaphylaxis (anaphylactic shock), which is the result of an IgE-basophil response to circulating (intravascular) antigen.

Japanese cedar (Sugi; *Cryptomeria japonica*) pollinosis is one of the most important allergic diseases in Japan. The number of patients suffering from this disease is on the increase and in some areas, more than 10% of the population are affected. Treatment of Japanese cedar pollinosis by administration of Japanese cedar pollen extract to effect hyposensitization to the allergen has been attempted. Hyposensitization using Japanese cedar pollen extract, however, has drawbacks in that it can elicit anaphylaxis if high doses are used, whereas when low doses are used to avoid anaphylaxis, treatment must be continued for several years to build up a tolerance for the extract.

The major allergen from Japanese cedar pollen has been purified and designated as Sugi basic protein (SBP) or Cry j I. This protein is reported to be a basic protein with a molecular weight of 41-50 kDa and a pI of 8.8. There appear to be multiple isoforms of the allergen, apparently due in part to differential glycosylation (Yasueda et al. (1983) *J. Allergy Clin. Immunol.* 71: 77-86; and Taniai et al. (1988) *FEBS Letters* 239: 329-332.

The sequence of the first twenty amino acids at the N-terminal end of Cry j I (SEQ ID NO: 18) and a sixteen amino acid sequence (SEQ ID NO: 19) at the carboxy terminus have been determined (Taniai supra).

A second allergen has recently been isolated from the pollen of *Cryptomeria japonica* (Japanese cedar) (Sakaguchi et al. (1990) *Allergy* 45:309-312). This allergen, designated Cry j II, has been reported to have a molecular weight of approximately 37 kDa and 45 kDa when assayed on sodium dodecyl sulfate-polyacrylamide gel electrophoresis (SDS-PAGE) under non-reducing and reducing conditions, respectively (Sukaguchi et al., supra). Cry j II was found to have no immunological cross-reactivity with Cry j I (Sakaguchi (1990) supra; Kawashima et al. (1992) *Int. Arch. Allergy Immunol.* 98:110-117). Most patients with Japanese cedar pollinosis were found to have IgE antibodies to both Cry j I and Cry j II, however, 29% of allergic patients had IgE that only reacted with Cry j I and 14% of allergic patients had IgE that only reacted with Cry j II (Sakaguchi (1990) supra). Isoelectric focusing of Cry j II indicated that this protein has a pI above 9.5, as compared to pI 8.6-8.8 for Cry j I (Sakaguchi (1990) supra).

In addition to hyposensitization of Japanese cedar pollinosis patients with low doses of Japanese cedar pollen extract, U.S. Pat. No. 4,939,239, issued Jul. 3, 1990 to Matsuhashi et al., discloses a hyposensitization agent comprising a saccharide covalently linked to a Japanese cedar pollen allergen for hyposensitization of persons sensitive to Japanese cedar pollen. This hyposensitization agent is reported to enhance the production of IgG and IgM antibodies, but reduce production of IgE antibodies which are specific to the allergen and responsible for anaphylaxis and allergy. The allergens used in the hyposensitization agent preferably have an $NH_2$-terminal amino acid sequence of Asp-Asn-Pro-Ile-Asp-Ser-X-Trp-Arg-Gly-Asp-Ser-Asn-Trp-Ala-Gln-Asn-Arg-Met-Lys-, wherein X is Ser, Cys, Thr, or His (SEQ ID NO: 18). Additionally, Usui et al. (1990) *Int. Arch. Allergy Appl. Immunol.* 91: 74-79 reported that the ability of a Sugi basic protein (i.e., Cry j I)-pullulan conjugate to elicit the Arthus reaction was markedly reduced, about 1,000 times lower than that of native Sugi basic protein and suggested that the Sugi basic protein-pullulan conjugate would be a good candidate for desensitization therapy against cedar pollinosis.

The Cry j I allergen found in *Cryptomeria japonica* has also been found to be cross-reactive with allergens in the pollen from other species of trees, including *Cupressus sempervirens*. Panzani et al. (*Annals of Allergy* 57: 26-30 (1986)) reported that cross reactivity was detected between allergens in the pollens of *Cupressus sempervirens* and *Cryptomeria japonica* in skin testing, RAST and RAST inhibition. A 50 kDa allergen isolated from Mountain Cedar (*Juniperus sabinoides*, also known as *Juniperus ashei*) has the $NH_2$-terminal sequence AspAsnProIleAsp (SEQ ID NO: 25) (Gross et al., (1978) *Scand. J. Immunol.* 8: 437-441) which is the same sequence as the first five amino acids of the $NH_2$ terminal end of the Cry j I allergen. The Cry j I allergen has also been found to be allergenically cross-reactive with the following species of trees: *Cupressus arizonica, Cupressus macrocarpa, Juniperus virginiana, Juniperus communis, Thuya orientalis*, and *Chamaecyparis obtusa*.

Despite the attention Japanese cedar pollinosis allergens have received, definition or characterization of the allergens responsible for its adverse effects on people is far from complete. Current desensitization therapy involves treatment with pollen extract with its attendant risks of anaphylaxis if high doses of pollen extract are administered, or long desensitization times when low doses of pollen extract are administered. Thus there is a pressing need for the development of compositions and methods that could be used in detecting sensitivity to Japanese cedar pollen allergens or other immunologically related allergens or in treating sensitivities to such allergens with reduced side effects. The present invention provides materials and methods having one or more of these utilities.

SUMMARY OF THE INVENTION

The present invention provides nucleic acid sequences coding for the *Cryptomeria japonica* major pollen allergen Cry j I and fragments thereof. The present invention also provides isolated Cry j I or at least one fragment or peptide thereof produced in a host cell transformed with a nucleic acid sequence coding for Cry j I (SEQ ID NO: I) or at least one fragment thereof and fragments of Cry j I prepared synthetically. The present invention also provides purified native Cry j I protein.

The present invention further provides Jun v I and Jun s I protein allergens which are immunologically cross-reactive with Cry j I and fragments of Jun v I and Jun s I produced in a host cell transformed with a nucleic acid sequence coding for Jun s I or Jun v I respectively and fragments of Jun s I and Jun v I prepared synthetically and purified native Jun s I and Jun v I. The present invention further provides nucleic acid sequences coding for Jun v I (SEQ ID NO: 94) and Jun s I (SEQ ID NO: 96) and fragments thereof. As used herein, a fragment of the nucleic acid sequence coding for the entire amino acid sequence of Cry j I, Jun s I or Jun v I refers to a nucleotide sequence having fewer bases than the nucleotide sequence coding for the entire amino acid sequence of Cry j I, (SEQ ID NO: 2) Jun s I (SEQ ID NO: 95) or Jun v I (SEQ ID NO: 97) and/or mature Cry j I, Jun s I or Jun v I. Cry j I, Jun s I or Jun v I and fragments thereof are useful for diagnosing, treating, and preventing Japanese cedar pollinosis as well as pollinosis caused by pollen from other species of trees wherein such pollen is immunologically cross-reactive with Japenese cedar pollen allergen.

The present invention also provides nucleic acid sequences coding for the *Cryptomeria japonica* major pollen allergen Cry j II (SEQ ID NO: 133) and fragments or peptides thereof. The present invention also provides purified Cry j II (SEQ ID NO: 134) and at least one fragment thereof produced in a host cell transformed with a nucleic acid sequence coding for Cry j II or at least one fragment thereof, fragments of Cry j II prepared synthetically, and purified native Cry j II protein purified to homogeneity. Cry j II and fragments thereof are useful for diagnosing, treating, and preventing Japanese cedar pollinosis.

As used herein the term "peptides" of the invention include full-length protein or fragments thereof. Peptides of the invention may be produced recombinantly, by chemical synthesis, or by chemical cleavage of the native protein allergen. Peptides within the scope of the invention preferably comprise at least one T cell epitope, and may comprise at least two T cell epitopes of Cry j I or Cry j II. The invention further provides peptides comprising at least two regions, each region comprising at least one T cell epitope of a Japanese cedar pollen protein allergen. The invention also provides modified peptides having similar or enhanced therapeutic properties as the corresponding, naturally-occurring allergen or portion thereof, but having reduced side effects, as well as modified peptides having improved properties such as increased solubility and stability. Peptides of the invention alone or in conjunction with other peptides of the invention when administered to a Japanese cedar pollen-sensitive individual or in an individual who is sensitive to an allergen cross-reactive with Japanese cedar pollen, are capable of modifying the allergic response of the individual to a Japanese cedar pollen allergen or an allergen cross-reactive with Japanese cedar pollen such as Jun s I or Jun v I. Methods of treatment or diagnosis of sensitivity to Japanese cedar pollen or a cross-reactive allergen in an individual and therapeutic compositions comprising one or more peptides of the invention are also provided. This invention is more particularly described in the appended claims and is described in its preferred embodiments in the following description.

BRIEF DESCRIPTION OF THE DRAWINGS

FIG. 1b shows an SDS-PAGE (12.5%) analysis of the fractions from the major peak shown in FIG. 1a;

FIGS. 4a-d show the composite nucleic acid sequence (SEQ ID NO: 1 from the two overlapping clones JC 71.6 and pUC19JC91a coding for Cry j I. The complete cDNA sequence for Cry j I (SEQ ID NO: 1) is composed of 1312 nucleotides, including 66 nucleotides of 5' untranslated sequence, an open reading frame starting with the codon for an initiating methionine of 1122 nucleotides, and a 3' untranslated region. FIGS. 4a-b also show the deduced amino acid sequence of Cry j I (SEQ ID NO: 2);

FIG. 7 is a graphic representation of the results of a competition ELISA using plasma from individual patients (indicated by patient numbers) wherein the coating antigen is soluble pollen extract (SPE) from Japanese cedar pollen and the competing antigen is purified native Cry j I;

FIG. 13 shows various peptides of desired lengths derived from Cry j I (SEQ ID NOs: 26-60);

FIG. 16a-c shows the nucleotide sequence (SEQ ID NO: 94) of Jun s I; this sequence is a composite from the two overlapping cDNA clones pUC19JS42e and pUC19JS45a as well as the full-length clone JS53iib coding for Jun s I; the complete cDNA sequence for Jun s I (SEQ ID NO: 94) is composed of 1170 nucleotides, including 25 nucleotides of 5' untranslated sequence, an open reading frame of 1,101 nucleotides, and a 3' untranslated region; FIG. 16 also shows the deduced amino acid sequence of Jun s I (SEQ ID NO: 95);

FIG. 17 shows the nucleotide sequence of Jun v I; this sequence is a composite from the two overlapping cDNA clones pUC19JV46a and pUC19JV49iia coding for Jun v I; the complete cDNA sequence for Jun v I (SEQ ID NO: 96) is composed of 1278 nucleotides, including 35 nucleotides of 5' untranslated sequence, an open reading frame of 1,110 nucleotides, and a 3' untranslated region; FIG. 17 also show the deduced amino acid sequence of Jun v I (SEQ ID NO: 97);

FIG. 18 shows various peptides of desired lengths derived from Cry j I (SEQ ID NOs: 71-93);

FIG. 19a shows RNA from C. japonica (U.S. and Japanese sources), J. sabinoides and J. virginiana probed with Cry j I cDNA; FIG. 19b shows RNA from J. sabinoides and C. arizonica probed with the same cDNA; the position of molecular weight standards are shown in each part of the Figure;

FIG. 20 shows various modified peptides of Cry j I (SEQ ID NOs: 119-132);

FIG. 28a-g shows the nucleic acid sequence (SEQ ID NO: 133) and the deduced amino acid sequence (SEQ ID NO: 134) coding for Cry j II;

FIG. 29 shows the deduced amino acid sequence of Cry j II (SEQ ID NO: 134);

FIG. 30 shows the long form and short form $NH_2$-terminii amino acid sequences of Cry j II determined by protein sequence analysis as discussed in Example 14 aligned with the ten amino acid sequence of Cry j II defined by Sakaguchi et al., supra (SEQ ID NOs: 262, 263, 138, 264, and 265);

FIG. 40 is a table which summarizes both the MAST scores performed on patient's plasma samples (Batch 1-3) and the direct ELISA results shown in FIGS. 31-39; a positive response is indicated by a (+) sign and the number of positive responses for each antigen is shown at the bottom of each column;

FIG. 41a-b shows various Cry j II peptides (SEQ ID NOs: 185-193);

FIG. 44 shows various modified Cry j I (SEQ ID NOs: 202-234, 127, 235-258, 130, and 259-261);

FIG. 45 is a graphic representation depicting T cell responses to various Cry j I peptides. The mean S.I. shown above each bar (in parenthesis) as well as the percentage of responses, the positivity index (mean S.I. multiplied by percentage of responses) is the Y axis.

DETAILED DESCRIPTION OF THE INVENTION

Figure 1A:
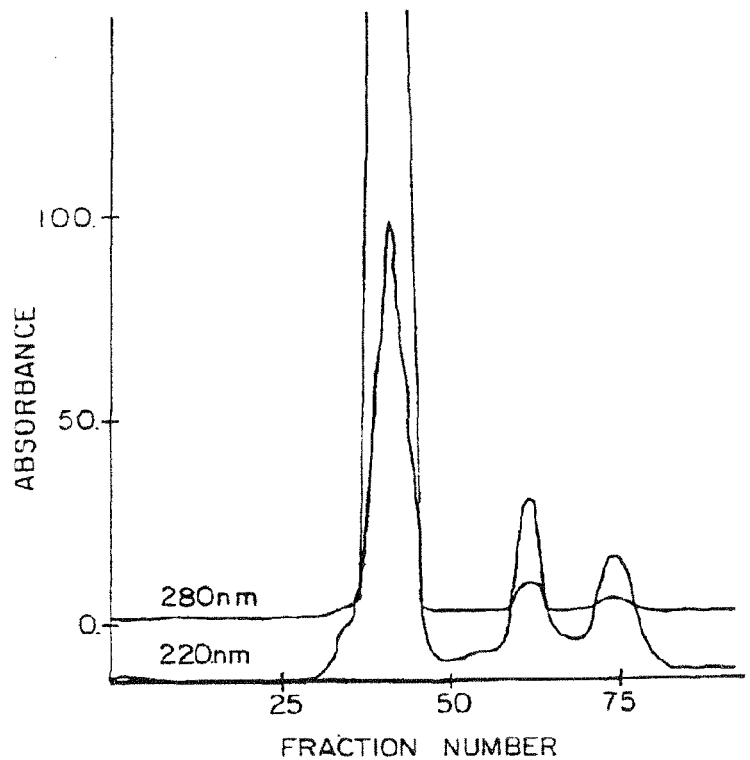
FIG. 1a is a graphic representation of affinity purified Cry j I on Superdex 75 (2.6 by 60 cm) equilibrated with 10 mM sodium acetate (pH 5.0) and 0.15 M NaCl.

The present invention provides nucleic acids encoding Cry j I, the major allergen found in Japanese cedar pollen as well as nucleic acids encoding Cry j II, Jun v I, and Jun s I. Preferably, the nucleic acid is a cDNA having a nucleotide sequence which encodes Cry j I, Cry j II, Jun v I or Jun s I. The nucleic acid sequence coding for Cry j I shown in FIGS. 4a and 4b (SEQ ID NO: 1) contains a 21 amino acid leader sequence from base 66 through base 128. This leader sequence is cleaved from the mature protein which is encoded by bases 129 through 1187. The deduced amino acid sequence of Cry j I is also shown in FIGS. 4a and 4b (SEQ ID NO: 2). The nucleic acid sequence of the invention codes for a protein having a predicted molecular weight of 38.5 kDa, with a pI of 7.8, and five potential N-linked glycosylation sites. Utilization of these glycosylation sites will increase the molecular weight and affect the pI of the mature protein. There are sequence polymorphisms observed in the nucleic acid sequence of the invention. For example, single independent nucleotide substitutions at the codons encoding amino acids 38, 51 and 74 (GGA vs. GAA, GTG vs. GCG, and GGG vs. GAG, respectively) of SEQ ID NO: 1 may result in amino acid polymorphisms (G vs. E, V vs. A, and G vs. E, respectively) at these sites. In addition, a single nucleotide substitution has been detected in one cDNA clone derived from *Cryptomeria japonica* pollen collected in Japan. This substitution in the codon for amino acid 60 (TAT vs. CAT) of SEQ ID NO: 1 may result in an amino acid polymorphism (Y vs. H) at this site. Additional silent nucleotide substitutions have been detected. It is expected that there are additional sequence polymorphisms, and it will be appreciated by one skilled in the art that one or more nucleotides (up to about 1% of the nucleotides) in the nucleic acid sequence coding for Cry j I may vary among individual *Cryptomeria japonica* plants due to natural allelic variation. Any and all such nucleotide variations and resulting amino acid polymorphisms are within the scope of the invention. Furthermore, there may be one or more family members of Cry j I. Such family members are defined as proteins related in function and amino acid sequence to Cry j I but encoded by genes at separate genetic loci. These family members are also within the scope of this invention.

The nucleic acid sequence coding for Cry j II shown in FIG. 28 (SEQ ID NO: 133) encodes a protein of 514 amino acids. The deduced Cry j II amino acid sequence is shown in FIGS. 28 and 29. (SEQ ID NO: 134) Direct protein sequence analysis of native purified Cry j II resulted in two separate overlapping NH$_2$-termini sequences, designated Long and Short corresponding respectively to amino acids 46 through 89 (SEQ ID NO: 136) and 51 through 89 (SEQ ID NO: 137) of FIGS. 28, 29 and 30. The full-length Cry j II sequence contains 20 cysteine residues and three potential N-linked glycosylation sites with the consensus sequence of Asn-Xxx-Ser/Thr. The amino acid sequence representing the long form of Cry j II is encoded by the nucleotide sequence extending from bases 177-1586 (SEQ ID NO: 139) as shown in FIG. 28, and the amino acid sequence representing the short form of Cry j II is encoded by the nucleotide sequence extending from 192-1586 (SEQ ID NO: 140) as shown in FIG. 28. A host cell transformed with a vector containing the cDNA insert coding for full-length Cry j II has been deposited with the American Type Culture Collection, ATCC No. 69105.

Fragments of the nucleic acid sequence coding for fragments of Cry j I or Cry j II or a cross-reactive allergen or equivalents thereof are also within the scope of the invention. The term "nucleic acid" as used herein is intended to include fragments or equivalents of the nucleic acid. An equivalent of an oligonucleotide sequence is one which is 1) a sequence capable of hybridizing to a complementary oligonucleotide to which the sequence (or corresponding sequence portions) of SEQ ID NO: 1 or SEQ. ID. NO.: 133 or fragments thereof hybridizes, or 2) the sequence (or corresponding sequence portion) complementary to SEQ ID NO: 1, or SEQ. ID. NO.: 133 and/or 3) a sequence which encodes a product (e.g., a polypeptide or peptide) having the same functional characteristics of the product encoded by the sequence (or corresponding sequence portion) of SEQ ID NO: 1 or SEQ. ID. NO: 133. Whether an equivalent of a nucleic acid must meet one or both criteria will depend on its use (e.g., if it is to be used only as an oligoprobe, it need meet only the first or second criteria and if it is to be used to produce a Cry j I or Cry j II, it need only meet the third criterion).

As used herein, the functional equivalent of a peptide includes peptides having the same or enhanced ability to bind MHC; peptides capable of stimulating the same T cell subpopulations; peptides having the same or increased ability to induce T cell responses such as stimulation (proliferation or cytokine secretion), peptides having the same or increased ability to induce T cell non-responsiveness or reduced responsiveness, peptides having reduced IgE binding, and peptides which elicit minimal IgE synthesis stimulating activity. Minimal IgE stimulating activity refers to IgE synthesis stimulating activity that is less than the amount of IgE production elicited by purified native Cry j I, Cry j II, Jun s I or Jun v I.

Preferred nucleic acids encode a peptide having at least about 50% homology to Cry j I (SEQ ID NO: 1) or Cry j II, (SEQ ID NO: 133) more preferably at least about 60% homology and most preferably at least about 70% homology with Cry j I (FIGS. 4a-b) or Cry j II (FIG. 28). Nucleic acids which encode peptides having at least about 90%, more preferably at least about 95%, and most preferably at least about 98-99% homology with Cry j I or Cry j II are also within the scope of the invention. Homology refers to sequence similarity between two peptides of Cry j I or Cry j II or between two nucleic acid molecules. Homology can be determined by comparing a position in each sequence which may be aligned for purposes of comparison. When a position in the compared sequence is occupied by the same base or amino acid, then molecules are homologous at that position. A degree of homology between sequences is a function of the number of matching or homologous positions shared by the sequences.

Preferred nucleic acid fragments encode peptides of at least 10 amino acid residues in length, preferably at least 15 amino acid residues in length, more preferably at least 20 amino acid residues in length and most preferably at least 30 amino acid residues in length. Nucleic acid fragments which encode peptides of at least 40 amino acid residues in length, at least 60 amino acid residues in length, at least 80 amino acid residues in length, at least 100 amino acid residues in length or more are also within the scope of this invention.

Nucleic acids within the scope of the invention include those coding for parts of Cry j I (or a cross-reactive allergen such as Jun v I (SEQ ID NO: 96) or Jun s I (SEQ ID NO: 94)) or Cry j II (SEQ ID NO: 133) which are antigenic i.e. induce an immune response in mammals, preferably humans, such as stimulation of minimal amounts of IgE; binding of IgE; eliciting the production of IgG and IgM antibodies; or the eliciting of a T cell response such as proliferation and/or lymphokine secretion and/or the induction of T cell non responsiveness or reduced T cell responsiveness.

Nucleotides within the scope of the invention also include those capable of hybridizing with nucleic acid from other plant species for use in screening protocols to detect allergens that are cross-reactive with Cry j I or Cry j II. Appropriate stringency conditions which promote DNA hybridization, for example, 6.0× sodium chloride/sodium citrate (SSC) at about 45° C., followed by a wash of 2.0×SSC at 50° are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

As used herein, a fragment of the nucleic acid sequence coding for Cry j I or Cry j II refers to a nucleotide sequence having fewer nucleotides than the nucleotide sequence coding for the entire amino acid sequence of Cry j I and/or mature Cry j I or Cry j II and/or mature Cry j II. Generally, the nucleic acid sequence coding for the fragment or fragments of Cry j I or Cry j II will be selected from the bases coding for the mature protein, however, in some instances it may be desirable to select all or a part of a fragment or fragments from the leader sequence portion of the nucleic acid sequence of the invention. Nucleic acid sequence of the invention may also contain linker sequences, modified restriction endonuclease sites and other sequences useful for cloning, expression or purification of Cry j I or Cry j II or fragments thereof.

Isolated nucleic acids encoding a Cry j I or Cry j II peptide, as described herein, and having a sequence that differs from the nucleotide sequence shown in FIG. 4a-b (SEQ ID NO: 1) or FIG. 28 (SEQ ID NO: 133) due to degeneracy in the genetic code are also within the scope of the invention. Such nucleic acids encode functionally equivalent protein or peptides (i.e., protein or peptides having at least a portion of the activity of Cry j I or Cry j II) but differ in sequence from the nucleic acid sequence of FIG. 4a-b (SEQ ID NO: 1) or FIG. 28 (SEQ ID NO: 133) due to the fact that a number of naturally-occurring amino acids are encoded by more than one nucleotide triplet. Codons that specify the same amino acid, or synonyms (for example, CAU and CAC are synonyms for histidine) may result in "silent" mutations which do not affect the amino acid sequence of the Cry j I or Cry j II protein. However, it is expected that DNA sequence polymorphisms that do lead to changes in the amino acid sequence of Cry j I or Cry j II will exist within Japanese cedar pollen. One skilled in the art will appreciate that these variations in one or more nucleotides (up to about 3-4% of the nucleotides) of the nucleic acids encoding proteins or peptides of Cry j I or Cry j II may exist. Any and all such nucleotide variations and resulting amino acid polymorphisms are within the scope of this invention. Furthermore, there may be one or more isoforms or related, cross-reacting family members of Cry j I or Cry j II. Such isoforms or family members are defined as proteins related in function and amino acid sequence to Cry j I or Cry j II, but are encoded by genes at different loci.

A nucleic acid sequence coding for Cry j I or Cry j II may be obtained from *Cryptomeria japonica* plants. However, Applicants have found that mRNA coding for Cry j I was very difficult to obtain from commercially available *Cryptomeria japonica* pollen. This inability to obtain mRNA from the pollen may be due to problems with storage or transportation of commercially available pollen. Applicants have found that fresh pollen and staminate cones are a good source of Cry j I or Cry j II mRNA. It may also be possible to obtain the nucleic acid sequence coding for Cry j I or Cry j II from genomic DNA. *Cryptomeria japonica* is a well-known species of cedar, and plant material may be obtained from wild, cultivated, or ornamental plants. The nucleic acid sequence coding for Cry j I or Cry j II may be obtained using the method disclosed herein or any other suitable techniques for isolation and cloning of genes. The nucleic acid sequence of the invention may be DNA or RNA.

The present invention provides expression vectors and host cells transformed to express the nucleic acid sequences of the invention. A nucleic acid sequence coding for Cry j I, Cry j II, Jun v I or Jun s I or at least one fragment thereof may be expressed in bacterial cells such as *E. coli*, insect cells (baculovirus), yeast, or mammalian cells such as Chinese hamster ovary cells (CHO). Suitable expression vectors, promoters, enhancers, and other expression control elements may be found in Sambrook et al. *Molecular Cloning: A Laboratory Manual*, second edition, Cold Spring Harbor Laboratory Press, Cold Spring Harbor, N.Y. (1989). Other suitable expression vectors, promoters, enhancers, and other expression elements are known to those skilled in the art. Expression in mammalian, yeast or insect cells leads to partial or complete glycosylation of the recombinant material and formation of any inter- or intra-chain disulfide bonds. Suitable vectors for expression in yeast include YepSec1 (Baldari et al. (1987) *Embo J.* 6: 229-234); pMFa (Kurjan and Herskowitz (1982) *Cell* 30: 933-943); JRY88 (Schultz et al. (1987) *Gene* 54: 113-123) and pYES2 (Invitrogen Corporation, San Diego, Calif.). These vectors are freely available. Baculovirus and mammalian expression systems are also available. For example, a baculovirus system is commercially available (PharMingen, San Diego, Calif.) for expression in insect cells while the pMSG vector is commercially available (Pharmacia, Piscataway, N.J.) for expression in mammalian cells.

For expression in *E. coli*, suitable expression vectors include, among others, pTRC (Amann et al. (1988) *Gene* 69: 301-315); pGEX (Amrad Corp., Melbourne, Australia); pMAL (N.E. Biolabs, Beverly, Mass.); pRIT5 (Pharmacia, Piscataway, N.J.); pET-11d (Novagen, Madison, Wis.) Jameel et al., (1990) *J. Virol.* 64:3963-3966; and pSEM (Knapp et al. (1990) *BioTechniques* 8: 280-281). The use of pTRC, and pET-11d, for example, will lead to the expression of unfused protein. The use of pMAL, pRIT5 pSEM and pGEX will lead to the expression of allergen fused to maltose E binding protein (pMAL), protein A (pRIT5), truncated β-galactosidase (PSEM), or glutathione S-transferase (pGEX). When Cry j I, Cry j II, fragment, or fragments thereof is expressed as a fusion protein, it is particularly advantageous to introduce an enzymatic cleavage site at the fusion junction between the carrier protein and Cry j I, Cry j II or fragment thereof. Cry j I, Cry j II or fragment thereof may then be recovered from the fusion protein through enzymatic cleavage at the enzymatic site and biochemical purification using conventional techniques for purification of proteins and peptides. Suitable enzymatic cleavage sites include those for blood clotting Factor Xa or thrombin for which the appropriate enzymes and protocols for cleavage are commercially available from, for example, Sigma Chemical Company, St. Louis, Mo. and N.E. Biolabs, Beverly, Mass. The different vectors also have different promoter regions allowing constitutive or inducible expression with, for example, IPTG induction (PRTC, Amann et al., (1988) supra; pET-11d, Novagen, Madison, Wis.) or temperature induction (pRIT5, Pharmacia, Piscataway, N.J.). It may also be appropriate to express recombinant Cry j I in different *E. coli* hosts that have an altered capacity to degrade recombinantly expressed proteins (e.g. U.S. Pat. No. 4,758,512). Alternatively, it may be advantageous to alter the nucleic acid sequence to use codons preferentially utilized by *E. coli*, where such nucleic acid alteration would not affect the amino acid sequence of the expressed protein.

Host cells can be transformed to express the nucleic acid sequences of the invention using conventional techniques such as calcium phosphate or calcium chloride co-precipitation, DEAE-dextran-mediated transfection, or electroporation. Suitable methods for transforming the host cells may be found in Sambrook et al. supra, and other laboratory textbooks.

Inducible non-fusion expression vectors include pTrc (Amann et al., (1988) *Gene* 69:301-315) and pET11d (Studier et al., *Gene Expression Technology: Methods in Enzymology* 185, Academic Press, San Diego, Calif. (1990) 60-89). While target gene expression relies on host RNA polymerase transcription from the hybrid trp-lac fusion promoter in pTrc, expression of target genes inserted into pET11d relies on transcription from the T7 gn10-lac 0 fusion promoter mediated by coexpressed viral RNA polymerase (T7 gn1). This viral polymerase is supplied by host strains BL21(DE3) or HMS174(DE3) from a resident X prophage harboring a T7 gn1 under the transcriptional control of the lacUV 5 promoter.

One strategy to maximize recombinant Cry j I, Cry j II, Jun s I, or Jun v I expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy would be to alter the nucleic acid sequence of the desired gene to be inserted into an expression vector so that the individual codons for each amino acid would be those preferentially utilized in highly expressed *E. coli* proteins (Wada et al., (1992) *Nuc. Acids Res.* 20:2111-2118). Such alteration of nucleic acid sequences of the invention could be carried out by standard DNA synthesis techniques.

The nucleic acids of the invention can also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,07 1, incorporated by reference herein).

The present invention also provides a method of producing isolated Japanese cedar pollen allergen Cry j I or Cry j II or at least one fragment thereof comprising the steps of culturing a host cell transformed with a nucleic acid vector directing expression of a nucleotide sequence encoding Japanese cedar pollen allergen Cry j I or Cry j II or at least one fragment thereof in an appropriate medium to produce a mixture of cells and medium containing said Japanese cedar pollen allergen Cry j I or Cry j II; and purifying the mixture to produce substantially pure Japanese cedar pollen allergen Cry j I, Cry j II or at least one fragment thereof. Host cells transformed with an expression vector containing DNA coding for Cry j I, Cry j II or at least one fragment thereof are cultured in a suitable medium for the host cell. Cry j I or Cry j II peptides can be purified from cell culture medium, host cells, or both using techniques known in the art for purifying peptides and proteins including ion-exchange chromatography, gel filtration chromatography, ultrafiltration, electrophoresis and immunopurification with antibodies specific for Cry j I or Cry j II or fragments thereof. The terms "isolated" and "purified" are used interchangeably herein and refer to peptides substantially free of cellular material or culture medium when produced by recombinant DNA techniques, or chemical precursors or other chemicals when synthesized chemically. The present invention also provides purified native Cry j I and Cry j II peptides as discussed in Examples 1 and 14 and purified native Jun s I and Jun v I as discussed in Example 9.

Another aspect of the invention provides preparations including therparutic compositions and formulations comprising Japanese cedar pollen allergen Cry j I (or a cross-reactive allergen such as Jun v I or Jun s I) or Cry j II, or at least one fragment thereof, synthesized in a host cell transformed with a nucleic acid sequence encoding all (or a portion of Japanese cedar pollen allergen Cry j I) or such cross-reactive allergen or Cry j II, or chemically synthesized, and isolated Japanese cedar pollen allergen Cry j I protein or a cross-reactive allergen such as Jun v I or Jun s I or Cry j II, or at least one antigenic fragment thereof produced in a host cell transformed with a nucleic acid sequence of the invention, or produced by chemically synthesis or produced by chemical cleavage of the native allergen. The present invention also provides preparations including therapeutic compositons and formulations comprising native purified Cry j I and Cry j II proteins or fragments thereof.

Antigenic fragments as defined herein refer to any protein fragment of Cry j I which induces an immune response. As used herein, the term "fragment" of a protein refers to an amino acid sequence having fewer residues than the entire amino acid sequence of the protein from which the fragment is derived. "Specific" antigenic fragments as defined herein refer to any antigenic fragment derived from Cry j I or Cry j II with the exception of the Cry j I fragments consisting of amino acids 1-20 or 325-340 as shown in FIGS. 4*a*-4*b* and the exception of Cry j II fragments which consist of amino acids 55-64 of FIGS. 28 and 30. Specific fragments may also include any fragment of said excepted Cry j I or Cry j II fragments, or any portions of said excepted Cry j I or Cry j II fragments in conjunction with amino acid sequence downstream or upstream of said excepted Cry j I or Cry j II fragments, or in conjunction with any other amino acid sequence.

Antigenic fragments of an allergen from Japanese cedar pollen, or a cross-reactive allergen such as Jun v I or Jun s I may be obtained, for example, by screening peptides recombinantly produced from the corresponding fragment of the nucleic acid sequence of the invention coding for such peptides or synthesized chemically using techniques known in the art, or fragments may be produced by chemical cleavage of the native allergen as is known in the art. The allergen may be arbitrarily divided into fragments of a desired length with no overlap of the peptides, or preferably divided into overlapping fragments of a desired length. The fragments are tested to determine their antigenicity (e.g. the ability of the fragment to induce an immune response). Additionally, antigenic fragments comprising "cryptic epitopes' may be determined. Cryptic epitopes are those determinants in a protein antigen which, due to processing and presentation of the native protein antigen to the appropriate MHC molecule, are not normally revealed to the immune system. However, a peptide comprising a cryptic epitope is capable of tolerizing T cells, and when a subject is primed with the peptide, T cells obtained from the subject will proliferate in vitro in response to the peptide or the protein antigen from which the peptide is derived. Peptides which comprise at least one cryptic epitope derived from a protein antigen are referred to herein as cryptic peptides. To confirm the presence of cryptic epitopes in the above-described assay, antigen-primed T cells are cultured in vitro in the presence of each peptide separately to establish peptide-reactive T cell lines. A peptide is considered to comprise at least one cryptic epitope if a T cell line can be established with a given peptide and T cells are capable of proliferation upon challenge with the peptide and the protein antigen from which the peptide is derived.

If fragments of Cry j I or Cry j II are to be used for therapeutic purposes, then the fragments of Cry j I or Cry j II which are capable of eliciting a T cell response such as stimulation (i.e., proliferation or lymphokine secretion) and/or are capable of inducing T cell non-responsiveness are particularly desirable and fragments of Japanese cedar pollen which have minimal IgE stimulating activity are also desirable. Additionally, for therapeutic purposes, it is preferable to use isolated Japanese cedar pollen allergens, e.g. Cry j I or Cry j II, or fragments thereof or a specific fragment thereof which are capable of eliciting T cell responses and which do not bind IgE specific for Japanese cedar pollen or bind such IgE to a substantially lesser extent (i.e., at least 100-fold less binding and more preferably at least 1,000-fold less binding) than the purified native Japanese cedar pollen allergen binds such IgE. If the isolated Japanese cedar pollen allergen or fragment or fragments thereof bind IgE, it is preferable that such binding does not result in the release of mediators (e.g. histamines) from mast cells or basophils. Furthermore, if Jun v I or Jun s I are to be used for therapeutic purposes, it is preferable to use Juniperus pollen allergens, e.g. Jun v I or Jun s I or a fragment thereof which are capable of eliciting T cell responses and which do not bind IgE specific for pollen from the species *Juniperus* or bind such IgE to a substantially lesser extent (as defined above) than the purified native *Juniperus* pollen allergen binds such IgE. If the isolated Jun v I or Jun s I or fragment or fragments thereof bind IgE, it is preferable that such binding does not result in the release of mediators (e.g. histamines) from mast cells or basophils.

Screening peptides of Cry j I or Cry j II as described herein can be accomplished using one or more of several different assays. For example, in vitro, Cry j I or Cry j II T cell stimulatory activity is assayed by contacting a protein or peptide known or suspected to be from Cry j I or Cry j II with an antigen presenting cell which presents appropriate MHC molecules in a T cell culture. Presentation of a peptide of Cry j I or Cry j II in association with appropriate MHC molecules to T cells in conjunction with the necessary costimulation has the effect of transmitting a signal to the T cell that induces the production of increased levels of cytokines, particularly of interleukin-2 and interleukin-4. The culture supernatant can be obtained and assayed for interleukin-2 or other known cytokines. For example, any one of several conventional assays for interleukin-2 can be employed, such as the assay described in *Proc. Natl. Acad. Sci USA*, 86:1333 (1989) the pertinent portions of which are incorporated herein by reference. A kit for an assay for the production of interferon is also available from Genzyme Corporation (Cambridge, Mass.).

A common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

In another embodiment, a Cry j I or Cry j II peptide is screened for the ability to reduce T cell responsiveness. The ability of a peptide known to stimulate T cells, to inhibit or completely block the activity of purified native Cry j I or Cry j II or portion thereof and induce a state of T cell nonresponsiveness or reduced T cell responsiveness, can be determined using subsequent attempts at stimulation of the T cells with antigen presenting cells that present native Cry j I or Cry j II following exposure to a Cry j I or Cry j II peptide activity. If the T cells are unresponsive to the subsequent activation attempts, as determined by interleukin-2 synthesis and T cell proliferation, a state of nonresponsiveness has been induced. See, e.g., Gimmi, et al. (1993) *Proc. Natl. Acad. Sci USA*, 90:6586-6590; and Schwartz (1990) *Science*, 248:1349-1356, for assay systems that can be used as the basis for an assay in accordance with the present invention.

In yet another embodiment, peptides of Cry j I or Cry j II or of an immunologically related allergen such as Jun s I or Jun v I, are identified by IgE binding activity. For therapeutic purposes, peptides of the invention preferably do not bind IgE specific for Japanese cedar pollen allergen, or bind such IgE to a substantially lesser extent (e.g. at least 100 fold less and more preferably, at least 1000 fold less binding) than the corresponding purified native Cry j I or Cry j II allergen binds IgE. If a peptide of the invention is to be used as a diagnostic reagent, it is not necessary that the peptide or protein have reduced IgE binding activity compared to the native Cry j I or Cry j II allergen. IgE binding activity of peptides can be determined by, for example, an enzyme linked immunosorbent assay (ELISA) using, for example, sera obtained from a subject, (i.e., an allergic subject) that has been previously exposed to the native Cry j I or Cry j II allergen. Briefly, a peptide to be tested is coated onto wells of a microtiter plate. After washing and blocking the wells, antibody solution consisting of the plasma of an allergic subject who has been exposed to the peptide being tested or the protein from which it was derived is incubated in the wells. The plasma is generally depleted of IgG before incubation. A labeled secondary antibody is added to the wells and incubated. The amount of IgE binding is then quantified and compared to the amount of IgE bound by a purified native Cry j I or Cry j II protein. Alternatively, the binding activity of a peptide can be determined by Western blot analysis. For example, a peptide to be tested is run on a polyacrylamide gel using SDS-PAGE. The peptide is then transferred to nitrocellulose and subsequently incubated with sera from an allergic subject. After incubation with the labeled secondary antibody, the amount of IgE bound is then determined and quantified.

Another assay which can be used to determine IgE binding activity of a peptide is a competition ELISA assay. Briefly, an IgE antibody pool is generated by combining plasma from Japanese cedar pollen allergic subjects that have been shown by direct ELISA to have IgE reactive with native Cry j I or Cry j II. This pool is used in ELISA competition assays to compare IgE binding to native Cry j I or Cry j II to the peptide tested. IgE binding for the native Cry j I or Cry j II protein and the peptide being tested is determined and quantified.

If a peptide of Cry j I or Cry j II binds IgE, and is to be used as a therapeutic agent, it is preferable that such binding does not result in the release of mediators (e.g. histamines) from mast cells or basophils. To determine whether a peptide which binds IgE results in the release of mediators, a histamine release assay can be performed using standard reagents and protocols obtained for example, from Amac, Inc. (Westbrook, Me.). Briefly, a buffered solution of a peptide to be tested is combined with an equal volume of whole heparinized blood from an allergic subject. After mixing and incubation, the cells are pelleted and the supernatants are processed an analyzed using a radioimmunoassay to determine the amount of histamine released.

Isolated protein allergens from Japanese cedar pollen or preferred antigenic fragments thereof, when administered to a Japanese cedar pollen-sensitive individual, or an individual allergic to an allergen cross-reactive with Japanese cedar pollen allergen, such as allergen from the pollen of *Juniperus virginiana* or *Juniperus sabinoides* etc. (discussed previously) arc capable of modifying the allergic response of the individual to Japanese cedar pollen or such cross-reactive allergen of the individual, and preferably are capable of modifying the B-cell response, T-cell response or both the B-cell and the T-cell response of the individual to the allergen. As used herein, modification of the allergic response of an individual sensitive to a Japanese cedar pollen allergen or cross-reactive allergen can be defined as non-responsiveness or diminution in symptoms to the allergen, as determined by standard clinical procedures (See e.g. Varney et al, *British Medical Journal,* 302:265-269 (1990)) including diminution in Japanese cedar pollen induced asthmatic symptoms. As referred to herein, a diminution in symptoms includes any reduction in allergic response of an individual to the allergen after the individual has completed a treatment regimen with a peptide or protein of the invention. This diminution may be subjective (i.e. the patient feels more comfortable in the presence of the allergen). Diminution in symptoms can be determined clinically as well, using standard skin tests as is known in the art.

Isolated Cry j I or Cry j II protein or fragments thereof are preferably tested in mammalian models of Japanese cedar pollinosis such as the mouse model disclosed in Tamura et al. (1986) *Microbiol. Immunol.* 30: 883-896, or U.S. Pat. No. 4,939,239; or the primate model disclosed in Chiba et al. (1990) *Int. Arch. Allergy Immunol.* 93: 83-88. Initial screening for IgE binding to the protein or fragments thereof may be performed by scratch tests or intradermal skin tests on laboratory animals or human volunteers, or in in vitro systems such as RAST (radioallergosorbent test), RAST inhibition, ELISA assay, radioimmunoassay (RIA), or histamine release (see Examples 7 and 8).

Antigenic fragments of the present invention which have T cell stimulating activity, and thus comprise at least one T cell epitope are particularly desirable. Specific peptides of Cry j I and Cry j II comprising at least one epitope are discussed later. T cell epitopes are believed to be involved in initiation and perpetuation of the immune response to a protein allergen which is responsible for the clinical symptoms of allergy. These T cell epitopes are thought to trigger early events at the level of the T helper cell by binding to an appropriate HLA molecule on the surface of an antigen presenting cell and stimulating the relevant T cell subpopulation. These events lead to T cell proliferation, lymphokine secretion, local inflammatory reactions, recruitment of additional immune cells to the site, and activation of the B cell cascade leading to production of antibodies. One isotype of these antibodies, IgE, is fundamentally important to the development of allergic symptoms and its production is influenced early in the cascade of events, at the level of the T helper cell, by the nature of the lymphokines secreted. A T cell epitope is the basic element or smallest unit of recognition by a T cell receptor, where the epitope comprises amino acids essential to receptor recognition. Amino acid sequences which mimic those of the T cell epitopes and which modify the allergic response to protein allergens are within the scope of this invention.

Exposure of Japanese cedar pollen patients to isolated peptides of the present invention or to the antigenic fragments of the present invention which comprise at least one T cell epitope and are derived from protein allergens, in a non-immunogenic form, may cause T cell non-responsiveness of appropriate T cell subpopulations such that they become unresponsive to the protein allergen and do not participate in stimulating an immune response upon such exposure or reduced T cell responsiveness. In addition, administration of a protein allergen of the invention or an antigenic fragment of the present invention which comprises at least one T cell epitope may modify the lymphokine secretion profile as compared with exposure to the naturally-occurring protein allergen or portion thereof (e.g. result in a decrease of IL-4 and/or an increase in IL-2). Furthermore, exposure to such protein allergen or antigenic fragment of such protein allergen may influence T cell subpopulations which normally participate in the response to the allergen such that these T cells are drawn away from the site(s) of normal exposure to the allergen (e.g., nasal mucosa, skin, and lung) towards the site(s) of therapeutic administration of the fragment or protein allergen. This redistribution of T cell subpopulations may ameliorate or reduce the ability of an individual's immune system to stimulate the usual immune response at the site of normal exposure to the allergen, resulting in a dimunution in allergic symptoms.

The isolated Cry j I and/or Cry j II peptides including antigenic fragments derived therefrom can be used in methods of diagnosing, treating and preventing allergic reactions to Japanese cedar pollen allergen or a cross reactive protein allergen. Thus the present invention provides therapeutic compositions comprising isolated Japanese cedar pollen allergen Cry j I or Cry j II or at least one antigenic fragment of specific antigenic fragment thereof produced in a host cell transformed to express Cry j I or Cry j II, or at least one antigenic fragment thereof, and a pharmaceutically acceptable carrier or diluent. The therapeutic compositions of the invention may also comprise Cry j I or Cry j II or at least one antigenic fragment thereof which may be prepared synthetically or by chemical cleavage of the allergen, and a pharmaceutically acceptable carrier or diluent. Administration of the therapeutic compositions of the present invention to an individual to be desensitized can be carried out using known techniques. Cry j I or Cry j II peptide may be administered to an individual in combination with, for example, an appropriate diluent, a carrier and/or an adjuvant or incomplete adjuvant. Pharmaceutically acceptable diluents include saline and aqueous buffer solutions. Pharmaceutically acceptable carriers include polyethylene glycol (Wie et al. (1981) *Int. Arch. Allergy Appl. Immunol.* 64:84-99) and liposomes (Strejan et al. (1984) *J. Neuroimmunol* 7: 27).

The therapeutic compositions of the invention are administered to Japanese cedar pollen-sensitive individuals or individuals sensitive to an allergen which is immunologically cross-reactive with Japanese cedar pollen allergen (i.e. *Juniperus virginiana*, or *Juniperus sabinoides*, etc.). For purposes of inducing T cell non-responsiveness, therapeutic compositions of the invention are preferably administered in non-immunogenic form, e.g. which does not contain adjuvant. While not intending to be limited to any theory, it is believed that T cell non responsivness or reduced T cell responsiveness is induced as a result of not providing a "second signal" Briefly, it is believed that stimulation of T cells requires two types of signals, the first is the recognition by the T cell via the T cell receptor of appropriate MHC-associated processed antigens on antigen presenting class (APCs) and the second type of signal is referred to as a "second signal" or "costimulatory signals" which may be provided by certain competent APCs. When a composition of the invention is administered without adjuvant, it is believed that competent APCs which are capable of producing the second signal or costimulatory signal are not engaged in the stimulation of appropriate T cells therefore resulting in T cell non responsiveness or reduced T cell responsiveness. In addition, there are a number of antibodies or other reagents capable of blocking the delivery of costimulatory signals such as the "second signal" which include, but are not limited to B7 (including B7-1, B7-2, and BB-1), CD28, CTLA4, CD40 CD40L CD54 and CD11a/18 (Jenkins and Johnson, *Current Opinion in Immunology*, 5:361-367 (1993), and Clark and Ledbetter, *Nature*, 367:425-428 (1994)) Thus, a peptide of the invention may be administered in nonimmunogenic form as discussed above, in conjunction with a reagent capable of blocking costimulatory signals such that the level of T cell nonresponsiveness is enhanced.

Administration of the therapeutic compositions of the present invention to an individual to be desensitized can be carried out using known procedures at dosages and for periods of time effective to reduce sensitivity (i.e., reduce the allergic response) of the individual to the allergen. Effective amounts of the therapeutic compositions will vary according to factors such as the degree of sensitivity of the individual to Japanese cedar pollen, the age, sex, and weight of the individual, and the ability of the protein or fragment thereof to elicit an antigenic response in the individual. The active compound (i.e., protein or fragment thereof) may be administered in a convenient manner such as by injection (subcutaneous, intravenous, etc.), oral administration, inhalation, transdermal application, or rectal administration. Depending on the route of administration, the active compound may be coated within a material to protect the compound from the action of enzymes, acids and other natural conditions which may inactivate the compound.

For example, preferably about 1 µg-3 mg and more preferably from about 20-500 µg of active compound (i.e., protein or fragment thereof) per dosage unit may be administered by injection. Dosage regimen may be adjusted to provide the optimum therapeutic response. For example, several divided doses may be administered daily or the dose may be proportionally reduced as indicated by the exigencies of the therapeutic situation.

To administer protein or peptide by other than parenteral administration, it may be necessary to coat the protein with, or co-administer the protein with, a material to prevent its inactivation. For example, protein or fragment thereof may be administered in an adjuvant, co-administered with enzyme inhibitors or in liposomes. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) *J. Neuroimmunol.* 7:27).

The active compound may also be administered parenterally or intraperitoneally. Dispersions can also be prepared in glycerol, liquid polyethyline glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions of dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glyceral, propylene glycol, and liquid polyetheylene glycol, and the like), suitable mixtures thereof, and vegetable oils. The proper fluidity can be maintained, for example, by the use of a coating such as licithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thirmerosal, and the like. In many cases, it will be preferable to include isotonic agents, for example, sugars, polyalcohols such as manitol and sorbitol or sodium chloride in the composition. Prolonged absorption of the injectable compositions can be brought about, including in the composition, an agent which delays absorption, for example, aluminum monostearate and gelatin.

Sterile injectable solutions can be prepared by incorporating active compound (i.e., protein or peptide) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile inectable solutions, the preferred methods of preparation are vacuum drying and freeze-drying which yields a powder of the active ingredient (i.e., protein or peptide) plus any additional desired ingredient from a previously sterile-filtered solution thereof.

When protein or peptide thereof is suitably protected, as described above, the protein may be orally administered, for example, with an inert diluent or an assimilable edible carrier. The protein and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the composition and preparations may, of course, be varied and may conveniently be between about 5 to 80% of the weight of the unit. The amount of active compound in such therapeutically useful compositions is such that a suitable dosage will be obtained. Preferred compositions or preparations according to the present invention are prepared so that an oral dosage unit contains between from about 10 µg to about 200 mg of active compound.

The tablets, troclics, pills, capsules and the like may also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservative, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. Dosage unit from as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the novel dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The Cry j I cDNA (SEQ ID NO: 1) or the Cry j II cDNA (SEQ ID NO: 133) (or the mRNAs from which they were transcribed) or a portion thereof can be used to identify similar sequences in any variety or type of plant and thus, to identify or "pull out" sequences which have sufficient homology to hybridize to the Cry j I or Cry j II cDNA or mRNA or portion thereof, for example, DNA from allergens of *Juniperus virginiana, Juniperus sabinoides* etc., under conditions of low stringency. Those sequences which have sufficient homology (generally greater than 40%) can be selected for further assessment using the method described herein. Homology can be determined as discussed previously. Alternatively, high stringency conditions can be used. In this manner, DNA of the present invention can be used to identify, in other types of plants, preferably related families, genera, or species such as *Juniperus*, or *Cupressus*, sequences encoding polypeptides having amino acid sequences similar to that of Japanese cedar pollen allergen Cry j I or Cry j II, and thus to identify allergens in other species. Thus, the present invention includes not only Cry j I or Cry j II, but also other allergens encoded by DNA which hybridizes to DNA of the present invention. The invention further includes isolated allergenic proteins or fragments thereof that are immunologically related to Cry j I or fragments thereof, such as by antibody cross-reactivity wherein the isolated allergenic proteins or fragments thereof are capable of binding to antibodies specific for the protein and peptides of the invention, or by T cell cross-reactivity wherein the isolated allergenic proteins or fragments thereof are capable of stimulating T cells specific for the protein and peptides of this invention.

Proteins or peptides encoded by the cDNA of the present invention can be used, for example as "purified" allergens. Such purified allergens are useful in the standardization of allergen extracts which are currently key reagents for the clinical diagnosis and treatment of Japanese cedar pollinosis.

Another aspect of the invention pertains to an antibody specifically reactive with Cry j I or Cry j II, or a fragment thereof. The antibodies of this invention can be used to standardize allergen extracts or to isolate the naturally-occurring or native form of Cry j I or Cry j II. For example, by using proteins or fragments thereof based on the cDNA sequence of Cry j I or Cry j II, anti-proteinlanti-peptide antisera or monoclonal antibodies can be made using standard methods. A mammal such as a mouse, a hamster or rabbit can be immunized with an immunogenic form of such protein or an antigenic fragment which is capable of eliciting an antibody response. Techniques for conferring immunogenicity on a protein or peptide include conjugation to carriers or other techniques well known in the art. Cry j I or Cry j II protein or fragments thereof can be administered in the presence of adjuvant. The progress of immunization can be monitored by detection of antibody titers in plasma or serum. Standard ELISA or other immunoassays can be used with the immunogen as antigen to assess the levels of antibodies.

Following immunization, anti-Cry j I or Cry j II antisera can be obtained and, if desired, polyclonal anti-Cry j I or Cry j II antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, for example the hybridoma technique originally developed by Kohler and Milstein, (*Nature* (1975) 256:495-497) as well as other techniques such as the human B cell hybridoma technique (Kozbar et al., *Immunology Today* (1983) 4:72) and the EBV-hybridoma technique to produce human monoclonal antibodies (Cole et al., *Monoclonal Antibodies and Cancer Therapy* (1985) Alan R. Liss, Inc. pp. 77-96). Hybridoma cells can be screened immunochemically for production of antibodies specifically reactive with Cry j I or Cry j II and the monoclonal antibodies isolated.

The term antibody as used herein is intended to include fragments thereof which are also specifically reactive with Cry j I or Cry j II. Antibodies can be fragmented using conventional techniques and the fragments screened for utility in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments. The antibody of the present invention is further intended to include bispecific and chimeric molecules having an anti-Cry j I or Cry j II portion.

Another aspect of this invention provides T cell clones and soluble T cell receptors specifically reactive with Cry j I or Cry j II or a fragment thereof. Monoclonal T cell populations (i.e., T cells genetically identical to one another and expressing identical T cell receptors) can be derived from an individual sensitive to Cry j I or Cry j II, followed by repetitive in vitro stimulation with Cry j I or Cry j II in the presence of MHC-matched antigen-presenting cells. Single Cry j I or Cry j II MRC responsive cells can then be cloned by limiting dilution and permanent lines expanded and maintained by periodic in vitro restimulation. Alternatively, Cry j I or Cry j II specific T-T hybridomas can be produced by a technique similar to B cell hybridoma production. For example, a mammal, such as a mouse can be immunized with Cry j I or Cry j II or fragments thereof, T cells from the mammal can be purified and fused with an autonomously growing T cell tumor line. From the resulting hybridomas, cells responding to Cry j I or Cry j II or fragments thereof are selected and cloned. Procedures for propagating monoclonal T cell populations are described in *Cellular and Molecular Immunology* (Abul K. Abbas et al. ed.), W.B. Saunders Company, Philadelphia, Pa. (1991) page 139. Soluble T cell receptors specifically reactive with Cry j I or Cry j II or fragments thereof can be obtained by immunoprecipitation using an antibody against the T cell receptor as described in *Immunology: A Synthesis* (Second Edition), Edward S. Golub et al., ed., Sinauer Associates, Inc., Sunderland, Mass. (1991) pages 366-269.

T cell clones specifically reactive with Cry j I or Cry j II or fragments thereof can to be used to isolate and molecularly clone the gene encoding the relevant T cell receptor. In addition, a soluble T cell receptor specifically reactive with Cry j I or Cry j II or fragments thereof can be used to interfere with or inhibit antigen-dependent activation of the relevant T cell subpopulation, for example, by administration to an individual sensitive to Japanese Cedar pollen. Antibodies specifically reactive with such a T cell receptor can be produced according to the techniques described herein. Such antibodies can be used to block or interfere with the T cell interaction with peptides presented by MHC.

Through use of the peptides of the present invention, preparations of consistent, well-defined composition and biological activity can be made and administered for therapeutic purposes (e.g. to modify the allergic response of a Japanese cedar sensitive individual to pollen of such trees). Administration of such peptides or protein may, for example, modify B-cell response to Cry j I or Cry j II, T-cell response to Cry j I or Cry j II or both responses. Isolated peptides can also be used to study the mechanism of immunotherapy of *Cryptomeria japonica* allergy and to design modified derivatives or analogues useful in immunotherapy.

Work by others has shown that high doses of allergens generally produce the best results (i.e., best symptom relief). However, many people are unable to tolerate large doses of allergens because of allergic reactions to the allergens. A peptide can be designed in such a manner to have the same or enhanced therapeutic properties as the corresponding naturally-occurring allergen but have reduced side effects (especially anaphylactic reactions) can be produced. These can be, for example, a peptide of the present invention (e.g., one having all or a portion of the amino acid sequence of Cry j I (SEQ ID NO: 2) or Cry j II (SEQ ID NO: 134)), or a modified peptide, or peptide analogue.

It is also possible to modify the structure of a peptide of the invention for such purposes as increasing solubility, enhancing therapeutic or preventive efficacy, or stability (e.g., shelf life ex vivo, and resistance to proteolytic degradation in vivo). A modified peptide can be produced in which the amino acid sequence has been altered, such as by amino acid substitution, deletion, or addition, to modify immunogenicity and/or reduce allergenicity, or to which a component has been added for the same purpose.

For example, a peptide can be modified so that it maintains the ability to induce T cell non-responsiveness or reduced T cell responsiveness and bind MHC proteins without to the ability to induce a strong proliferative response or possibly, and proliferative response when administered in immunogenic form. In this instance, critical binding residues for the T cell receptor can be determined using known techniques (e.g., substitution of each residue and determination of the presence or absence of T cell reactivity). Those residues shown to be essential to interact with the T cell receptor can be modified by replacing the essential amino acid with another, preferably similar amino acid residue (a conservative substitution) whose presence is shown to enhance, diminish but not eliminate or not affect T cell activity. In addition, those amino acid residues which are not essential for T cell receptor interaction can be modified by being replaced by another amino acid whose incorporation may enhance, diminish but not eliminate or not affect T cell activity but does not eliminate binding to relevant MHC.

Additionally, peptides of the invention can be modified by replacing an amino acid shown to be essential to interact with the MHC protein complex with another, preferably similar amino acid residue (conservative substitution) whose presence is shown to enhance, diminish but not eliminate or not affect T cell activity. In addition, amino acid residues which are not essential for interaction with the MHC protein complex but which still bind the MHC protein complex can be modified by being replaced by another amino acid whose incorporation may enhance, not affect, or diminish but not eliminate T cell reactivity. Preferred amino acid substitutions for non-essential amino acids include, but are not limited to substitutions with alanine, glutamic acid, or a methyl amino acid.

In order to enhance stability and/or reactivity, peptides of the invention can also be modified to incorporate one or more polymorphisms in the amino acid sequence of the protein allergen resulting from natural allelic variation. Additionally, D-amino acids, non-natural amino acids or non-amino acid analogues can be substituted or added to produce a modified protein or peptide within the scope of this invention. Furthermore, peptides of the present invention can be modified using the polyethylene glycol (PEG) method of A. Sehon and co-workers (Wie et al. supra) to produce a protein or peptide conjugated with PEG. In addition, PEG can be added during chemical synthesis of a protein or peptide of the invention. Modifications of proteins or peptides or portions thereof can also include reduction/ alyklation (Tarr in: *Methods of Protein Microcharacterization*, J. E. Silvered. Humana Press, Clifton, N.J., pp 155-194 (1986)); acylation (Tarr, supra); chemical coupling to an appropriate carrier (Mishell and Shiigi, eds, *Selected Methods in Cellular Immunology*, WH Freeman, San Francisco, Calif. (1980); U.S. Pat. No. 4,939, 239; or mild formalin treatment (Marsh *International Archives of Allergy and Applied Immunology,* 41:199-215 (1971)).

To facilitate purification and potentially increase solubility of proteins or peptides of the invention, it is possible to add reporter group(s) to the peptide backbone. For example, polyhistidine can be added to a peptide to purify the peptide on immobilized metal ion affinity chromatography (Hochuli, E. et al., *Bio/Technology,* 6:1321-1325 (1988)). In addition, specific endoprotease cleavage sites can be introduced, if desired, between a reporter group and amino acid sequences of a peptide to facilitate isolation of peptides free of irrelevant sequences.

In order to successfully desensitize an individual to a peptide, it may be necessary to increase the solubility of a peptide for use in buffered aqueous solutions, such as pharmaceutically acceptable carriers or diluents, by adding functional groups to the peptide, terminal portions of the peptide, or by not including hydrophobic T cell epitopes or regions containing hydrophobic epitopes in the peptides or hydrophobic regions of the protein or peptide. For example, to increase solubility, charged amino acids or charged amino acid pairs or triplets may be added to the carboxy or amino terminus of the peptide. Examples of charged amino acids include, but are not limited to arginine (R), lysine (K), histidine (H), glutamic acid (E), and aspartic acid (D).

To potentially aid proper antigen processing of T cell epitopes within a peptide, canonical protease sensitive sites can be recombinantly or synthetically engineered between regions, each comprising at least one T cell epitope. For example, charged amino acid pairs, such as KK or RR, can be introduced between regions within a peptide during recombinant construction of the peptide. The resulting peptide can be rendered sensitive to cathepsin and/or other trypsin-like enzymes cleavage to generate portions of the peptide containing one or more T cell epitopes.

Site-directed mutagenesis of DNA encoding a peptide or protein of the invention (e.g. Cry j I or Cry j II or a fragment thereof) can be used to modify the structure of the peptide or protein by methods known in the art. Such methods may, among others, include PCR with degenerate oligonucleotides (Ho et al., *Gene,* 77:51-59 (1989)) or total synthesis of mutated genes (Hostomsky, Z. et al., *Biochem. Biophys, Res. Comm.,* 161:1056-1063 (1989)). To enhance bacterial expression, the aforementioned methods can be used in conjunction with other procedures to change the eucaryotic codons in DNA constructs encoding protein or peptides of the invention to ones preferentially used in *E. coli*, yeast, mammalian cells, or other eukaryotic cells.

Using the structural information now available, it is possible to design Cry j I or Cry j II peptides which, when administered to a Japanese cedar pollen sensitive individual in sufficient quantities, will modify the individual's allergic response to Japanese cedar pollen. This can be done, for example, by examining the structure of Cry j I or Cry j II, producing peptides (via an expression system, synthetically, chemical cleavage of the native allergen or otherwise) to be examined for their ability to influence B-cell and/or T-cell responses in Japanese cedar pollen sensitive individuals and selecting appropriate peptides which contain epitopes recognized by the cells. In referring to an epitope, the epitope will be the basic element or smallest unit of recognition by a receptor, particularly immunoglobulins, histocompatibility antigens and T cell receptors where the epitope comprises amino acids essential to receptor recognition. Amino acid sequences which mimic those of the epitopes and which are capable of down regulating allergic response to Cry j I or Cry j II can also be used.

It is now also possible to design an agent or a drug capable of blocking or inhibiting the ability of Japanese cedar pollen allergen to induce an allergic reaction in Japanese cedar pollen sensitive individuals. Such agents could be designed, for example, in such a manner that they would bind to relevant anti-Cry j I IgEs, thus preventing IgE-allergen binding and subsequent mast cell degranulation. Alternatively, such agents could bind to cellular components of the immune system, resulting in suppression or desensitization of the allergic response to *Cryptomeria japonica* pollen allergens.

Peptides of the present invention can also be used for detecting and diagnosing Japanese cedar pollinosis. For example, this could be done by combining blood or blood products obtained from an individual to be assessed for sensitivity to Japanese cedar pollen with an isolated antigenic peptide or peptides of Cry j I, or isolated Cry j I protein, under conditions appropriate for binding of components in the blood (e.g., antibodies, T-cells, B-cells) with the peptide(s) or protein and determining the extent to which such binding occurs. Other diagnostic methods for allergic diseases which the peptides of the present invention can be used include radio-allergergosorbent test (RAST), paper radioimmunosorbent test (PRIST), enzyme linked immunosorbent assay (ELISA), radioimmunoassays (RIA), immuno-radiometric assays (IRMA), luminescence immunoassays (LIA), histamine release assays and IgE immunoblots.

The presence in individuals of IgE specific for at least one protein allergen and the ability of T cells of the individuals to respond to T cell epitope(s) of the protein allergen can be determined by administering to the individuals an Immediate Type Hypersensitivity test and a Delayed Type Hypersensitivity test. The individuals are administered an Immediate Type Hypersensitivity test (see e.g. *Immunology* (1985) Roitt, I. M., Brostoff, J., Male, D. K. (eds), C.V. Mosby Co., Gower Medical Publishing, London, N.Y., pp. 19.2-19.18, pp. 22.1-22.10) utilizing a peptide of the protein allergen, or a modified form of the peptide, each of which binds IgE specific for the allergen. The same individuals are administered a Delayed Type Hypersensitivity test prior to, simultaneously with, or subsequent to administration of the Immediate Type Hypersensitivity test. Of course, if the Immediate Type Hypersensitivity test is administered prior to the Delayed Type Hypersensitivity test, the Delayed Type Hypersensitivity test would be given to those individuals exhibiting a specific Immediate Type Hypersensitivity reaction. The Delayed Type Hypersensitivity test utilizes a modified form of the protein allergen or a portion thereof, the protein allergen produced recombinantly, or peptide derived from the protein allergen, each of which has human T cell stimulating activity and each of which does not bind IgE specific for the allergen in a substantial percentage of the population of individuals sensitive to the allergen (e.g., at least about 75%). Those individuals found to have both a specific Immediate Type Hypersensitivity reaction and a specific Delayed Type Hypersensitivity reaction are diagnosed as having sensitivity to Japanese cedar pollen allergen and may, if need be, administered a therapeutically effective amount of a therapeutic composition. The therapeutic composition comprises the modified form of the protein or portion thereof, the recombinantly produced protein allergen, or peptide, each as used in the Delayed Type Hypersensitivity test, and a pharmaceutically acceptable carrier or diluent.

Peptides comprising at least two regions, each region comprising at least one T cell epitope of Japanese cedar pollen are also within the scope of the invention. Isolated peptides or regions of isolated peptides, each comprising at least two T cell epitopes of a Japanese cedar pollen protein allergen or use of more than one peptide having one T cell epitope may be desirable for increased therapeutic effectiveness. Peptides which are immunologically related (e.g., by antibody or T cell cross-reactivity) to peptides of the present invention are also within the scope of the invention.

Isolated peptides of the invention can be produced as discussed previously. With regard to isolated Jun v I or Jun s I peptides, peptides may be produced by biochemically purifying the native Jun v I or Jun s I proteins from *Juniperus virginiana* or *Juniperus sabinoides* pollen as is known in the art, or by recombinant or chemical synthetic techniques as described herein.

To obtain isolated Cry j I or Cry j II peptides of the present invention, Cry j I or Cry j II is divided into non-overlapping peptides of desired length or overlapping peptides of desired lengths which can be produced recombinantly, or synthetically or by chemical cleavage. Peptides comprising at least one T cell epitope are capable of eliciting a T cell response, such as T cell proliferation or lymphokine secretion, and/or are capable of reducing T cell responsiveness. To determine peptides comprising at least one T cell epitope, isolated peptides are tested by, for example, T cell biology techniques, to determine whether the peptides elicit a T cell response or induce T cell non-responsivenss. Those peptides found to elicit a T cell response or induce T cell non-responsiveness are defined as having T cell stimulating activity.

As discussed in Examples 6, 11, and 19 human T cell stimulating activity can be tested by culturing T cells obtained from an individual sensitive to Japanese cedar pollen allergen, (i.e., an individual who has an IgE mediated immune response to Japanese cedar pollen allergen) with a peptide derived from the allergen and determining whether proliferation of T cells occurs in response to the peptide as measured, e.g., by cellular uptake of tritiated thymidine. Stimulation indices for responses by T cells to peptides can be calculated as the maximum counts per minute (CPM) in response to a peptide divided by the control CPM. A stimulation index (S.I.) equal to or greater than two times the background level is considered "positive". Positive results are used to calculate the mean stimulation index for each peptide for the group of patients tested. Preferred peptides of this invention comprise at least one T cell epitope and have a mean T cell stimulation index of greater than or equal to 2.0. A peptide having a mean T cell stimulation index of greater than or equal to 2.0 is considered useful as a therapeutic agent. Preferred peptides have a mean T cell stimulation index of at least 2.5, more preferably at least 3.5, more preferably at least 4.0, more preferably at least 5, even more preferably at least 7 and and most preferably at least about 9. For example, Cry j I peptides of the invention having a mean T cell stimulation index of at least 5, as shown in FIG. 14, include CJ1-2 (SEQ ID NO: 27), CJ1-7 (SEQ ID NO: 32), CJ1-10 (SEQ ID NO: 35), CJ1-16 (SEQ ID NO: 41), CJ1-17 (SEQ ID NO: 42), CJ1-20 (SEQ ID NO: 45), CJ1-22 (SEQ ID NO: 47), CJ1-23 (SEQ ID NO: 48), CJ1-24 (SEQ ID NO: 49), CJ1-27 (SEQ ID NO: 52), CJ1-31 (SEQ ID NO: 56), CJ1-32 (SEQ ID NO: 57) and CJ1-35 (SEQ ID NO: 60). Peptides of the invention having a mean T cell stimulation index of at least 7, as shown in FIG. 14, include CJ1-16 (SEQ ID NO: 41), CJ1-20 (SEQ ID NO: 45, CJ1-22 (SEQ ID NO: 47), and CJ1-32 (SEQ ID NO: 57).

For therapeutic purposes, preferred peptides are recognized by at least 10%, more preferably at least 20%, more preferably at least 30% and even more preferably at least 40% or more of individuals in a population of individuals sensitive to Japanese cedar pollen. In addition, preferred Cry j I peptides have a positivity index (P.I.) of at least about 100, more preferably at least about 250 and most preferably at least about 350. The positivity index for a peptide is determined by multiplying the mean T cell stimulation index by the percent of individuals, in a population of individuals sensitive to Japanese cedar pollen (e.g., preferably at least 15 individuals, more preferably at least 30 individuals or more), who have a T cell stimulation index to such peptide of at least 2.0. Thus, the positivity index represents both the strength of a T cell response to a peptide (S.I.) and the frequency of a T cell response to a peptide in a population of individuals sensitive to Japanese cedar pollen. For example, as shown in FIG. 14, peptide CJ1-22 (SEQ ID NO: 47) has a mean S.I. of 14.5 and 60.0% of positive responses in the group of individuals tested resulting in a positivity index of 870.00. Peptides of Cry j I having a positivity index of at least about 100 and a mean T cell stimulation index of at least about 4 include: CJ1-16 (SEQ ID NO: 41), CJ1-17 (SEQ ID NO: 42), CJ1-20 (SEQ ID NO: 45), CJ1-22 (SEQ ID NO: 47), CJ1-23 (SEQ ID NO: 48), CJ1-24 (SEQ ID NO: 49), CJ1-26 (SEQ ID NO: 51), CJ1-27 (SEQ ID NO: 52), CJ1-32 (SEQ ID NO: 57) and CJ1-35 (SEQ ID NO: 60).

In order to determine precise T cell epitopes by, for example, fine mapping techniques, a peptide having T cell stimulating activity and thus comprising at least one T cell epitope as determined by T cell biology techniques is modified by addition or deletion of amino acid residues at either the amino or carboxy terminus of the peptide and tested to determine a change in T cell reactivity to the modified peptide. If two or more peptides which share an area of overlap in the native protein sequence are found to have human T cell stimulating activity, as determined by T cell biology techniques, additional peptides can be produced comprising all or a portion of such peptides and these additional peptides can be tested by a similar procedure. Following this technique, peptides are selected and produced recombinantly or synthetically. Example 11 discusses preferred peptides of the invention produced in accordance with these techniques.

For therapeutic purposes, peptides are selected based on various factors, including the strength of the T cell response to the peptide (e.g., stimulation index), the frequency of the T cell response to the peptide in a population of individuals sensitive to Japanese cedar pollen, and the potential cross-reactivity of the peptide with other allergens from other species of trees as discussed earlier (e.g. *Cupressus sempervirens, Cupressus arizonica, Juniperus virginiana, Juniperus sabinoides, Chamae cyparisobtusa*, etc.) or ragweed (Amb a 1.1). The physical and chemical properties of these selected peptides (e.g., solubility, stability) are examined to determine whether the peptides are suitable for use in therapeutic compositions or whether the peptides require modification as described herein.

To determine whether a peptide (candidate peptide) or a combination of candidate peptides are likely to comprise a sufficient percentage of the T cell epitopes of the protein antigen of interest to induce T cell nonresponsiveness in a substantial percentage of a population of individuals sensitive to the protein antigen, an algorithm can be used. In accordance with one such algorithm, a set of overlapping peptides is produced by systematically dividing the protein sequence of the allergen or other antigen into at least two overlapping peptide regions of desired lengths (e.g., of about 12-30 amino acid residues in length, preferably not longer than about 25 amino acid residues in length with about 5-15 amino acid residues of overlap). This division into peptide regions can be arbitrary, can be made according to an algorithm, or can be wholly or partially based on regions of the protein antigen known to comprise at least one T cell epitope. Preferably, at least 50% of the entire protein sequence of the protein allergen or other protein antigen and more preferably, the entire protein sequence of the protein allergen or other protein antigen and more preferably, the entire protein sequence of the protein allergen or other protein antigen is divided into two or more peptides. A human T cell stimulation index is determined for each of the peptides in an in vitro T cell proliferation assay as described herein for each individual tested in a population of individuals sensitive to the protein antigen. A candidate peptide or combination of candidate peptides is selected based, at least in part, on the mean human T cell stimulation index of the candidate peptide in the set of peptides tested and the positivity index of the candidate peptide in the set of peptides tested. The human T cell stimulation index for the candidate peptide(s) is summed. For each individual, the human T cell stimulation index for the candidate peptide(s) is divided by the sum of the human T cells stimulation indices of the remaining peptides in the set of peptides tested to determine a percent of T cell reactivity as shown below:

$$\% \text{ T Cell Reactivity of a candidate peptide(s)} = \frac{\text{Candidate} S.I.}{\text{Sum of } S.I. \text{ of the set of Overlapping peptides}} \times 100 \quad (1)$$

Alternatively, the presence of T cell epitopes in the candidate peptide dependent on amino acids residues in an overlapping peptide located at either the N-terminus or C-terminus of the candidate peptide in the amino acid sequence of the protein antigen, but which epitopes are not present in the candidate peptide can be considered in calculating the percent of T cell reactivity in the candidate peptide by use of the following formula:

$$\% \text{ T Cell Reactivity of a candidate peptide(s)} = \quad (2)$$

$$\frac{N_T \text{ flanking peptide } S.I. + \text{Candidate peptide } S.I. + C_T \text{ flanking peptide } S.I.}{\text{Sum of } S.I. \text{ of the set of overlapping peptides}} \times 100$$

In this formula, "$N_T$ flanking peptide" refers to a peptide which comprises amino acid residues which overlap with amino acid residues located at the N-terminus of the candidate peptide in the amino acid sequence of the protein antigen from which the peptide is derived; "$C_T$ flanking peptide" refers to a peptide which comprises amino acid residues which overlap with amino acid residues located a the C-terminus of the candidate peptide in the amino acid sequence of the protein antigen from which the peptide is derived. In this calculation stimulation indices for the candidate peptide, the N-terminal flanking peptide and the C-terminal flanking peptide are added and divided by the sum total of the stimulation indices for the entire set of overlapping peptides obtain a percent of T cell reactivity for the candidate peptide. If a combination of two or more candidate peptides is selected each of which contains amino acid residues which overlap, this calculation cannot be used to determine a percent of T cell reactivity for each candidate peptide separately. However, a total percent of T cell reactivity for the combination of candidate peptides can be obtained. In this situation, the stimulation indices for all of the candidate peptides which overlap is included in the calculation.

The values obtained for the percentage of T cell reactivity for the candidate peptide or combination of peptides in each individual tested can be expressed as a range of the lower and higher values of the results of the above described calculations. By either of the above calculations, the percent is obtained for at least about twenty (20) and preferably at least about thirty (30) individuals sensitive to the protein antigen and a mean percent is determined. For use in the compositions of the invention, the candidate peptide or combination of candidate peptides has the following criteria: (I) the candidate peptide or combination of candidate peptides has a mean percent of at least about 10%, preferably at least about 20%, more preferably at least about 30%, more preferably at least about 40% and more preferably at least about 50-60% or greater; and (2) in the population of individuals tested at least about 60%, preferably at least about 75%, and more preferably at least about 90-100% have positive T call responses (S.I. equal to or greater than 2.0) in response to the candidate peptide or combination of candidate peptides. A candidate peptide or combination of candidate peptides meeting the above criteria is likely to comprise a sufficient percentage of the T cell epitopes of the protein antigen to induce T cell nonresponsiveness in a substantial percentage of a population of individuals sensitive to the protein antigen.

As an illustrative embodiment of the above-described algorithm, a set of overlapping peptides derived from Cry j I were produced and tested. Secondary T cell cultures determined to be reactive with Cry j I protein antigen were derived from 36 Cry j I-allergic subjects and analyzed for reactivity to the overlapping set of peptides in an in vitro T cell proliferation assay as described herein. The results are shown in FIG. 45. The highest stimulation index greater than or equal to 2.0 in response to each peptide was recorded for each subject tested. The data were then analyzed by the equations above. The results and calculations of the percent of T cell reactivity for a single Cry j I-allergic subject are shown below using formulas (1) and (2).

| T CELL REACTIVITY FOR PATIENT 1308 | |
|---|---|
| PEPTIDE | STIMULATION INDEX |
| CJ1-1 | 10.9 |
| CJ1-2 | 16.1 |
| CJ1-3 | 8.8 |
| CJ1-4 | 0 |
| CJ1-5 | 3.2 |
| CJ1-6 | 0 |
| CJ1-7 | 2.5 |
| CJ1-8 | 0 |
| CJ1-41 | 8.9 |
| CJ1-11 | 0 |
| CJ1-12 | 0 |
| CJ1-13 | 0 |
| CJ1-14 | 0 |
| CJ1-15 | 0 |
| CJ1-42.5 | 17.6 |
| CJ1-18 | 0 |
| CJ1-19 | 0 |
| CJ1-20 | 0 |
| CJ1-21 | 0 |
| CJ1-43.39 | 25.6 |
| CJ1-23 | 5.3 |
| CJ1-24.5 | 6.9 |
| CJ1-25 | 9.4 |
| CJ1-26 | 11.9 |
| CJ1-27 | 5.5 |
| CJ1-28 | 0 |
| CJ1-29 | 2.9 |
| CJ1-30 | 0 |
| CJ1-44.8 | 21.5 |
| CJ1-33 | 20.9 |
| CJ1-34 | 17.8 |
| CJ1-35 | 0 |
| SUM OF STIMULATION INDICES: | 195.7 (DENOMINATOR) |

% Reactivity of Peptides 44.8 for patient 1308

$$\frac{CJ1-44.8(S.I.)}{195.7} = \frac{21.5}{195.7} \times 100 = 11\% \quad (1)$$

$$\frac{CJ1-30 + CJ1-44.8 + CJ1-33(S.I.s)}{195.7} = \quad (2)$$

$$\frac{0 + 21.5 + 20.9}{195.7} \times 100 = 21.7\%$$

Therefore the estimated range of T cell reactivity for Peptide 44.8 for this patient is 11%-21.7% of the total reactivity of the Cry j I protein. The above calculation is repeated for any potential candidate peptides. In the population of 36 Cry j I-allergic subjects tested the following results were obtained:

| Candidate Peptides | Range of mean percentage T Cell Reactivity | Frequency of response at least one peptide |
| --- | --- | --- |
| CJ1-24.5 + CJ1-43.3 + CJ1-44.8 | 36-53% | 97% |

Additionally, for therapeutic purposes, preferred T cell epitope-containing peptides of the invention do not bind immunoglobulin E (IgE) or bind IgE to a substantially lesser extent (i.e., preferably at least 100-fold less or more preferably at least 1,000-fold less) than the protein allergen from which the peptide is derived binds IgE. The major complications of standard immunotherapy are IgE-mediated responses such as anaphylaxis. Immunoglobulin E is a mediator of anaphylactic reactions which result from the binding and cross-linking of antigen to IgE on mast cells or basophils and the release of mediators (e.g., histamine, serotonin, eosinophil chemotacic factors). Thus, anaphylaxis in a substantial percentage of a population of individuals sensitive to Cry j I or Cry j II could be avoided by the use in immunotherapy of a peptide or peptides which do not bind IgE in a substantial percentage (e.g., at least about 75%) of a population of individuals sensitive to Cry j I allergen, or if the peptide binds IgE, such binding does not result in the release of mediators from mast cells or basophils. The risk of anaphylaxis could be reduced by the use in immunotherapy of a peptide or peptides which have reduced IgE binding. Moreover, peptides which have minimal IgE stimulating activity are desirable for therapeutic effectiveness. A T cell epitope-containing peptide of the invention, when administered to a Japanese cedar pollen-sensitive individual, is capable of modifying the allergic response of the individual to the allergen.

A preferred isolated peptide of the invention comprises at least one T cell epitope of the Japanese cedar pollen allergen, Cry j I or Cry j II and accordingly the peptide comprises at least approximately seven amino acid residues. For purposes of therapeutic effectiveness, therapeutic compositions of the invention may comprise peptides having at least two T cell epitopes of Cry j I or Cry j II, and accordingly, the peptide comprises at least approximately eight amino acid residues and preferably at least fifteen amino acid residues. Alternatively, the individual sensitive to Cry j I or Cry j II may be administered more than one peptide of the invention comprising at least one T cell epitope. Additionally, therapeutic compositions comprising preferred isolated peptides of the invention preferably comprise a sufficient percentage of the T cell epitopes of the entire protein allergen such that a therapeutic regimen of administration of the composition to an individual sensitive to Japanese cedar pollen, results in T cells of the individual being renedered non-responsive to the protein allergen. Peptides of the invention produced by chemical synthesis comprising up to approximately forty-five amino acid residues in length, and most preferably up to approximately thirty amino acid residues in length are particularly desirable as increases in length may result in difficulty in peptide synthesis. Peptides of the invention may also be produced recombinantly as described above or by chemical cleavage of the native allergen.

Preferred peptides comprise all or a portion of the areas of major T cell reactivity within Cry j I or Cry j II. Areas of major T cell reactivity within Cry j I are designated herein as, Region 1, Region 2, Region 3, Region 4 and Region 5. Each major area of T cell activity is defined as follows and is shown in FIG. 4*a-b*. Region 1 comprises amino acid residues 1-50 of Cry j I (SEQ ID NO: 61); Region 2 comprises amino acid residues 61-120 of Cry j I (SEQ ID NO: 62); Region 3 comprises amino acid residues 131-180 of Cry j I (SEQ ID NO: 63); Region 4 comprises amino acid residues 191-280 of Cry j I (SEQ ID NO: 64); Region 5 comprises amino acid residues 291-353 of the Cry j I (SEQ ID NO: 65). Preferred areas of major T cell reactivity within each Region as shown in FIG. 4*a-b* and comprise: amino acid residues 1-40 (SEQ ID NO: 66); amino acid residues 81-110 (SEQ ID NO: 67); amino acid residues 151-180 (SEQ ID NO: 68); amino acid residues 191-260 (SEQ ID NO: 69); and amino acid residues 291-330 (SEQ ID NO: 70).

Peptides derived from the Cry j I protein allergen which can be used for therapeutic purposes comprise all or a portion of the following peptides: CJ1-1 (SEQ ID NO: 26). CJ1-2 (SEQ ID NO: 27), CJ1-3 (SEQ ID NO: 28), CJ1-4 (SEQ ID NO: 29), CJ1-7 (SEQ ID NO: 32), CJ1-8 (SEQ ID NO: 33), CJ1-9 (SEQ ID NO: 34), CJ1-10 (SEQ ID NO: 35), CJ1-11 (SEQ ID NO:36), CJ1-12 (SEQ ID NO:37), CJ1-14 (SEQ ID NO: 39), CJ1-15 (SEQ ID NO: 40), CJ1-16 (SEQ ID NO: 41), CJ1-17 (SEQ ID NO: 42), CJ1-18 (SEQ ID NO: 43), CJ1-19 (SEQ ID NO: 44), CJ1-20 (SEQ ID NO: 45), CJ1-21 (SEQ ID NO: 46), CJ1-22 (SEQ ID NO: 47), CJ1-23 (SEQ ID NO: 48), CJ1-24 (SEQ ID NO: 49), CJ1-25 (SEQ ID NO: 50), CJ1-26 (SEQ ID NO: 51), CJ1-27 (SEQ ID NO: 52), CJ1-28 (SEQ ID NO: 53), CJ1-30 (SEQ ID NO: 55), CJ1-31 (SEQ ID NO: 56), CJ1-32 (SEQ ID NO: 57), CJ1-33 (SEQ ID NO: 58), CJ1-34 (SEQ ID NO: 59) and CJ1-35 (SEQ ID NO: 60) wherein the portion of the peptide preferably has a mean T cell stimulation index equivalent to, or greater than the mean T cell stimulation index of the peptide from which it is derived as shown in FIG. 14.

Preferably peptides derived from the Cry j I protein allergen which can be used for therapeutic purposes comprise all or a portion of the following peptides: CJ1-2 (SEQ ID NO: 27), CJ1-9 (SEQ ID NO: 34), CJ1-10 (SEQ ID NO: 35), CJ1-16 (SEQ ID NO: 41), CJ1-17 (SEQ ID NO: 42), CJ1-20 (SEQ ID NO: 45), CJ1-22 (SEQ ID NO: 47), CJ1-23 (SEQ ID NO: 48), CJ1-24 (SEQ ID NO: 49), CJ1-25 (SEQ ID NO: 50), CJ1-26 (SEQ ID NO: 51), CJ1-27 (SEQ ID NO: 52), CJ1-30 (SEQ ID NO: 53), CJ1-31 (SEQ ID NO: 54), CJ1-32 (SEQ ID NO: 56)and CJ1-35 (SEQ ID NO: 60) wherein the portion of the peptide preferably has a mean T cell stimulation index equivalent to, or greater than the mean T cell stimulation index of the peptide from which it is derived as shown in FIG. 14.

Additionally, other peptides useful for therapeutic purposes comprise the following peptides: CJ1-41 (SEQ ID NO: 71), CJ1-41.1 (SEQ ID NO: 72), CJ1-41.2 (SEQ ID NO: 73), CJ1-41.3 (SEQ ID NO: 74), CJ1-42 (SEQ ID NO: 75), CJ1-42.1 (SEQ ID NO: 76), CJ1-42.2 (SEQ ID NO: 77), CJ1-43 (SEQ ID NO: 78), CJ1-43.1 (SEQ ID NO: 79), CJ1-43.6 (SEQ ID NO: 80), CJ1-43.7 (SEQ ID NO: 81), CJ1-43.8 (SEQ ID NO: 82), CJ1-43.9 (SEQ ID NO: 83), CJ1-43.10 (SEQ DD NO: 84), CJ1-43.11 (SEQ ID NO: 85), CJ1-43.12 (SEQ ID NO: 86), CJ1-45 (SEQ ID NO: 87), CJ1-45.1 (SEQ ID NO: 88), CJ1-45.2 (SEQ ID NO: 89), CJ1-44 (SEQ ID NO: 90), CJ1-44.1 (SEQ ID NO: 91), CJ1-44.2 (SEQ ID NO: 92) and CJ1-44.3 (SEQ ID NO: 93), all as shown in FIG. 18. Some of these peptides have been further modified for the purpose of increasing their solubility Such modified peptides derived from Cry j I comprise all or a portion of the following peptides: CJ1-42.3, CJ1-42.4, CJ1-42.5 (SEQ ID NO: 119), CJ1-42.6, CJ1-42.7, CJ1-42.8 (SEQ ID NO: 120), CJ1-42.9, CJ1-42.10, CJ1-42.1 1, CJ1-42.12, CJ1-42.13, CJ1-42.14, 42.15, CJ1-43.2, CJ1-43.3, CJ1-43.4, 43.5, CJ1-43.12, CJ1-43.13, CJ1-43.14, CJ1-43.15, CJ1-43.16, CJ1-43.17, CJ1-43.18, CJ1-43.19, CJ1-43.20, CJ1-43.21, CJ1-43.22, CJ1-43.23, CJ1-43.24, CJ1-43.26, CJ1-43.26 (SEQ ID NO: 12 1), CJ1-43.27 (SEQ ID NO: 122), CJ1-43.28, CJ1-43.29, CJ1-43.30 (SEQ ID NO: 123), CJ1-43.31 (SEQ ID NO: 124), CJ1-43.32 (SEQ ID NO: 125), CJ1-43.33, CJ1-43.34, CJ1-43.35 (SEQ ID NO: 126), CJ1-43.36 (SEQ ID NO: 127), CJ1-43.37, CJ1-43.38, CJ1-43.39 (SEQ ID NO: 128), CJ1-43.40, CJ1-43.41, CJ1-43.42, CJ1-43.43, CJ1-43.44, CJ1-43.45, C1-43.46, CJ1-43.47, CJ1-43.48, CJ1-43.49, CJ1-43.50, CJ1-43.51, CJ1-43.52, CJ1-43.53, CJ1-43.54, CJ1-43.55, CJ1-43.56, CJ1-43.57, CJ1-43.58, CJ1-43.59, CJ1-43.60, CJ1-24.2, CJ1-24.5 (SEQ ID NO: 129), CJ1-44.5 (SEQ ID NO: 130), CJ1-44.6 (SEQ ID NO: 131), CJ1-44.7, CJ1-44.8 (SEQ ID NO: 132), CJ1-44.9, CJ1-44.10 all as shown in FIG. 18, 20, or 44). Preferred peptides which have been modified for enhanced solubility include the following peptides: CJ1-42.5 (SEQ ID NO: 119), CJ1-42.8 (SEQ ID NO: 120), CJ1-43.26 (SEQ ID NO: 121), CJ1-43.27 (SEQ ID NO: 122), CJ1-43.30 (SEQ ID NO: 123), CJ1-43.31 (SEQ ID NO: 124), CJ1-43.32 (SEQ ID NO: 125), CJ1-43.35 (SEQ ID NO: 126), CJ1-43.36 (SEQ ID NO: 127), CJ1-43.39 (SEQ ID NO: 128), CJ1-24.5 (SEQ ID NO: 129), CJ1-44.5 (SEQ ID NO: 130), CJ1-44.6 (SEQ ID NO: 131), CJ1-44.8 (SEQ ID NO: 132) and CJ1-44.9, all as shown in FIGS. 20 and 44.

Of the above group of modified peptides, several peptides have been identified as "unique" modified peptides. A "unique" modified peptide is defined herein as a modified peptide which 1) possesses the characteristic of "superior solubility"; 2) has T cell reactivity which is similar to that of the "parent" peptide from which the "unique" modified peptide is derived; and 3) is stable in an aqueous buffer at a pH ranging from pH6 to pH8. "Superior solubility" is defined herein as solubility of greater than 5 mg/ml over a pH range of pH6 to pH8 in an aqueous buffer. Certain modified peptides are characterized as "unique" due to the difficulties encountered when developing a modified peptide which meets all of the stringent requirements of a "unique" peptide defined herein. In many cases, multiple modifications of a parent peptide are attempted prior to identifying a modified derivitive peptide which meets all the characteristics of a "unique" modified peptide. Unique modified peptides are particularly useful as candidate peptides for formulating injectable multipeptide therapeutic formulations of the invention because "unique" modified peptides are soluble and stable in the same physiologically acceptable pH range as well as elicit the necessary T cell reactivity of a therapeutic peptide of the invention. "Unique" modified peptides of the invention include but are not limited to the following group of modified peptides: CJ1-24.5, CJ1-43.39, CJ1-43.50, CJ1-44.8, and CJ1-44.9 all as shown in FIGS. 20 and 44. Example 21 describes the development and identification of "unique" modified peptides of the invention.

Preferred peptides of Cry j II which may comprise T cell epitopes include: Cry j IIA (SEQ ID NO: 185) Cry j IIB (SEQ ID NO: 186) and Cry j IIQ (SEQ ID NO: 193) (FIG. 41). Preferred Cry j II peptides comprising T cell epitopes include: Cry j IIC, Cry j IID, Cry j IIE, (SEQ ID NO: 189) Cry j IIF (SEQ ID NO: 190), Cry j IIG (SEQ ID NO: 191) and Cry j IIH (SEQ ID NO: 192) all as shown in FIG. 41.

Figure 14:
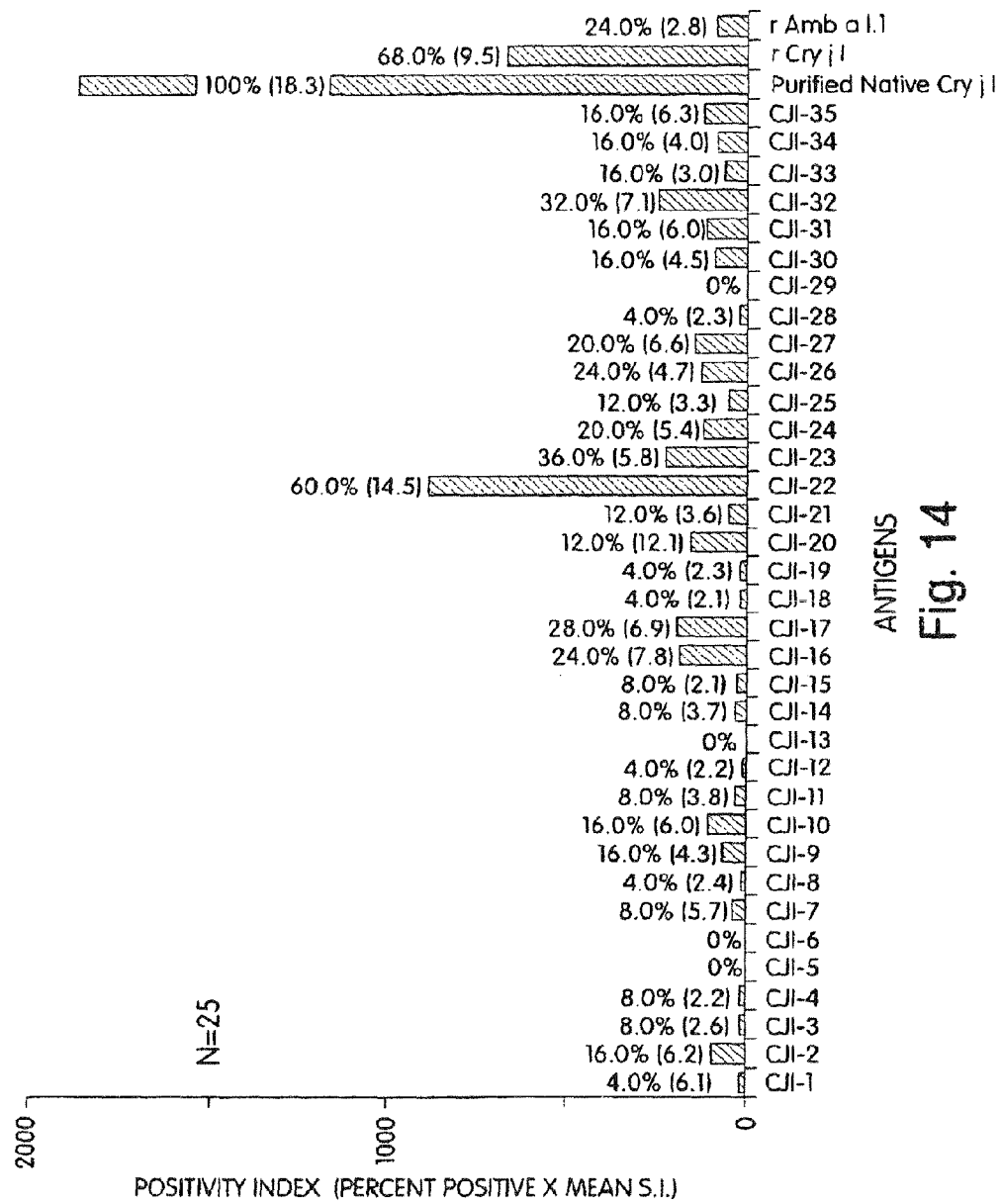
FIG. 14 is a graphic representation depicting responses of T cell lines from twenty-five patients primed in vitro with purified native Cry j I and analyzed for response to various Cry j I peptides by percent of responses (positive) with an S.I of at least two (shown over each bar), the mean stimulation index of positive response for the peptide (shown over each bar in parenthesis) and the positivity index (Y axis)

One embodiment of the present invention features a peptide or portion thereof of Cry j I which comprises at least one T cell epitope of the protein allergen and has a formula $X_n$-Y-$Z_m$. According to the formula, Y is an amino acid sequence selected from the group of Cry j I peptides consisting of CJI-1 (SEQ ID NO: 26), CJI-2 (SEQ ID NO: 27), CJI-3 (SEQ ID NO: 28), CJI-4 (SEQ ID NO: 29), CJI-7 (SEQ ID NO: 32), CJI-8 (SEQ ID NO: 33), CJI-9 (SEQ ID NO: 34), CJI-10 (SEQ ID NO: 35), CJI-11 (SEQ ID NO: 36), CJI-12 (SEQ ID NO: 37), CJI-14 (SEQ ID NO: 39), CJI-15 (SEQ ID NO: 40), CJI-16 (SEQ ID NO: 41), CJI-17 (SEQ ID NO: 42), CJI-18 (SEQ ID NO: 43), CJI-19 (SEQ ID NO: 44), CJI-20 (SEQ ID NO: 45), CJI-21 (SEQ ID NO: 46), CJI-22 (SEQ ID NO: 47), CJI-23 (SEQ ID NO: 48), CJI-24 (SEQ ID NO: 49), CJI-25 (SEQ ID NO: 50), CJI-26 (SEQ ID NO: 51), CJI-27 (SEQ ID NO: 52), CJI-28 (SEQ ID NO: 53), CJI-30 (SEQ ID NO: 55), CJI-31 (SEQ ID NO: 56), CJI-32 (SEQ ID NO: 57), CJI-33 (SEQ ID NO: 58), CJI-34 (SEQ ID NO: 59), CJI-35 (SEQ ID NO: 60), CJI-41, CJI-42.5 (SEQ ID NO: 119), CJI-42.8 (SEQ ID NO: 120), CJI-43.26 (SEQ ID NO: 121), CJI-43.27 (SEQ ID NO: 122), CJI-43.30 (SEQ ID NO: 123), CJI-43.31 (SEQ ID NO: 124), CJI-43.32 (SEQ ID NO: 125), CJI-43.35 (SEQ ID NO: 126), CJI-43.36 (SEQ ID NO: 127), CJI-43.39 (SEQ ID NO: 128), CJI-24.5 (SEQ ID NO: 129), CJI-44.5 (SEQ ID NO: 130), CJI-44.6 (SEQ ID NO: 131), CJI-44.8 (SEQ ID NO: 132) and preferably selected from the group consisting of CJI-2 (SEQ ID NO: 27), CJI-9 (SEQ ID NO: 29), CJI-10 (SEQ ID NO: 30), CJI-16 (SEQ ID NO: 41), CJI-17 (SEQ ID NO: 42), CJI-20 (SEQ ID NO: 45), CJI-22 (SEQ ID NO: 47), CJI-23 (SEQ ID NO: 48), CJI-24 (SEQ ID NO: 49), CJI-25 (SEQ ID NO: 50), CJI-26 (SEQ ID NO: 51), CJI-27 (SEQ ID NO: 52), CJI-30 (SEQ ID NO: 55), CJI-31 (SEQ ID NO: 56), CJI-32 (SEQ ID NO: 57), CJI-35 (SEQ ID NO: 60) CJI-41, CJI-24,5 (SEQ ID NO: 129), CJI-43.39 (SEQ ID NO: 128) and CJI-44.8 (SEQ ID NO: 132). In addition, $X_n$ are amino acid residues contiguous to the amino terminus of Y in the amino acid sequence of the protein allergen and $Z_m$ are amino acid residues contiguous to the carboxy terminus of Y in the amino acid sequence of the protein allergen. Preferably, the amino acids comprising the amino terminus of X and the carboxy terminus of Z are selected from charged amino acids, i.e., arginine (R), lysine (K), histidine (H), glutamic acid (E) or aspartic acid (D); amino acids with reactive side chains, e.g., cysteine (C), asparagine (N) or glutamine (Q); or amino acids with sterically small side chains, e.g. alanine (A) or glycine (G). In the formula, n is preferably 0-30 and m is preferably 0-30. Preferably n and m are 0-5, and most preferably n+m is less than 10. Preferably, the peptide or portion thereof has a mean T cell stimulation index equivalent to or greater than the mean T cell stimulation index of Y as shown in FIG. 14. Y may also be selected from the group of Cry j II peptides consisting of Cry j IIA (SEQ ID NO: 185), Cry j IIB (SEQ ID NO: 186), Cry j IIC (SEQ ID NO: 187), Cry j IID (SEQ ID NO: 188), Cry j IIE (SEQ ID NO: 189), Cry j IIF (SEQ ID NO: 190), Cry j IIG (SEQ ID NO: 191), Cry j IIH (SEQ ID NO: 192), or Cry j IIQ (SEQ ID NO: 193) all as shown in FIG. 41.

Another embodiment of the present invention provides peptides comprising at least two regions, each region comprising at least one T cell epitope of Cry j I or Cry j II and accordingly each region comprises at least approximately seven amino acid residues. These peptides comprising at least two regions can comprise as many amino acid residues as desired and preferably comprise 14 amino acid residues of a Cry j I or Cry j II allergen, or even more preferably about 30 amino acid residues and most preferably at least about 40 amino acid residues of Cry j I or Cry j II allergen. If desired, the amino acid sequences of the regions can be produced and joined by a linker to increase sensitivity to processing by antigen-presenting cells. Such linker can be any non-epitope amino acid sequence or other appropriate linking or joining agent. To obtain preferred peptides comprising at least two regions, each comprising at least one T cell epitope, the regions are arranged in a configuration different from a naturally-occurring configuration of the regions in the allergen. For example, the regions containing T cell epitope(s) can be arranged in a noncontiguous configuration and can preferably be derived from the same protein allergen. Noncontiguous is defined as an arrangement of regions containing T cell epitope(s) which is different than that of an amino acid sequence present in the protein allergen from which the regions are derived. Furthermore, the noncontiguous regions containing T cell epitopes can be arranged in a nonsequential order (e.g., in an order different from the order of the amino acids of the native protein allergen from which the region containing T cell epitope(s) are derived in which amino acids are arranged from an amino terminus to a carboxy terminus). A peptide for use as a therapeutic can comprise at least 15%, at least 30%, at least 50% or up to 100% of the T cell epitopes of Cry j I or Cry j II but does not comprise the whole protein sequence of the allergen.

The individual peptide regions can be produced and tested to determine which regions bind immunoglobulin E specific for Cry j I and which of such regions would cause the release of mediators (e.g., histamine) from mast cells or basophils. Those peptide regions found to bind immunoglobulin E and cause the release of mediators from mast cells or basophils in greater than approximately 10-15% of the allergic sera tested are preferably not included in the peptide regions arranged to form preferred peptides of the invention.

Additionally, regions of a peptide of the invention preferably comprise all or a portion of the above discussed preferred areas of major T cell reactivity within Cry j II or Cry j I (i.e., Regions 1-5 of Cry j I) or the above discussed preferred areas of major T cell activity within each Region (i.e. amino acids from residues 1-40, 81-110, 151-180, 191-260 and 291-330 of Cry j (SEQ ID NO: 2)). For example, with regard to Cry j I, one region can comprise all or a portion of Region I (amino acid residues 1-51) (SEQ ID NO: 61) and one region can comprise all or a portion of Region 2 (amino acid residues 61-120). (SEQ ID NO: 62) Peptides of the invention can comprise all or a portion of two or more of these Regions (i.e., Regions 1-5) and preferred resulting peptides do not bind IgE and cause the release of mediators from most cells or basophils. Preferred peptides derived from Cry j I comprise all or a portion of Region 3 (SEQ ID NO: 63), Region 4 (SEQ ID NO: 64) and Region 5 (SEQ ID NO: 65), and, optionally, Region 1 (SEQ ID NO: 61) or Region 2.(SEQ ID NO: 62) Further, if one of these Regions is found to bind IgE and cause the release of mediators from mast cells or basophils, then it is preferred that the peptide not comprise such Region, but rather comprises various regions derived from such Region which do not bind IgE or cause release of mediators from mast cells or basophils.

Examples of preferred regions of Cry j I include: CJ1-1 (SEQ ID NO: 26), CJ1-2 (SEQ ID NO: 27), CJ1-3 (SEQ ID NO: 28), CJ1-4 (SEQ ID NO: 29), CJ1-7 (SEQ ID NO: 32), CJ1-8 (SEQ ID NO: 33), CJ1-9 (SEQ ID NO: 34), CJ1-10 (SEQ ID NO: 35), CJ1-11 (SEQ ID NO: 36), CJ1-12 (SEQ ID NO: 37), CJ1-14 (SEQ ID NO: 39), CJ1-15 (SEQ ID NO: 40), CJ1-16 (SEQ ID NO: 41), CJ1-17 (SEQ ID NO: 42), CJ1-18 (SEQ ID NO: 43), CJ1-19 (SEQ ID NO: 44), CJ1-20 (SEQ ID NO: 45), CJ1-21 (SEQ ID NO: 46), CJ1-22 (SEQ ID NO: 47), CJ1-23 (SEQ ID NO: 48), CJ1-24 (SEQ ID NO: 49), CJ1-25 (SEQ ID NO: 50), CJ1-26 (SEQ ID NO: 51), CJ1-27 (SEQ ID NO: 52), CJ1-28 (SEQ ID NO: 53), CJ1-30 (SEQ ID NO: 55), CJ1-31 (SEQ ID NO: 56), CJ1-32 (SEQ ID NO: 57), CJ1-33 (SEQ ID NO: 58), CJ1-34 (SEQ ID NO: 59), CJ1-35 (SEQ ID NO: 60), CJ1-42.5 (SEQ ID NO: 119), CJ1-42.8 (SEQ ID NO: 120), CJ1-43.26 (SEQ ID NO: 121), CJ1-43.27, (SEQ ID NO: 122) CJ1-43.30 (SEQ ID NO: 123), CJ1-43.31 (SEQ ID NO: 124), CJ1-43.32 (SEQ ID NO: 125), CJ1-43.35 (SEQ ID NO: 126), CJ1-43.36 (SEQ ID NO: 127), CJ1-43.39 (SEQ ID NO: 128), CJ1-24.5 (SEQ ID NO: 129), CJ1-44.5 (SEQ ID NO: 130), CJ1-44.6 (SEQ ID NO: 131), CJ1-44.8 (SEQ ID NO: 132), the amino acid sequences of such regions being shown in FIG. 13 and FIG. 20, or portions of said regions comprising at least one T cell epitope.

Preferred peptides comprise various combinations of two or more regions, each region comprising all or a portion of the above-discussed preferred areas of major T cell reactivity. Preferred peptides comprise a combination of two or more regions (each region having an amino acid sequence as shown in FIG. 13 and FIG. 20), including:

```
CJ1-1,            (SEQ ID NO: 26)

CJ1-2             (SEQ ID NO: 27)
and

CJ1-3;            (SEQ ID NO: 28)

CJ1-1             (SEQ ID NO: 26)
and

CJ1-2;            (SEQ ID NO: 27)

CJ1-9             (SEQ ID NO: 34)
and

CJ1-10;           (SEQ ID NO: 35)

CJ1-14,           (SEQ ID NO: 39)

CJ1-15,           (SEQ ID NO: 40)

CJ1-16            (SEQ ID NO: 41)
and

CJ1-17;           (SEQ ID NO: 42)

CJ1-20,           (SEQ ID NO: 45)

CJ1-21,           (SEQ ID NO: 46)

CJ1-22,           (SEQ ID NO: 47)

CJ1-23;           (SEQ ID NO: 48)

CJ1-20,           (SEQ ID NO: 45)

CJ1-22            (SEQ ID NO: 47)
and

CJ1-23;           (SEQ ID NO: 48)

CJ1-22            (SEQ ID NO: 47)
and

CJ1-23;           (SEQ ID NO: 48)

CJ1-22,           (SEQ ID NO: 47)

CJ1-23            (SEQ ID NO: 48)
and

CJ1-24;           (SEQ ID NO: 49)
```

-continued

| | |
|---|---|
| CJ1-24 and | (SEQ ID NO: 49) |
| CJ1-25; | (SEQ ID NO: 50) |
| CJ1-30, | (SEQ ID NO: 55) |
| CJ1-31 and | (SEQ ID NO: 56) |
| CJ1-32; | (SEQ ID NO: 57) |
| CJ1-31 and | (SEQ ID NO: 56) |
| CJ1-32; | (SEQ ID NO: 57) |
| CJ1-22, | |
| CJ1-23, | (SEQ ID NO: 48) |
| CJ1-16 and | (SEQ ID NO: 41) |
| CJ1-17; | (SEQ ID NO: 42) |
| CJ1-22, | (SEQ ID NO: 47) |
| CJ1-23, | (SEQ ID NO: 48) |
| CJ1-31 and | (SEQ ID NO: 56) |
| CJ1-32; | (SEQ ID NO: 57) |
| CJ1-16, | (SEQ ID NO: 41) |
| CJ1-17, | (SEQ ID NO: 42) |
| CJ1-31 and | (SEQ ID NO: 56) |
| CJ1-32; | (SEQ ID NO: 57) |
| CJ1-9, | (SEQ ID NO: 34) |
| CJ1-10 and | (SEQ ID NO: 35) |
| CJ1-16; | (SEQ ID NO: 41) |
| CJ1-16 and | (SEQ ID NO: 41) |
| CJ1-17; | (SEQ ID NO: 42) |
| CJ1-17, | (SEQ ID NO: 42) |
| CJ1-22 and | (SEQ ID NO: 47) |
| CJ1-23; | (SEQ ID NO: 48) |
| CJ1-16, | (SEQ ID NO: 41) |
| CJ1-17 and | (SEQ ID NO: 42) |
| CJ1-20; | (SEQ ID NO: 45) |
| CJ1-31, | (SEQ ID NO: 56) |
| CJ1-32 and | (SEQ ID NO: 57) |
| CJ1-20; | (SEQ ID NO: 45) |
| CJ1-22, | (SEQ ID NO: 47) |
| CJ1-23, | (SEQ ID NO: 48) |
| CJ1-1, and | (SEQ ID NO: 26) |
| CJ1-2 and | (SEQ ID NO: 27) |
| CJ1-3; | (SEQ ID NO: 28) |
| CJ1-16, | (SEQ ID NO: 41) |
| CJ1-17, | (SEQ ID NO: 42) |
| CJ1-22 and | (SEQ ID NO: 47) |
| CJ1-23, | (SEQ ID NO: 48) |
| CJ1-31 and | (SEQ ID NO: 56) |
| CJ1-32; | (SEQ ID NO: 57) |
| CJ1-9, | (SEQ ID NO: 34) |
| CJ1-10, | (SEQ ID NO: 35) |
| CJ1-16, | (SEQ ID NO: 41) |
| CJ1-17, | (SEQ ID NO: 42) |
| CJ1-22 and | (SEQ ID NO: 47) |
| CJ1-23; | (SEQ ID NO: 48) |
| CJ1-9, | (SEQ ID NO: 34) |
| CJ1-10, | (SEQ ID NO: 35) |
| CJ1-16, | (SEQ ID NO: 41) |
| CJ1-17, | (SEQ ID NO: 42) |
| CJ1-31 and | (SEQ ID NO: 56) |
| CJ1-32; | (SEQ ID NO: 57) |
| CJ1-9, | (SEQ ID NO: 34) |
| CJ1-10, | (SEQ ID NO: 35) |
| CJ1-22, | (SEQ ID NO: 47) |
| CJ1-23, | (SEQ ID NO: 48) |
| CJ1-31 and | (SEQ ID NO: 56) |
| CJ1-32; | (SEQ ID NO: 57) |
| CJ1-9, | (SEQ ID NO: 34) |
| CJ1-10, | (SEQ ID NO: 35) |
| CJ1-16, | (SEQ ID NO: 41) |
| CJ1-17, | (SEQ ID NO: 42) |
| CJ1-22 | (SEQ ID NO: 47) |
| CJ1-23, | (SEQ ID NO: 48) |
| CJ1-31 and | (SEQ ID NO: 56) |
| CJ1-32; | (SEQ ID NO: 57) |
| CJ1-1, | (SEQ ID NO: 26) |
| CJ1-2, | (SEQ ID NO: 27) |

-continued

| | |
|---|---|
| CJ1-16, | (SEQ ID NO: 41) |
| CJ1-17, | (SEQ ID NO: 42) |
| CJ1-22 and | (SEQ ID NO: 47) |
| CJ1-23; | (SEQ ID NO: 48) |
| CJ1-22, | (SEQ ID NO: 47) |
| CJ1-23, | (SEQ ID NO: 48) |
| CJ1-24, | (SEQ ID NO: 49) |
| CJ1-9, and | (SEQ ID NO: 34) |
| CJ1-10; | (SEQ ID NO: 35) |
| CJ1-22, | (SEQ ID NO: 47) |
| CJ1-23, | (SEQ ID NO: 48) |
| CJ1-24, | (SEQ ID NO: 49) |
| CJ1-9, | (SEQ ID NO: 34) |
| CJ1-10, | (SEQ ID NO: 35) |
| CJ1-16, and | (SEQ ID NO: 41) |
| CJ1-17; | (SEQ ID NO: 42) |
| CJ1-22, | (SEQ ID NO: 47) |
| CJ1-23, | (SEQ ID NO: 48) |
| CJ1-24, | (SEQ ID NO: 49) |
| CJ1-16, | (SEQ ID NO: 41) |
| CJ1-17, | (SEQ ID NO: 42) |
| CJ1-31 and | (SEQ ID NO: 56) |
| CJ1-32; | (SEQ ID NO: 57) |
| CJ1-22, | (SEQ ID NO: 47) |
| CJ1-23, | (SEQ ID NO: 48) |
| CJ1-24, | (SEQ ID NO: 49) |
| CJ1-16, and | (SEQ ID NO: 41) |
| CJ1-17; | (SEQ ID NO: 42) |
| CJ1-22, | (SEQ ID NO: 47) |
| CJ1-23, | (SEQ ID NO: 48) |
| CJ1-24, | (SEQ ID NO: 49) |
| CJ1-9, | (SEQ ID NO: 34) |
| CJ1-10, | (SEQ ID NO: 35) |
| CJ1-31 and | (SEQ ID NO: 56) |
| CJ1-32; | (SEQ ID NO: 57) |
| CJ1-22, | (SEQ ID NO: 47) |
| CJ1-23, | (SEQ ID NO: 48) |
| CJ1-24, | (SEQ ID NO: 49) |

-continued

| | |
|---|---|
| CJ1-9, | (SEQ ID NO: 34) |
| CJ1-10, | (SEQ ID NO: 35) |
| CJ1-16, | (SEQ ID NO: 41) |
| CJ1-17, | (SEQ ID NO: 42) |
| CJ1-31 and | (SEQ ID NO: 56) |
| CJ1-32; | (SEQ ID NO: 57) |
| CJ1-22, | (SEQ ID NO: 47) |
| CJ1-23, | (SEQ ID NO: 48) |
| CJ1-24, | (SEQ ID NO: 49) |
| CJ1-31 and | (SEQ ID NO: 56) |
| CJ1-32; | (SEQ ID NO: 57) |
| CJI-42.5, | (SEQ ID NO: 119) |
| CJI-43.32, | (SEQ ID NO: 125) |
| CJI-43.39, | (SEQ ID NO: 128) |
| CJI-24.5 and | (SEQ ID NO: 129) |
| CJI-44.8; | (SEQ ID NO: 132) |
| CJI-42.5, | (SEQ ID NO: 119) |
| CJI-43.39, | (SEQ ID NO: 128) |
| CJI-24.5 and | (SEQ ID NO: 129) |
| CJI-44.8; | (SEQ ID NO: 132) |
| CJI-42.5, | (SEQ ID NO: 119) |
| CJI-43.39, | (SEQ ID NO: 128) |
| CJI-24.5 and | (SEQ ID NO: 129) |
| CJI-44.8; | (SEQ ID NO: 132) |
| CJI-42.5, | (SEQ ID NO: 119) |
| CJI-43.39 and | (SEQ ID NO: 128) |
| CJI-24.5; | (SEQ ID NO: 129) |
| CJI-42.5, and | (SEQ ID NO: 119) |
| CJI-43.39; | (SEQ ID NO: 128) |
| CJI-43.39, | (SEQ ID NO: 128) |
| CJI-24.5 and | (SEQ ID NO: 129) |
| CJI-44.8; | (SEQ ID NO: 132) |
| CJI-43.39 and | (SEQ ID NO: 128) |
| CJI-24.5; | (SEQ ID NO: 129) |

-continued

```
CJI-43.39          (SEQ ID NO: 128)
and

CJI-44.8;          (SEQ ID NO: 132)

CJI-24.5,          (SEQ ID NO: 129)

CJI-44.8           (SEQ ID NO: 132)
and

CJI-42.5;          (SEQ ID NO: 119)

CJI-24.5           (SEQ ID NO: 129)
and

CJI-44.8;          (SEQ ID NO: 132)

CJI-44.8,          (SEQ ID NO: 132)

CJI-42.5           (SEQ ID NO: 119)
and

CJI-43.32;         125)

CJI-44.8           (SEQ ID NO: 132)
and

CJI-42.5;          (SEQ ID NO: 119)
and

CJI-44.8           (SEQ ID NO: 132)
and

CJI-43.32.         (SEQ ID NO: 125)
```

Isolated Cry j I or Cry j II peptides within the scope of the invention can be used in methods of treating and preventing allergic reactions to Japanese cedar pollen. Thus, one aspect of the present invention provides therapeutic compositions comprising a peptide of Cry j I or Cry j II or a combination of peptides of both Cry j I or Cry j II, each peptide including at least one T cell epitope, and a pharmaceutically acceptable carrier or diluent. In another aspect, the therapeutic composition comprises a pharmaceutically acceptable carrier or diluent and a peptide comprising at least two regions, each region comprising at least one T cell epitope of Cry j I or Cry j II.

Preferred therapeutic compositions comprise a sufficient percentage of the T cell epitopes of Cry j I or Cry j II or T cell epitopes of both Cry j I and Cry j II such that a therapeutic regimen of administration of the composition to an individual sensitive to Japanese cedar pollen allergen, results in reduced T cell responsiveness. More preferably, the composition comprises a sufficient percentage of the T cell epitopes such that at least about 40%, and more preferably at least about 60% of the T cell reactivity of Cry j I or Cry j II or both Cry j I or Cry j II are included in the composition. Such compositions can be administered to an individual to treat or prevent sensitivity to Japanese cedar pollen or to an allergen which is immunologically cross-reactive with Japanese cedar pollen allergen such as pollen from Jun s or Jun v.

In yet another aspect of the present invention, a composition is provided comprising at least two peptides (e.g., a physical mixture of at least two peptides), each comprising at least one T cell epitope of Cry j I or Cry j II. Such compositions can be administered in the form of a therapeutic composition with a pharmaceutically acceptable carrier or diluent. A therapeutically effective amount of one or more of such compositions can be administered simultaneously or sequentially to an individual sensitive to Japanese cedar pollen. In another aspect of the invention, Cry j I or Cry j II peptides are provided which can be administered simultaneously or sequentially. Such combinations may comprise therapeutic compositions composing only one peptide, or more peptides if desired. Such compositions may be administered simultaneously or sequentially in preferred combinations.

Preferred compositions and preferred combinations of Cry j I peptides which can be administered simultaneously or sequentially (comprising peptides having amino acid sequences shown in FIG. 13 and FIG. 20) include the following combinations:

```
CJ1-1,             (SEQ ID NO: 26)

CJ1-2              (SEQ ID NO: 27)
and

CJ1-3;             (SEQ ID NO: 28)

CJ1-1              (SEQ ID NO: 26)
and

CJ1-2;             (SEQ ID NO: 27)

CJ1-9              (SEQ ID NO: 34)
and

CJ1-10;            (SEQ ID NO: 35)

CJ1-14,            (SEQ ID NO: 39)

CJ1-15,            (SEQ ID NO: 40)

CJ1-16             (SEQ ID NO: 41)
and

CJ1-17;            (SEQ ID NO: 42)

CJ1-20,            (SEQ ID NO: 45)

CJ1-21,            (SEQ ID NO: 46)

CJ1-22             (SEQ ID NO: 47)
and

CJ1-23;            (SEQ ID NO: 48

CJ1-20,            (SEQ ID NO: 45)

CJ1-22             (SEQ ID NO: 47)
and

CJ1-23;            (SEQ ID NO: 48)

CJ1-22             (SEQ ID NO: 47)
and

CJ1-23;            (SEQ ID NO: 48)

CJ1-22,            (SEQ ID NO: 47)

CJ1-23             (SEQ ID NO: 48)
and

CJ1-24;            (SEQ ID NO: 49)

CJ1-24             (SEQ ID NO: 49)
and

CJ1-25;            (SEQ ID NO: 50)

CJ1-30,            (SEQ ID NO: 55)

CJ1-31             (SEQ ID NO: 56)
and

CJ1-32;            (SEQ ID NO: 57)
```

-continued

| | |
|---|---|
| CJ1-31 and | (SEQ ID NO: 56) |
| CJ1-32; | (SEQ ID NO: 57) |
| CJ1-22, | (SEQ ID NO: 47) |
| CJ1-23, | (SEQ ID NO: 48) |
| CJ1-16 and | (SEQ ID NO: 41) |
| CJ1-17; | (SEQ ID NO: 42) |
| CJ1-22, | (SEQ ID NO: 47) |
| CJ1-23, | (SEQ ID NO: 48) |
| CJ1-31 and | (SEQ ID NO: 56) |
| CJ1-32; | (SEQ ID NO: 57) |
| CJ1-16, | (SEQ ID NO: 41) |
| CJ1-17, | (SEQ ID NO: 42) |
| CJ1-31 and | (SEQ ID NO: 56) |
| CJ1-32; | (SEQ ID NO: 57) |
| CJ1-9, | (SEQ ID NO: 34) |
| CJ1-10 and | (SEQ ID NO: 35) |
| CJ1-16; | (SEQ ID NO: 41) |
| CJ1-16 and | (SEQ ID NO: 41) |
| CJ1-17; | (SEQ ID NO: 42) |
| CJ1-17, | (SEQ ID NO: 42) |
| CJ1-22 and | (SEQ ID NO: 47) |
| CJ1-23; | (SEQ ID NO: 48) |
| CJ1-16, | (SEQ ID NO: 41) |
| CJ1-17 and | (SEQ ID NO: 42) |
| CJ1-20; | (SEQ ID NO: 45) |
| CJ1-31, | (SEQ ID NO: 56) |
| CJ1-32 and | (SEQ ID NO: 57) |
| CJ1-20; | (SEQ ID NO: 45) |
| CJ1-22, | (SEQ ID NO: 47) |
| CJ1-23, | (SEQ ID NO: 48) |
| CJ1-1, | (SEQ ID NO: 26) |
| CJ1-2 and | (SEQ ID NO: 27) |
| CJ1-3; | (SEQ ID NO: 28) |
| CJ1-16, | (SEQ ID NO: 41) |
| CJ1-17, | (SEQ ID NO: 42) |
| CJ1-22, | (SEQ ID NO: 47) |
| CJ1-23, | (SEQ ID NO: 48) |
| CJ1-31 and | (SEQ ID NO: 56) |
| CJ1-32; | (SEQ ID NO: 57) |
| CJ1-9, | (SEQ ID NO: 34) |
| CJ1-10, | (SEQ ID NO: 35) |
| CJ1-16, | (SEQ ID NO: 41) |
| CJ1-17, | (SEQ ID NO: 42) |
| CJ1-22 and | (SEQ ID NO: 47) |
| CJ1-23; | (SEQ ID NO: 48) |
| CJ1-9, | (SEQ ID NO: 34) |
| CJ1-10, | (SEQ ID NO: 35) |
| CJ1-16, | (SEQ ID NO: 41) |
| CJ1-17, | (SEQ ID NO: 42) |
| CJ1-31 and | (SEQ ID NO: 56) |
| CJ1-32; | (SEQ ID NO: 57) |
| CJ1-9, | (SEQ ID NO: 34) |
| CJ1-10, | (SEQ ID NO: 35) |
| CJ1-22, | (SEQ ID NO: 47) |
| CJ1-23, | (SEQ ID NO: 48) |
| CJ1-31 and | (SEQ ID NO: 56) |
| CJ1-32; | (SEQ ID NO: 57) |
| CJ1-9, | (SEQ ID NO: 34) |
| CJ1-10, | (SEQ ID NO: 35) |
| CJ1-16, | (SEQ ID NO: 41) |
| CJ1-17, | (SEQ ID NO: 42) |
| CJ1-22, | (SEQ ID NO: 47) |
| CJ1-23, | (SEQ ID NO: 48) |
| CJ1-31 and | (SEQ ID NO: 56) |
| CJ1-32; | (SEQ ID NO: 57) |
| CJ1-1, | (SEQ ID NO: 26) |
| CJ1-2, | (SEQ ID NO: 27) |
| CJ1-16, | (SEQ ID NO: 41) |
| CJ1-17, | (SEQ ID NO: 42) |
| CJ1-22 and | (SEQ ID NO: 47) |
| CJ1-23; | (SEQ ID NO: 48) |
| CJ1-22, | (SEQ ID NO: 47) |
| CJ1-23, | (SEQ ID NO: 48) |

-continued

| | |
|---|---|
| CJ1-24, | (SEQ ID NO: 49) |
| CJ1-9, and | (SEQ ID NO: 34) |
| CJ1-10; | (SEQ ID NO: 35) |
| CJ1-22, | (SEQ ID NO: 47) |
| CJ1-23, | (SEQ ID NO: 48) |
| CJ1-24, | (SEQ ID NO: 49) |
| CJ1-9, | (SEQ ID NO: 34) |
| CJ1-10, | (SEQ ID NO: 35) |
| CJ1-16, and | (SEQ ID NO: 41) |
| CJ1-17; | (SEQ ID NO: 42) |
| CJ1-22, | (SEQ ID NO: 47) |
| CJ1-23, | (SEQ ID NO: 48) |
| CJ1-24, | (SEQ ID NO: 49) |
| CJ1-16, | (SEQ ID NO: 41) |
| CJ1-17, | (SEQ ID NO: 42) |
| CJ1-31 and | (SEQ ID NO: 56) |
| CJ1-32; | (SEQ ID NO: 57) |
| CJ1-22, | (SEQ ID NO: 47) |
| CJ1-23, | (SEQ ID NO: 48) |
| CJ1-24, | (SEQ ID NO: 49) |
| CJ1-16, and | (SEQ ID NO: 41) |
| CJ1-17; | (SEQ ID NO: 42) |
| CJ1-22, | (SEQ ID NO: 47) |
| CJ1-23, | (SEQ ID NO: 48) |
| CJ1-24, | (SEQ ID NO: 49) |
| CJ1-9, | (SEQ ID NO: 34) |
| CJ1-10, | (SEQ ID NO: 35) |
| CJ1-31 and | (SEQ ID NO: 56) |
| CJ1-32; | (SEQ ID NO: 57) |
| CJ1-22, | (SEQ ID NO: 47) |
| CJ1-23, | (SEQ ID NO: 48) |
| CJ1-24, | (SEQ ID NO: 49) |
| CJ1-9, | (SEQ ID NO: 34) |
| CJ1-10, | (SEQ ID NO: 35) |
| CJ1-16, | (SEQ ID NO: 41) |
| CJ1-17, | (SEQ ID NO: 42) |
| CJ1-31 and | (SEQ ID NO: 56) |
| CJ1-32; | (SEQ ID NO: 57) |

-continued

| | |
|---|---|
| CJ1-22, | (SEQ ID NO: 47) |
| CJ1-23, | (SEQ ID NO: 48) |
| CJ1-24, | (SEQ ID NO: 49) |
| CJ1-31, and | (SEQ ID NO: 56) |
| CJ1-32; | (SEQ ID NO: 57) |
| CJI-42.5, | (SEQ ID NO: 119) |
| CJI-43.32, | (SEQ ID NO: 125) |
| CJI-43.39, | (SEQ ID NO: 128) |
| CJI-24.5 and | (SEQ ID NO: 129) |
| CJI-44.8; | (SEQ ID NO: 132) |
| CJI-42.5, | (SEQ ID NO: 119) |
| CJI-43.39, | (SEQ ID NO: 128) |
| CJI-24.5 and | (SEQ ID NO: 129) |
| CJI-44.8; | (SEQ ID NO: 132) |
| CJI-42.5, | (SEQ ID NO: 119) |
| CJI-43.39 and | (SEQ ID NO: 128) |
| CJI-24.5; | (SEQ ID NO: 129) |
| CJI-42.5, and | (SEQ ID NO: 119) |
| CJI-43.39; | (SEQ ID NO: 128) |
| CJI-43.39, | (SEQ ID NO: 128) |
| CJI-24.5 and | (SEQ ID NO: 129) |
| CJI-44.8; | (SEQ ID NO: 132) |
| CJI-43.39 and | (SEQ ID NO: 128) |
| CJI-24.5; | (SEQ ID NO: 129) |
| CJI-43.39 and | (SEQ ID NO: 128) |
| CJI-44.8; | (SEQ ID NO: 132) |
| CJI-24.5, | (SEQ ID NO: 129) |
| CJI-44.8 and | (SEQ ID NO: 132) |
| CJI-42.5; | (SEQ ID NO: 119) |
| CJI-24.5 and | (SEQ ID NO: 129) |
| CJI-44.8; | (SEQ ID NO: 132) |
| CJI-44.8, | (SEQ ID NO: 132) |
| CJI-42.5 and | (SEQ ID NO: 119) |
| CJI-43.32; | (SEQ ID NO: 125) |

```
CJI-44.8         (SEQ ID NO: 132)
and

CJI-42.5;        (SEQ ID NO: 119)
and

CJI-44.8         (SEQ ID NO: 132)
and

CJI-43.32.       (SEQ ID NO: 125)
```

Preferred compositions and preferred combinations of Cry j I peptides which can be administered simultaneously and/or sequentially may include any of the above preferred Cry j I combinations and in addition, may also include compositions comprising at least one peptide, or a combination of peptides derived from Cry j II such as Cry j IIA (SEQ ID NO: 185), Cry j IIB (SEQ ID NO: 186), Cry j IIC (SEQ ID NO: 187), Cry j IID (SEQ ID NO: 188), Cry j IIE, (SEQ ID NO: 189) and Cry j IIF (SEQ ID NO: 190), Cry j IIG (SEQ ID NO: 191), Cry j IIH (SEQ ID NO: 192), and Cry j IIQ (SEQ ID NO: 193) all as shown in FIG. 41.

Another aspect of this invention pertains to a multipeptide formulation suitable for pharmaceutical administration to ragweed sensitive individuals. The multipeptide formulation includes at least two or more peptides of Japanese cedar pollen protein allergen having human T cell stimulating activity in an in vitro T cell proliferation assay (i.e., comprising at least one T cell epitope). Special considerations when preparing a multipeptide formulation include maintaining the solubility and stability of all peptides in the formulation at a physiologically acceptable pH (e.g. . pH4-pH9 and even more preferably pH5.5-pH8.5). This requires choosing one or more pharmaceutically acceptable carriers such as excipients which are compatible with all the peptides in the multipeptide formulation. For example, suitable excipients include sterile water, sodium phosphate, mannitol or both sodium phosphate and mannitol or any combination thereof. Other suitable excipients include but are not limited to sorbitol, sucrose, dextrose, lactose dextran and PVP. Additionally due to the potential for dimerization of the peptides in a multipeptide formulation, there may also be included an agent such as EDTA to prevent dimerization. Alternatively, any material or procedures known in the art to prevent dimerization may be used. In addition, pharmaceutically acceptable counter ions may be added during the preparation of the multipeptide formulation. Examples of pharmaceutically acceptable counter ions include acetate, HCl, and citrate. A preferred multipeptide formulation includes at least two peptides derived from Japanese cedar pollen protein allergen each having human T cell stimulating activity and each soluble and stable at a physiologically acceptable pH. In a preferred embodiment, the multipeptide formulation includes Cry j I peptides CJ1-24.5, CJ1-43.39 and CJ1-44.8 and sodium phosphate and mannitol. For this embodiment, a suitable counter ion such as acetate may be added during the preparation of the formulation, and the formulation is preferably prepared in the form of a lyophilized powder which is reconstituted in a physiologically acceptable carrier, such as sterile water, prior to use. One, non-limiting example of a preferred multipeptide formulation of the invention is described below. The Cry j I peptides CJ1-24.5, CJ1-43.39 and CJ1-44.8 will preferably be combined during manufacturing with the appropriate counter ion to produce a vial containing a sterile, pyrogen free, lyophilized powder having the following composition:

Active: Cry j I peptides CJ1-24.5, CJ1-43.39 and CJ1-44.8
In concentration of 7.5-1500 μg per peptide Inactives: 0.05 M Sodium Phosphate pH 6.0-8.0
5% w/v Mannitol, U.S.P.
Diluent: Sterile Water for Injection, U.S.P. (initial reconstitution)
0.9% Sodium Chloride for Injection (dilution beyond initial reconstitution)

The multipeptide formulation of the invention can be provided in the form of a kit, including instructions for use.

The invention is further illustrated by the following non-limiting examples.

EXAMPLE 1

Purification of Native Japanese Cedar Pollen Allergen (Cry j I)

The following is a description of the work done to biochemically purify the major allergen, Cry j I in the native form. The purification was modified from published procedures (Yasueda et al., *J. Allergy Clin. Immunol.* 71:77, 1983).

100 g of Japanese cedar pollen obtained from Japan (Hollister-Stier, Spokane, Wash.) was defatted in 1 L diethyl ether three times, the pollen was collected after filtration and the ether was dried off in a vacuum.

The defatted pollen was extracted at 4° C. overnight in 2 L extraction buffer containing 50 mM tris-HCL, pH 7.8, 0.2 M NaCl and protease inhibitors in final concentrations: soybean trypsin inhibitor (2 μg/ml), leupeptin (1 μg/ml), pepstatin A (1 μg/ml) and phenyl methyl sulfonyl fluoride (0.17 mg/ml). The insoluble material was reextracted with 1.2 L extraction buffer at 4° C. overnight and both extracts were combined together and depigmented by batch absorption with Whatman DE-52 DEAE cellulose (200 g dry weight) equilibrated with the extraction buffer.

The depigmented material was then fractionated by ammonium sulfate precipitation at 80% saturation (4° C.), which removed much of the lower molecular weight material. The resultant partially purified Cry j I was either dialyzed in PBS buffer and used in T cell studies (see Example 6) or subjected to further purification (biochemically or by monoclonal affinity chromatography) as described below.

The enriched Cry j I material was then dialyzed against 50 mM Na-acetate, pH 5.0 at 4° C. with 50 mM Na-acetate, pH 5.0 with protease inhibitors. The sample was next applied to a 100 ml DEAE cellulose column (Whatman DE-52) equilibrated at 4° C. with 50 mM Na-acetate pH 5.0 with protease inhibitors. The unbound material (basic proteins) was then applied to a 50 ml cation exchange column (Whatman CM-52) which was equilibrated at 4° C. with 10 mM Na-acetate, pH 5.0 with protease inhibitors. Cry j I was eluted in the early fractions of a linear gradient 0.3 M NaCl. The enriched Cry j I material was lyophilized and was then purified by FPLC over a 300 ml Superdex 75 column (Pharmacia) at a flow rate of 30 ml/h in 10 mM Na-acetate, pH 5.0 at 25° C.

Figure 1B:
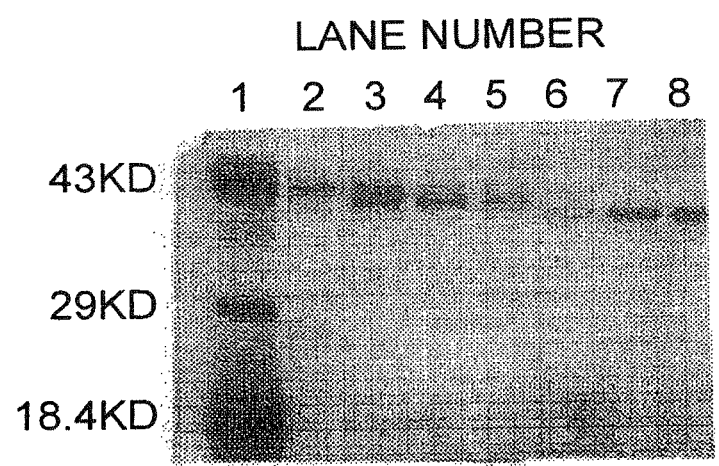

The purified Cry j I was further applied to FPLC S-Sepharose 16/10 column chromatography (Pharmacia) with a linear gradient of 0-1 M NaCl at 25° C. Cry j I, eluted as the major peak, was subjected to a second gel filtration chromatography. FPLC Superdex 75 column (2.6 by 60 cm) (Pharmacia, Piscataway, N.J.) was eluted with a downward flow of 10 mM Na-acetate, pH 5.0 with 0.15 M NaCl at a flow rate of 30 ml/h at 25° C. FIG. 1a shows the chromatography on gel filtration. Only Cry j I was detected (FIG. 1b, lane 2 to lane 8). Cry j I was fractionated into 3 bands as analyzed by SDS-PAGE using silver staining (FIG. 1b) As shown in FIG. 1b, SDS PAGE (12.5%) analysis of the fractions from the major peak shown in FIG. 1a was performed under reducing conditions. The gel was silver stained using the silver staining kit from Bio-Rad. The samples in each lane were as follows: Lane 1, prestained standard proteins (Gibco BRL) including ovalbumin (43,000 kD), carbonic anhydrase (29,000 kD), and a-lactoglobulin (18,400 kD); lane 2, fraction 36; lane 3 fraction 37; lane 4 fraction 38; lane 5 fraction 39 ; lane 6 fraction 41, lane 7 fraction 43; and lane 8 fraction 44. All fractions are shown in FIG. 1a.

Figure 2:
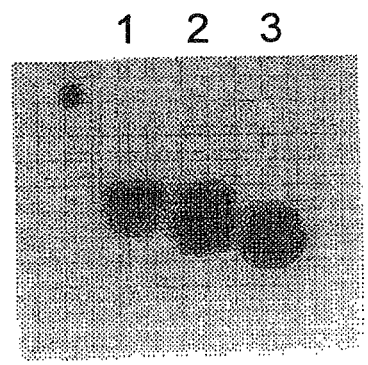
FIG. 2 shows a Western blot of isoforms of purified native Cry j I proteins separated by SDS-PAGE and probed with mAB CBF2.

These proteins were also analyzed by Western blotting using mouse monoclonal antibody CBF2 (FIG. 2). As shown in FIG. 2, an aliquot of fraction 36 (lane 1), fraction 39, (lane 2) and fraction 43 (lane 3) purified from the Superdex 75 as shown in FIG. 1 was separated by SDS-PAGE, electroblotted onto nitrocelluslose and probed with mAB CBF2. Biotinylated goat anti-mouse Ig was used for the second antibody and bound antibody was revealed by $^{125}$I-streptavidin. The monoclonal CBF2 was raised against ragweed allergen Amb a I by Dr. D. Klapper (Chapel Hill, N.C.). Because of the homology between the Amb a I and Cry j I sequences, a number of antibodies raised against Amb a I were tested for reactivity with Cry j I. The results showed that CBF2 recognized denatured Cry j I as detected by ELISA and Western blotting. In addition, Western blotting also demonstrated that no other bands were detected by CBF2, other than Cry j I in the expected molecular weight range (FIG. 2). These results were consistent with the findings from protein sequencing. When fraction 44 and fraction 39 (FIG. 1b) were subjected to N-terminal sequencing, only Cry j I sequence was detected.

Figure 3:
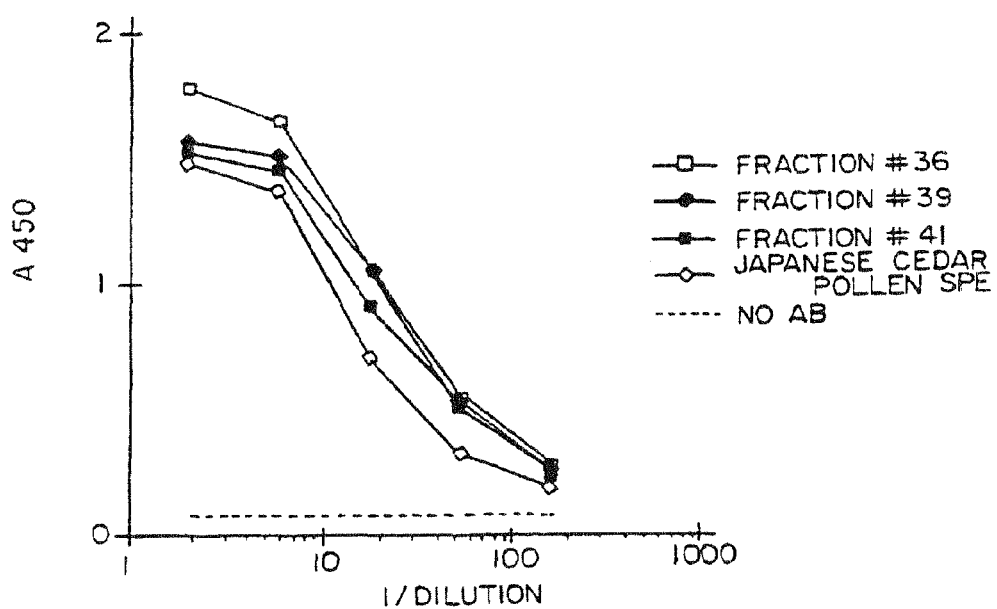
FIG. 3 is a graphic representation of allergic sera titration of different purified fractions of purified native Cry j I using plasma from a pool of fifteen allergic patients.

In summary, three Cry j I isoforms of different molecular weight were purified from pollen extract. The molecular weights estimated by SDS-PAGE ranged from 40-35 kD under both reducing and non-reducing conditions. The isoelectric point of these isoforms is approximately 9.5-8.6, with an average pI of 9.0. The N-terminal 20 amino acid sequence was the same in these 3 bands and was identical to previously published Cry j I sequence (Taniai et al, supra). The 3 isoforms are all recognized by monoclonal antibody CBF2 as shown in the allergic sera titration of different purified subfractions of Cry j I using a pool of fifteen allergic patient plasma. They all bind allergic patient IgE (FIG. 3). The difference in molecular weight and isoelectric point in these isoforms might in part be due to post-translational modification, e.g. glycosylation, phosphorylation or lipid content. The possibility that these different isoforms might be due to protease degradation cannot be ruled out at present even though it is unlikely due to the fact that four different protease inhibitors were used during extraction and purification. The other possibility could be due to polymorphism in the gene or alternate splicing in the mRNA though only one major form of Cry j I protein has been detected in cDNA cloning studies (see Example 4).

Another approach which may be used to purify native Cry j I or recombinant Cry j I is immunoaffinity chromatography. This technique provides a very selective protein purification due to the specificity of the interaction between monoclonal antibodies and antigen. For the purpose of producing Cry j I-reactive monoclonal antibodies, female Balbl/c mice were obtained from Jackson Labs. Each mouse was initially immunized intraperitoneally with 70-100 µg purified native Cry j I, (>99% purity lower band, as shown in FIG. 1b), emulsified in Freund's complete adjuvant. One further intravenous injection of 10 µg purified native Cry j I in PBS was given 54 days after the initial injection. The spleen was removed 3 days later and myeloma fusion was conducted as described (Current Protocols in Immunology, 1991, Coligan et al, eds.) using the myeloma line SP2.0. The cells were cultured in 10% fetal calf serum (Hybrimax), hypoxanthine and azaserine and wells containing colonies of hybridoma cells were screened for antibody production using antigen-binding ELISA.

Cells from positive wells were cloned at three-tenths cell/well in 10% fetal calf serum (Hybrimax), hypoxanthine and positive clones were subcloned one more time in hypoxanthine medium. Capture ELISA (see Example 7) was used for secondary and tertiary screening. This assay offers the advantage that a clone that recognizes the native protein may be selected and thus may be useful for immunoaffinity purification. For example, two monoclonal antibodies (4B11. 8B11) were generated. These antibodies were purified by Gammabind G. Sepharose (Pharmacia, Piscataway, N.J.) according to manufacturer's procedures and were immobilized to cyanogen bromide—activated Sepharose 4B (Pharmacia, Piscataway, N.J.) according to the procedures described by Pharmacia. The ammonium sulphate preparation containing Cry j I was applied to the resin and unbound material was washed extensively with PBS. Cry j I was eluted with 2 column volumes of 0.1 M glycine, pH 2.7. Silver staining of the eluate fractions run on SDS PAGE showed that Cry j I was purified almost to homogeneity. These fractions did not contain detectable levels of Cry j II. Other methods to immobilize MAb 8B11 were also tested. Similar results were obtained using purified MAb 8B11 covalently cross-linked to Gammabind G Sepharose by dimethylpimelimidate (Schneider C., et al, J. Biol. Chem. (1982) volume 257:10766-10769). However, experiments using purified MAb 8B11 covalently cross-linked to Affi-gel 10 (Biorad, Richmond, Calif.) showed that although greater than 90% of the monoclonal antibody was covalently coupled to Affi-gel 10, the yield of Cry j I purified over this resin was significantly less than that purified from MAb 8B11 cross-linked to cyanogen bromide-activated Sepharose 4B (data not shown). Nevertheless, the purified Cry j I from these monoclonal antibodies immobilized on different resins is still intact and can be recognized by MAb 8B11 and 4B11 by capture ELISA. Thus, these MAbs will provide a useful tool in purification of Cry j I from pollen extracts. Similarly, monoclonal antibodies that bind to recombinant Cry j I can also be used for immunoaffinity chromatography. In addition, the monoclonal antibodies generated may be useful for diagnostic purposes. It may also be possible to raise different MAbs that show some specificity towards these different isoforms of Cry j I and thus would provide a useful tool to characterize these isoforms.

EXAMPLE 2

Attempted Extraction of RNA From Japanese Cedar Pollen

Multiple attempts were made to obtain RNA from commercially-available, non-defatted, *Cryptomeria japonica* (Japanese cedar) pollen (Hollister Stier, Seattle, Wash.). Initially, the method of Sambrook et al., *Molecular Cloning. A Laboratory Manual*, Cold Spring Harbor Laboratory Press, Cold Spring Harbor, N.Y. (1989) was used in which the sample was suspended and lysed in 4 M guanidine buffer, ground under liquid nitrogen, and pelleted through 5.7 M cesium chloride by ultracentrifugation. Various amounts (3, 5 and 10 g) of pollen in varying amounts of guanidine lysis buffer (10 and 25 ml) were tried. Centrifugation through cesium resulted in viscous material in the bottom of the tube, from which it was not possible to recover an RNA pellet. Although it was possible to obtain RNA from defatted *Ambrosia artemisiifolia* (ragweed) pollen (Greer Laboratories, Lenior, N.C.) using this protocol, defatting the *Cryptomeria japonica* pollen with acetone before guanidine extraction also did not yield any RNA, as determined by absorbance at $A_{260}$.

An acid phenol extraction of RNA according to the method in Sambrook et al., supra was attempted from *Cryptomeria japonica* pollen. The pollen was ground and sheared in 4.5 M guanidine solution, acidified by addition of 2 M sodium acetate, and extracted with water-saturated phenol plus chloroform. After precipitation, the pellet was washed with 4 M lithium chloride, redissolved in 10 mM Tris/5 mM EDTA/1% SDS, chloroform extracted, and re-precipitated with NaCl and absolute ethanol. It was possible to extract *Ambrosia artemisiifolia* but not *Cryptomeria japonica* RNA with this procedure.

Next, 4 g of *Cryptomeria japonica* pollen was suspended in 10 ml extraction buffer (50 mM Tris, pH 9.0, 0.2 M NaCl, 10 mM Mg acetate and diethylpyrocarbonate (DEPC) to 0.1%), ground in a mortar and pestle on dry ice, transferred to a centrifuge tube with 1% SDS, 10 mM EDTA and 0.5% N-lauroyl sarcosine, and the mixture was extracted five times with warm phenol. The aqueous phase was recovered after the final centrifugation, 2.5 vol. absolute ethanol was added, and the mixture was incubated overnight at 4° C. The pellet was recovered by centrifugation, resuspended in 1 ml $dH_2O$ by heating to 65° C., and reprecipitated by the addition of 0.1 vol. 3 M Na acetate and 2.0 vol. of ethanol. No detectable RNA was recovered in the pellet as judged by absorbance at $A_{260}$ and gel electrophoresis.

Finally, 500 mg of *Cryptomeria japonica* pollen was ground by mortar and pestle on dry ice and suspended in 5 ml of 50 mM Tris pH 9.0 with 0.2 M NaCl, 1 mM EDTA, 1% SDS that had been treated overnight with 0.1% DEPC, as previously described in Frankis and Mascarhenas (1980) *Ann. Bot.* 45: 595-599. After five extractions with phenol/chloroform/isoamyl alcohol (mixed at 25:24:1), material was precipitated from the aqueous phase with 0.1 volume 3 M sodium acetate and 2 volumes ethanol. The pellet was recovered by centrifugation, resuspended in $dH_2O$ and heated to 65° C. to solubilize the precipitated material. Further precipitations with lithium chloride were not done. There was no detectable RNA recovered, as determined by absorbance at $A_{260}$ and gel electrophoresis.

In summary, it has not been possible to recover RNA from the commercial pollen. It is not known whether the RNA has been degraded during storage or shipment, or whether the protocols used in this example did not allow recovery of extant RNA. However, RNA was recovered from fresh *Cryptomeria japonica* pollen and staminate cone samples. (See Example 3)

EXAMPLE 3

Extraction of RNA From Japanese Cedar Pollen and Staminate Cones and Cloning of Cry j I Fresh pollen and staminate cone samples, collected from a single *Cryptomeria japonica* (Japanese cedar) tree at the Arnold Arboretum (Boston, Mass.), were frozen immediately on dry ice. RNA was prepared from 500 mg of each sample, essentially as described by Frankis and Mascarenhas, supra. The samples were ground by mortar and pestle on dry ice and suspended in 5 ml of 50 mM Tris pH 9.0 with 0.2 M NaCl, 1 mM EDTA, 1% SDS that had been treated overnight with 0.1% DEPC. After five extractions with phenol/chloroform/isoamyl alcohol (mixed at 25:24:1), the RNA was precipitated from the aqueous phase with 0.1 volume 2 M sodium acetate and 2 volumes ethanol. The pellets were recovered by centrifugation, resuspended in $dH_2O$ and heated to 65° C. for 5 min. Two ml of 4 M lithium chloride were added to the RNA preparations and they were incubated overnight at 0° C. The RNA pellets were recovered by centrifugation, resuspended in 1 ml $dH_2O$, and again precipitated with 3 M sodium acetate and ethanol overnight. The final pellets were resuspended in 100 µl $dH_2O$ and stored at –80° C.

First strand cDNA was synthesized from 8 µg flowerhead and 4 µg pollen RNA using a commercially available kit (cDNA synthesis systems kit, BRL, Gaithersburg, Md.) with oligo dT priming according to the method of Gubler and Hoffman (1983) Gene 25:263-269. An attempt was made to amplify cDNA encoding Cry j I using the degenerate oligonucleotide CP-1 (which has the sequence 5'-GATAATC-CGATAGATAG-3'(SEQ ID NO:3), wherein T at position 3 can also be C; T at position 6 can also be C; G at position 9 can also be A,T, or C; A at position 12 can also be T, or C; T at position 15 can also be C; A at position 16 can also be T; and G at position 17 can also be C) and primers EDT and ED. Primer EDT has the sequence 5°-GGAATTCTCTAGACTG-CAGGTTTTTTTTTTTTTTT-3'(SEQ ID NO: 24). Primer ED has the sequence 5'-GGAATTCTCTAGACTGCAGGT-3' (SEQ ID NO: 23). CP-1 is the degenerate oligonucleotide sequence encoding the first six amino acids of the amino terminus (AspAsnProIleAspSer (SEQ ID NO: 266), amino acids 1-6 of SEQ ID NO: 1) of Cry j I. EDT will hybridize with the poly A tail of the gene. All oligonucleotides were synthesized by Research Genetics, Inc. Huntsville, Ala. Polymerase chain reactions (FOR) were carried out using a commercially available kit (GeneAmp DNA Amplification kit, Perkin Elmer Cetus, Norwalk, Conn.) whereby 10 µl 10× buffer containing dNTPs was mixed with 1 µg of CP-1 and 1 µg of ED/EDT primers (ED:EDT in a 3:1 M ratio), cDNA (3-5 µl of a 20 µl first strand cDNA reaction mix), 0.5 µl Amplitaq DNA polymerase, and distilled water to 100 µl.

The samples were amplified with a programmable thermal controller (MJ Research, Inc., Cambridge, MA). The first 5 rounds of amplification consisted of denaturation at 94° C. for 1 minute, annealing of primers to the template at 45° C. for 1.5 minutes, and chain elongation at 70° C. for 2 minutes. The final 20 rounds of amplification consisted of denaturation as above, annealing at 55° C. for 1.5 minutes, and elongation as above. Five percent (5 µl) of this initial amplification was then used in a secondary amplification with 1 µg each of CP-2 (which has the sequence 5'-GGGAATTCAATTGGGCGCA-GAATGG-3' wherein T at position 11 can also be C; G at position 17 can also be A, T, or C; G at position 20 can also be A; T at position 23 can also be C; and G at position 24 can also be C) (SEQ ID NO: 4), a nested primer, and ED, as above. The sequence 5'-GGGAATTC-3' (SEQ ID NO: 160) (bases 1 through 8 of SEQ ID NO: 4) in primer CP-2 represents an Eco RI site added for cloning purposes; the remaining degenerate oligonucleotide sequence encodes amino acids 13-18 of Cry j I (AsnTrpAlaGlnAsnArg (SEQ ID NO: 267), amino acids 13 through 18 of SEQ ID NO: 1). Multiple DNA bands were resolved on a 1% GTG agarose gel (FMC, Rockport, ME), none of which hybridized with $^{32}P$ end- labeled probe CP-3 (SEQ ID NO: 5) in a Southern blot performed according to the method in Sambrook et al. supra. Therefore, it was not possible to select a specific Cry j I DNA band and this approach was not pursued. CP-3 has the sequence 5'-CTGCAGC-CATTTTCIACATTAAA-3' wherein A at position 9 can also be G; Tat position 12 can also be C; A at position 18 can also be G; and A at position 21 can also be G) (SEQ ID NO: 5). Inosine (I) is used at position 15 in place of G or A or T or C to reduce degeneracy (Knoth et al. (1988) Nucleic Acids Res, 16: 10932). The sequence 5'-CTGCAG-3' (bases 1 through 6 of SEQ ID NO: 5) in primer CP-3 represent a Pst I site added for cloning purposes; the remaining degenerate oligonucleotide sequence is the non-coding strand sequence corresponding to coding strand sequence encoding amino acids PheAsnValGluAsnGly (SEQ ID NO: 268) (amino acids 327 through 332 of SEQ ID NO: 1) from the internal sequence of Cry jI.

A primary PCR was also performed on first-strand cDNA using CP-1 (SEQ ID NO: 3) and CP-3 (SEQ ID NO: 5), as above. A secondary PCR was performed using 5% of the primary reaction using CP-2 (SEQ ID NO: 4) and CP-3 (SEQ ID NO: 5). Again, multiple bands were observed, none of which could be specifically identified in a Southern blot as Cry j I, and this approach was also not pursued.

Double-stranded cDNA was then synthesized from approximately 4 μg (pollen) or 8 μg (flowerhead) RNA using a commercially available kit (cDNA Synthesis System kit, BRL, Gaithersburg, MD). After a phenol extraction and ethanol precipitation, the cDNA was blunted with T4 DNA polymerase (Promega, Madison, WI), and ligated to ethanol precipitated, self-annealed, AT (SEQ ID NO: 20) and AL (SEQ ID NO: 22) oligonucleotides for use in a modified Anchored PCR reaction, according to the method in Rafnar et al. (1991) *J. Biol. Chem.* 266: 1229-1236; Frohman et al. (1990) *Proc. Natl. Acad. Sci. USA* 85: 8998-9002; and Roux et al. (1990) *BioTech.* 8: 48-57. Oligonucleotide AT has the sequence 5'-GGGTCTAGAGGTACCGTCCGATCGATCATT-3' (SEQ ID NO: 20) (Rafnar et al. supra). Oligonucleotide AL has the sequence 5'-AATGATCGATGCT-3' (SEQ ID NO: 22) (Rafnar et al. supra. The amino terminus of Cry j I was amplified from the linkered cDNA (3 μl from a 20 μl reaction) with 1 μg each of oligonucleotides AP (SEQ ID NO: 21) and degenerate Cry j I primer CP-7 (which has the sequence 5'-TTCATICGATTCTGGGCCCA-3' wherein G at position 8 can also be T; A at position 9 can also be G; C at position 12 can also be T; and G at position 15 can also be A, T, or C)(SEQ ID NO: 6). Inosine (I) is used at position 6 in place of G or A or T or C to reduce degeneracy (Knoth et al. supra). The degenerate oligonucleotide CP-7 (SEQ ID NO: 6) is the non-coding strand sequence corresponding to coding strand sequence encoding amino acids 14-20 (TrpAlaGlnAsnArgMetLys (SEQ ID NO: 269)) from the amino terminus of Cry j I (amino acids 14-20 of SEQ ID NO: 1). Oligonucleotide AP has the sequence 5'-GGGTCTAGAGGTACCGTCCG-3' (SEQ ID NO: 21).

The primary PCR reaction was carried out as described herein. Five percent (5 μl) of this initial amplification was then used in a secondary amplification with 1 .μg each of AP (SEQ ID NO: 21) and degenerate Cry j I primer CP-8 (SEQ ID NO: 7) an internally nested Cry j I oligonucleotide primer, as described herein. Primer CP-8 has the sequence 5'-CCTGCAGCGATTCTGGGCCCAAATT-3' wherein G at position 9 can also be T; A at position 10 can also be G; C at position 13 can also be T; G at position 16 can also be A, T, or C; and A at position 23 can also be G)(SEQ ID NO: 7). The nucleotides 5'-CCTGCAG-3' (bases 1 through 7 of SEQ ID NO: 7) represent a Pst I restriction site added for cloning purposes. The remaining degenerate oligonucleotide sequence is the non-coding strand sequence corresponding to coding strand sequence encoding amino acids 13-18 of Cry j I (AsnTrpAlaGlnAsnArg (SEQ ID NO: 267), amino acids 13-18 of SEQ ID NO: 1) from the amino terminus of Cry j I. The dominant amplified product was a DNA band of approximately 193 base pairs, as visualized on an ethidium bromide (EtBr)-stained 3% GTG agarose gel.

Amplified DNA was recovered by sequential chloroform, phenol, and chloroform extractions, followed by precipitation at −20° C. with 0.5 volumes of 7.5 ammonium acetate and 1.5 volumes of isopropanol. After precipitation and washing with 70% ethanol, the DNA was simultaneously digested with Xba I and Pst I in a 15 μl reaction and electrophoresed through a preparative 3% GTG NuSieve low melt gel (FMC, Rockport, Me.). The appropriate sized DNA band was visualized by EtBr staining, excised, and ligated into appropriately digested M13mp18 for sequencing by the dideoxy chain termination method (Sanger et al. (1977) *Proc. Natl Acad Sci. USA* 74: 5463-5476) using a commercially available sequencing kit (Sequenase kit, U.S. Biochemicals, Cleveland, Ohio). It was initially thought that ligatable material could only be derived from staminate cone-derived RNA. However, upon subsequent examination, it was shown that ligatable material could be recovered from PCR product generated from pollen-derived RNA, and from staminate cone-derived RNA.

The clone designated JC71.6 was found to contain a partial sequence of Cry j I. This was confirmed as an authentic clone of Cry j I by having complete identity to the disclosed $NH_2$-terminal sequence of Cry j I (Taniai et al. supra). The amino acid at position 7 was determined to be cysteine (Cys) in agreement with the sequence disclosed in U.S. Pat. No. 4,939,239. Amino acid numbering is based on the sequence of the mature protein; amino acid 1 corresponds to the aspartic acid (Asp) disclosed as the $NH_2$-terminus of Cry j I (Taniai et al. supra) The initiating methionine was found to be amino acid −21 relative to the first amino acid of the mature protein. The position of the initiating methionine was supported by the presence of upstream in-frame-stop codons and by 78% homology of the surrounding nucleotide sequence with the plant consensus sequence that encompasses the initiating methionine, as reported by Lutcke et al. (1987) *EMBO J.* 6:4348.

The cDNA encoding the remainder of Cry j I gene was cloned from the linkered cDNA by using oligonucleotides CP-9 (which has the sequence 5'ATGGATTCCCCTTGCTTA-3')(SEQ ID NO: 8) and AP (SEQ ID NO: 21) in the primary PCR reaction. Oligonucleotide CP-9 (SEQ ID NO: 8) encodes amino acids MetAspSerProCysLeu (SEQ ID NO: 270) of Cry j I (amino acids −21 through −16 of SEQ ID NO: 1) from the leader sequence of Cry j I, and is based on the nucleotide sequence determined for the partial Cry j I clone JC76.1.

A secondary PCR reaction was performed on 5% of the initial amplification mixture, with 1 μg each of AP (SEQ ID NO: 21) and CP-10 (which has the sequence 5'-GGGAATTCGATAATCCCATAGACAGC-3')(SEQ ID NO: 9), the nested primer. The nucleotide sequence 5'-GGGAATTC-3' of primer CP-10 (bases 1 through 8 of SEQ ID NO: 9) represent an Eco RI restriction site added for cloning purposes. The remaining oligonucleotide sequence encodes amino acids 1-6 of Cry j I (AspAsnProlleAspSer (SEQ ID NO: 266)) (amino acids 1 through 6 of SEQ ID NO: 1), and is based on the nucleotide sequence determined for the partial Cry j I clone JC76.1. The amplified DNA product was purified and precipitated as above, followed by digestion with Eco RI and Xba I and electrophoresis through a preparative 1% low melt gel. The dominant DNA band was excised and ligated into M13 mp 19 and pUC19 for sequencing. Again, ligatable material was recovered from cDNA generated from pollen-derived RNA, and from staminate cone-derived RNA. Two clones, designated pUC19JC91a and pUC19JC91d, were selected for full-length sequencing. They were subsequently found to have identical sequences.

DNA was sequenced by the dideoxy chain termination method (Sanger et al. supra) using a commercially available kit (sequenase kit (U.S. Biochemicals, Cleveland, OH). Both strands were completely sequenced using M13 forward and reverse primers (N.E. Biolabs, Beverly, MA) and internal sequencing primers CP-13 (SEQ ID NO: 10), CP-14 (SEQ ID NO: 11), CP-15 (SEQ ID NO: 12), CP-16 (SEQ ID NO: 13), CP-18 (SEQ ID NO: 15), CP-19 (SEQ ID NO: 16), and CP-20 (SEQ ID NO: 17). CP-13 has the sequence 5'-ATGCCTAT-GTACATTGC-3' (SEQ ID NO: 10). CP-13 (SEQ ID NO: 10) encodes amino acids 82-87 of Cry j I (MetProMetTyrIleAla (SEQ ID NO: 271), amino acids 82 through 87 of SEQ ID NO: 1). CP-14 has the sequence 5'-GCAATGTACATAG-GCAT-3' (SEQ ID NO: 11) and corresponds to the non-coding strand sequence of CP-13 SEQ ID NO: 10). CP-15 has the sequence 5'-TCCAATTCTTCTGATGGT-3' ((SEQ ID NO: 12) which encodes amino acids 169-174 of Cry j I (SerAsnSerSerAspGly (SEQ ID NO: 272), amino acids 169 through 174 of SEQ ID NO: 1). CP-16 has the sequence 5'-TTTTGTCAATTGAGGAGT-3' (SEQ ID NO: 13) which is the non-coding strand sequence which corresponds to coding strand sequence encoding amino acids 335-340 of Cry j I (ThrProGlnLeuThrLys (SEQ ID. NO: 273), amino acids 335 through 340 of SEQ ID NO: 1). CP-18 has the sequence 5'-TAGCAACTCCAGTCGAAGT-3' (SEQ ID NO: 15) which is the non-coding strand sequence which substantially corresponds to coding strand sequence encoding amino acids 181 through 186 of Cry j I (ThrSerThrGlyValThr (SEQ ID NO: 274), amino acids 181 through 186 of SEQ ID NO: 1) except that the fourth nucleotide of CP-18 (SEQ ID NO: 15) was synthesized as a C rather than the correct nucleotide, T. CP-19 which has the sequence 5'-TAGCTCTCATTTG-GTGC-3' (SEQ ID NO: 16) is the non-coding strand sequence which corresponds to coding strand sequence encoding amino acids 270 through 275 of Cry j I (AlaProAsnGluSerTyr (SEQ ID NO: 275), amino acids 270 through 275 of SEQ ID NO: 1). CP-20 has the sequence 5'-TATGCAATTGGTGG-GAGT-3' (SEQ ID NO: 17) which is the coding strand sequence for amino acids 251-256 of Cry j I (TyrAlaIleG-lyGlySer (SEQ ID NO: 276), amino acids 251 through 256 of SEQ ID NO: 1). The sequenced DNA was found to have the sequence shown in FIGS. 4*a* and 4*b* (SEQ ID NO: 1). This is a composite sequence from the two overlapping clones JC 71.6 and pUC19J91a. The complete cDNA sequence for Cry j I is composed of 1312 nucleotides, including 66 nucleotides of 5' untranslated sequence, an open reading frame starting with the codon for an initiating methionine, of 1122 nucleotides, and a 3' untranslated region. There is a consensus polyadenylation signal sequence in the 3' untranslated region 25 nucleotides 5' to the poly A tail (nucleotides 1279-1283 of FIG. 4 and SEQ. ID NO: 1). Nucleotides 1313-1337 of FIG. 4 and SEQ. ID NO: 1 represent vector sequences. The position of the initiating methionine is confirmed by the presence of in-frame upstream stop codons and by 78% homology with the plant consensus sequence that encompasses the initiating methionine (AAAAAUGGA (bases 62 through 70 of SEQ ID NO: 1)) found in Cry j I compared with the AACAAUGGC consensus sequence for plants, Lutcke et al. (1987) EMBO J. 6:43-48). The open reading frame encodes a protein of 374 amino acids of which the first 21 amino acids comprise a leader sequence that is cleaved from the mature protein. The amino terminus of the mature protein was identified by comparison with the published $NH_2$-terminal sequence (Taniai et al. (1988) supra) and with sequence determined by direct amino acid analysis of purified native Cry j I (Example 1). The deduced amino acid sequence of the mature protein, comprised of 353 amino acids has complete sequence identity with the published protein sequence for Cry j I (Taniai et al. supra), including the first twenty amino acids for the $NH_2$-terminal and sixteen contiguous internal amino acids. The mature protein also contains five potential N-linked glycosylation sites corresponding to the consensus sequence N-X-S/T.

EXAMPLE 4

Extraction of RNA from Japanese Cedar Pollen Collected in Japan

Fresh pollen collected from a pool of *Cryptomeria japonica* (Japanese cedar) trees in Japan was frozen immediately on dry ice. RNA was prepared from 500 mg of the pollen, essentially as described by Frankis and Mascarenhas *Ann. Bot.* 45:595-599. The samples were ground by mortar and pestle on dry ice and suspended in 5 ml of 50 mM Tris pH 9.0 with 0.2 M NaCl, 1 mM EDTA, 1% SDS that had been treated overnight with 0.1% DEPC. After five extractions with phenol/chloroform/isoamyl alcohol (mixed at 25:24:1), the RNA was precipitated from the aqueous phase with 0.1 volume 3 M sodium acetate and 2 volumes ethanol. The pellets were recovered by centrifugation, resuspended in $dH_2O$ and heated to 65° C. for 5 minutes. Two ml of 4 M lithium chloride were added to the RNA preparations and they were incubated overnight at 9° C. The RNA pellets were recovered by centrifugation, resuspended in 1 ml $dH_2O$, and again precipitated with 3 M sodium acetate and ethanol overnight. The final pellets were resuspended in 100 µl $dH_2O$ and stored at −80° C.

Double stranded cDNA was synthesized from 8 µg pollen RNA using the cDNA Synthesis Systems kit (BRL) with oligo dT priming according to the method of Gubler and Hoffman (1983) *Gene* 25:263-269. Polymerase chain reactions (PCR) were carried out using the GeneAmp DNA Amplification kit (Perkin Elmer Cetus) whereby 10 µl 10× buffer containing dNTPs was mixed with 100 pmol each of a sense oligonucleotide and an anti-sense oligonucleotide, (10 µl of a 400 µl double stranded cDNA reaction mix), 0.5 µl. Amplitaq DNA polymerase, and distilled water to 100 µl.

The samples were amplified with a programmable thermal controller from MJ Research, Inc. (Cambridge, Mass.). The first 5 rounds of amplification consisted of denaturation at 94° C. for 1 minute, annealing of primers to the template at 45° C. for 1 minute, and chain elongation at 72° C. for 1 minute. The final 20 rounds of amplification consisted of denaturation as above, annealing at 55° C. for 1 minute, and elongation as above.

Seven different Cry j I primer pairs were used to amplify the double stranded cDNA as follows: CP-9 (SEQ ID NO: 8) and CP-17 (SEQ ID NO: 14), CP-10 (SEQ ID NO: 9) and CP-17 (SEQ ID NO: 14), CP-10 (SEQ ID NO: 9) and CP-16 (SEQ ID NO: 13), CP-10 (SEQ ID NO: 9) and CP-19 (SEQ ID NO: 16), CP-10 (SEQ ID NO: 9) and CP-18 (SEQ ID NO: 15), CP-13 (SEQ ID NO: 10) and CP-17 (SEQ ID NO: 14), and CP-13 (SEQ ID NO: 10) and CP-19 (SEQ ID NO: 16). CP-17 has the sequence 5'-CCTGCAGAAGCTTCATCAA-CAACGTTTAGA-3' (SEQ ID NO: 14) and corresponds to non-coding strand sequence that corresponds to coding strand sequence encoding amino acids SKRC* (SEQ ID NO: 277) (amino acids 350-353 and the stop codon of SEQ ID NO: 1). The nucleotide sequence 5'-CCTGCAGAAGCTT-3' (SEQ ID NO: 278) (bases 1 through 13 of SEQ ID NO: 14) represents Pst I and Hin dIII restriction sites added for cloning purposes. The nucleotide sequence 5'-TCA-3' (bases 13 through 15 of SEQ ID NO: 14) correspond to the non-coding strand sequence of a stop codon. All of the amplifications yielded products of the expected size when viewed on ethidium bromide (EtBr)-stained agarose gels. Two of these primer pairs were used in amplifications whose products were cloned into pUC19 for full-length sequencing. The PCR reaction with CP-10 (SEQ ID NO: 9) and CP-16 (SEQ ID NO: 13) on the double stranded cDNA yielded a band of approximately 1.1 kb, and was called JC130. A separate first strand cDNA reaction was done with 8 pg pollen RNA as described above and amplified with oligonucleotide primers CP-10 (SEQ ID NO: 9) and CP-17 (SEQ ID NO: 14). This amplification yielded a full-length cDNA, named JC135, from the amino terminus of the mature protein to the stop codon.

Amplified DNA was recovered by sequential chloroform, phenol, and chloroform extractions, followed by precipitation at −20° C. with 0.5 volumes of 7.5 ammonium acetate and 1.5 volumes of isopropanol. After precipitation and washing with 70% ethanol, the DNA was blunted with T4 polymerase followed by digestion with Eco RI, in the case of JC130, or simultaneously digested with Eco RI and Pst I, in the case of JC135, in a 15 µl reaction and electrophoresed through a preparative 1% SeaPlaque low melt gel (FMC). Appropriate sized DNA bands were visualized by EtBr staining, excised, and ligated into appropriately digested pUC19 for dideoxy DNA sequencing by the dideoxy chain termination method (Sanger et al. (1977) *Proc. Natl. Acad. Sci. USA* 74:5463-5476) using a commercially available sequencing kit (Sequenase kit, U.S. Biochemicals, Cleveland, Ohio).

Both strands were sequenced using M13 forward and reverse primers (N.E. Biolabs, Beverly, Mass.) and internal sequencing primers CP-13 (SEQ ID NO: 10), CP-15 (SEQ ID NO: 12), CP-16 (SEQ ID NO: 13), CP-18 (SEQ ID NO: 15), CP-19 (SEQ ID NO: 16) and CP-20 (SEQ ID NO: 17). Two clones from amplification JC130 (JC130a and JC130b) and one clone from amplification JC135 (JC135g) were found to be Cry j I clones upon sequencing. The nucleotide and deduced amino acid sequences of clones JC130a and JC135g were identical to previously known Cry j I sequence (SEQ ID NO: 1). Clone JC130b was found to contain a single nucleotide difference from the previously known Cry j I sequence (SEQ ID NO: 1). Clone JC130b had a C at nucleotide position 306 of SEQ ID NO: 1. This nucleotide change results in a predicted amino acid change from a Tyr to a His at amino acid 60 of the mature Cry j I protein. This polymorphism has not yet been confirmed in an independently-derived PCR clone or by direct amino acid sequencing. However, such polymorphisms in primary nucleotide and amino acid sequences are expected.

EXAMPLE 5

Expression of Cry j I

Expression of Cry j I was performed as follows. Ten µg of pUC19JC91a was digested with Xba I, precipitated, then blunted with T4 polymerase. BamH I linkers (N.E. Biolabs, Beverly, Mass.) were blunt-end ligated to pUC19JC91a overnight and excess linkers were removed by filtration through a NACS ion exchange minicolumn (BRL, Gaithersburg, Md.). The Tinkered cDNA was then digested simultaneously with EcoR I and BamH I. The Cry j I insert (extending from the nucleotides encoding the amino terminus of the mature protein through the stop codon) was isolated by electrophoresis of this digest through a 1% SeaPlaque low melt agarose gel. The insert was then ligated into the appropriately digested expression vector pET-11d (Novagen, Madison, Wis.; Jameel et al. (1990) *J. Virol.* 64:3963-3966) modified to contain a sequence encoding 6 histidines (His 6) immediately 3' of the ATG initiation codon followed by a unique EcoR I endonuclease restriction site. A second EcoR I endonuclease restriction site in the vector, along with neighboring Cla I and Hind III endonuclease restriction sites, had previously been removed by digestion with EcoR I and Hind III, blunting and religation.

The histidine (His6) sequence was added for affinity purification of the recombinant protein (Cry j I) on a $Ni^{2+}$ chelating column (Hochuli et al. (1987) *J. Chromatog.* 411:177-184; Hochuli et al. (1988) *Bio/Tech.* 6:1321-1325.). A recombinant clone was used to transform *Escherichia coli* strain BL21-DE3 which harbors a plasmid that has an isopropyl-β-D-thiogalactopyranoside (IPTG)-inducible promoter preceding the gene encoding T7 polymerase. Induction with IPTG leads to high levels of 17 polymerase expression, which is necessary for expression of the recombinant protein in pET-11d, which has a T7 promoter. Clone pET-11dΔHRhis$_6$JC91a.d was confirmed by dideoxy sequencing (Sanger et al. supra) with CP-14 (SEQ ID NO: 11) to be a Cry j I clone in the correct reading frame for expression.

Expression of the recombinant protein was confirmed in an initial small culture (50 ml). An overnight culture of clone pET-11dΔHRhis$_6$JC91a.d was used to inoculate 50 ml of media (Brain Heart Infusion Media, Difco) containing ampicillin (200 µg/ml), grown to an $A_{600}$=1.0 and then induced with IPTG (1 mM, final concentration) for 2 hrs. One ml aliquots of the bacteria were collected before and after induction, pelleted by centrifugation, and crude cell lysates prepared by boiling the pellets for 5 minutes in 50 mM Tris HCl, pH 6.8, 2 mM EDTA, 1% SDS, 1% β-mercaptoethanol, 10% glycerol, 0.25% bromophenol blue (Studier et al., (1990) *Methods in Enzymology* 185:60-89). Recombinant protein expression was visualized as a band with the predicted molecular weight of approximately 38 kDa on a Coomassie blue-stained SDS-PAGE gel, according to the method in Sambrook et al., supra, on which 40 µl of the crude lysate was loaded. A negative control consisted of crude lysates from uninduced bacteria containing the plasmid with Cry j I and an induced lysate from bacteria carrying no plasmid.

The pET-11dΔHRhis$_6$JC91a.d clone was then grown on a large scale for recombinant protein expression and purification. A 2 ml culture bacteria containing the recombinant plasmid was grown for 8 hr, then streaked onto solid media (e.g. 6 petri plates (100×15 mm) with 1.5% agarose in LB medium (Gibco-BRL, Gaithersburg, Md.) containing 200 µg/ml ampicillin), grown to confluence overnight, then scraped into 9 L of liquid media (Brain Heart Infusion media, Difco) containing ampicillin (200 µg/ml). The culture was grown until the $A_{600}$ was 1.0, IPTG added (1 mM final concentration), and the culture grown for an additional 2 hours.

Bacteria were recovered by centrifugation (7,930×g, 10 min), and lysed in 90 ml of 6M Guanidine-HCl, 0.1M $Na_2HPO_4$, pH 8.0 for 1 hour with vigorous shaking. Insoluble material was removed by centrifugation (11,000×g, 10 min, 4° C.). The pH of the lysate was adjusted to pH 8.0, and the lysate applied to an 80 ml Nickel NTA agarose column (Qiagen) that had been equilibrated with 6 M Guanidine HCl, 100 mM $Na_2HPO_4$, pH 8.0. The column was sequentially washed with 6 M Guanidine HCl, 100 mM $Na_2HPO_4$, 10 mM Tris-HCl, pH 8.0, then 8 M urea, 100 mM $Na_2HPO_4$, pH 8.0, and finally 8 M urea, 100 mM sodium acetate, 10 mM Tris-HCl, pH 6.3. The column was washed with each buffer until the flow through had an $A_{280} \leq 0.05$.

The recombinant protein, Cry j I, was eluted with 8 M u.ea, 100 mM sodium acetate, 10 mM Tris-HCl, pH 4.5, and collected in 10 ml aliquots. The protein concentration of each fraction was determined by absorbance at $A_{280}$ and the peak fractions pooled. An aliquot of the collected recombinant protein was analyzed on SDS-PAGE according to the method in Sambrook et al., supra.

The first 9 L prep, JCpET-1, yielded 30 mg of Cry j I with approximately 78% purity, as determined by densitometry (Shimadzu Flying Spot Scanner, Shimadzu Scientific Instruments, Inc., Braintree, Mass.) of the Coomassie-blue stained SDS-PAGE gel. A second 9 L prep prepared the same way, JCpET-2, yielded 41 mg of Cry j I with approximately 77% purity.

EXAMPLE 6

Japanese Cedar Pollen Allergic Patient T Cell Studies with Cry j I—the Primary Cedar Pollen Antigen.
Synthesis of Overlapping Peptides Japanese cedar pollen Cry j I overlapping peptides were synthesized using standard Fmoc/tBoc synthetic chemistry and purified by Reverse Phase HPLC. FIG. 13 shows Cry j I peptides used in these studies. The peptide names are consistent throughout.

T Cell Responses to Cedar Pollen Antigenic Peptides

Peripheral blood mononuclear cells (PBMC) were purified by lymphocyte separation medium (LSM) centrifugation of 60 ml of heparinized blood from Japanese cedar pollen-allergic patients who exhibited clinical symptoms of seasonal rhinitis and were MAST and/or skin test positive for Japanese cedar pollen. Long term T cell lines were established by stimulation of $2\times10^6$ PBL/ml in bulk cultures of complete medium (RPMI-1640, 2 mM L-glutamine, 100 U/ml penicillin/streptomycin, $5\times10^{-5}$M 2-mercaptoethanol, and 10 mM HEPES supplemented with 5% heat inactivated human AB serum) with 20 μg/ml of partially purified native Cry j I (75% purity containing three bands similar to the three bands in FIG. 2) for 7 days at 37° C. in a humidified 5% $CO_2$ incubator to select for Cry j I reactive T cells. This amount of priming antigen was determined to be optimal for the activation of T cells from most cedar pollen allergic patients. Viable cells were purified by LSM centrifugation and cultured in complete medium supplemented with 5 units recombinant human IL-2/ml and 5 units recombinant human IL-4/ml for up to three weeks until the cells no longer responded to lymphokines and were considered "rested". The ability of the T cells to proliferate to selected peptides, recombinant Cry j I (rCry j I), purified native Cry j I, or recombinant Amb aI.1 (rAmb aI.1) or a positive control, phyto-hemaglutinin (PHA) was then assessed. For assay, $2\times10^4$ rested cells were restimulated in the presence of $2\times10^4$ autologous Epstein-Barr virus (EBV)-transformed B cells (prepared as described below) (gamma-irradiated with 25,000 RADS) with 2-50 μg/ml of selected peptides, Cry j I, purified native Cry j I or rAmb a I.1 or PHA, in a volume of 200 μl complete medium in duplicate or triplicate wells in 96-well round bottom plates for 2-4 days. The optimal incubation was found to be 3 days. Each well then received 1 μCi tritiated thymidine for 16-20 hours. The counts incorporated were collected onto glass fiber filter mats and processed for liquid scintillation counting. FIG. 12 shows the effect of varying antigen dose in assays with recombinant Cry j I, purified native Cry j I, and recombinant Amb a I.1 and several antigenic peptides synthesized as described above. Some peptides were found to be inhibitory at high concentrations in these assays. The titrations were used to optimize the dose of peptides in T cell assays. The maximum response in a titration of each peptide is expressed as the stimulation index (S.I.). The S.I. is the counts per minute (CPM) incorporated by cells in response to peptide, divided by the CPM incorporated by cells in medium only. An S.I. value equal to or greater than 2 times the background level is considered "positive" and indicates that the peptide contains a T cell epitope. The positive results were used in calculating mean stimulation indices for each peptide for the group of patients tested. The results shown in FIG. 12 demonstrate that patient #999 responds well to recombinant Cry j I (SEQ ID NO: 1), and purified native Cry j I, as well as to peptides CJ1-2 (SEQ ID NO: 27), 3 (SEQ ID NO: 28), 20 (SEQ ID NO: 45), and 22 (SEQ ID NO: 47) but not to recombinant Amb a I.1. This indicates that Cry j I T cell epitopes are recognized by T cells from this particular allergic patient and that rCry j I and peptides (SEQ ID NO: 27), 3 (SEQ ID NO: 28), 20 (SEQ ID NO: 45), and 22 (SEQ ID NO: 47) contain such T cell epitopes. Furthermore, the epitopes were often not detected with the adjacent overlapping peptides, and therefore probably span the non-overlapping central residues of the reactive peptides. No significant cross-reactivity was found in T cell assays using T cells primed with control antigens or with Cry j I primed T cells against other antigens.

The above procedure was followed with a number of other patients. Individual patient results were used in calculating the mean S.I. for each peptide if the patient responded to the Cry j I protein at an S.I. of 2.0 or greater and the patient responded to at least one peptide derived from Cry j I at an S.I. of 2.0 or greater. A summary of positive experiments from twenty-five patients is shown in FIG. 14. The bars represent the positivity index. Above each bar is the percent of positive responses with an S.I. of at least two to the peptide or protein in the group of patients tested. In parenthesis above each bar are the mean stimulation indices for each peptide or protein for the group of patients tested. All twenty-five T cell lines responded to purified native Cry j I and 68.0% of the T cell lines responded to rCry j I. These twenty-five T cell lines also responded at a significantly lower level to rAmb a I.1 indicating that the Amb a I allergens share a degree of homology with Cry j I and that "shared" T cell epitopes might exist between Cry j I and Amb a I. This panel of Japanese cedar allergic patients responded to peptides CJ1-1 (SEQ ID NO: 26), CJ1-2 (SEQ ID NO: 27), CJ1-3 (SEQ ID NO: 28), CJ1-4 (SEQ ID NO: 29), CJ1-7 (SEQ ID NO: 32), CJ1-8 (SEQ ID NO: 33), CJ1-9 (SEQ ID NO: 34), CJ1-10 (SEQ ID NO: 35), CJ1-11 (SEQ ID NO: 36), CJ1-12 (SEQ ID NO: 37), CJ1-14 (SEQ ID NO: 39), CJ1-15 (SEQ ID NO: 40), CJ1-16 (SEQ ID NO: 41), CJ1-17 (SEQ ID NO: 42), CJ1-18 (SEQ ID NO: 43), CJ1-19 (SEQ ID NO: 44), CJ1-20 (SEQ ID NO: 45), CJ1-21 (SEQ ID NO: 46), CJ1-22 (SEQ ID NO: 47), CJ1-23 (SEQ ID NO: 48), CJ1-24 (SEQ ID NO: 49), CJ1-25 (SEQ ID NO: 50), CJ1-26 (SEQ ID NO: 51), CJ1-27 (SEQ ID NO: 52), CJ1-28 (SEQ ID NO: 53), CJ1-30 (SEQ ID NO: 55), CJ1-31 (SEQ ID NO: 56), CJ1-32 (SEQ ID NO: 57), CJ1-33 (SEQ ID NO: 58), CJ1-34 (SEQ ID NO: 59) and CJ1-35 (SEQ ID NO: 60) indicating that these peptides contain T cell epitopes.

Preparation of (EBV)-Transformed B Cells for Use as Antigen Presenting Cells

Autologous EBV-transformed cell lines were γ-irradiated with 25,000 Rad and used as antigen presenting cells in secondary proliferation assays and secondary bulk stimulations. These EBV-transformed cell lines were made by incubating $5\times10^6$ PBL with 1 ml of B-59/8 Marmoset cell line (ATCC CRL1612, American Type Culture Collection, Rockville, Md.) conditioned medium in the presence of 1 μg/ml phorbol 12-myristate 13-acetate (PMA) at 37° C. for 60 minutes in 12×75 mm polypropylene round-bottom Falcon snap cap tubes (Becton Dickinson Labware, Lincoln Park, N.J.). These cells were then diluted to $1.25\times10^6$ cells/ml in RPMI-1640 as described above except supplemented with 10% heat-inactivated fetal bovine serum and cultured in 200 μl aliquots in flat bottom culture plates until visible colonies were detected. They were then transferred to larger wells until the cell lines were established.

EXAMPLE 7

Cry j I as the Major Cedar Pollen Allergen

Figure 5A:
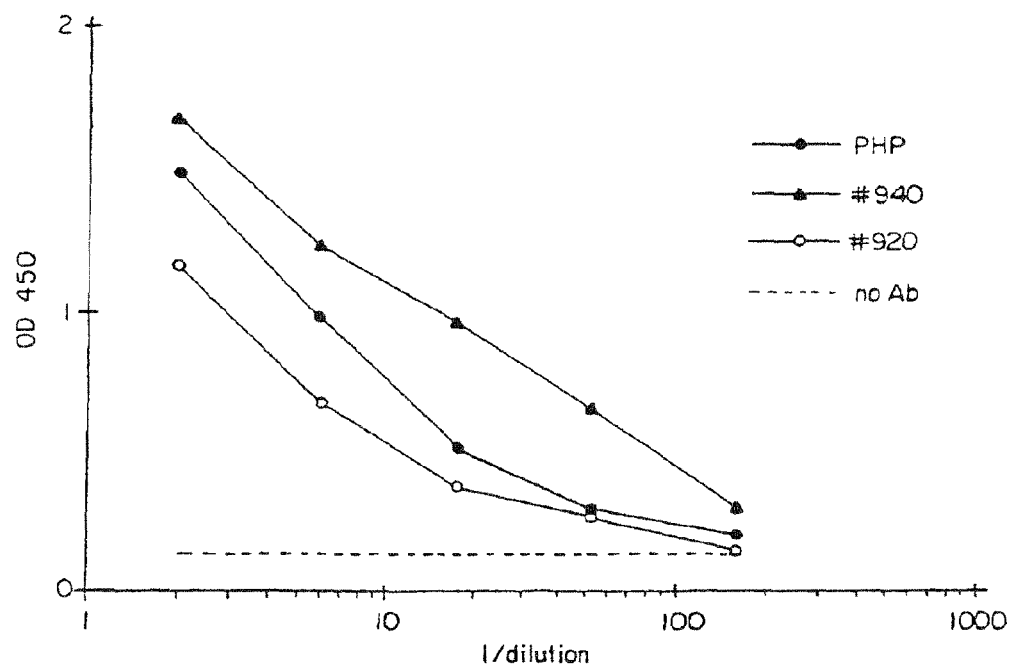
FIG. 5a is a graphic representation of the results of IgE binding reactivity wherein the coating antigen is soluble pollen extract (SPE) from Japanese cedar pollen.
Figure 5B:
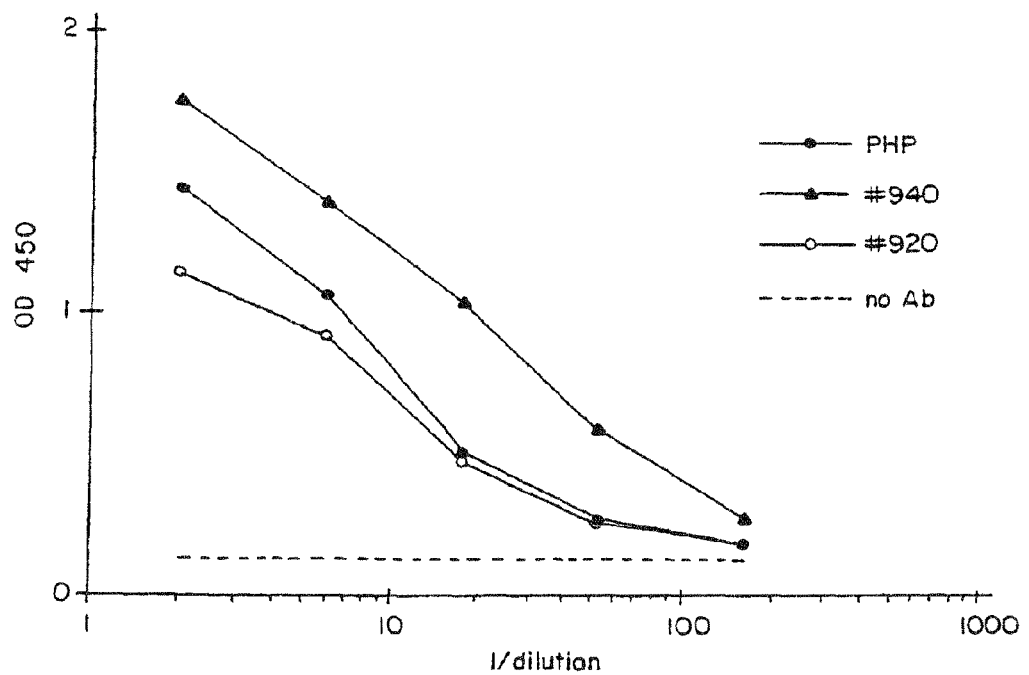
FIG. 5b is a graphic representation of the results of IgE binding reactivity wherein the coating antigen is purified native Cry j I.

To examine the importance of Cry j I, reported as the major allergen of Japanese cedar pollen, both direct and competition ELISA assays were performed. For the direct ELISA assays, wells were coated with either soluble pollen extract (SPE) of Japanese cedar pollen or purified native Cry j I (assayed at 90% purity by protein sequencing) and human IgE antibody binding to these antigens was analyzed. Pooled human plasma, consisting of an equal volume of plasma from 15 patients with a Japanese cedar pollen MAST score of 2.5 or greater, and two individual patient plasma samples were compared in this assay. FIG. 5 shows the results of the binding reactivity with these two antigens. The overall pattern of binding is very similar whether the coating antigen is SPE (FIG. 5a) or purified native Cry j I (FIG. 5b).

Figure 6:
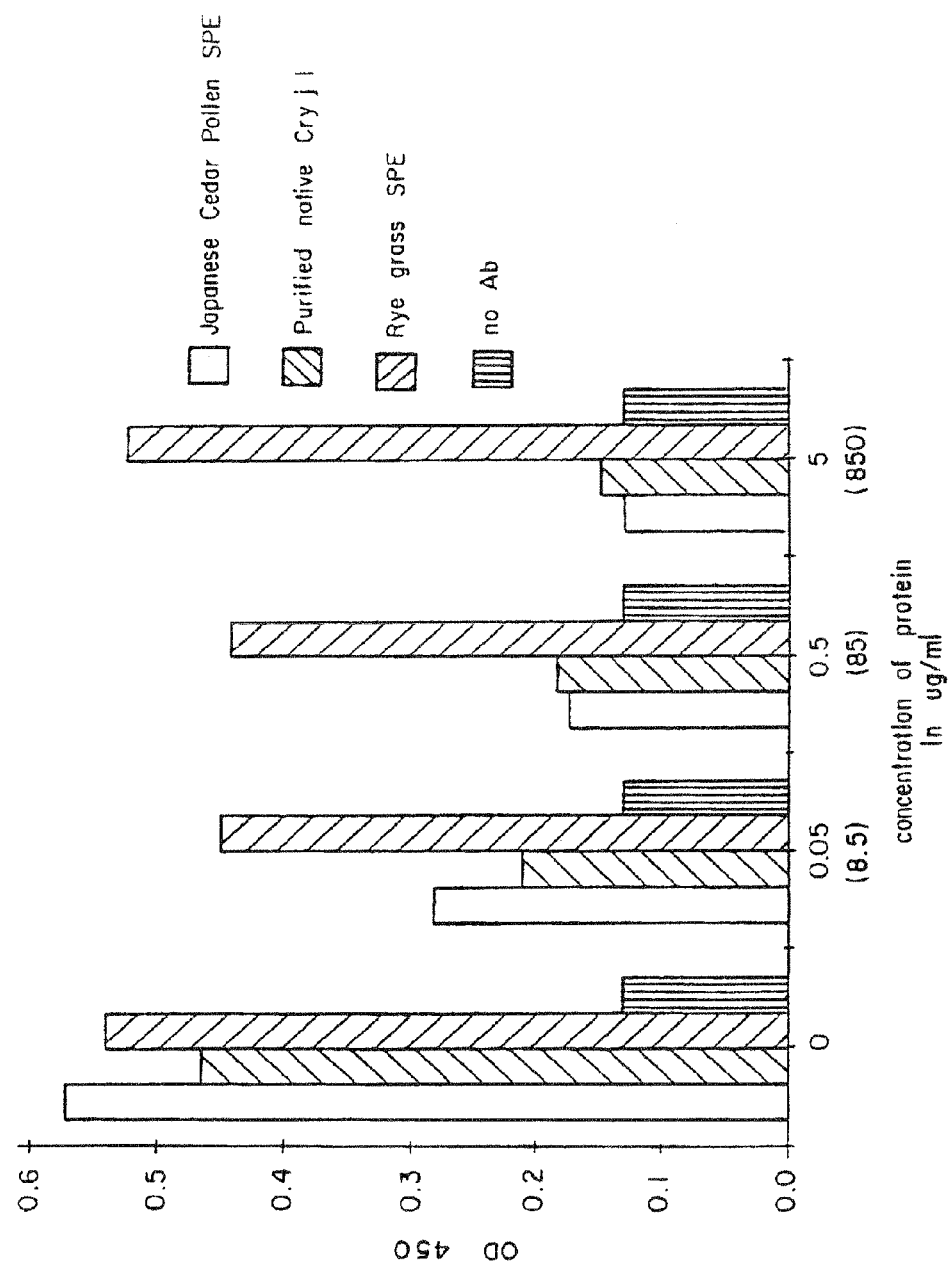
FIG. 6 is a graphic representation of the results of a competition ELISA with pooled human plasma (PHP) from 15 patients wherein the coating antigen is soluble pollen extract (SPE) from Japanese cedar pollen.

In the competition assay, ELISA wells were coated with Japanese cedar pollen SPE and then allergic patient IgE binding was measured in the presence of competing purified native Cry j I in solution. The source of allergic IgE in these assays was either the pool of plasma from 15 patients (denoted PHP) or seven individual plasma samples from patients with a Japanese cedar MAST score of 2.5 or greater. The competition assay using the pooled human plasma samples compares the competitive binding capacity of purified native Cry j I to Japanese cedar pollen SPE and an irrelevant allergen source, rye grass SPE. FIG. 6 shows the graphed results of the competition ELISA with pooled human plasma. The concentration of protein present in the Japanese cedar pollen SPE is approximately 170 times greater at each competing point than is the purified native Cry j I. From this analysis it is clear that the purified native Cry j I competes very well for IgE binding to the whole range of proteins present in the Japanese cedar pollen soluble pollen extract. This implies that most of the anti-Cry j IgE reactivity is directed against native Cry j I. The negative control shows no specific competitive activity and the competing SPE in solution can completely remove binding to the coated wells. This assay was repeated with individual patients as a measure of the range of the IgE response within the allergic population. FIG. 7 shows this result where the competition of binding to SPE was performed with purified native Cry j I. The results demonstrate that although the patients show different dose response to Japanese cedar pollen SPE, each of the seven patients' IgE binding to Japanese cedar pollen SPE could be competed with purified native Cry j I. The implications of these data are that for each patient the IgE reactivity directed against Cry j I is predominant but that there is variation in this reactivity between patients. The overall conclusion is that these data support the previous findings (Yasueda et al., (1988) supra) that Cry j I is the major allergen of Japanese cedar pollen.

Figure 8A:
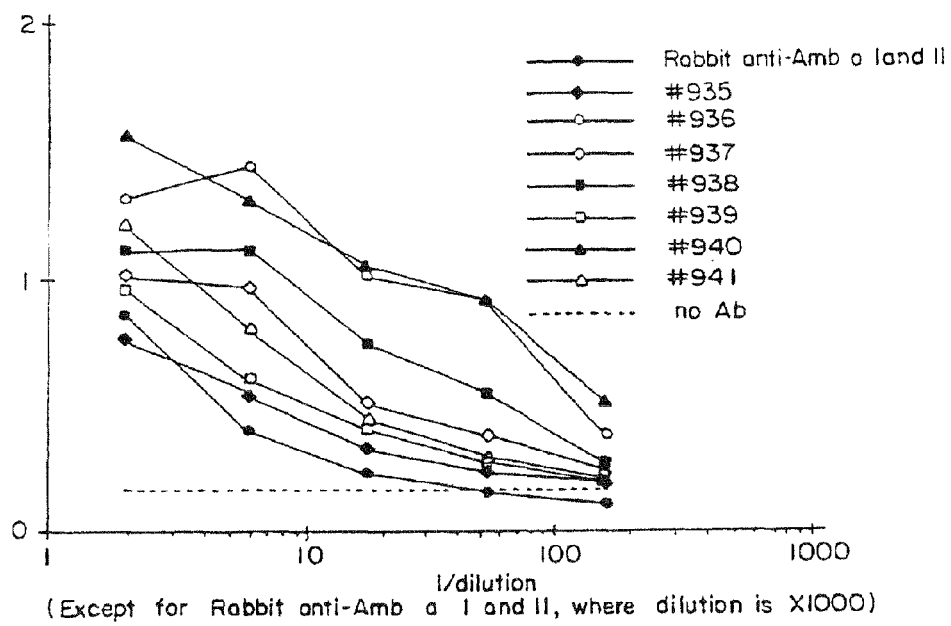
FIG. 8a is a graphic representation of the results from a direct binding ELISA using plasma from seven individual patients (indicated by patient numbers) wherein the coating antigen is soluble pollen extract (SPE) from Japanese cedar pollen.
Figure 8B:
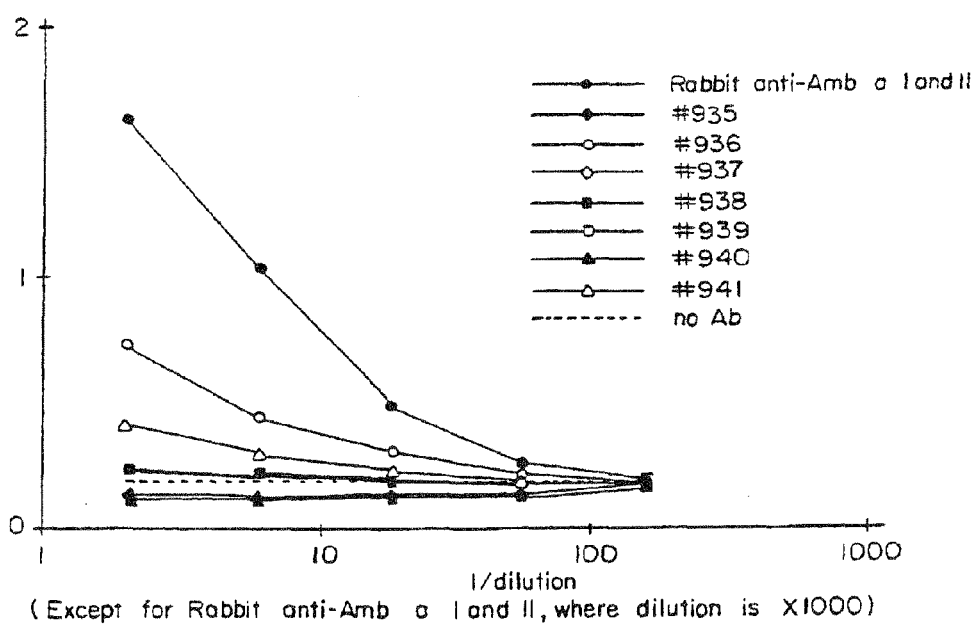
FIG. 8b is a graphic representation of the results from a direct binding ELISA using plasma from seven individual patients (indicated by patient numbers) wherein the coating antigen is denatured soluble pollen extract which has been denatured by boiling in the presence of a reducing agent, DTT.

The reactivity of IgE from cedar pollen allergic patients to the pollen proteins is dramatically reduced when these proteins are denatured. One method of analyzing this property is through direct binding ELISA where the coating antigen is the Japanese cedar pollen SPE or denatured Japanese cedar pollen SPE which has been denatured by boiling in the presence of a reducing agent DTT. This is then examined with allergic patient plasma for IgE binding reactivity. FIG. 8a, shows the direct binding assay to the SPE with seven individual plasma samples. In FIG. 8b, the binding results with the denatured SPE demonstrates the marked decrease in reactivity following this treatment. To determine the extent of Cry j I binding to the ELISA wells, Cry j I was detected with a rabbit polyclonal antisera against the Amb a I & II protein family. These ragweed proteins have high sequence identity (46%) with Cry j I and this antisera can be used as a cross reactive antibody detection system. In conclusion, these data demonstrate a marked loss in IgE reactivity following denaturation of the Japanese cedar pollen SPE.

EXAMPLE 8

IgE Reactivity and Histamine Release Analysis

Figure 9:
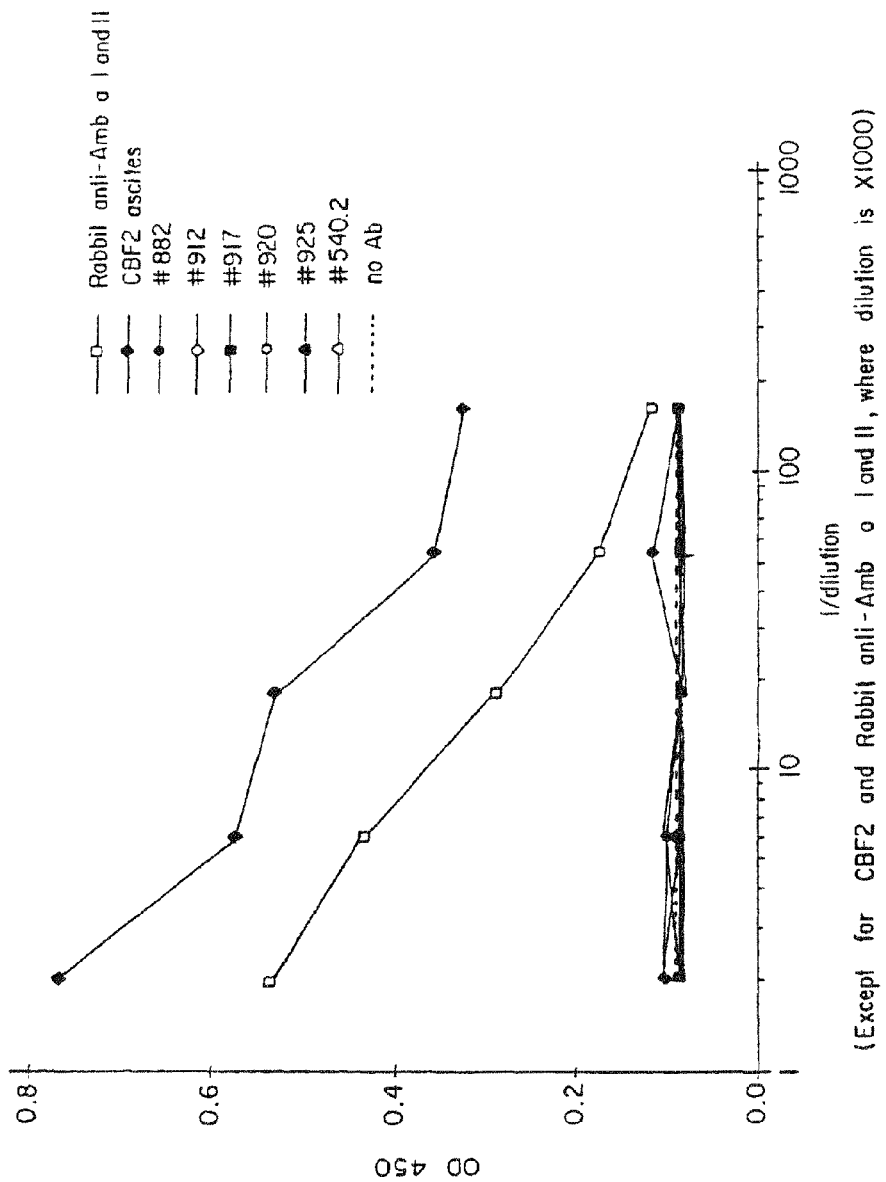
FIG. 9 is a graphic representation of a direct ELISA where the wells were coated with recombinant Cry j I (rCry j I) and IgE binding was assayed on individual patients.

The recombinant Cry j I protein (rCry j I), expressed in bacteria and then purified (as described in Example 5), has been examined for IgE reactivity. The first method applied to this examination was direct ELISA where wells were coated with the recombinant Cry j I and IgE binding was assayed on individual patients. FIG. 9 is the graphic representation of this direct ELISA. The only positive signals on this data set are from the two control antisera rabbit polyclonal anti-Amb a I & II prepared by conventional means (Rabbit anti-Amb a I & II) and CBE2, a monoclonal antibody raised against Amb a I that cross reacts with Cry j I. By this method all patients tested showed no IgE reactivity with the recombinant Cry j I.

Figure 10A:
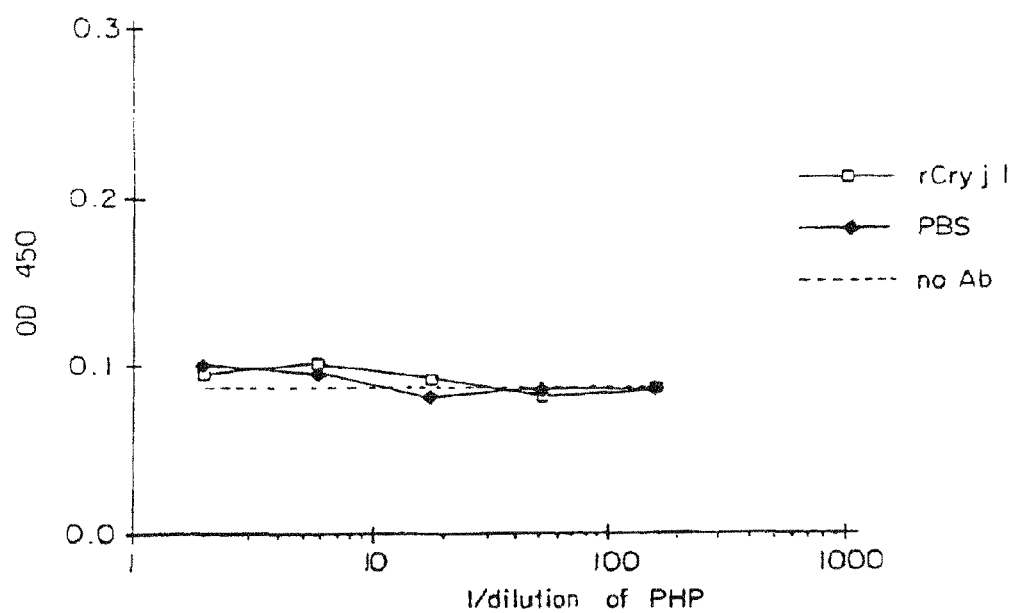
FIG. 10a is a graphic representation of the results of a capture ELISA using pooled human plasma from fifteen patients wherein the wells were coated with CBF2 (IgG) mAb, PBS was used as a negative antigen control, and the antigen was purified recombinant Cry j I.
Figure 10B:
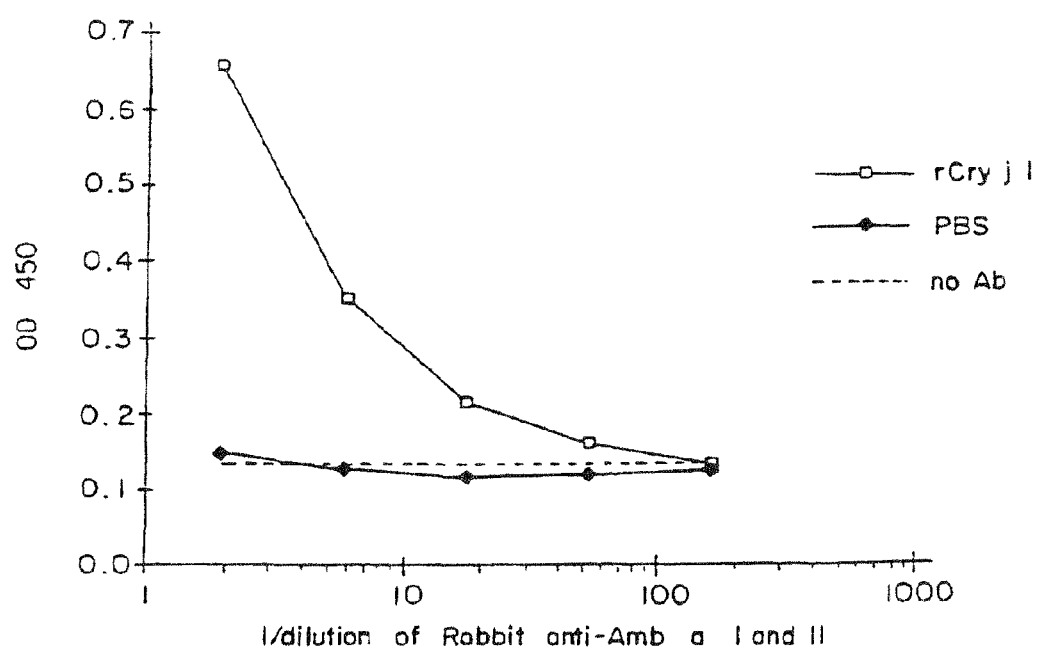
FIG. 10b is a graphic representation of the results of a capture ELISA using rabbit anti-Amb aI and II, wherein the wells were coated with 20 μg/ml CBF2 (IgG), PBS was used as a negative antigen control and the antigen was purified recombinant Cry j I.

Another method of analysis that was applied to the examination of IgE reactivity to the recombinant Cry j I was a capture ELISA. This analysis relies on the use of a defined antibody, in this case CBF2 to bind the antigen and allow for the binding of antibodies to other epitope sites. The format of this capture ELISA is 1) wells are coated with MAb CBF2, 2) antigen or PBS (as one type of negative control) is added and captured by specific interaction with the coated MAb, 3) either the control antibody anti-Amb a I & II (FIG. 10b) or human allergic plasma (FIG. 10a) is added as the detecting antibody, and 4) detection of antibody binding is assayed. FIGS. 10a and 10b are the graphed results of these assays. For the IgE analysis, the pooled human plasma (PHP) (15 patients) was used. The conclusion from these results is that there is no indication of any specific binding of human allergic IgE to rCry j I by this method of analysis. However, the capture of rCry j I works as evidenced by the control antibody binding curve, shown in FIG. 10b. The lack of IgE binding to E. coli expressed rCry j I may be due to absence of carbohydrate or any other post-translational modification and/or that the majority of IgE cannot react with denatured Cry j I. RAST, competition ELISA and Western blotting data also demonstrates no specific IgE reactivity to the rCry j I (data not shown).

Figure 11:
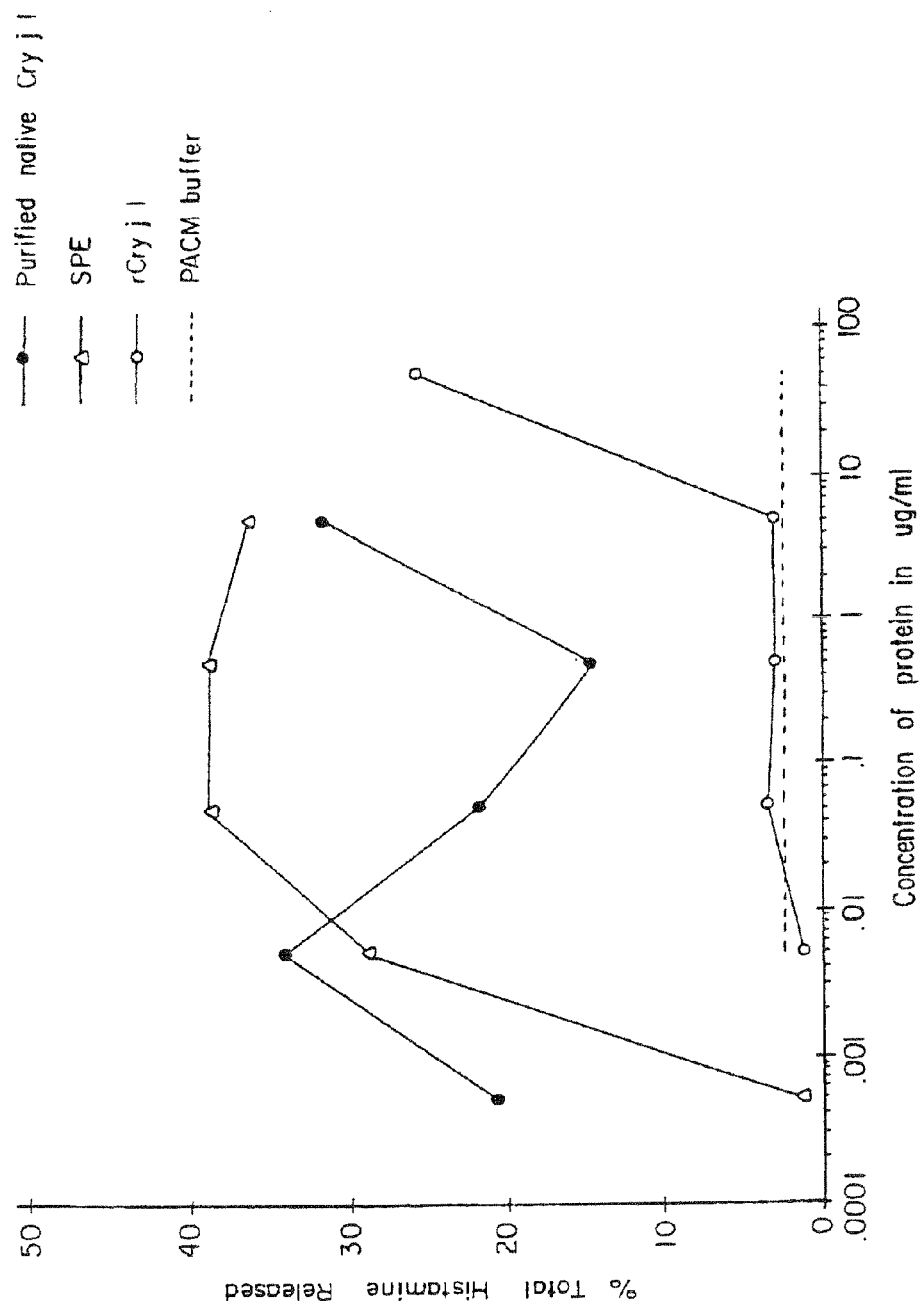
FIG. 11 is a graphic representation of a histamine release assay performed on one Japanese cedar pollen allergic patient using SPE from Japanese cedar pollen, purified native Cry j I and recombinant Cry j I as the added antigens.
Figure 12:
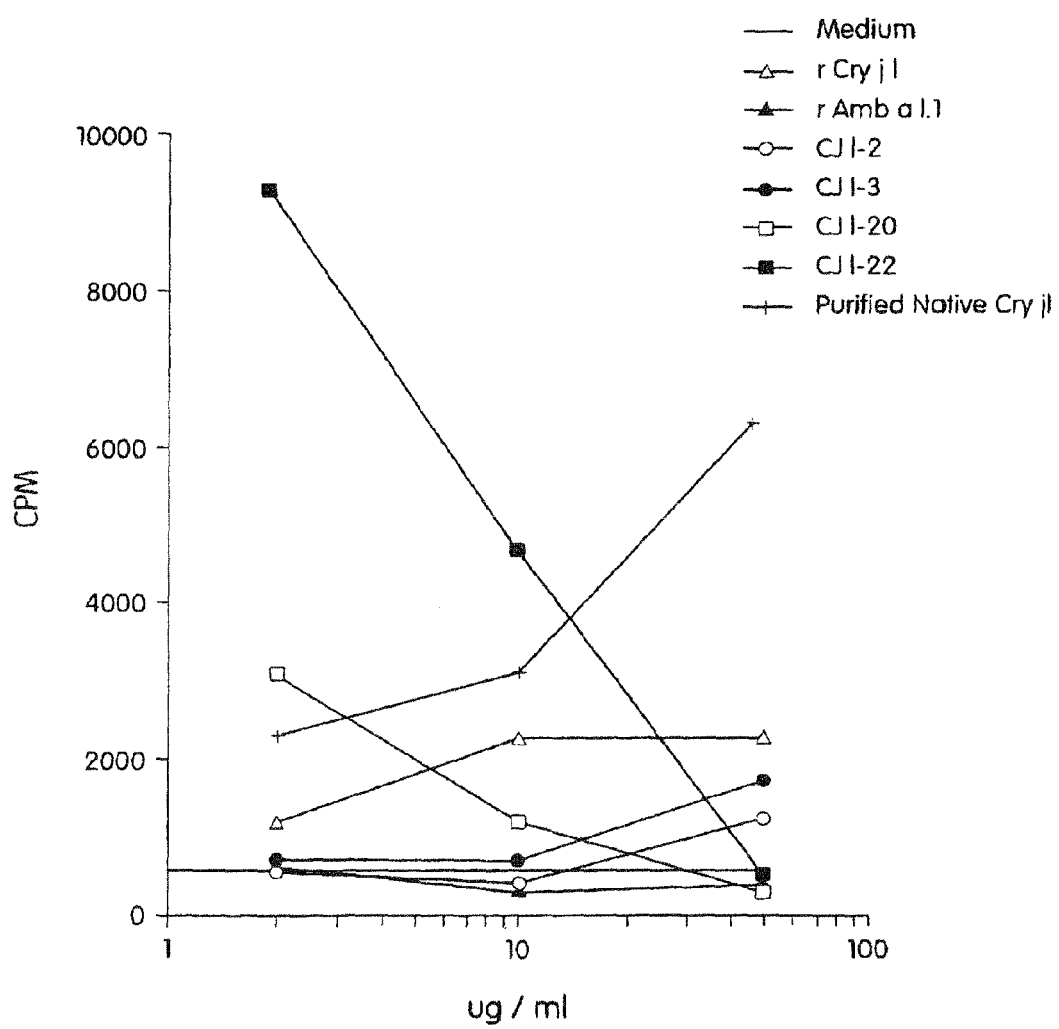
FIG. 12 is a graphic representation of the results of a T cell proliferation assay using blood from patient #999 wherein the antigen is recombinant Cry j I protein, purified native Cry j I protein, or selected Cry j I peptides recombinant Amb a 1.1.

A histamine release assay was performed on one Japanese cedar pollen allergic patient using Japanese cedar pollen SPE, purified native Cry j I and rCry j I as the added antigens. This assay is a measure of IgE reactivity through human basophil mediator release. The results of this assay, shown in FIG. 11, demonstrate strong histamine release with both purified native Cry j I and the Japanese cedar pollen SPE over a wide concentration range. The only point where there is any measurable histamine release with the Cry j I is at the highest concentration, 50 µg/ml. Two possible explanations for this release by the rCry j I are: 1) specific reactivity with a very low proportion of the anti-Cry j I IgE capable of recognizing the recombinant form of Cry j I, or 2) non-specific release caused by low abundance of bacterial contaminants observed only at the highest antigen concentration. Thus far, this result has only been shown in a single patient. In addition, the data shown are from single data points at each protein concentration.

It may be possible to use this recombinantly expressed Cry j I protein for immunotherapy as E. coli expressed material has T cell reactivity (Example 6), but does not appear to bind IgE from *Crytpomeria japonica* atopes nor cause histamine release from the mast cells and basophils of such atopes in vitro. Expression of rCry j I which is capable of binding IgE could possibly be achieved in yeast, insect (baculovirus) or mammalian cells (e.g. CHO, human and mouse). A specific example of mammalian cell expression could be the use of the pcDNA l/Amp mammalian expression vector (Invitrogen, San Diego, Calif.) expressing recombinant Cry j I in COS cells. A rCry j I capable of actively binding IgE may be important for the use of recombinant material for diagnostic purposes.

Figure 15A:
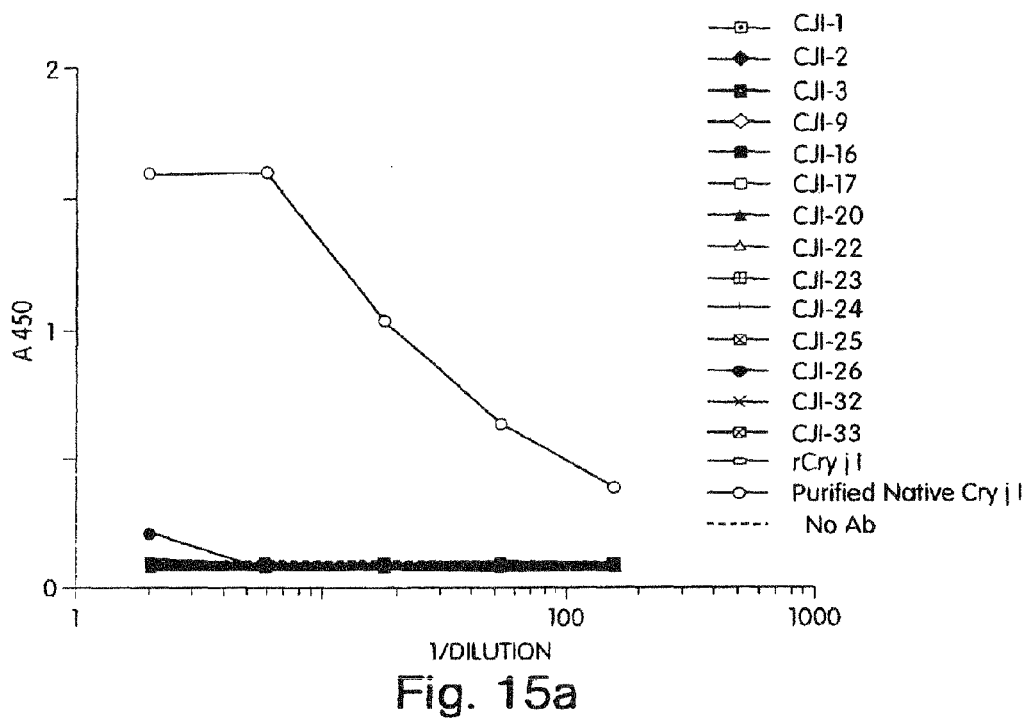
FIG. 15 is a graphic representation of the results of a direct binding assay of IgE to certain Cry j I peptides, purified native Cry j I and rCry j I.
Figure 15B:
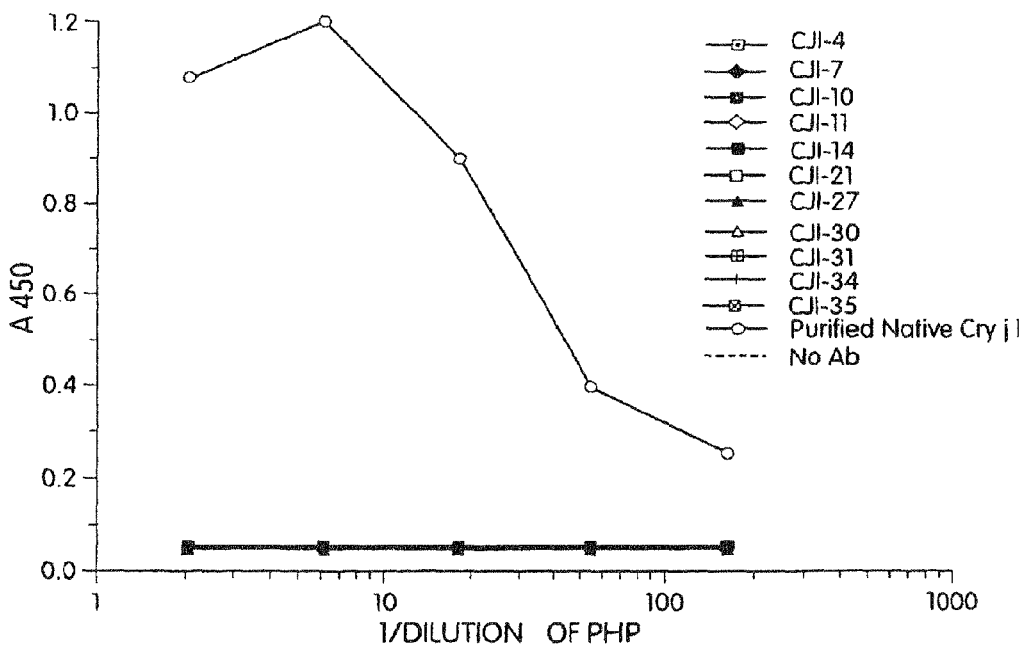

To analyze IgE reactivity to selected Cry j I peptides a direct ELISA format was used. ELSIA wells were coated with 25 peptides derived from Cry j I and assayed for IgE binding. FIG. 15a and 15b are graphs of these binding results using PHP (15 patients) as the cedar pollen allergic IgE source. This pool of plasma was formulated for enrichment of IgE that could bind to denatured SPE (as determined by direct ELISA) and therefore increase the chance of reactivity toward the peptides. In this assay, the peptide IgE binding capacity was compared to that of purified native Cry j I and to rCry j I. The only specific IgE detected in this assay was to purified native Cry j I which supports the finding that Japanese cedar allergic patient IgE does not bind to recombinant Cry j I or the recombinant Cry j I peptides tested (FIG. 15).

EXAMPLE 9

Extraction of RNA from *Juniperus sabinoides, Juniperus virginana* and *Cupressus arizonica* Pollens and the Cloning of Jun s I and Jun v I, Homologs of Cry j I.

Fresh pollen was collected from a single *Juniperus virginiana* tree at the Arnold Arboretum (Boston, Mass.), and was frozen immediately on dry ice; *Juniperus sabinoides* and *Cupressus arizonica* pollens were purchased from Greer Laboratories, Inc. (Lenoir, N.C.). Total RNA was prepared from *J. virginiana, J. sabinoides*, and *C. arizonica* pollens as described in Example 3. Single stranded cDNA was synthesized from 5 µg total pollen RNA from *J. virginiana* and 5 µg total pollen RNA from *J. sabinoides* using the cDNA Synthesis System kit (BRL, Gaithersburg, Md.), as described in Example 3.

The initial attempt at cloning Cry j I homologue from the two juniper species was made using various pairs of Cry j I-specific oligonucleotides in PCR amplifications on both juniper cDNAs. PCRs were carried out as described in Example 3. The oligonucleotide primer pairs used were: CP-9 (SEQ ID NO: 8)/CP-17 (SEQ ID NO: 14), CP10 (SEQ ID NO: 9)/CP-17 (SEQ ID NO: 14), CP-10 (SEQ ID NO: 9)/CP-16 (SEQ ID NO: 13), CP-1O (SEQ ID NO: 9)/CP-19 (SEQ ID NO: 16), CP-10 (SEQ ID NO: 9)/CP-18 (SEQ ID NO: 15), CP-13 (SEQ ID NO: 13)/CP-17 (SEQ ID NO: 14), and CP-13 (SEQ ID NO: 10)/CP-19. CP-10 (SEQ ID NO: 9) was used in the majority of the reactions as the 5' primer since it has been reported by Gross et. al. (1978) *Scand. J. Immunol.* 8: 437-441 that the first 5 amino-terminal amino acids of *J. sabinoides* are identical to those of Cry j I. These oligonucleotides and oligonucleotide primers pairs are described in Example 3. None of the primer pairs cited above resulted in a PCR product for either *juniperus* species when viewed on an EtBr-stained 1% agarose (FMC Bioproducts, Rockland, Me.) minigel.

The next series of PCR amplifications attempting to clone the Cry j I homologues from *J. sabinoides* and *J. virginiana* from were made on double stranded linkered cDNA synthesized from RNA from each species. Double stranded cDNA was synthesized from 5 µg of *J. virginiana* and 5 µg *J. sabinoides* pollen RNA as described in Example 3. The double-stranded cDNA was ligated to ethanol precipitated, self annealed, AT (SEQ ID NO: 20) and AL (SEQ ID NO: 22) oligonucleotides for use in a modified Anchored PCR as described in Example 3. A number of Cry j I primers were then used in combination with AP (SEQ ID NO: 21) in an attempt to isolate the Cry j I homologues from the two juniper species. The sequences of AR (SEQ ID NO: 20), AL (SEQ ID NO: 22) and AP (SEQ ID NO: 21) are given in Example 3. First, a primary PCR was carried out with 100 pmol each of the oligonucleotides CP-10 (SEQ ID NO: 9) and AP (SEQ ID NO: 21). Three percent (3 µl) of this initial amplification was then used in a secondary PCR with 100 pmoles each of CP-10 (SEQ ID NO: 9) and APA (SEQ ID NO: 98), which has the sequence 5'-GGGCTCGAGCTG-CAGTTTTTTTTTTTTTTTG-3', where nucleotides 1-15 represent Pst I and Xho I endonuclease restriction sites added for cloning purposes, and nucleotide 33 can also be an A or C. A broad smear, with no discreet band, was revealed upon examination of the secondary PCR reactions on an EtBr-stained agarose gel. Attempts to clone Cry j I homologues from these PCR products were not successful. This approach would have cloned a carboxyl portion of these genes. The degenerate Cry j I primers CP-1 (SEQ ID NO: 3), CP-4 (SEQ ID NO: 194), and CP-7 (SEQ ID NO: 6) as described in Example 3 were then each used in primary PCRs with AP (SEQ ID NO: 21) on the double stranded tinkered *J. virginiana* and *J. sabinoides* cDNAs. Various primer pair combinations were used in secondary PCRs as follows: CP-2 (SEQ ID NO: 4)/AP (SEQ ID NO: 21) and CP-4 (SEQ ID NO: 194)/AP (SEQ ID NO: 21) on the CP-1 (SEQ ID NO: 3)/AP (SEQ ID NO: 21) primary PCR amplification mixture, CP-2 (SEQ ID NO: 4)/AP (SEQ ID NO: 21) and CP-5 (SEQ ID NO: 195)/AP (SEQ ID NO: 21) on the CP-4 (SEQ ID NO: 194)/AP (SEQ ID NO: 21) primary PCR amplification mixture, and CP-8 (SEQ ID NO: 7)/AP (SEQ ID NO: 21) on the CP-7 (SEQ ID NO: 6)/AP (SEQ ID NO: 21) primary PCR amplification mixture. Only the last amplification, the CP-8 (SEQ ID NO: 7)/AP (SEQ ID NO: 21) secondary PCR amplification, yielded a band upon examination on an EtBr-stained minigel; the others gave smears that could not be cloned into pUC19. Both the *J. virginiana* and *J. sabinoides* secondary PCRs with CP-8 (SEQ ID NO: 7) and AP (SEQ ID NO: 21), described in Example 3, called JV21 and JS17, respectively, resulted in amplified products that were approximately 200 base pairs long. The amplified DNA was recovered as described in Example 3 and simultaneously digested with Xba I and Pst I in a 50 µl reaction, precipitated to reduce the volume to 10 µl, and electrophoresed through a preparative 2% GTG NuSeive low melt gel (FMC, Rockport, Me.). The appropriate sized DNA band was visualized by EtBr staining, excised, and ligated into appropriately digested pUC19 for sequencing by the dideoxy chain termination method of Sanger et al. (supra) using a commercially available sequencing kit (Sequenase kit, U.S. Biochemicals, Cleveland, Ohio). Two JS17 clones (pUC19JS17d and pUC19JS17f) and one JV21 clone (pUC19JV21g) were sequenced, and found to contain sequences homologous to the Cry j I nucleotide and deduced amino acid sequences. The Cry j I homologues isolated from *J. sabinoides* and *J. virginiana* RNA were designated Jun s I and Jun v I, respectively.

The Cry j I primers CP-9 (SEQ ID NO: 8) and CP-10 (SEQ ID NO: 9) should work in primary and secondary PCRs, respectively, with AP to amplify the carboxyl portion of the Jun s I and Jun v I cDNAs. The sequence of these primers are essentially identical to the sequences of Jun s I (SEQ ID NO: 94) and Jun v I (SEQ ID NO: 96), with the exception of 2 nucleotides in CP-9 (SEQ ID NO: 8) (T instead of A in position 5 of CP-9 (SEQ ID NO: 8), C instead of A in position 12), and 1 in CP-10 (SEQ ID NO: 9) (C instead of A in position 12 for Jun s I only). However, primary PCRs with CP-9 (SEQ ID NO: 8) and AP (SEQ ID NO: 21) and secondary PCRs with CP-10 (SEQ ID NO: 9) and AP (SEQ ID NO: 21) did not yield identifiable Jun s I nor Jun v I product when viewed on an EtBr-stained agarose gel. Oligonucleotide J1 (SEQ ID NO: 99) was synthesized. J1 and all subsequent oligonucleotides were synthesized on an ABI 394 DNA/RNA synthesizer (Applied Biosystems, Foster City, Calif.). Primary PCRs were carried out using AP (SEQ ID NO: 21) and J1 (SEQ ID NO: 99) with *J. virginiana* and *J. sabinoides* cDNAs. J1 has the sequence 5'-CTAAAAATGGCTTC-CCCA-3', which corresponds to nucleotides 20-37 of Jun s I (FIG. 16) (SEQ ID NO: 94) and nucleotides 30-47 of Jun v I (FIG. 17) (SEQ ID NO: 96). A secondary PCR amplification was performed on the primary J1 (SEQ ID NO: 99)/AP (SEQ ID NO: 21) amplification of *J. sabinoides* cDNA using primers J2 (SEQ ID NO: 100) and AP (SEQ ID NO: 21). J2 (SEQ ID NO: 100) has the sequence 5'-CGGGAATTCTAGATGT-GCAATTGTATCTTGTTA-3', whereby nucleotides 1-13 represent EcoR I and Xba I endonuclease restriction sites added for cloning purposes, and the remaining nucleotides correspond to nucleotides 65-84 in the Jun s I sequence (FIG. 16) (SEQ ID NO: 94). The secondary amplification from *J. virginiana* cDNA was performed with AP (SEQ ID NO: 21) and J3 (SEQ ID NO: 101), which has sequence 5'-CGG-GAATTCTAGATGTGCAATAGTATCTTGTTG-3' whereby nucleotides 1-13 represent EcoR I and Xba I endonuclease restriction sites added for cloning purposes and the remaining nucleotides correspond to nucleotides 75-94 in the Jun v I sequence (FIG. 17) (SEQ ID NO: 96). No specific amplified product was observed in either secondary reaction. The primers designated ED (SEQ ID NO: 102) and EDT (SEQ ID NO: 103) were used at a molar ratio of 3:1 (ED:EDT) in conjunction with primers J1 (SEQ ID NO: 99), J2 (SEQ ID NO: 100) and J3 (SEQ ID NO: 101), as described below. EDT (SEQ ID NO: 103) has the sequence 5'-GGAATTCTCTAGACTG-CAGGTTTTTTTTTTTTTTT-3'. The nucleotides 1 through 20 of EDT (SEQ ID NO: 103) were added to the poly-T track to create EcoR I, Xba I, and Pst I endonuclease restriction sites for cloning purposes. ED (SEQ ID NO: 102) has the sequence 5'-GGAATTCTCTAGACTGCAGGT-3', corresponding to nucleotides 1 to 21 of EDT (SEQ ID NO: 103). These oligonucleotides and their use have been previously described (Morgenstern et al. (1991) *Proc. Natl. Acad Sci. USA* 88:9690-9694). ED (SEQ ID NO: 102)/EDT (SEQ ID NO: 103) were used in primary PCRs with oligonucleotide J1 (SEQ ID NO: 99) for amplifications from *J. sabinoides* and *J. virginiana* cDNAs, followed by secondary PCRs with oligonucleotides J2 (SEQ ID NO: 100) and APA (SEQ ID NO: 98) (for *J. sabinoides*) or J3 (SEQ ID NO: 101) and APA (SEQ ID NO: 98) (for *J. virginiana*). No specific product was identified from these amplifications. A final set of PCRs with J1 (SEQ ID NO: 99), J2 (SEQ ID NO: 100), and J3 (SEQ ID NO: 101) was tried with oligonucleotide APA (SEQ ID NO: 98). APA was used in a primary PCR reaction with J1 (SEQ ID NO: 99) for *J. sabinoides* and *J. virginiana*, followed by secondary amplifications with J2 (SEQ ID NO: 100) (for *J. sabinoides*) or J3 (SEQ ID NO: 101) (for *J. virginiana*) and APA (SEQ ID NO: 98). No specific product was identified from these amplifications. The degenerate primer CP-57 (SEQ ID NO: 104) was then synthesized. CP-57 (SEQ ID NO: 104) has the sequence 5'-GGCCTGCAGTTAACAGCGTTTGCA-GAAGGTGCA-3', wherein T at position 10 can also be C, T at position 11 can also be C, A at position 13 can also be G, G at position 16 can also be A, T, or C, G at position 18 can also be T, T at position 19 can also be C, G at position 22 can also be A, T or C, C at position 23 can also be G, A at position 24 can also be C, G at position 25 can also be A, T, or C, A at position 27 can also be G, G at position 28 can also be A, T, or C, G at position 29 can also be C, T at position 30 can also be A, and G at position 31 can also be A. The nucleotides 1 through 9 of CP-57 (SEQ ID NO: 104) were added to create a Pst I site for cloning purposes, the nucleotides 10 through 12 are complementary to a stop codon and nucleotides 13 through 33 are complementary to coding strand sequence essentially encoding the amino acids CysSerLeuSerLysArg-Cys (amino acids 347 through 353 of FIG. 4*b* (SEQ ID NO: 2), corresponding to nucleotides 1167 through 1187 of FIG. 4*b* (SEQ ID NO: 1)). This was used in a primary PCR with J1 (SEQ ID NO: 99) on both *J. sabinoides* and *J. virginiana* double stranded Tinkered cDNA, followed by a secondary PCRs with CP-57 (SEQ ID NO: 104) and J2 (SEQ ID NO: 100) for J. sabinoides and CP-57 (SEQ ID NO: 104) and J3 (SEQ ID NO: 101) for *J. virginiana*. No PCR products were recovered. Three additional degenerate Cry j I oligonucleotides were synthesized. CP-62 (SEQ ID NO: 105) has sequence 5'-CCACTAAATATTATCCA-3', wherein A at position 3 can also be G, A at position 6 can also be G, T at position 9 can also be A or G, and T at position 12 can also be A or G; this degenerate oligonucleotide sequence is complementary to the coding strand sequence essentially encoding the amino acids TrpIleIlePheSerGly (amino acids 69 through 74 of FIG. 4*a* (SEQ ID NO: 2), corresponding to nucleotides 333 through 349 of FIG. 4*a* (SEQ ID NO: 1)). CP-63 (SEQ ID NO: 106) has sequence 5'-GCATCCCCATCTTGGGGATG-3', wherein A at position 3 can also be G, A at position 9 can also be G, T at position 12 can also be C, G at position 15 can also be A, T, or C, and A at position 18 can also be G; this degenerate oligonucleotide sequence is complementary to the sequence capable of encoding the amino acids HisProGl-nAspGlyAspAla (amino acids 146-152 of FIG. 4*a* (SEQ ID NO: 2), corresponding to nucleotides 564 to 583 of FIG. 4*a* (SEQ ID NO: 1)). CP-64 (SEQ ID NO: 107) has the sequence 5'-GTCCATGGATCATAATTATT-3', wherein T at position 6 can also be C, A at position 9 can also be G, A at position 12 can also be G, A at position 15 can also be G, and A at position 18 can also be G; this degenerate oligonucleotide sequence is complementary to the coding strand sequence capable of encoding the amino acids AsnAsnTyrAspProTrpThr (amino acids 243-249 of FIG. 4*b* (SEQ ID NO: 2), corresponding to nucleotides 855 through 874 of FIG. 4*b* (SEQ ID NO: 1)). AP was used in a primary PCR amplification with CP-62 (SEQ ID NO: 105), CP-63 (SEQ ID NO: 106), CP-64 (SEQ ID NO: 107) and CP-3 (SEQ ID NO: 5) (described in Example 3) for both *J. sabinoides* and *J. virginiana* double-stranded Tinkered cDNA. A diagnostic PCR was performed on each primary reaction mixture. In this diagnostic PCR, 3% of the primary reaction was amplified as described above using AP and CP-8. For both *J. sabinoides* and *J. virginiana*, the expected bands of approximately 200 base pairs were observed in diagnostic PCRs from the primary PCR with AP (SEQ ID NO: 21) and CP-63 (SEQ ID NO: 106).

The degenerate primer CP-65 (SEQ ID NO: 108) was then synthesized. CP-65 (SEQ ID NO: 108) has the sequence 5'-GCCCTGCAGTCCCCATCTTGGGGATGGAC-3', wherein A at position 15 can also be G, T at position 18 can also be C, G at position 21 can also be G, A, T, or C, A at position 24 can also be G, and G at position 27 can also be A, T, or C. Nucleotides 1-9 of CP-65 (SEQ ID NO: 108) were added to create a Pst I restriction site for cloning purposes, while the remaining degenerate oligonucleotide sequence is complementary to coding strand sequence essentially capable of encoding the amino acids ValHisProGlnAspGlyAsp (amino acids 145-151 of FIG. 4a (SEQ ID NO: 2), corresponding to nucleotides 561 through 580 of FIG. 4a (SEQ ID NO: 1)). AP was used in conjunction with CP-65 (SEQ ID NO: 108) in a secondary PCR of the primary AP (SEQ ID NO: 21)/CP-63 (SEQ ID NO: 106) amplifications of *J. sabinoides* and *J. virginiana* described above. These reactions were designated JS42 for *J. sabinoides* and JV46 for *J. virginiana*. Both secondary PCRs gave bands of approximately 600 base pairs when examined on 1% agarose minigels stained with EtBr. The DNA from the JS42 and JV46 PCRs was recovered as described in Example 3, simultaneously digested with Xba I and Pst I in 15 µl reactions then electrophoresed through a preparative 2% GTG SeaPlaque low melt gel (FMC, Rockport, Me.). The appropriate sized DNA bands were visualized by EtBr staining, excised, and ligated into appropriately digested pUC19 for sequencing by the dideoxy chain termination method (Sanger et al., supra) using a commercially available sequencing kit (Sequenase kit, U.S. Biochemicals, Cleveland, Ohio). Clones were sequenced using M13 forward and reverse primers (N.E. Biolabs, Beverly, Mass.) and internal sequencing primer J4 (SEQ ID NO: 109) for both Jun s I and Jun v I. J4 (SEQ ID NO: 109) has the sequence 5'-GCTC-CACCATGGGAGGCA-3' (nucleotides 177-194 of FIG. 16 (SEQ ID NO: 94) and nucleotides 187-204 of FIG. 17 (SEQ ID NO: 96)), which is the coding strand sequence that essentially encodes amino acids SerSerThrMetGlyGly (amino acids 30 through 35 of Jun s I (SEQ ID NO: 94) and Jun v I (SEQ ID NO: 96) as shown in FIGS. 16 and 17, respectively).

The sequence of the Jun s I (SEQ ID NO: 94) clone designated pUC19JS42e was found to be identical to that of clones pUC19JS17d and pUC19JS17f in their regions of overlap, although they had different lengths in the 5' untranslated region. Clone pUC 19JS 17d had the longest 5' untranslated sequence. Nucleotides 1 through 141 of FIG. 16 (SEQ ID NO: 94) correspond to sequence of clone pUC19JS17d. Clone pUC19JS42e corresponds to nucleotides 1 through 538 of FIG. 16 (SEQ ID NO: 94).

The sequences of the Jun v I (SEQ ID NO: 96) clones designated pUC19JV46a and pUC19JV46b were identical to the sequence of clone pUC19JV21g in their regions of overlap, with the exception that nucleotide 83 of FIG. 17 (SEQ ID NO: 96) was A in clone pUC19JV21g rather than the T shown. This nucleotide difference does not result in a predicted amino acid change. Clones pUC19JV46a, pUC19JV46b and pUC19JV21g correspond to nucleotides 1 through 548, 1 through 548 and 2 through 151 of FIG. 17 (SEQ ID NO: 96), respectively.

The cDNAs encoding the remainder of the Jun s I (SEQ ID NO: 94) and Jun v I (SEQ ID NO: 96) genes were cloned from the respective linkered cDNAs by using degenerate oligonucleotide CP66 (SEQ ID NO: 110), which has the sequence 5'-CATCCGCAAGATGGGGATGC-3', wherein T at position 3 can also be C, G at position 6 can also be A, T, or C, A at position 9 can also be G, T at position 12 can also be C, and T at position 18 can also be C, and AP (SEQ ID NO: 21) in a primary PCR. The sequence of CP-66 (SEQ ID NO: 110) is complementary to that of CP-63 (SEQ ID NO: 106). A secondary PCR was performed on 3% of the initial amplification mixture, with 100 pmoles each of AP (SEQ ID NO: 21) and CP-67 (SEQ ID NO: 111), which has the sequence 5'-CGG-GAATTCCCTCAAGATGGGGATGCGCT-3', wherein A at position 15 can also be G, T at position 18 can also be C, T at position 24 can also be C, G at position 27 can also be A, T, or C, and C at position 28 can be T. The nucleotide sequence 5'-CGGGAATTC-3' of primer CP-67 (SEQ ID NO: 111) (bases 1 through 9 of SEQ ID NO: 111) were added to create an EcoR I restriction site for cloning purposes. The remaining oligonucleotide sequence essentially encodes amino acids ProGlnAspGlyAspAlaLeu (amino acids 147 through 153 of FIG. 4a (SEQ ID NO: 2), corresponding to nucleotides 567 through 586 of FIG. 4a (SEQ ID NO: 1)). The amplified DNA products, designated JS45 from the *J. sabinoides* amplification and JV49ii from the *J. virginiana* amplification, were purified as described in Example 3, digested with EcoR I and Xba I (JS45) or EcoR I and Asp718 I (JV49ii) and electrophoresed through a preparative 1% low melt gel. The dominant DNA bands, which were approximately 650 bp in length, were excised and ligated into pUC19 for sequencing. DNA was sequenced by the dideoxy chain termination method (Sanger et al. supra) using a commercially available kit (sequenase kit, U.S. Biochemicals, Cleveland, Ohio).

Two clones, designated pUC19JS45a and pUC19JV49iia for Jun s I (SEQ ID NO: 94) (and Jun v I (SEQ ID NO: 96), respectively, were sequenced using M13 forward and reverse primers (N.E. BioLabs, Beverly, MA) and internal sequencing primers J8 (SEQ ID NO: 112), J9 (SEQ ID NO: 113), and J12 (SEQ ID NO: 114) for Jun s I, and J6 (SEQ ID NO: 115) and J11 (SEQ ID NO: 116) for Jun v I. J8(SEQ ID NO: 112) has the sequence 5'-TAGGACATGATGATACAT-3' (nucleotides 690-707 of FIG. 16 (SEQ ID NO: 94)), which is the coding strand sequence essentially encoding amino acids LeuGlyHisAspAspThr of Jun s I (SEQ ID NO: 282) (amino acids 201-206 of FIG. 16 (SEQ ID NO: 95)). J9 (SEQ ID NO: 113) has the sequence 5'-GAGATCTACACGAGATGC-3' (nucleotides 976-993 of FIG. 16 (SEQ ID NO: 94)) which is the coding strand sequence essentially encoding amino acids ArgSerThrArgAspAla of Jun s I, (SEQ ID NO: 283) (amino acids 297-302 of FIG. 16 (SEQ ID NO: 95)). J12 (SEQ ID NO: 114 has the sequence 5'-AAAACTATTCCCTTCACT-3', wherein A at position 1 can also be G, and A at position 4 can also be T. This is the non-coding strand sequence that corresponds to coding strand sequence (nucleotides 875-892 of FIG. 16 (SEQ ID NO: 94) encoding amino acids SerGluG-lyAsnSerPhe (SEQ ID NO: 279) of Jun SI (amino acids 263-268 of FIG. 16 (SEQ ID NO: 95)). J6(SEQ ID NO: 115) has the sequence 5'-TAGGACATAGTGATTCAT-3' (nucleotides 700-717 of FIG. 17 (SEQ ID NO: 96)), which is the coding strand sequence essentially encoding amino acids LeuGlyHisSerAspSer (SEQ ID NO: 280) of Jun v I (amino acids 201-206 of FIG. 17 (SEQ ID NO: 97)). J11 (SEQ ID NO: 116) has the sequence 5'-CCGGGATCCTTA-CAAATAACACATTAT-3', where nucleotides 1-9 encode a BamH I restriction site for cloning purposes and nucleotides 10-27 correspond to noncoding strand sequence complementary to nucleotides 1165-1182 of FIG. 17 (SEQ ID NO: 96) in the 3' untranslated region of Jun v I. The sequence of clone pUC19JS45a corresponds to nucleotides 527 through 1170 of FIG. 16 (SEQ ID NO: 94). The sequence of clone pUC29JV49iia corresponds to nucleotides 537 through 1278 of FIG. 17 (SEQ ID NO: 96).

A full length clone of Jun s I was amplified using PCR. Oligonucleotides J7 (SEQ ID NO: 117) and J10 (SEQ ID NO: 118) were used in a PCR reaction as above with J. sabinoides double stranded, linkered cDNA. J7 (SEQ ID NO: 117) has the sequence 5'-CCCGAATTCATGGCTTCCCCAT-GCTTA-3', where nucleotides 1-9 encode an EcoR I restriction site added for cloning purposes and nucleotides 10-27 (corresponding to nucleotides 2643 of FIG. 16 (SEQ ID NO: 94)) are the coding strand sequence that encode amino acids MetAlaSerProCysLeu (SEQ ID NO: 281) of Jun s I (amino acids −21 to −16, FIG. 16 (SEQ ID NO: 95)). J10 (SEQ ID NO: 118) has the sequence 5'-CCGGGATCCCGTTTCAT-AAGCAAGATT-3', where nucleotides 1-9 encode a BamH I restriction site added for cloning purposes and nucleotides 10-27 are the non-coding strand sequence complementary to nucleotides 1140-1157 from the 3' untranslated region of Jun s I (FIG. 16 (SEQ ID NO: 94)). The PCR product, designated JS53ii, gave a band of approximately 1200 bp when examined on a 1% agarose minigel stained with EtBr. The DNA from the JS53ii PCR was recovered as described in Example 3. After precipitation and washing with 70% EtOH, the DNA was simultaneously digested with EcoR I and BamH I in a 15 µl reaction and electrophoresed through a preparative 1% GTG SeaPlaque low melt gel (FMC, Rockport, ME). The appropriate sized DNA band was visualized by EtBr staining, excised, and ligated into appropriately digested pUC19 for sequencing by the dideoxy chain termination method (Sanger et al. (1977) supra) using a commercially available sequencing kit (Sequenase kit, U.S. Biochemicals, Cleveland, OH). The resultant clone, pUC19JS53iib was partially sequenced using M13 forward and reverse primers (N.E. Biolabs, Beverly, MA) and internal sequencing primer J4 (SEQ ID NO: 109). The sequence of pUC19JS53iib that was determined was identical to that obtained from clones pUC19JS17d, pUC19JS42e, and pUC19JS45a. The nucleotide sequence of clone pUC19JS53iib corresponds to nucleotides 26 through 1157 of FIG. 16 (SEQ ID NO: 94).

The nucleotide and predicted amino acid sequences of Jun s I are shown in FIG. 16 (SEQ ID NO: 64 and 65). Jun s I has an open reading frame of 1101 nucleotides, corresponding to nucleotides 26 through 1126 of FIG. 16 (SEQ ID NO: 94), that can encode a protein of 367 amino acids. Nucleotides 1-25 and 1130-1170 of FIG. 16 (SEQ ID NO: 94) are untranslated 5' and 3' regions, respectively. The initiating Met, encoded by nucleotides 26-28 of FIG. 16 (SEQ ID NO: 94), has been identified through the 89% identity of nucleotides 23 through 30 (AAAAATGGC) of FIG. 16 (SEQ ID NO: 94) with the consensus sequence encompassing the initiating Met in plants (AACAATGGC; Lutcke, supra). There is also an in-frame stop codon just 5' of the codon encoding the initiating Met. Amino acids −21 to −1 of FIG. 16 (SEQ ID NO: 95) correspond to a predicted leader sequence. The amino terminus of the mature form of Jun s I was identified as amino acid 1 of FIG. 16 (SEQ ID NO: 95) through direct protein sequence analysis of purified Jun s I (Gross et al supra). The mature form of Jun s I, corresponding to amino acids 1 through 346 of FIG. 16 (SEQ ID NO: 95), has a predicted molecular weight of 37.7 kDa. Jun s I has three potential N-linked glycosylation sites with the consensus sequence of Asn-Xxx-Ser/Thr.

The nucleic and predicted amino acid sequences of Jun v I are shown in FIG. 17 (SEQ ID NO: 96 and 97). Nucleotides 1-35 and 1130-1170 of SEQ ID NO: 96 are untranslated 5' and 3' regions, respectively. The initiating Met, encoded by nucleotides 36-38 of FIG. 17 (SEQ ID NO: 96), was identified through the 89% identity of nucleotides 23 through 30 (AAAAATGGC) of FIG. 17 (SEQ ID NO: 96) with the consensus sequence encompassing the initiating Met in plants (AACAATGGC; Lutcke, supra). The nucleic acids of Jun s I (FIG. 16 (SEQ ID NO: 94)) and Jun v I (FIG. 17 (SEQ ID NO: 96)) are identical in this region surrounding the initiating Met. There are also 2 in-frame stop codons in the 5' untranslated region of FIG. 17 (SEQ ID NO: 96). Jun v I has an open reading frame of 1,110 nucleotides, corresponding to nucleotides 36 through 1145 of FIG. 17 (SEQ ID NO: 96), that can encode a protein of 370 amino acids. Nucleotides 1146-1148 of FIG. 17 (SEQ ID NO: 96) encode a stop codon. Amino acids −21 to −1 of Jun v I (FIG. 17 (SEQ ID NO: 97)) correspond to a predicted leader sequence. The amino terminus of the mature form of Jun v I was identified as amino acid 1 of FIG. 17 (SEQ ID NO: 97) by comparison with the sequences of Cry j I (FIG. 4a) (SEQ ID NO: 2) and Jun s I (FIG. 16) (SEQ ID NO: 95). The mature form of Jun v I, corresponding to amino acids 1 through 349 of FIG. 17 (SEQ ID NO: 97) has a predicted molecular weight of 38.0 kDa. Jun v I has four potential N-linked glycosylation sites with the consensus sequence of Asn-Xxx-Ser/Thr.

As shown in Table 1, the amino acid sequences of the mature forms of Jun s I and Jun v I are 80.9% homologous (75.4% identity and 5.5% similarity) with each other. The amino acid sequences of the mature forms of Jun s I and Cry j I are 87% homologous (80.1% identity, 6.9% similarity) and the sequences of the mature forms of Jun v I and Cry j I are 80.5% homologous (72.5% identity, 8% similarity). The homologies between Cry j I peptide sequences identified in Example 6 as containing T cell epitopes and the corresponding Jun s I and Jun v I sequences are also very high. For example, peptide CJ1-22 (SEQ ID NO: 47) (FIG. 13), corresponding to amino acids 211-230 of Cry j I (FIG. 4b) (SEQ ID NO: 2), contains a major T cell epitope (FIG. 14). CJ1-22 (SEQ ID NO: 47) has 95% identity (19/20 identical amino acids) and 85% homology (16/20 identical amino acids, 1/20 similar amino acid) with the corresponding regions of Jun s I (SEQ ID NO: 95) and Jun v I (SEQ ID NO: 97), respectively (see Table I). This high degree of sequence homology suggests that an immunotherapy effective in treating allergic disease caused by Cry j I may also be effective in treating allergic diseases caused by Cry j I homologues. All nucleic and amino acid analyses were performed using software contained in PCGENE (Intelligenetics, Mountain View, Calif.).

TABLE I

| Protein/Peptide Comparisons | Identity | Similarity | Total Homology |
|---|---|---|---|
| Jun s I vs. Jun v I | 75.4% | 5.5% | 80.9% |
| Jun s I vs. Cry j I | 80.1% | 6.9% | 87.9% |
| Jun v I vs. Cry j I | 72.5% | 8.0% | 80.5% |
| CJ1-22 vs. Jun s $I_{211-230}$ | 95.0% | 0.0% | 95.0% |
| CJ1-22 vs. Jun v $I_{211-230}$ | 80.0% | 5.0% | 85.0% |

Native Jun s I or Jun v I can also be biochemically purified using known techniques or purified by other means to a high degree of purity by amino acid sequencing of the purified native product and comparing the sequence of the purified native product to the amino acid sequence of Jun s I or Jun v I provided herein.

EXAMPLE 10

Northern blot analysis of *C. japonica, J. sabinoides, J. virginiana* and *C. arizonica* RNA.

Figure 19A:
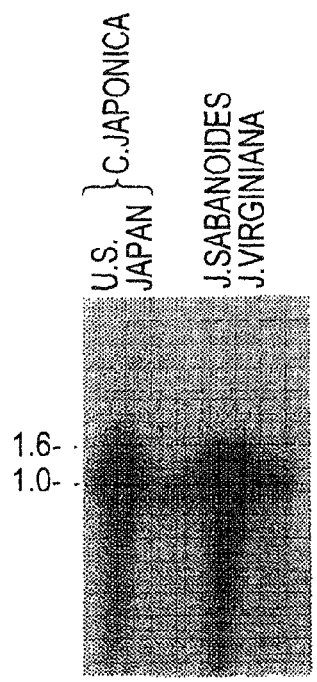
FIGS. 19a and 19b show Northern blots of pollen-derived RNA probed with Cry j cDNA for identification of mRNA capable of encoding Cry j I or a Cry j I homologue.
Figure 19B:
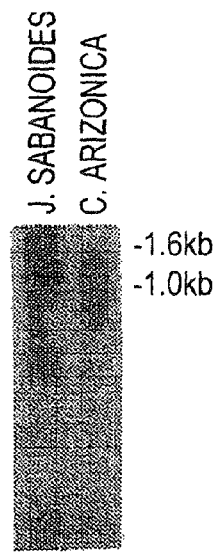

A Northern blot analysis was performed on RNA isolated from *C. japonica, J. sabinoides* and *J. virginiana* pollens. RNA from *C. japonica* pollens collected in both the United States (Example 3) and Japan (Example 4) were examined. Using essentially the method of Sambrook, supra, 15 µg of each RNA were run on a 1.2% agarose gel containing 38% formaldehyde and 1×MOPS (20×=0.4M MOPS, 0.02M EDTA, 0.1 M NaOAc, pH 7.0) solution. The RNA samples (first precipitated with 1/10 volume sodium acetate, 2 volumes ethanol to reduce volume and resuspended in 5.5 µl dH2O) were run with 10 µl formaldehyde/formamide buffer containing loading dyes with 15.5% formaldehyde, 42% formamide, and 1.3×MOPS solution, final concentration. The samples were transferred to Genescreen Plus (NEN Research Products, Boston, Mass.) by capillary transfer in 10×SSC (20×=3M NaCl, 0.3M Sodium Citrate), after which the membrane was baked 2 hr. at 80° C. and UV irradiated for 3 minutes. Prehybridization of the membrane was at 60° C. for 1 hour in 4 ml 0.5M NaPO4 (pH 7.2), 1 mM EDTA, 1% BSA, and 7% SDS. The antisense probe was synthesized by asymmetric PCR (McCabe, P. C., in: PCR Protocols. A Guide to Methods and Applications, Innis, M., et al., eds. Academic Press, Boston, (1990), pp 76-83) on the JC91a amplification in low melt agarose (described in Example 3), where 2 µl DNA is amplified with 2 µl dNTP mix (0.167 mM dATP, 0.167mM dTTP, 0.167mM dGTP, and 0.033mM dCTP), 2 µl 10×buffer, 10 µl $^{32}$P-dCTP (100 µCi; Amersham, Arlington Heights, Ill.), 1 µl (100 pmoles) antisense primer CP-17 (SEQ ID NO: 14), 0.5 µl Taq polymerase, and dH$_2$O to 20 µl; the 10×PCR buffer, dNTPs and Taq polymerase were from Perkin Elmer Cetus (Norwalk, Conn.). Amplification consisted of 30 rounds of denaturation at 94° C. for 45 sec, annealing of primer to the template at 60° C. for 45 sec, and chain elongation at 72° C. for 1 min. The reaction was stopped by addition of 100 µl TE, and the probe recovered over a 3 cc G-50 spin column (2 ml G-50 Sephadex [Pharmacia, Uppsala, Sweden] in a 3 cc syringe plugged with glass wool, equilibrated with TE) and counted on a 1500 TriCarb Liquid Scintillation Counter (Packard, Downers Grove, Ill.). The probe was added to the prehybridizing buffer at $10^6$ cpm/ml and hybridization was carried out at 60° C. for 16 hrs. The blot was washed in high stringency conditions: 3×1 min at 65° C. with 0.2×SSC/ 1% SDS, followed by wrapping in plastic wrap and exposure to film at −80° C. A seven hour exposure of this Northern blot revealed a single thick band at approximately 1.2 kb for *C. japonica* (United States) (FIG. 19*a*, lane 1), *C. japonica* (Japan) (FIG. 19*a*, lane 2), *J. sabinoides* (FIG. 19*a*, lane 3) and *J. virginiana* (FIG. 19*a*, lane 4) RNAs. This band is the expected size for Cry j I, Jun s I and Jun v I as predicted by PCR analysis of the cDNA. The different band intensities in each lane may reflect differences in the amount of RNA loaded on the gel. The position of 1.6 and 1.0 kb molecular weight standards are shown on the FIGS. 19*a* and 19*b*.

RNA isolated from *J. sabinoides* and *C. arizonica* were analyzed in a separate Northern blot. Five µg of total RNA from *J. sabinoides* and 5 µg of total RNA from *C. arizonica* were probed as described. The 1.2 kb band was observed in this blot for both *J. sabinoides* (FIG. 19*b*, lane 1) and *C. arizonica* (FIG. 19*b*, lane 2), indicating that *C. arizonica* has a Cry j I homologue. Other, related, trees are also expected to have a Cry j I homologue.

EXAMPLE 11

Japanese Cedar Pollen Allergic Patient T Cell Studies with Cry j I—the Primary Cedar Pollen Antigen.
Synthesis of Peptides Japanese cedar pollen Cry j I peptides were synthesized using standard Fmoc/tBoc synthetic chemistry and purified by Reverse Phase HPLC. FIG. 20 shows Cry j I peptides used in these studies. The peptide names are consistent throughout.
T Cell Responses to Cedar Pollen Antigen Peptides Peripheral blood mononuclear cells (PBMC) were purified by lymphocyte separation medium (LSM) centrifugation of 60 ml of heparinized blood from Japanese cedar pollen-allergic patients who exhibited clinical symptoms of seasonal rhinitis and were MAST and/or skin test positive for Japanese cedar pollen. Long term T cell lines were established by stimulation of $2\times10^6$ PBL/ml in bulk cultures of complete medium (RPMI-1640, 2 mM L-glutamine, 100 U/ml penicillin/streptomycin, $5\times10^{-5}$M 2-mercaptoethanol, and 10 mM HEPES supplemented with 5% heat inactivated human AB serum) with 20 µg/ml of partially purified native Cry j I (75% purity containing three bands similar to the three bands in FIG. 2) for 6 days at 37° C. in a humidified 5% CO$_2$ incubator to select for Cry j I reactive T cells. This amount of priming antigen was determined to be optimal for the activation of T cells from most cedar pollen allergic patients. Viable cells were purified by LSM centrifugation and cultured in complete medium supplemented with 5 units recombinant human IL-2/ml and 5 units recombinant human IL4/ml for up to three weeks until the cells no longer responded to lymphokines and were considered "rested". The ability of the T cells to proliferate to selected Cry j I peptides, partially purified Cry j I, affinity purified Cry j I, or positive (PHA) controls or negative controls (medium only) was then assessed. For assay, $2\times10^4$ rested cells were restimulated in the presence of $2\times10^4$ autologous Epstein-Barr virus (EBV)-transformed B cells (prepared as described below) (gamma-irradiated with 25,000 RADS) with 2-50 µg/ml of rCry j I, purified native Cry j I in a volume of 200 µl complete medium in duplicate or triplicate wells in 96-well round bottom plates for 2-4 days. The optimal incubation was found to be 3 days. Each well then received 1 µCi tritiated thymidine for 16-20 hours. The counts incorporated were collected onto glass fiber filter mats and processed for liquid scintillation counting. Titrations using T cells from one individual were conducted which showed the effect of varying antigen dose in assays with purified native Cry j I and several the peptides synthesized as described above. The titrations were used to optimize the dose of peptides in T cell assays.

The maximum response in a titration of each peptide is expressed as the stimulation index (S.I.). The S.I. is the counts per minute (CPM) incorporated by cells in response to peptide, divided by the CPM incorporated by cells in medium only. An S.I. value equal to or greater than 2 times the background level is considered "positive" and indicates that the peptide contains a T cell epitope. The positive results were used in calculating mean stimulation indices for each peptide for the individual patient tested.

Figure 21:
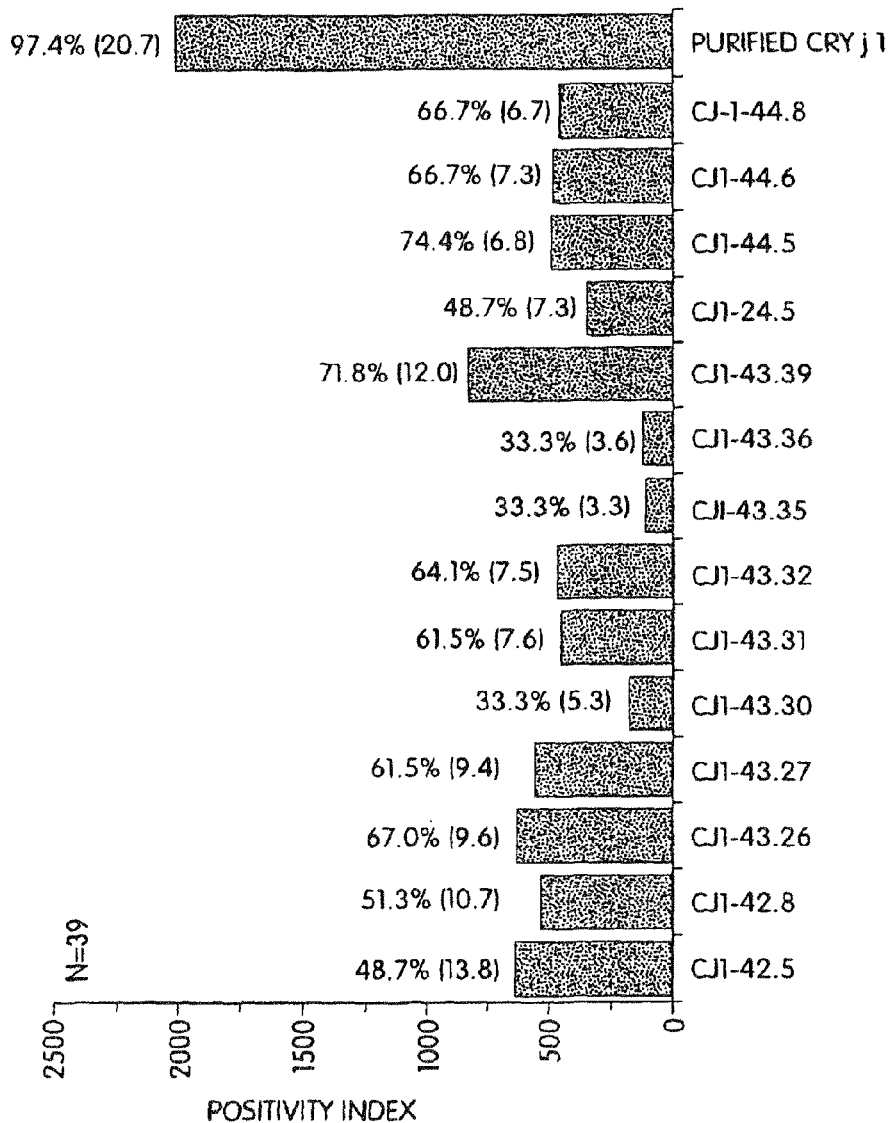
FIG. 21 is a graphic representation depicting regions of T cell lines from 26 patients primed in vitro with and analyzed for response to various Cry j I peptides and affinity purified Cry j I peptides by percent of responses.

The above procedure was followed with 39 patients. Individual patient results were used in calculating the mean S.I. for each peptide if the patient responded to the Cry j I protein at an S.I. of 2.0 or greater and the patient responded to at least one peptide derived from Cry j I at an S.I. of 2.0 or greater. A summary of positive experiments from thirty-nine (n=39) patients is shown in FIG. 21. The bars represent the positivity index. Above each bar is the percent of positive responses with an S.I. of at least two to the peptide or protein in the group of patients tested. In parenthesis above each bar are the mean stimulation indices for each peptide or protein for the group of patients tested. All but one of the thirty-nine T cell lines responded to purified native Cry j I. However, the one T cell line which did not respond to purified native Cry j I did respond to peptides derived from Cry j I. This panel of Japanese cedar allergic patients responded to peptides: CJ1-42.5 (SEQ ID NO: 119), CJ1-42.8 (SEQ ID NO: 120), CJ1-43.26 (SEQ ID NO: 121), CJ1-43.27 (SEQ ID NO: 122), CJ1-43.30 (SEQ ID NO: 123), CJ1-43.31 (SEQ ID NO: 124), CJ1-43.32 (SEQ ID NO: 125), CJ1-43.35 (SEQ ID NO: 126), CJ1-43.36 (SEQ ID NO: 127), CJ1-43.39 (SEQ ID NO: 128), CJ1-24.5 (SEQ ID NO: 129), CJ1-44.5 (SEQ ID NO: 130), CJ1-44.6 (SEQ ID NO: 131), CJ1-44.8 (SEQ ID NO: 132) all as shown in FIG. 20, indicating that these peptides contain T cell epitopes. Preparation of (EBV)-transformed B Cells for Use as Antigen Presenting Cells was described in Example 6, supra.

EXAMPLE 12

Figure 22:
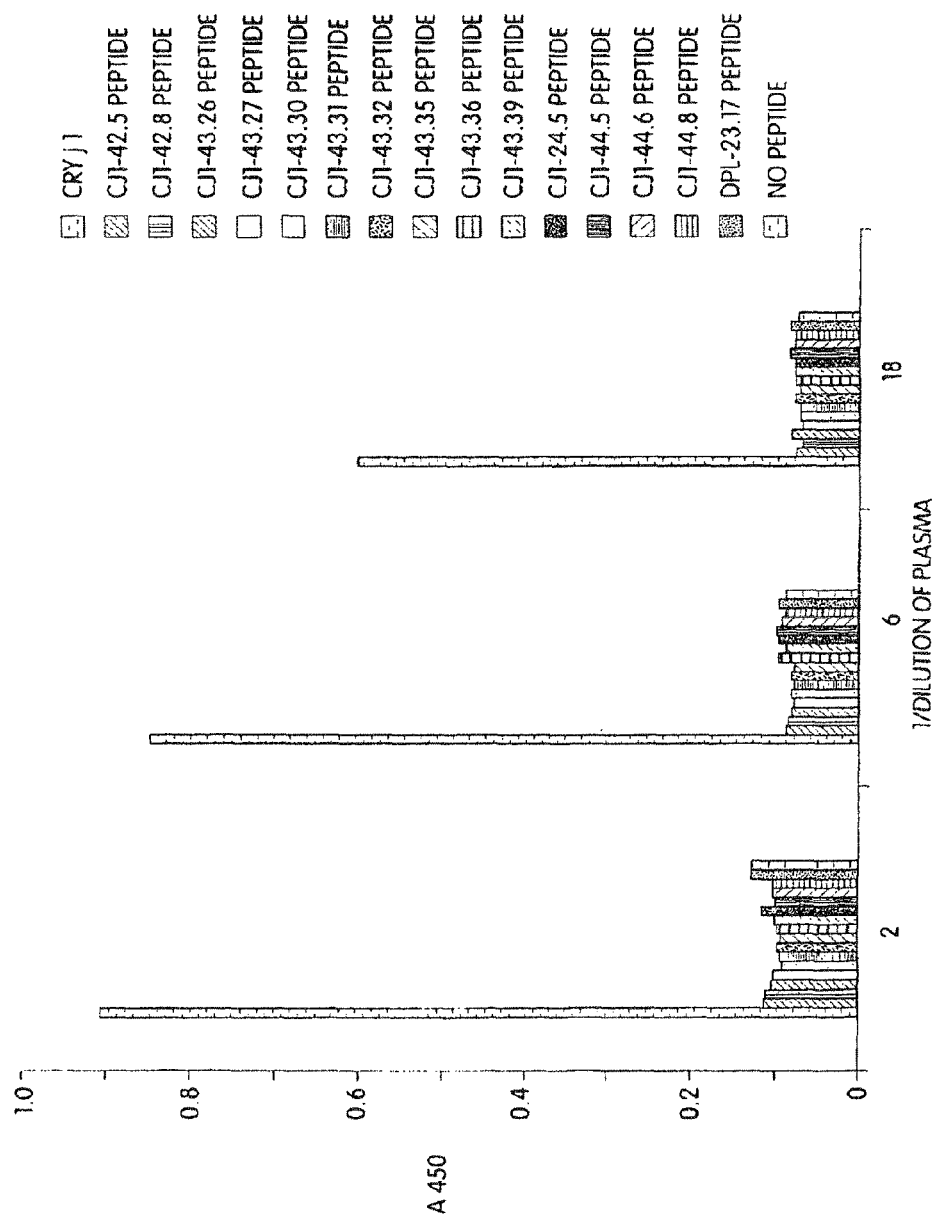
FIG. 22 is a graphic representation of a direct ELISA assay wherein wells were coated with peptides derived from Cry j I and then assayed for IgE binding to patient plasma pool A (PHP-A)
Figure 23:
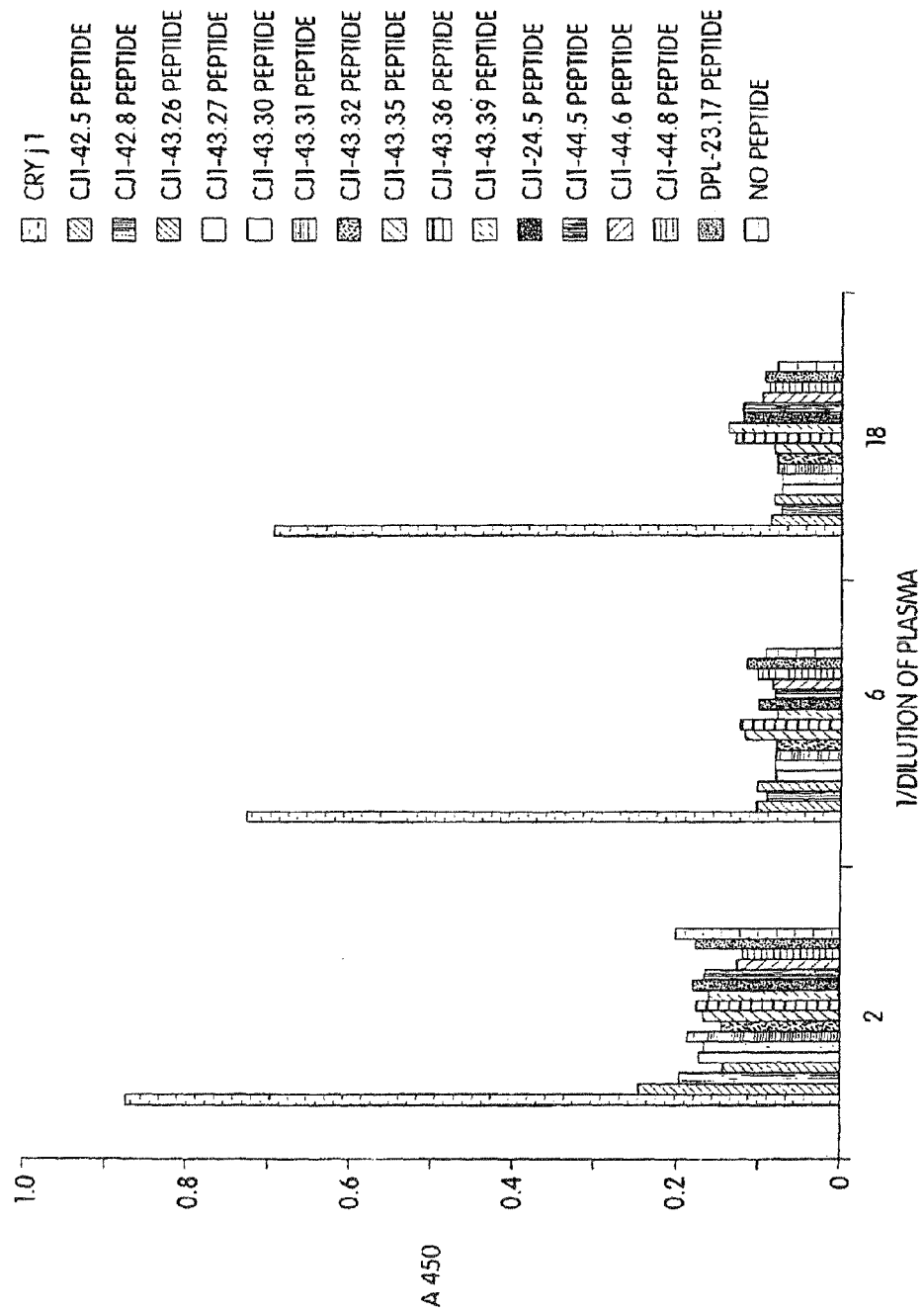
FIG. 23 is a graphic representation of a direct ELISA assay wherein wells were coated with peptides derived from Cry j I and then assayed for IgE binding to patient plasma pool D (PHP-D)
Figure 24:
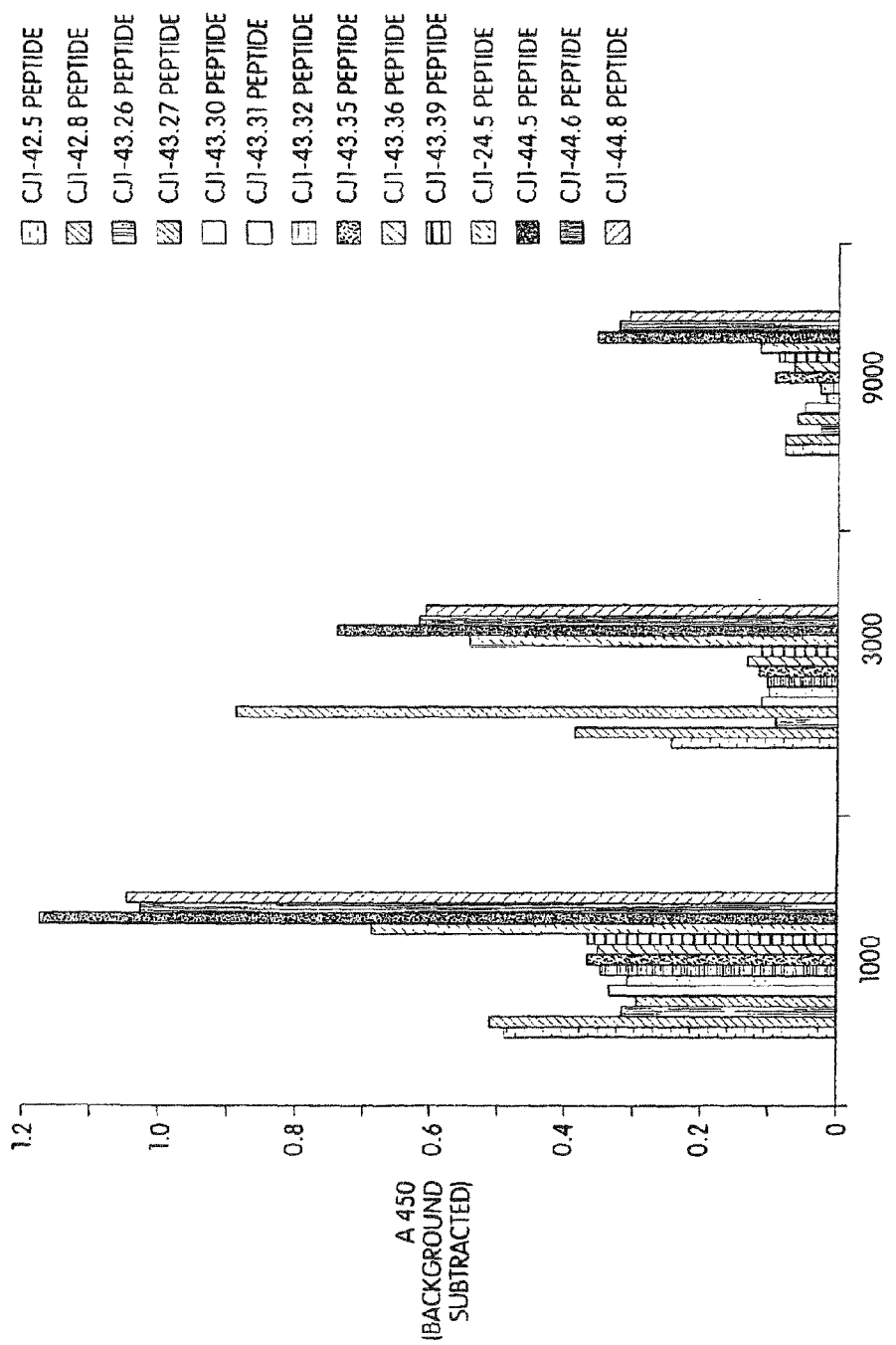
FIG. 24 is a graphic representation of a direct ELISA used to control for the presence of Cry j I peptide coating the wells; mouse polyclonal antisera was generated to the peptides

Cry j I Peptide Screen.
To analyze IgE reactivity to the selected peptides discussed in example 11 and shown in FIG. 20, a direct ELISA format was used. ELISA wells were coated with the selected peptides derived from Cry j I and then assayed for IgE binding. FIGS. 22 and 23 are graphs of these binding results using two different pools of Cry j allergic patient plasma. Patient plasma pool A (denoted PHP-A) (FIG. 22) was formulated by mixing equal volumes of plasma from 22 patients that were all shown to be positive for direct IgE binding to native purified Cry j I by ELISA. The second pool (PHP-D) (FIG. 23) was formulated by the combination of equal plasma volumes from 8 patients that had IgE binding by direct ELISA to both native and denatured purified Cry j I. This pool was generated to increase the chance of detecting reactivity towards peptides. Both pools in this assay set show direct binding to the native purified Cry j I, FIG. 22 and FIG. 23. There was no detectable IgE binding reactivity to any of the peptides at any of the plasma concentrations used. To control for the presence of peptide coating the wells, mouse polyclonal antisera was generated to the peptides. These antisera were then used in direct ELISA binding to demonstrate that the peptides were coating the wells. The results of these assays are shown in FIG. 24, and indicate that peptides were coating the wells.

In addition, 20 allergic patients which demonstrated IgE binding to Cry j I were examined for IgE reactivity to peptides CJ1-24.5, CJ1-43.39, and CJ1-44.8 using essentially the same protocol described above. No patient showed IgE binding to peptides CJ1-24.5, CJ1-43.39, and CJ1-44.8, or to the controls of patient plasma on oncoated blocked wells (gelatin) or to an irrelevant peptide (data not shown).

EXAMPLE 13

Purification of Native Japanese Cedar Pollen Allergen (Cry j II)

The following purification of native Cry j II from Japanese cedar pollen was modified from previously published reports (Yasueda et al, *J. Allergy Clin. Immunol.* 71:77 (1983); Sukaguchi et al., *Allergy*, 45:309 (1990)).

100 g of Japanese cedar pollen obtained from Japan (Hollister-Stier, Spokane, Wash.) was defatted in 1 L diethyl ether three times, the pollen was collected after filtration and the ether was dried off in a vacuum.

The defatted pollen was extracted at 4° C. overnight in 2 L extraction buffer containing 50 mM tris-HCl, pH 7.8, 0.2 M NaCl and protease inhibitors in final concentrations: soybean trypsin inhibitor (2 μg/mL), leupeptin (1 μg/mL), pepstatin A (1 μg/mL) and phenyl methyl sulfonyl fluoride (0.17 mg/mL). The insoluble material was re-extrated with 1.2 L extraction buffer at 4° C. overnight and both extracts were combined together and depigmented by batch absorption with Whatman DE-52 (200 g dry weight) equilibrated with the extraction buffer.

The depigmented material was then fractionated by ammonium sulfate precipitation at 80% saturation (4° C.), which removed much of the lower molecular weight material. The resulting pellet was resuspended in 0.4 L of 50 mM Na-acetate, pH 5.0 containing protease inhibitors and was dialyzed extensively against the same buffer.

The sample was further subjected to purification by either one of the two methods described below.

Method A

The sample was applied to a 100 mL DEAE cellulose column (Whatman DE-52) equilibrated at 4° C. with 50 mM Na-acetate, pH 5.0 with protease inhibitors. The unbound material (basic proteins) from the DEAE cellulose column was then applied to a 50 ml cation exchange column (Whatman CM-52) which was equilibrated with 10 mM Na-acetate, pH 5.0 at 4° C. with protease inhibitors. A linear gradient of 0-0.3 M NaCl was used to elute the proteins. The early fractions were enriched in Cry j I whereas the later fractions were enriched in Cry j II. Fractions containing Cry j II were pooled and next applied to an 1 mL Mono S HR 5/5 column (Pharmacia, Piscataway, N.J.) in 10 mM Na-acetate, pH 5.0, and proteins were eluted with a linear gradient of NaCl at room temperature. Residual Cry j I was eluted at –0.2 M NaCl and Cry j II was eluted between 0.3 to 0.4 M NaCl. The Cry j II peak was pooled and concentrated to twofold by lyophilization and subjected to gel filtration chromatography.

Figure 25A:
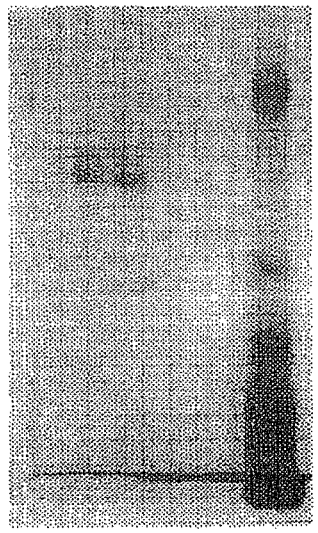
FIG. 25a shows an SDS-PAGE (12%) analysis of Cry j II under non-reducing conditions.

The sample was applied to FPLC Superdex 75 16/60 column (Pharmacia, Piscataway, N.J.) in 10 mM acetate buffer, pH 5.0 and 0.15 M NaCl at a flow rate of 30 ml/min. at room temperature. Purified Cry j II was recovered in the 35-30 kD region. Cry j II migrated as two broad bands lower than Cry j I under non-reducing conditions (FIG. 25*a*) but both bands shifted upward and migrated as Cry j I under reducing condition (FIG. 25*b*) when analyzed by silver-stained SDS-PAGE. This highly purified Cry j II still contained a small amount (–5%) of Cry j I as detected by Western blot using MAb CBF2, which has been shown to bind to Cry j I and by N-terminal protein sequencing. This Cry j II preparation was used to generate primary protein sequence of Cry j II as described below.

Method B

The dialyzed sample from the ammonium sulfate precipitation was applied at 1 ml/min to an 5.0 ml Q-Sepharose Econapac anion exchange cartridge (BioRad, Richmond, Calif.) equilibrated with 50 mM Na-acetate, pH 5.0 with protease inhibitors at 4° C. Elution was performed with the above buffer containing 0.5 M NaCl. The basic unbound material was then applied to a 5.0 ml CM-Sepharose Econopac cation exchange cartridge (BioRad, Richmond, Calif.) equilibrated in 50 mM sodium acetate pH 5.0 with protease inhibitors. Basic proteins were eluted with a linear gradient up to 0.1 M sodium phosphate pH 7.0, 0.3 M NaCl at 1 ml/min at 4° C. A Cry j II-enriched peak was collected late in the gradient and further purified by gel filtration chromatography.

FPLC gel filtration was performed using a 320 mL Superdex 75 26/60 (Pharmacia, Piscataway, N.J.) column at 0.5 ml/min in 20 mM sodium acetate, pH 5.0, in the presence of 0.15 M NaCl. The major peak containing mostly Cry j II eluted between 160 and 190 ml. Contaminating Cry j I was next removed by FPLC using a 1.0 ml Mono 5 S 5/5 (Pharmacia, Piscataway, N.J.) cation exchange column equilibrated with 10 mM sodium acetate pH 5.0. A stepwise gradient of 0-1 M NaCl was utilized by holding isocratically at 0.2 M, 0.3 M, 0.4 M and 1 M salt concentration.

Figure 26:
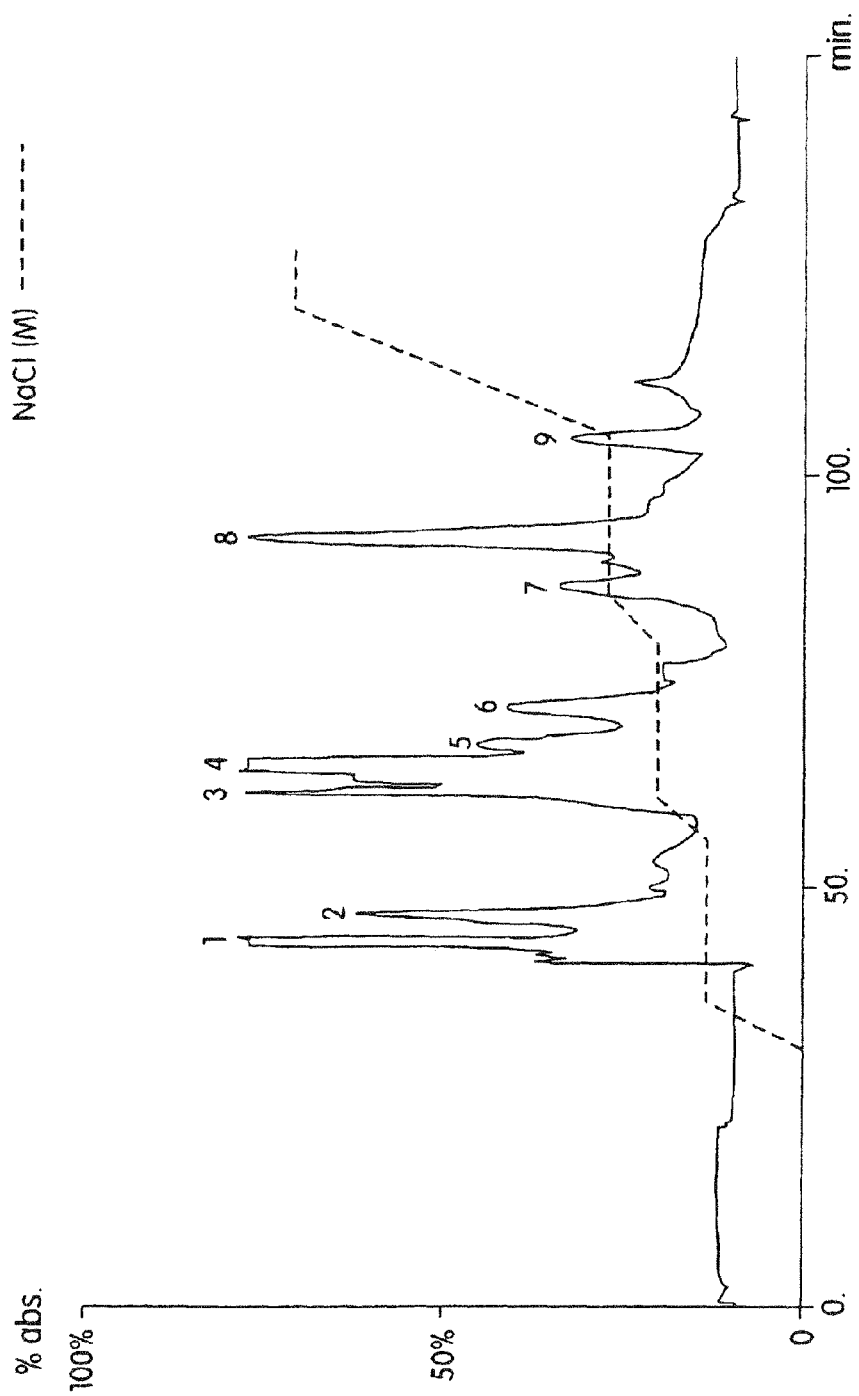
FIG. 26 shows the results of mono S column chromatography of Cry j II eluted with a step gradient of NaCl in 10 mM sodium acetate buffer, pH 5.0.
Figure 27:
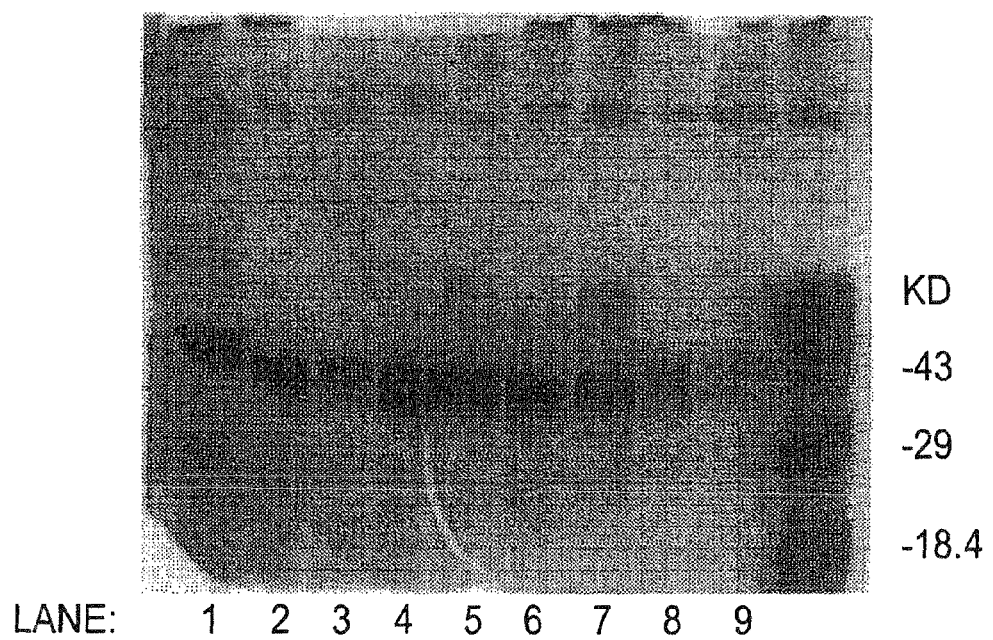
FIG. 27 shows an SDS-PAGE (12%) of purified subfractions of Cry j II analyzed under reducing conditions.

Multiple peaks (up to nine peaks) were obtained (FIG. 26) and analyzed by silver stained SDS-PAGE under reducing conditions (FIG. 27). Cry j I with a reported pI of 8.6-8.9 (Yasueda et al, *J. Allergy Clin. Immunol.*, 17 (1983)), eluted in the earlier peaks and displayed a molecular weight of about 40 kD. Cry j II was purified to homogeneity as two bands (FIG. 27) and eluted in the later multiple peaks, suggesting the existence of isoforms. ELISA analysis using the mouse monoclonal 8B11 IgG antibody which was raised against biochemically purified Cry j I confirmed the absence of Cry j I in these purified Cry j II preparation. This purified Cry j II was used in the human IgE reactivity studies (Example 18).

Physical Properties of Cry j II

Figure 25B:
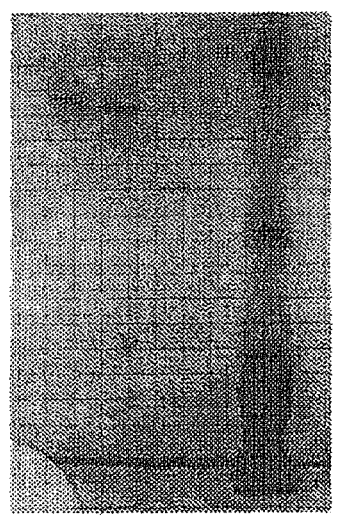
FIG. 25b shows an SDS-PAGE (12%) analysis of Cry j II under reducing conditions.

The physiochemical properties of Cry j II were studied and summarized as below. Under non-reducing SDS-PAGE conditions Cry j II consists of two bands with molecular weights ranged 34000-32000. The molecular weights of both bands are shifted higher to about 38-36 kD under reducing conditions (FIG. 25*b*). This shift in SDS-polyacrylamide gel has also been observed by others (Sakaguchi et al, *Allergy*

45:309-312 (1990)). These results suggest that intra-disulfide bonds are probably present in the protein, and it is supported by the present findings that cloned Cry j II contains 20 cysteines deduced from the nucleotide sequence (Example 15). The pI of Cry j II estimated from IEF gel is about 10. The purified Cry j II binds human IgE of some allergic patients.

The two molecular weight bands of Cry j II were separated on a 12% SDS-polyacrylamide gel and was then electroblotted onto PVDF membrane (Applied Biosystems, Foster City, Calif.). The blot was stained with coomassie brilliant blue and was cut and subjected to N-terminal amino acid sequencing. (Example 14). The results showed that the upper and lower molecular weight bands had identical N-terminal sequences except the lower molecular weight band missed the first five amino acids. The estimated molecular weight of the upper band based on the cDNA sequence is about 52,000, which is significantly higher than the molecular weight estimated from SDS-polyacrylamide gel either in the presence or absence of reducing reagent. It is also higher than that obtained from gel filtration and preliminary mass spectroscopy analysis. These are several possibilities to account for this difference. One possibility is that Cry j II protein is processed. It is probable that the N-terminal and C-terminal of the protein are cleaved. It is not clear at the present time whether this processing occurs in the cell or due to proteolysis during purification even though four different protease inhibitors were added in most of the purification steps. Nevertheless, the two N-terminal sequences obtained from the purified Cry j II (Example 14) also contained the N-terminal sequence (10 amino acid) published by Sakaguchi et al (*Allergy*, 45:309-312(1990)) suggesting that the N-terminal of Cry j II is probably hydrolyzed. Since Sakaguchi et al. (supra), did not use any protease inhibitors in their purification, a higher degree of hydrolysis might have occurred. This could explain why the N-terminal amino acid sequence that Sakaguchi et al. obtained was downstream of the N-terminal sequences as discussed in Example 14.

Another approach which may be used to purify native Cry j II or recombinant Cry j II is immunoaffinity chromatography. This technique provides a very selective protein purification due to the specificity of the interaction between monoclonal antibodies and antigen. Murine polyclonal and monoclonal antibodies are generated against purified Cry j II. These antibodies are used for purification, characterization, analysis and diagnosis of the allergen Cry j II.

EXAMPLE 14

Protein Sequencing of Purified Cry j II

Cry j II protein was isolated as in Example 1. The doublet band shown on SDS-PAGE (FIG. 25a) was electroblotted onto ProBlott (Applied Biosystems, Foster City, Calif.). Sequencing was performed with the Beckman/Porton Microsequencer (model LF3000, Beckman Instruments, Carlsbad, Calif.), a Programmable Solvent Module (Beckman System Gold Model 126, Beckman Instuments, Carlsbad, Calif.) and a Diode Array Detector Module for PTH-amino acid detection (Beckman System Gold Model 168, Beckman Instruments, Carlsbad, Calif.) following manufacturers specifications.

A single N-terminal sequence analysis of the upper doublet band and multiple N-terminal sequence analyses of the lower doublet band showed that both bands contained two N-termini, designated "long" and "short". The lower doublet band contained approximately 3.3 picomoles of the long form and 8.3 picomoles of the short form. This difference in yields was sufficient to make sequence assignments according to the quantitation at each sequencer cycle. The upper doublet band contained approximately 8.3 picomoles of both sequences. The revealed long sequence was $NH_2$—RKVEHSRHDAIN-IFNVEKYGAVGDGKHDCTEAFSTAW(Q) ( ) ( ) ( ) KNP ( ) —COOH (SEQ ID NO: 136), where (Q) indicates a tentative identification of glutamine at position 38 and 0 indicated unknown residues at positions 39-41 and 45. The revealed "short" sequence was $NH_2$—SRHDAINIFN-VEKYGAVGDGKHDCTEAFSTAWS—COOH (SEQ ID NO: 137). Thus the long Cry j II sequence had five additional amino terminal residues than the short form and the sequence of the short form exactly matched that of the long form. In addition, both the long and short forms of Cry j II contained the ten amino acids, $NH_2$-AINIFNVEKY—COOH (SEQ ID NO: 138), previously described for Cry j II (Sakaguchi et al. 1990, supra). The previously published 10 amino acids (Sakaguchi et al. 1990, supra) correspond to amino acids ten through 19 of the long form described above (SEQ ID NO: 136).

EXAMPLE 15

Extraction of RNA From Japanese Cedar Pollen and Staminate Cones and Cloning of Cry j II Fresh pollen and staminate cone samples, collected from a single *Cryptomeria japonica* (Japanese Cedar) tree at the Arnold Arboretum (Boston, Mass.), were frozen immediately on dry ice. RNA was prepared from 500 mg of each sample, essentially as described by Frankis and Mascarhenas (1980) *Ann. Bot.* 45: 595-599. The samples were ground by mortar and pestle on dry ice and suspended in 5 ml of 50 mM Tris pH 9.0 with 0.2 M NaCl, 1 mM EDTA, 0.1% SDS that had been treated overnight with 0. 1% diethyl pyrocarbonate (DEPC). After five extractions with phenol/chlorofom/isoamyl alcohol (mixed 25:24:1), the RNA was precipitated from the aqueous phase with 0.1 volume 3M sodium acetate and 2 volumes ethanol. The pellets were recovered by centrifugation, resuspended in 2 ml $dH_2O$ and heated to 65° C. for 5 minutes. Two ml 4M lithium chloride was added to the preparation and the RNA was precipitated overnight at 0° C. The RNA pellets were recovered by centrifugation, resuspended in 1 ml $dH_2O$, and again precipitated with 3M sodium acetate and ethanol on dry ice for one hour. The final pellet was washed with 70% ethanol, air dried and resuspended in 100 µl DEPC-treated $dH_2O$ and stored at −80° C.

Double stranded cDNA was synthesized from 4 µg pollen RNA or 8 µg flowerhead RNA using a commercially available kit (cDNA Synthesis System kit, BRL, Gaithersburg, Md.). The double-stranded cDNA was phenol extracted, ethanol precipitated, blunted with T4 DNA polymerase (Promega, Madison, Wis.), and then ligated to ethanol precipitated, self annealed, AT and AL oligonucleotides for use in a modified Anchored PCR reaction, according to the method of Rafnar et al. (1990) *J. Biol. Chem.* 266: 1229-1236 ; Frohman et al. (1990) *Proc. Natl. Acad. Sci. USA* 85: 8998-9002; and Roux et al. (1990) *BioTech.* 8: 48-57. Oligonucleotide AT has the sequence 5'-GGGTCTAGAGGTACCG-TCCGTCCGATC-GATCATT-3' (SEQ ID NO: 20) (Rafnar et al. supra). Oligonucleotide AL has the sequence 5'-AATGATCGATGCT (SEQ ID NO: 22) (Rafnar et al. supra).

The first attempts at amplifying the amino terminus of Cry j II from the linkered cDNA (2 µl of a 20 µl reaction) was made using the degenerate oligonucleotide CP-11 and oligonucleotide AP. CP-11 has the sequence 5'-ATACTTCTClACGT-TGAA-3' (SEQ ID NO: 142), wherein A at positon 1 can be G, C at position 4 can be T, C at position 7 can be T, I at position 10 is inosine to reduce degeneracy (Knoth et al.

(1988) *Nucleic Acids Res.* 16: 10932), G at position 13 can be A, and G at position 16 can be A). AP, which has the sequence 5'-GGGTCTAGAGGTA-CCGTCCG-3' (SEQ ID NO: 21), corresponds to nucleotides 1 through 20 of the oligonucleotide AT (SEQ ID NO: 20). CP-11 (SEQ ID NO: 142) is the degenerate oligonucleotide sequence that is complementary to the coding strand sequence substantially encoding amino acids PheAsnValGluLysTyr (SEQ ID NO: 143)(amino acids 59 to 64 of (SEQ ID NO: 134), (FIG. 28) which correspond to the carboxy terminus of the previously published Cry j II sequence (Sakaguchi et al., supra) shown in FIG. 28. All oligonucleotides were synthesized by Research Genetics Inc., Huntsville, Ala.

Polymerase chain reactions (PCR) were carried out using a commercially available kit (GeneAmp DNA Amplification kit, Perkin Elmer Cetus, Norwalk, Conn.) whereby 10 µl 10× buffer containing dNTPs was mixed with 100 pmoles of each oligonucleotide, cDNA (3-5 µl of a 20 µl first strand cDNA reaction mix), 0.5 µl Amplitaq DNA polymerase, and distilled water to 100 µl.

The samples were amplified with a programmable thermal controller (MJ Research, Inc., Cambridge, Mass.). The first 5 rounds of amplification consisted of denaturation at 94° C. for 1 min, annealing of primers to the template at 45° C. for 1 min, and chain elongation at 72° C. for 1 min. The final 20 rounds of amplification consisted of denaturation as above, annealing at 55° C. for 1 min, and elongation as above. The primary PCR reaction was carried out with 100 pmol each of the oligonucleotides AP (SEQ ID NO: 21) and CP-11 (SEQ ID NO: 142). Five percent (5 µl) of this initial amplification was then used in a secondary amplification with 100 pmoles each of AP (SEQ ID NO: 21) and CP-12. CP-12 has the sequence 5'-CCTGCAGTACTTCT-CIACGTTGAAIAT-3' (SEQ ID NO: 144), wherein C at position 10 can be T, C at position 13 can be T, I at positions 16 and 25 are inosines to reduce degeneracy as above, G at position 19 can be A, and G at position 22 can be A. The sequence 5'-CCTGCAG-3' (SEQ ID NO: 145) (bases 1 through 7 of CP-12) (SEQ ID NO: 144) represents a Pst I site added for cloning purposes; the remaining degenerate oligonucleotide sequence is complementary to the coding strand sequence that substantially encodes the amino acids IlePheAsnValGluLysT (SEQ ID NO: 146) (amino acids 58-64 of SEQ ID NO: 134; FIG. 28). Amplified DNA was recovered by sequential chloroform, phenol, and chloroform extractions, followed by precipitation on dry ice with 0.5 volumes of 7.5M ammonium acetate and 1.5 volumes of isopropanol. After precipitation and washing with 70% ethanol, the DNA was simultaneously digested with Xba I and Pst I in a 50 µl reaction, precipitated to reduce the volume to 10 µl, and electrophoresed through a preparative 2% GTG NuSeive low melt gel (FMC, Rockport, Me.). The appropriate sized DNA area was visualized by ethidium bromide (EtBr) staining, excised, and ligated into appropriately digested pUC19 for sequencing by the dideoxy chain termination method of Sanger et al. (1977) *Proc. Natl. Acad. Sci. USA* 74: 5463-5476) using a commercially available sequencing kit (Sequenase kit, U.S. Biochemicals, Cleveland, Ohio). All resultant clones were sequenced, and none were found to contain Cry j II sequence. An alternate 2° PCR reaction was performed with AP (SEQ ID NO: 21) and the nested oligonucleotide CP-21. CP-21 has the sequence 5'-CCTGCAGTACTTCTCIACGTTGAAGAT-3' (SEQ ID NO: 147) wherein C at position 10 can be T, C at position 13 can be T, I at position 16 is inosine to reduce degenerscy as above, G at position 19 can be A, G at position 22 can be A, and G at position 25 can be A or T. The sequence 5'-CCTG-CAG-3' (SEQ ID NO: 145) (bases 1 through 7 of CP-21)

(SEQ ID NO: 147) represent a Pst I site added for cloning purposes; the remaining degenerate oligonucleotide sequence is the non-coding strand sequence corresponding to coding strand sequence substantially encoding amino acids IlePheAsnValGluLysTyr (SEQ ID NO: 146) (amino acids 58 to 64 of SEQ ID NO: 134; FIG. 28).

A primary PCR was also performed on double-stranded, Tinkered cDNA using CP-23D (SEQ ID NO: 148) and AP (SEQ ID NO: 21), as above, to attempt to amplify the 3' end of the Cry j II cDNA. A secondary PCR was performed using 5% of the primary reaction, using CP-24D (SEQ ID NO: 150) and AP (SEQ ID NO: 21). CP-23D (sequence 5'-GCIAT-TAATATTTTAA-3',(SEQ ID NO: 148) wherein the T at position 6 can be C or A, T at position 9 can be C, T at position 12 can be C or A, and T at position 15 can be C ) is the coding strand sequence substantially encoding amino acids AlalleAsnIlePheAsn (SEQ ID NO: 149) (amino acids 55 to 60 of SEQ ID NO: 134; FIG. 28); CP-24D (sequence 5'-GGAAT-TCCGCIATTAATATTTTAATGT-3' (SEQ ID NO: 150), wherein the T at position 14 can be C or A, T at position 17 can be C, T at position 20 can be C or A, T at position 23 can be C, and T at position 26 can be C ) contains the sequence 5'-GGAATTCC-3' (SEQ ID NO: 151) (bases I through 8 of CP-24D (SEQ ID NO: 150)), which represents an Eco RI site added for cloning purposes. The remaining degenerate oligonucleotide sequence of CP-24D (SEQ ID NO: 150) substantially encodes amino acids AlaIleAsnIlePheAsnVal (SEQ ID NO: 152) (amino acids 55 to 61 of SEQ ID NO: 134; FIG. 28). Again, multiple clones were sequenced, none of which could be identified as Cry j II, and this approach was not pursued further.

Upon the characterization of novel Cry j II protein sequence data described in Example 14, new degenerate oligonucleotides for cloning Cry j II were designed and synthesized. All oligonucleotides mentioned hereafter were synthesized on an ABI 394 DNA/RNA Synthesizer (Applied Biosystems, Foster City, Calif.), and purified on NAP-10 columns (Pharmacia, Uppsala, Sweden) as per the manufacturers' instructions. Degenerate oligonucleotide CP-35 (SEQ ID NO: 153) was used with AP (SEQ ID NO: 21) on the double-stranded tinkered cDNA in a primary PCR reaction carried out as described herein. CP-35 has the sequence 5'-GCTTCGGTACAATCATGTTT-3 (SEQ ID NO: 153), wherein T at position 3 can also be C; G at position 6 can also be A, T or C; A at position 9 can also be G; A at position 12 can also be G; A at position 15 can be G; and T at position 18 can also be C; this degenerate oligonucleotide sequence is the non-coding strand sequence corresponding to coding strand sequence substantially encoding amino acids LysHisAsp-CysThrGluAla (SEQ ID NO: 154) of Cry j II (amino acids 71 to 77 of SEQ ID NO: 134; FIG. 28). Five percent (5 µl) of this initial amplification, designated JC136, was then used in a secondary amplification with 100 pmoles each of AP (SEQ ID NO: 21) and degenerate Cry j II primer CP-36, an internally nested Cry j II oligonucleotide primer with the sequence 5'-GGCTGCAGGTACAATCATGTTTGCCATC-3' (SEQ ID NO: 155) wherein A at position 11 can also be G; A at position 14 can also be G; A at position 17 can also be G; T at position 20 can also be C; G at position 23 can also be A, T, or C; and A at position 26 can also be G. The nucleotides 5'-GGCTGCAG-3' (SEQ ID NO: 156) (bases 1 through 8 of CP-36 (SEQ ID NO: 155)) represent a Psi I restriction site added for cloning purposes. The remaining degenerate oligonucleotide sequence of CP-36 (SEQ ID NO: 155) is the non-coding strand sequence corresponding to coding strand sequence substantially encoding amino acids AspGlyLysHisAspCysThr (SEQ ID NO: 157) of Cry j II (amino acids 69 to 75 of (SEQ ID NO: 134; FIG. 28). The dominant amplified product, designated JC137, was a DNA band of approximately 265 base pairs, as visualized on an EtBr-stained 2% GTG agarose gel.

Amplified DNA was recovered by sequential chloroform, phenol, and chloroform extractions, followed by precipitation at −20° C. with 0.5 volumes of 7.5 ammonium acetate and 1.5 volumes of isopropanol. After precipitation and washing with 70% ethanol, the DNA was simultaneously digested with Xba I and Psi I in a 15 µl reaction and electrophoresed through a preparative 2% GTG SeaPlaque low melt gel (FMC, Rockport, Me.). The appropriate sized DNA band was visualized by EtBr staining, excised, and ligated into appropriately digested pUC19 for sequencing by the dideoxy chain termination method (Sanger et al. (1977) Proc. Natl Acad Sci. USA 74: 5463-5476) using a commercially available sequencing kit (Sequenase kit, U.S. Biochemicals, Cleveland, Ohio).

The clones designated pUC19JC137a, pUC19JC137b, and pUC19JC137e were found to contain sequences encoding the amino terminus of Cry j II. All three clones had identical sequence in their regions of overlap, although all three clones had different lengths in the 5' untranslated region. Clone pUC19JC137b was the longest clone. The translated sequence of these clones had complete identity to the disclosed 10 amino acid sequence of Cry j II (Sakaguchi et al., supra.), as well as to the Cry j II amino acid sequence described in Example 14. Amino acid numbering is based on the sequence of the full length protein; amino acid 1 corresponds to the initiating methionine (Met) of Cry j II. The position of the initiating Met was supported by the presence of an upstream in-frame-stop codon and by 78% homology of the surrounding nucleotide sequence with the plant consensus sequence that encompasses the initiating Met, as reported by Lutcke et al. (1987) EMBO J. 6:43-48.

The cDNA encoding the remainder of Cry j II gene was cloned from the linkered cDNA by using oligonucleotides CP-37 (which has the sequence 5'-ATGTTGGACAGTGT-TGTCGAA-3' (SEQ ID NO: 158)) and AP (SEQ ID NO: 21) in a primary PCR, designated JC138ii. Oligonucleotide CP-37 (SEQ ID NO: 158) corresponds to nucleotides 129 to 149 of SEQ ID NO: 133; FIG. 28, and is based on the nucleotide sequence determined for the partial Cry j II clone pUC19JC137b.

A secondary PCR reaction was performed on 5% of the initial amplification mixture, with 100 pmoles each of AP (SEQ ID NO: 21) and CP-38 (which has the sequence 5'-GG-GAATTCAGAAAAGTTGAGCATTCTCGT-3' (SEQ ID NO: 159)), the nested primer. The nucleotide sequence 5'-GGGAATTC-3' (SEQ ID NO: 159) (bases 1 through 8 of CP-38 (SEQ ID NO: 162)) represents an Eco RI restriction site added for cloning purposes. The remaining oligonucleotide sequence corresponds to nucleotides 177 to 197 of SEQ ID NO: 133; FIG. 28, and is based on the nucleotide sequence determined for the partial Cry j II clone pUC19JC137b. The amplified DNA product, designated JC140iii, was purified and precipitated as above, followed by digestion with Eco RI and Asp 718 and electrophoresis through a preparative 1% low melt gel. The dominant DNA band, which was approximately 1.55 kb in length, was excised and ligated into pUC19 for sequencing. DNA was sequenced by the dideoxy chain termination method (Sanger et al. supra) using a commercially available kit (sequenase kit (U.S. Biochemicals, Cleveland, Ohio). Both strands were completely sequenced using M13 forward and reverse primers (N.E. Biolabs, Beverly, Mass.) and internal sequencing primers CP-35 (SEQ ID NO: 153), CP-38 (SEQ ID NO: 159), CP-40 (SEQ ID NO: 161), CP-41 (SEQ ID NO: 162), CP-42 (SEQ ID NO: 163), CP-43 (SEQ ID NO: 164), CP-44 (SEQ ID NO: 165), CP-45 (SEQ ID NO: 166), CP-46 (SEQ ID NO: 167), CP-47 (SEQ ID NO: 168), CP-48 (SEQ ID NO: 169), CP-49 (SEQ ID NO: 170), CP-50 (SEQ ID NO: 171), and CP-51 (SEQ ID NO: 172). CP-40 has the sequence 5'-GTTCTTCAATGGGCCATGT-3' (SEQ ID NO: 161) and corresponds to nucleotides 359 to 377 of SEQ ID NO: 133; FIG. 28. CP-41 has the sequence 5'-GTGTTRAGGACT-GTCTCTCGG-3' (SEQ ID NO: 162), which is the non-coding strand sequence that corresponds to nucleotides 720 to 739 of SEQ ID NO: 133; FIG. 28. CP-42 has the sequence 5'-TGTCCAGGCCATGGAATAAG-3' (SEQ ID NO: 163), which corresponds to nucleotides 864 to 883 of SEQ ID NO: 133; FIG. 28 except that the first nucleotide was synthesized as a T rather than the correct G. CP43 has the sequence 5'-GCCTTACATGGACTGCAACC-3' (SEQ ID NO: 164), which is the non-coding strand sequence that corresponds to nucleotides 1476 to 1495 of SEQ ID NO: 135; FIG. 28. CP-44 has the sequence 5'-TCCACGGGTCT-GATAATCCA-3', (SEQ ID NO: 165) which corresponds to nucleotides 612 to 631 of SEQ ID NO: 133; FIG. 28. CP-45 has the sequence 5'-AGGCAGGAAGCAATAACCC-3' (SEQ ID NO: 166), which is the non-coding strand sequence that corresponds to nucleotides 1254 to 1273 of SEQ ID NO: 133; FIG. 28. CP-46 has the sequence 5'-TACTGCACT-TCAGCT-TCTGC-3' (SEQ ID NO: 167), which corresponds to nucleotides 1077 to 1096 of SEQ ID NO: 133; FIG. 28. CP-47 has the sequence 5'-GGGGGTCTCCGAATTTATCA-3', (SEQ ID NO: 168) which is the non-coding strand sequence that substantially corresponds to nucleotides 1039 to 1058 of SEQ ID NO: 133; FIG. 28, except that the fifth nucleotide of CP-47 was synthesized as a G rather than the correct nucleotide, T. CP48, which has the sequence 5'-GGATATTTCAGTGGACACGT-3' (SEQ ID NO: 169), corresponds to nucleotides 1290 to 1309 of SEQ ID NO: 133; FIG. 28. CP-49 has the sequence 5'-TATTAGAAGACC-CT-GTGCCT-3' (SEQ ID NO: 170), which is the non-coding strand sequence that corresponds to nucleotides 821 to 840 of SEQ ID NO: 133; FIG. 28. CP-50 has the sequence 5'-CCAT-GTAAGGCCAAGTTAGT-3' (SEQ ID NO: 171), which corresponds to nucleotides 1485 to 1504 of SEQ ID NO: 133; FIG. 28. CP-51 has the sequence 5'-ACACCATTAC-CCATTAGAGT-3', (SEQ ID NO: 172) which is the non-coding strand sequence that corresponds to nucleotides 486 to 505 of SEQ ID NO: 133; FIG. 28.

Three clones, designated pUC19JC140iiia, pUC19JC140iiid and pUC19JC140iiie, were subsequently found to contain partial Cry j II sequence. The sequence of clone pUC19JC140iiid was chosen as the consensus sequence since it had the longest 3' untranslated region. The sequences of pUC19JC140iiid and pUC19JC137b were used to construct the composite Cry j II sequence shown in FIG. 28 (SEQ ID NO: 133). In this composite, nucleotide 230 is reported as the A found in pUC19JC137b (also, pUC19JC137a, pUC19JC140iiia and pUC19JC140iiie) not as the G found in pUC19JC140iiid; however both A and G at nucleotide 230 encode Lys at amino acid 63 (SEQ ID NO: 134). The sequence of clone pUC19JC140iiia was identical to that of pUC19JC140iiid except for the following: pUC19JC140iiia has a T at nucleotide 357 in place of a C (no predicted change in amino acid 106), has C at nucleotide 754 instead of T (changes amino acid 238 from Ile to Thr), C at nucleotide 1246 instead of T (changes amino acid 402 from Leu to Pro), and T at nucleotide 1672 instead of C (untranslated region). The sequence of clone pUC19JC140iiie was identical to that of pUC19JC140iiid except for G at nucleotide 794 instead of A (changes amino acid 251 from Ile to Met), and T at nucleotide 357 in place of C (no predicted change in amino acid 106).

An earlier attempt at cloning the JC140iii PCR product using an Eco RI/Xba I digest (oligonucleotide AP has both Xba I and Asp 718 restriction enzyme sites) yielded cDNA that was cut in half due to an internal Xba I restriction site in the Cry j II cDNA, giving rise to 800 and 750 bp bands; the 750 bp band was succesfully cloned into Eco RI/Xba I digested pUC19 and sequenced. Two 750 bp clones were sequenced and found to be the 5' half of the Cry j II molecule: clones pUC19JC140-2a and pUC19JC140-2b. Clone pUC19JC140-2a has C for nucloeotide 297 instead of T (changes amino acid 86 from Cys to Arg) and clone pUC19JC140-2b has G for nucleotide 753 instead of A (changes amino acid 238 from Ile to Val). Both clone pUC19JC140-2a and clone pUC19JC140-2b have a T at nucleotide 357 in place of C (no predicted change in amino acid 106).

Two different PCR amplifications were also sequenced directly to verify the clonal Cry j II sequence using the Amplitaq Cycle Sequencing kit (Perkin Elmer Cetus, Norwalk, Conn.). This procedure involves the [$^{32}$P]-end-labelling of oligonucleotide sequencing primers which are then annealled (1.6 pmoles in 1 µl) to template DNA and elongated with dideoxy NTPs (methodology of Sanger et al. (1977) *Proc. Natl. Acad Sci. USA* 74:5463-5476) in a PCR reaction also containing 4 µl 10× Cycling Mix (contains 0.5 U/µl Amplitaq DNA Polymerase), 5 µl template DNA (10-100 fmoles) and dH$_2$O to 20 µl. The dGTP in the termination mixes in this kit have been replaced by 7-deaza-dGTP, which provides increased resolution of sequences containing high G+C regions of DNA. The template DNA was a PCR product that was recovered by sequential chloroform, phenol, and chloroform extractions, precipitated at −20° C. with 0.5 volumes of 7.5 ammonium acetate and 1.5 volumes of isopropanol, then electrophoresed through a preparative 1 or 2% SeaPlaque low melt gel (FMC). Appropriate sized DNA bands were visualized by EtBr staining, excised, and treated with Gelase (Epicentre Technologies, Madison, Wis.) to remove the agarose. The DNA was again precipitated, and resuspended in 50 µl TE (10 mM Tris, pH 7.4, 1 mM EDTA, pH 8.0) containing 20 µg/1 ml RNAse (Boehringer Mannheim, Indianapolis, Ind.). Two secondary amplifications which had been used to clone Cry j II were repeated, and used as template DNA for PCR cycle sequencing: JC137ii, the 5' end PCR, (amplified from the 1° PCR JC136 above) was reamplified With oligonucleotides AP and CP-36; and JC140ii, the 3' end PCR, (amplified from the 1° PCR JC138ii above) was reamplified with oligonucleotides AP and CP-38. Both of the 1° amplifications used were precipitated, electrophoresed through a preparative 1 or 2% SeaPlaque low melt gel (FMC), and the appropriate sized bands were visualized by EtBr staining and excised. Two µl of each 1° amplification was then used in the corresponding 2° PCR reaction. The 2° PCR product was then prepared as DNA template for PCR cycle sequencing as described above. The oligonucleotides used as primers in PCR cycle sequencing, many of which were used to sequence the clones, are as follows: for JC137ii, CP-36 (SEQ ID NO: 155) and CP-39, which has the sequence 5'-CTGTCCAACATAATTGGGC-3' (SEQ ID NO: 173) and is the non-coding strand sequence corresponding to nucleotides 120 to 139 of SEQ ID NO: 133; FIG. 28. The oligonucleotide primers used for sequencing JC140ii were CP-38 (SEQ ID NO: 159), CP-40 (SEQ ID NO: 161), CP-41 (SEQ ID NO: 162), CP-42 (SEQ ID NO: 163), CP-43 (SEQ ID NO: 164), CP-44 (SEQ ID NO: 165), CP-45 (SEQ ID NO: 166), CP-46 (SEQ ID NO: 167), CP-47 (SEQ ID NO: 168), CP-49 (SEQ ID NO: 170), CP-50 (SEQ ID NO: 171), CP-54 (SEQ ID NO: 173), which has the sequence 5'-CATGGCAGGGTGGTTCAGGC-3' (SEQ ID NO: 173), corresponds to nucleotides 985 to 1004 of SEQ ID NO: 133; FIG. 28, CP-55, which has the sequence 5'-TAGCCCCATT-TACGTGCACG-3' (SEQ ID NO: 174) and is the non-coding strand sequence that corresponds to nucleotides 929 to 948 of SEQ ID NO: 133; FIG. 28, and CP-56, which has the sequence 5'-TTGGGGTCGAGGCCTCCGAA-3' (SEQ ID NO: 175) and corresponds to nucleotides 1437 to 1456 of SEQ ID NO: 133; FIG. 28. The sequence of this full-length PCR cycle sequencing had only 2 nucleotide changes from the composite pUC19JC137b/pUC19JC140iiid Cry j II sequence shown in FIG. 28 (SEQ ID NO: 133), neither of which lead to an amino acid change. There was a T instead of C at nucleotide 357 (no predicted change in amino acid 106), and a C instead of A at nucleotide 635 (no amino acid change).

The nucleotide and predicted amino acid sequences of Cry j II are shown in FIGS. 28 and 29 (SEQ ID NO: 133 and 134). This is a composite nucleotide sequence from the two overlapping clones pUC19JC137b and pUC19JC140iiid. Sequencing of multiple independent clones and cycle sequencing of PCR product confirmed the nucleotide sequence of FIG. 4 (SEQ ID NO: 133). There were several nucleotide changes resulting in predicted amino acid changes, as cited above. However, all nucleotide polymorphisms, with the exception of the T for C substitition at nucleotide 357, were only observed in single clones or sequencing reactions. Although T was seen at nucleotide 357 in all clones except pUC19JC140iiid, both C and T encode Leu at amino acid 106.

The complete cDNA sequence for Cry j II is composed of 1726 nucleotides, including 41 nucleotides of 5' untranslated sequence, an open reading frame of 1542 nucleotides starting with the codon for an initiating Met (nucleotides 42-44 of SEQ ID NO: 133; FIG. 28), and a 143 bp 3' untranslated region. There is a consensus polyadenylation signal sequence in the 3' untranslated region 64 nucleotides 5' to the poly A tail (nucleotides 1654-1659 of SEQ ID NO: 133; FIG. 28). The position of the initiating Met is confirmed by the presence of an in-frame upstream stop codon and by 78% homology with the plant consensus sequence that encompasses the initiating Met (TAAAAUGGC (bases 38 through 46 of (SEQ ID NO: 133); FIG. 28) found in Cry j II compared with the AACAAUGGC consensus sequence for plants, Lutcke et al. (1987) *EMBO J.* 6: 4348). The open reading frame encodes a deduced protein of 514 amino acids that has complete sequence identity with the published partial protein sequence for Cry j II (Sakaguchi et al. supra), which corresponds to amino acids 55 through 64 of SEQ ID NO: 134; FIG. 28. The predicted Cry j II protein has 20 Cys, contains four potential N-linked glycosylation sites corresponding to the consensus sequence N—X—S/T, has a predicted molecular weight of 56.6 kDa and a predicted pI of 9.08.

Detection of three separate NH$_2$ termini sequences for Cry j II (the long form and the short form as determined in Example 14 and the NH$_2$ terminus determined by Sakaguchi et al., supra, as shown in FIG. 6) may suggest that the amino terminus of the mature Cry j II protein is blocked and that the sequences obtained by sequence analysis of purified protein represent proteolytic cleavage products. As shown in FIG. 6, the amino acid sequence of the long form of Cry j II begins at amino acid 46 and the amino acid sequence of the short form of Cry j II begins at amino acid 51; and the NH2-terminal sequence determined by Sakaguchi et al. begins at amino acid 54. It is also possible that amino acids 1 to 45 represent the leader/pre-pro position of Cry j II that is enzymatically cleaved to give a functionally active protein beginning at amino acid 46 of SEQ ID NO: 134; FIG. 28. The sequences beginning at amino acids 51 and 54 represent breakdown products of the protein beginning at amino acid 46. There is a predicted cleavage site between amino acids 22 and 23 of SEQ ID NO: 134; FIG. 28 using the method of von Heijne (Nucleic Acids Res. (1986) 14:4683-4690). If the mature Cry j II protein started at amino acid 23 of SEQ ID NO: 134; FIG. 28, the protein would be 492 amino acids long with a predicted molecular weight of 54.2 kDa and a predicted pI of 9.0.

Searching the Swiss-Prot data base with the Cry j II sequence demonstrated that Cry j II is 43.3% homologous (33.3% identical to polygalacturonase of tomato (*Lycopersicon esculentum*) and 48.4% homologous (32.6% identical) to polygalacturonase of corn, *Zea mays*. All nucleotide and amino acid sequence analyses were performed using PCCENE (Intelligenetics, Mountain View, Calif.).

EXAMPLE 16

Extraction of RNA from Japanese Cedar Pollen Collected in Japan and Expression of Recombinant Cry j II Fresh pollen collected from a pool of *Cryptomeria japonica* (Japanese cedar) trees in Japan was frozen immediately on dry ice. RNA was prepared from 500 mg of the pollen, essentially as described by Frankis and Mascarenhas *Ann. Bot.* 45:595-599. The samples were ground by mortar and pestle on dry ice and suspended in 5 ml of 50 mM Tris pH 9.0 with 0.2 M NaCl, 1 mM EDTA, 1% SDS that had been treated overnight with 0.1% DEPC. After five extractions with phenol/chloroform/isoamyl alcohol (mixed at 25:24:1), the RNA was precipitated from the aqueous phase with 0.1 volume 3 M sodium acetate and 2 volumes ethanol. The pellets were recovered by centrifugation, resuspended in 2 ml dH$_2$O and heated to 65° C. for 5 minutes. Two ml of 4 M lithium chloride were added to the RNA preparations and they were incubated overnight at 0° C. The RNA pellets were recovered by centrifugation, resuspended in 1 ml dH$_2$O, and again precipitated with 3 M sodium acetate and ethanol overnight. The final pellets were resuspended in 100 µl dH$_2$O and stored at –80° C.

Double stranded cDNA was synthesized from 8 µg pollen RNA using the cDNA Synthesis Systems kit (BRL) with oligo dT priming according to the method of Gubler and Hoffman (1983) *Gene* 25:263-269. PCRs were carried out using the GeneAmp DNA Amplification kit (Perkin Elmer Cetus) whereby 10 µl 10× buffer containing dNTPs was mixed with 100 pmol each of a sense oligonucleotide and an anti-sense oligonucleotide, cDNA (10 µl of a 400 µl double stranded cDNA reaction mix), 0.5 µl Amplitaq DNA polymerase, and distilled water to 100 µl.

The samples were amplified with a programmable thermal controller from MJ Research, Inc. (Cambridge, Mass.). The first 5 rounds of amplification consisted of denaturation at 94° C. for 1 min, annealing of primers to the template at 45° C. for 1 min, and chain elongation at 72° C. for 1 min. The final 20 rounds of amplification consisted of denaturation as above, annealing at 55° C. for 1 min, and elongation as above.

A new set of primer pairs was synthesized for amplification of a Cry j II cDNA from the initiating Met to the stop codon. CP-52 has the sequence 5'-GCCGAATTCATGGCCAT-GAAATTAATT-3' (SEQ ID NO: 179) where the nucleotide sequence 5'-GCCGAATTC-3' (SEQ ID NO: 180) (bases I through 9 of CP-52 (SEQ ID NO: 179) represents an Eco RI restriction site added for cloning purposes, and the remaining sequence corresponds to nucleotides 42 to 59 of SEQ ID NO: 133; FIG. 28. CP-53 has the sequence 5'-CGGGGATCCT-CATTATGGATG-GTAGAT-3' (SEQ ID NO: 181) where the nucleotide sequence 5'-CGGGGATCC-3' (SEQ ID NO: 182) (bases 1 through 9 of CP-53 (SEQ ID NO: 181)) represents a Bam HI restriction site added for cloning purposes, and the remaining oligonucleotide sequence of CP-53 (SEQ ID NO: 181) is complementary to coding strand sequence corresponding to nucleotides 1572 to 1589 of SEQ ID NO: 133; FIG. 28. The PCR reaction with CP-52 (SEQ ID NO: 179) and CP-53 (SEQ ID NO: 181) on the double stranded Japanese Cedar pollen cDNA yielded a band of approximately 1.55 kb on an EtBr-stained agarose minigel, and was called JC145. Amplified DNA was recovered by sequential chloroform, phenol, and chloroform extractions, followed by precipitation at –20° C. with 0.5 volumes of 7.5 ammonium acetate and 1.5 volumes of isopropanol. After precipitation and washing with 70% ethanol, the DNA was simultaneously digested with Eco RI and Bam HI in a 15 µi reaction, and electrophoresed through a preparative 1% SeaPlaque low melt gel (FMC). Appropriate sized DNA bands were visualized by EtBr staining, excised, and ligated into appropriately digested pUC19 for sequencing by the dideoxy chain termination method (Sanger et al. (1977) *Proc. Natl. Acad. Sci. USA* 74:5463-5476) using a commercially available sequencing kit (Sequenase kit, U.S. Biochemicals, Cleveland, Ohio).

Clones pUC19JC145a and pUC19JC145b were completely sequenced using M13 forward and reverse primers (N.E. Biolabs, Beverly, Mass.) and internal sequencing primers CP-41 (SEQ ID NO: 162), CP-42 (SEQ ID NO: 163), CP-44 (SEQ ID NO: 165), CP-46 (SEQ ID NO: 167), and CP-51 (SEQ ID NO: 172). The nucleotide and deduced amino acid sequences of clones pUC19JC145a and pUC19JC145b were identical to the Cry j II sequence of FIG. 28 (SEQ ID NO: 133 and 134), with the following exceptions. Clone pUC19JC145a was found to contain a single nucleotide difference from the previously known Cry j II sequence: it has a C at nucleotide position 1234 of SEQ ID NO: 133; FIG. 28 rather than the previously described T. This nucleotide change results in a predicted amino acid change from Ile to Thr at amino acid 398 of the Cry j II protein (SEQ ID NO: 134). Clone pUC19JC145b has a G at nucleotide position 1088 of SEQ ID NO: 133; FIG. 28 rather than the previously described A, and an A for a G at nucleotide 1339. The nucleotide change at 1088 is silent and does not result in a predicted amino acid change. The nucleotide change at position 1339 results in a predicted amino acid change from Ser to Asn at amino acid 433 of the Cry j II protein. None of these polymorphisms have yet been confirmed by independently-derived PCR clones or by direct amino acid sequencing and may be due to the inherent error rate of Taq polymerase (approximately $2\times10^{-4}$, Saiki et al. (1988) *Science* 239:487-491). However, such polymorphisms in primary nucleotide and amino acid sequences are expected.

Expression of Cry j II was performed as follows. Ten µg of pUC19JC145b was digested simultaneously with Eco RI and Bam HI. The nucleotide insert encoding Cry j II (extending from nucleotide 42 through 1589 of (SEQ ID NO: 133) FIG. 28) was isolated by electrophoresis of this digest through a 1% SeaPlaque low melt agarose gel. The insert was then ligated into the appropriately digested expression vector pET-11d (Novagen, Madison, Wis.; Jameel et al. (1990) *J. Virol.* 64:3963-3966) modified to contain a sequence encoding 6 histidines (His 6) immediately 3' of the ATG initiation codon followed by a unique Eco RI endonuclease restriction site. A second Eco RI endonuclease restriction site in the vector, along with neighboring Cla I and Hind III endonuclease restriction sites, had previously been removed by digestion with Eco RI and Hind III, blunting and religation. The histidine (His$_6$) sequence was added for affinity purification of the recombinant protein (Cry j I) on a Ni$^{2+}$ chelating column (Hochuli et al. (1987) *J. Chromatog.* 411:177-184; Hochuli et al. (1988) *Bio/Tech.* 6:1321-1325.). A recombinant clone was used to transform *Escherichia coli* strain BL21-DE3, which harbors a plasmid that has an isopropyl-β-D-thiogalactopyranoside (IPTG)-inducible promoter preceding the gene encoding T7 polymerase. Induction with IPTG leads to high levels of T7 polymerase expression, which is necessary for expression of the recombinant protein in pET-11d. Clone pET-11dΔHRhis$_6$JC145b.a was confirmed to be a Cry j II clone in the correct reading frame for expression by dideoxy sequencing (Sanger et al. supra) with CP-39.

Expression of the recombinant protein was examined in an initial small culture. An overnight culture of clone pET-11dΔHRhis$_6$JC145b.a was used to innoculate 50 ml of media (Brain Heart Infusion Media, Difco) containing ampicillin (200 µg/ml), grown to an A$_{600}$=1.0 and then induced with IPTG (1 mM, final concentration) for 2 hrs. One ml aliquots of the bacteria were collected before and after induction, pelleted by centrifugation, and crude cell lysates prepared by boiling the pellets for 5 minutes in 50 mM Tris HCl, pH 6.8, 2 mM EDTA, 1% SDS, 1% β-mercaptoethanol, 10% glycerol, 0.25% bromophenol blue (Studier et al., (1990) *Methods in Enzymology* 185:60-89). Recombinant protein expression was examined on a 12% Coomassie blue-stained SDS-PAGE gel, according to the method in Sambrook et al., supra, on which 25 µl of the crude lysates were loaded. A negative control consisted of crude lysate from uninduced bacteria containing the plasmid with Cry j II. There was no notable increase in production of any recombinant *E. coli* protein in the range of 58 Kd, the size predicted for the recombinant Cry j II with the His$_6$ leader.

The pET-11dΔHRhis$_6$JC145b.a clone was then grown on a larger scale to examine if there was any recombinant protein being expressed. A 2 ml culture of bacteria containing the recombinant plasmid was grown for 8 hr, then 3 µl was spread onto each of 6 (100×15 mm) petri plates with 1.5% agarose in LB medium (Gibco-BRL, Gaithersburg, Md.) containing 200 µg/ml ampicillin, grown to confluence overnight, then scraped into 6 L of liquid media (Brain Heart Infusion media, Difco) containing ampicillin (200 µg/ml). The culture was grown until the absorbance at A600 was 1.0, IPTG added (1 mM final concentration), and the culture grown for an additional 2 hours.

Bacteria were recovered by centrifugation (7,930×g, 10 min) and lysed in 50 ml of 6M Guanidine-HCl, 0.1M Na$_2$HPO$_4$, pH 8.0, for 1 hour with vigorous shaking. Insoluble material was removed by centrifugation (11,000×g, 10 min, 4° C.). The pH of the lysate was adjusted to pH 8.0, and the lysate applied to a 50 ml Nickel NTA agarose column (Qiagen) that had been equilibrated with 6 M Guanidine HCl, 100 mM Na$_2$HPO$_4$, pH 8.0. The column was sequentially washed with 6 M Guanidine HCl, 100 mM Na$_2$HPO$_4$, 10 mM Tris-HCl, pH 8.0, then 8 M urea, 100 mM Na$_2$HPO$_4$, pH 8.0, and finally 8 M urea, 100 mM sodium acetate, 10 mM Tris-HCl, pH 6.3. The column was washed with each buffer until the flow through had an A$_{280}$≦0.05.

The recombinant Cry j II protein was eluted with 8 M urea, 100 MM sodium acetate, 10 mM Tris-HCl, pH 4.5, and collected in 10 ml aliquots. The protein concentration of each fraction was determined by A$_{280}$ and the peak fractions pooled. An aliquot of the collected recombinant protein was analyzed on SDS-PAGE according to the method in Sambrook et al. supra.

This 6L prep, JC11pET-1, yielded 1.5 mg of recombinant Cry j II, which was resolved into 2 major bands on SDS-PAGE at 58 kDa and 24 kDa. The 58 kDa band, which represents recombinant Cry j II, was approximately 9-10% of the total protein as determined by densitometry measurement (Shimadzu Flying Spot Scanner, Shimadzu Scientific Instruments, Inc., Braintree, Mass.). The 24 kDa band accounts for about 90% of the total protein and may represent a degradation product of the recombinant Cry j II or an *E. coli* contaminant.

Another Cry j II expression construct was made by the ligation of the pUC19JC140iiid Cry j II insert into appropriately digested pET11dΔHR (with the 6 histidine leader). The vector was derived from another pET11dΔHR construct whose insert supplied an EcoR I site (at the 5' pET11dΔHR-insert junction) and an Asp 718site (at the 3' end of the insert); the construct was digested with these two enzymes, run on a low melt minigel as above, and the vector recovered as a band in low melt agarose. The pUC19JC140iiid construct was digested with Eco R I and Asp 718 to release the Cry j II insert, which was isolated on a low melt minigel and ligated into the Eco R I/Asp 718 digested pET11dΔHR vector prepared above. Five clones were found to contain the correct nucleotide sequence at the insert/vector 5' junction, when sequenced by dideoxy sequencing (as above) with CP-39. This new construct, when expressed, would begin at amino acid 46 of Cry j II as shown in FIGS. 28 and 29. This recombinant protein is designated rCry j II Δ46. A 50 ml small scale expression test (as performed above) showed that the expression level of rCry j II Δ46 from this construct, designated pET11dΔHRJC140iiid2, would be much greater than the initial expression level from pET11dΔHRJC145b2. A 9L prep, JC11pET-3, was processed as above, and yielded 200 mg of rCry j II Δ46 at 80% purity as determined by densitometry of a Coomasie blue stained 12% SDS-PAGE gel.

EXAMPLE 17

Northern Blot on RNA from Japanese Cedar Pollen Sources

A northern blot analysis was performed on the RNA isolated from Japanese Cedar pollen from both the Arnold Arboretum tree and the pooled trees from Japan. Using essentially the method of Sambrook, supra, ten µg of RNA isolated from Japanese cedar pollen collected from the Arnold Arboretum (Boston, Mass.) and 15 µg pooled RNA from Japanese cedar pollen collected from trees in Japan were run on a 1.2% agarose gel containing 38% formaldehyde and 1×MOPS (20x=0.4M MOPS, 0.02M EDTA, 0.1M NaOAc, pH 7.0) solution. The RNA samples (first precipitated with 1/10 volume sodium acetate, 2 volumes ethanol to reduce volume and resuspended in 5.5 µl dH2O) were run with 10 µl formaldehyde/formamide buffer containing loading dyes with 15.5% formaldehyde, 42% formamide, and 1.3×MOPS solution, final concentration. The samples were transferred to Genescreen Plus (NEN Research Products, Boston, Mass.) by capillary transfer in 10×SSC (20x=3M NaCl, 0.3M Sodium Citrate), after which the membrane was baked 2 hrs at 80° C. and UV irradiated for 3 minutes. Prehybridization of the membrane was at 60° C. for 1 hour in 4 ml 0.5M NaPo4 (pH 7.2), 1 mM EDTA, 1% BSA, and 7% SDS. The antisense probe was synthesized by asymmetric PCR on the JC 145 amplification in low melt agarose (above), where 2 µl DNA is amplified with 2 µl dNTP mix (0.167 mM dATP, 0.167 mM dTTP, 0.167 mM dGTP, and 0.033 mM dCTP), 2 µl 10×PCR buffer, 10 µl $^{32}$P-dCTP (100 µCi; Amersham, Arlington Heights, Ill.), 1 µl (100 pmoles) antisense primer CP-53, 0.5 µl Taq polymerase, and dH2O to 20 µl; the 10×PCR buffer, dNTPs and Taq polymerase were from Perkin Elmer Cetus (Norwalk, Conn.). Amplification consisted of 30 rounds of denaturation at 94° C. for 45 sec, annealing of primer to the template at 60° C. for 45 sec. and chain elongation at 72° C. for 1 min. The reaction was stopped by addition of 100 μl TE, and the probe recovered over a 3 cc G-50 spin column (2 ml G-50 Sephadex [Pharmacia, Uppsala, Sweden] in a 3 cc syringe plugged with glass wool, equilibrated with TE) and counted on a 1500 TriCarb Liquid Scintillation Counter (Packard, Downers Grove, Ill.). The probe was added to the prehybridizing buffer at $10^6$ cpm/ml and hybridization was carried out at 60° C. for 16 hrs. The blot was washed in high stringency conditions: 3×15 min at 65° C. with 0.2%SSC/1% SDS, followed by wrapping in plastic wrap and exposure to film at −80° C. A seven hour exposure of this Northern blot analysis revealed a single thick band at approximately 1.7 kb for both RNA collected from the Arboretum tree and the RNA collected from the pooled trees from Japan. This message is the expected size for Cry j II as predicted by PCR analysis of the cDNA.

EXAMPLE 18

Direct Binding Assay of IgE to Cry j I, Cry j II and Recombinant Cry j II.

Costar assay plates were coated with Cry j I or Cry j II at 2 μg/mL or recombinant Cry j II preparation at 10 μg/mL (approximately 20% pure) in a volume of 50 μL overnight at 4° C. The coating antigens were removed and the wells were blocked with 0.5% gelatin, PVP (polyvinyl pyrolidine) 1 mg/mL in PBS, 200 μL/well for 2 hours at room temperature. The anti-Cry j I monoclonal antibody, 4B11, was serially diluted in PBS-Tween 20 starting at a 1:1000 dilution. The human plasma were serially diluted in PBS-Tween at a starting dilution of 1:2. For this set 23 plasma samples from patients symptomatic for Japanese cedar pollen allergy chosen for IgE binding analysis. The first antibody incubation proceeded overnight at 4° C. Following three washes with PBS-Tween the second antibodies were added (biotinylated goat anti-mouse Ig or goat anti-human IgE both at 1:2000) and incubated for two hours at room temperature at 100 μL/well. After washing 3 times, 100 μL of TMB substrate was added per well (Kirkgaard Perry Labs). This solution was removed and streptavidin-HRPO diluted to 1:10,000, was added at 100 μL/well. The color was allowed to develop for 2-5 minutes. The reaction was stopped by the addition of 100 μL/well of 1M phosphoric acid. Plates were read on a Microplate IL310 Autoreader (Biotek Instruments, Winooski, Vt.) with a 450 nm filter. The absorbance levels of duplicate wells were averaged. The graphed results (log of the dilution vs. absorbance) of the ELISA assays are shown in FIGS. 31 to 39. The summary of the results are given in FIG. 40. A positive binding result, indicated by a plus sign is determined to be a reading of two-fold or greater above background (no first antibody) at the second dilution of plasma (1:6).

Figure 31:
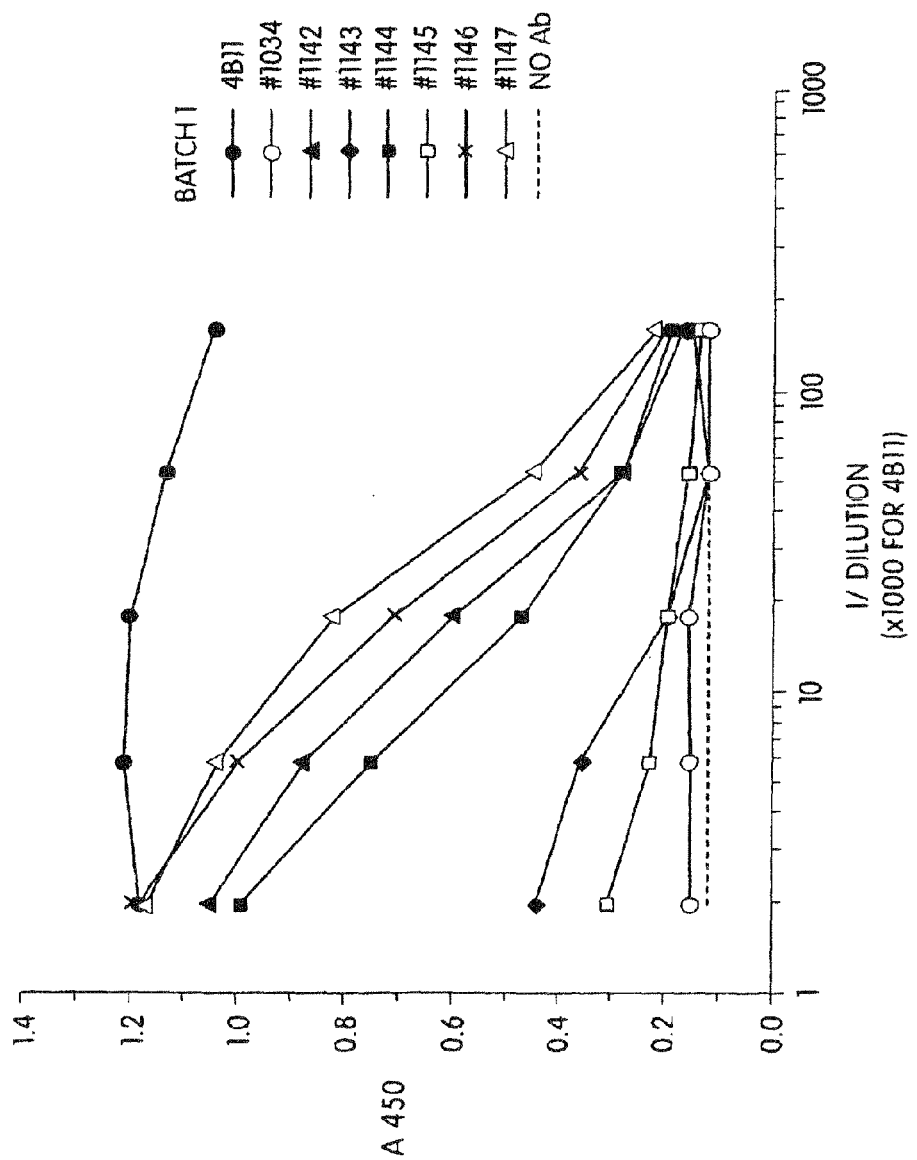
FIG. 31 is a graphic representation of the results of a direct ELISA assay showing the binding response of the monoclonal antibody 4B11 and seven patients' (Batch 1) plasma IgE to purified Cry j I as the coating antigen.
Figure 32:
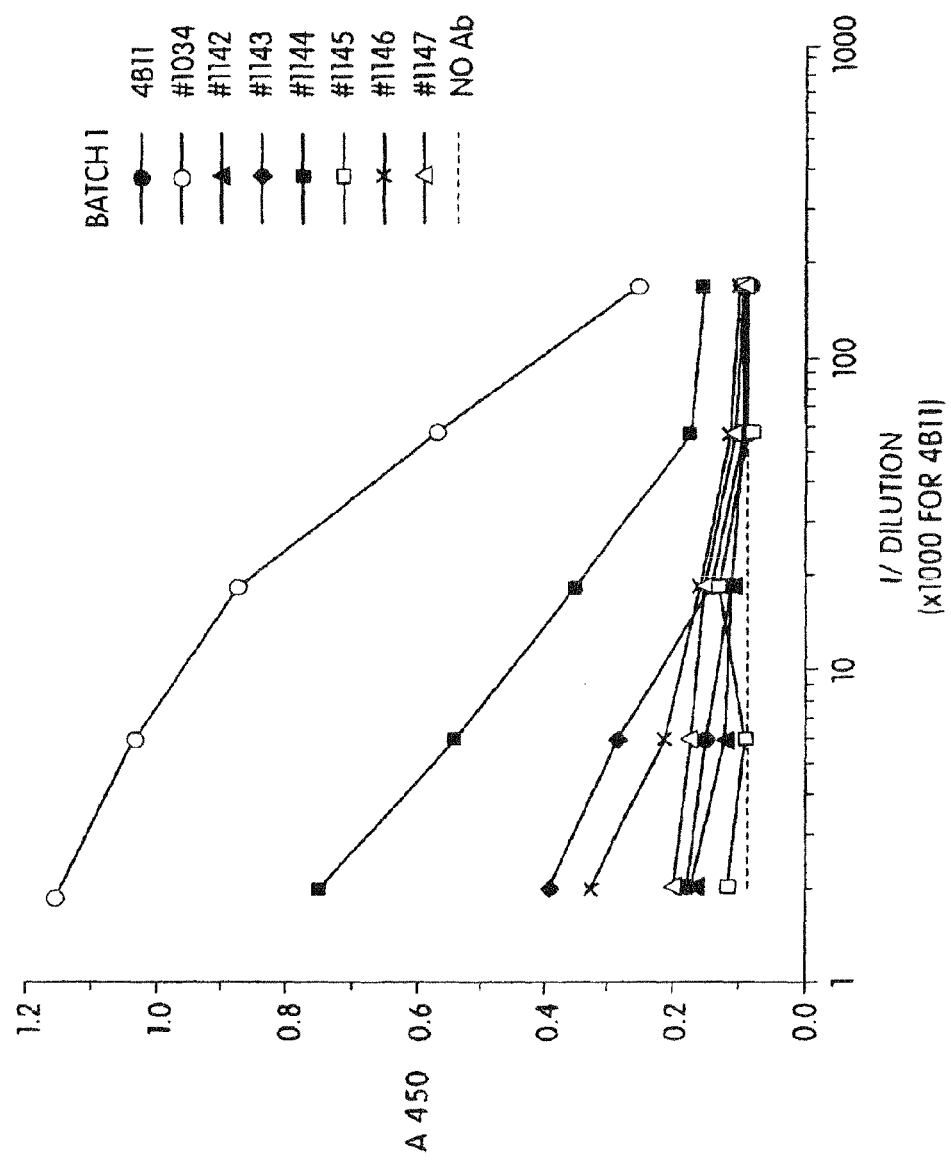
FIG. 32 is a graphic representation of a direct ELISA assay showing the binding response of the monoclonal antibody 4B11, and seven patients' (Batch 1) plasma IgE to purified native Cry j II as the coating antigen.
Figure 33:
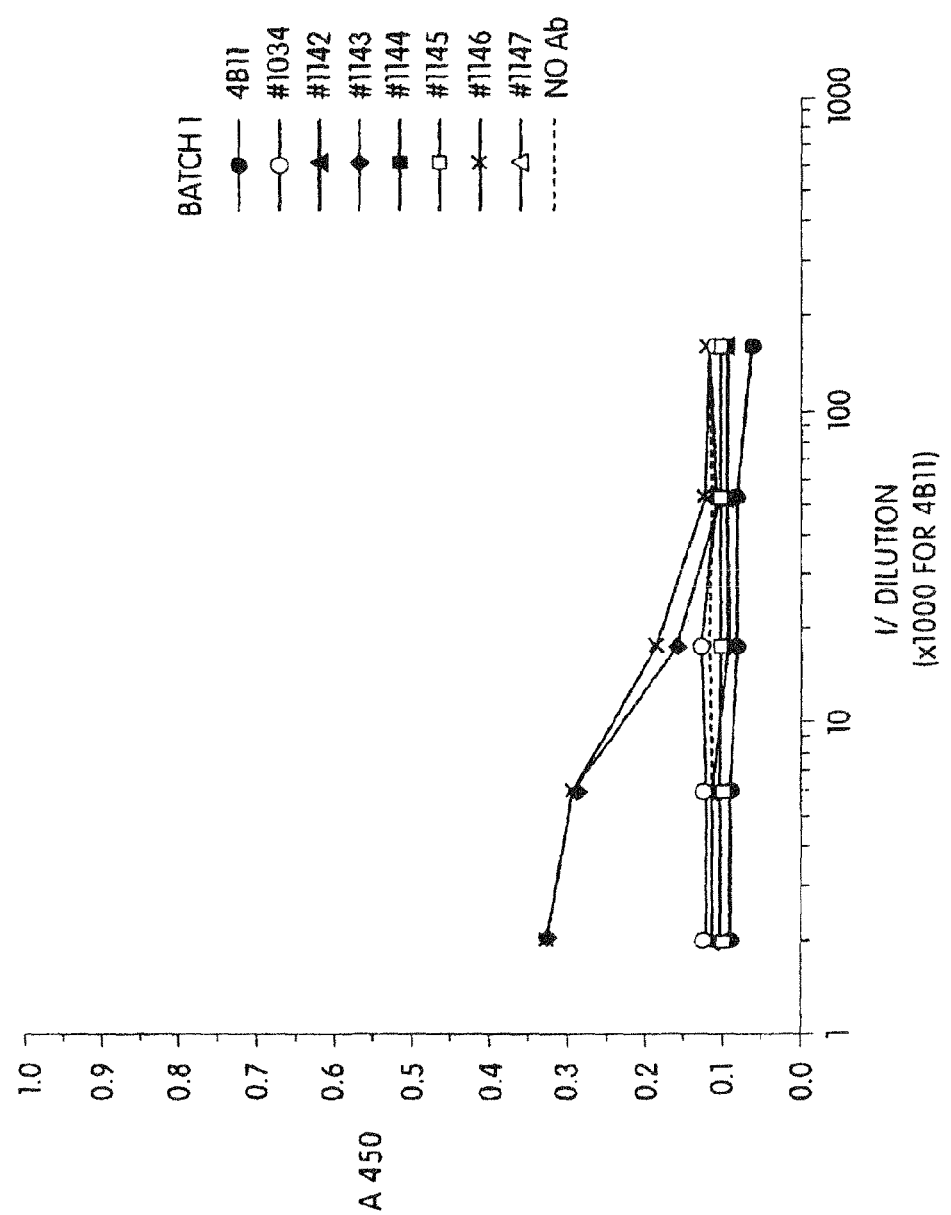
FIG. 33 is a graphic representation of a direct ELISA assay showing the binding response of the monoclonal antibody, 4B11, and seven patients' (Batch 1) plasma IgE to recombinant Cry j II (rCry j II) as the coating antigen.
Figure 34:
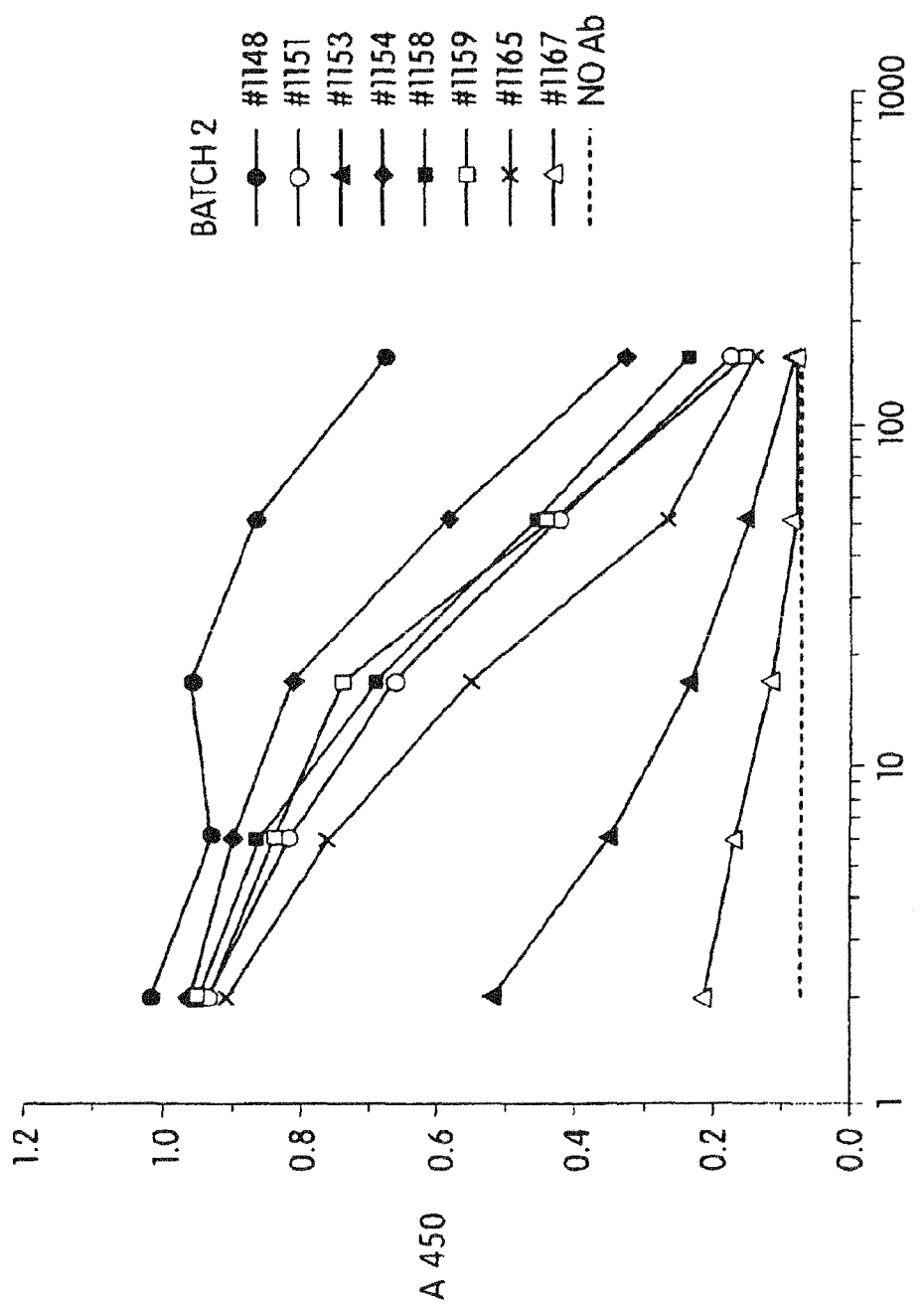
FIG. 34 is a graphic representation of a direct ELISA assay showing the binding response of eight patients' (Batch 2) plasma IgE to purified native Cry j I.
Figure 35:
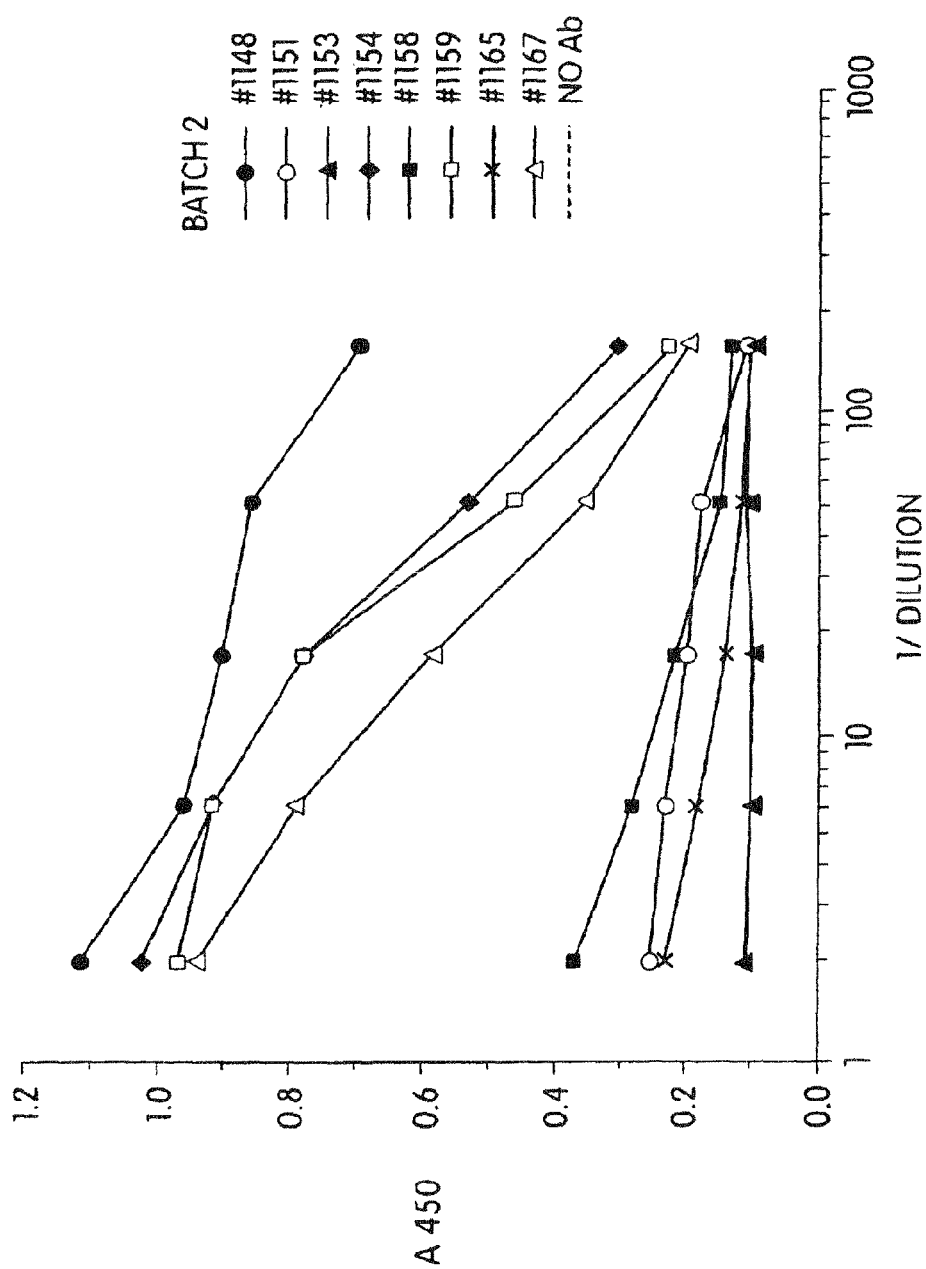
FIG. 35 is a graphic representation of a direct ELISA assay showing the binding response of eight patients' (Batch 2) plasma IgE to purified native Cry j II.
Figure 36:
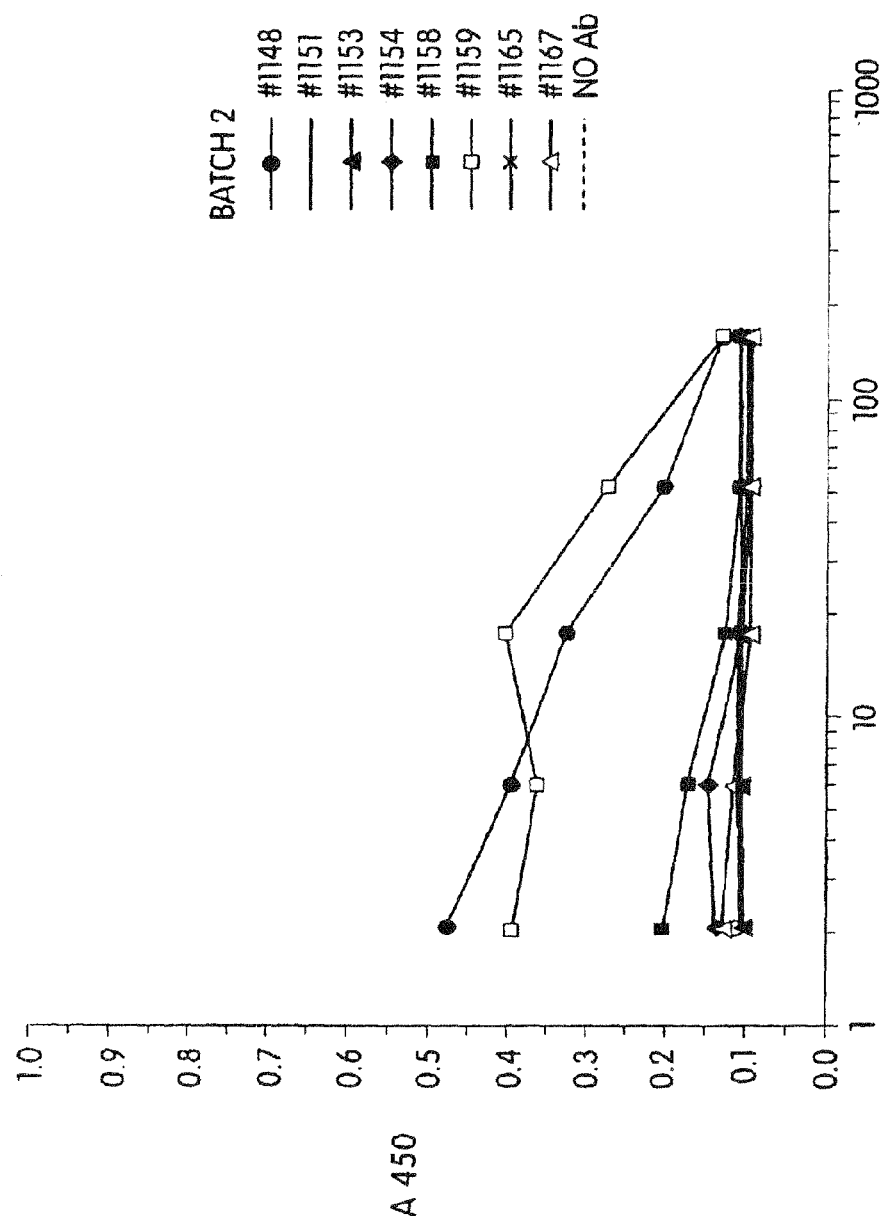
FIG. 36 is a graphic representation of a direct ELISA assay showing the binding response of eight patients' (Batch 2) plasma IgE to recombinant Cry j II.
Figure 37:
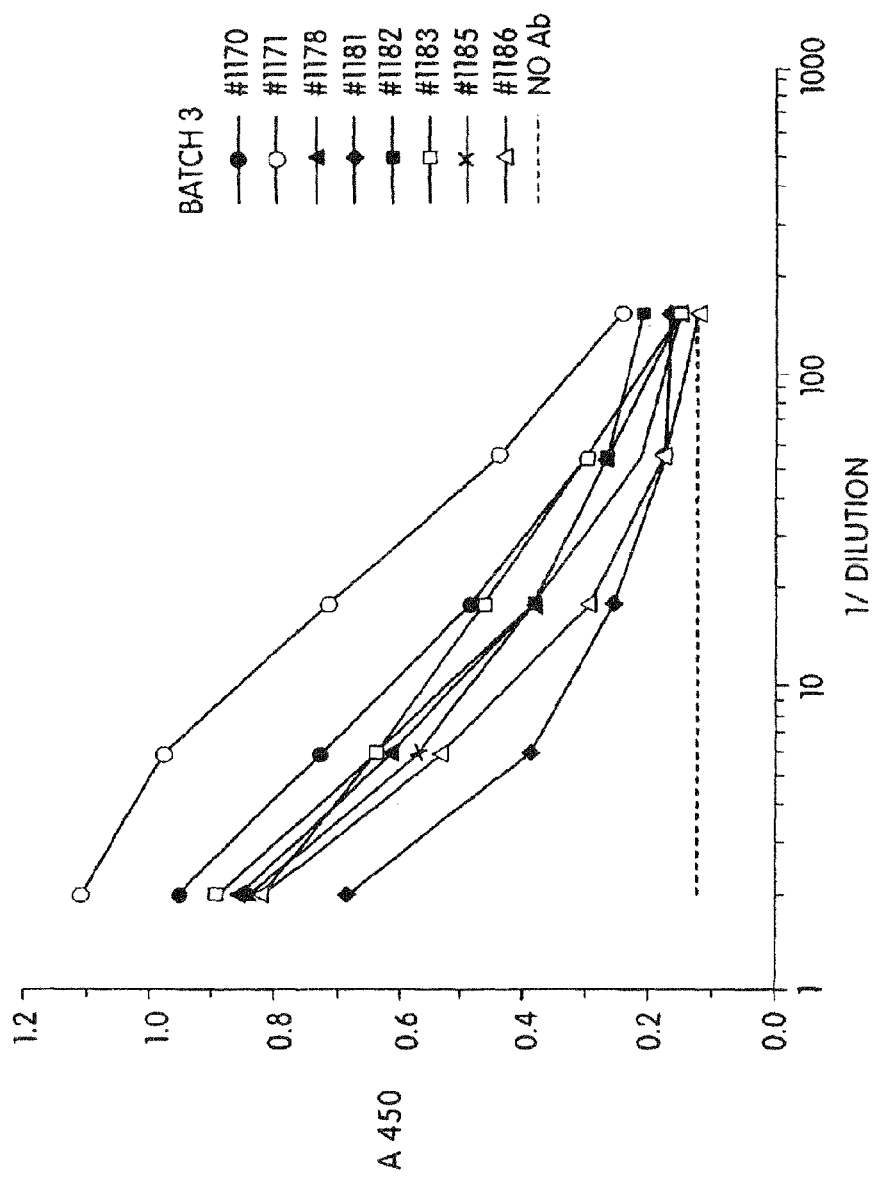
FIG. 37 is a graphic representation of a direct ELISA assay showing the binding response of eight patients' (Batch 3) plasma IgE to purified native Cry j I.
Figure 38:
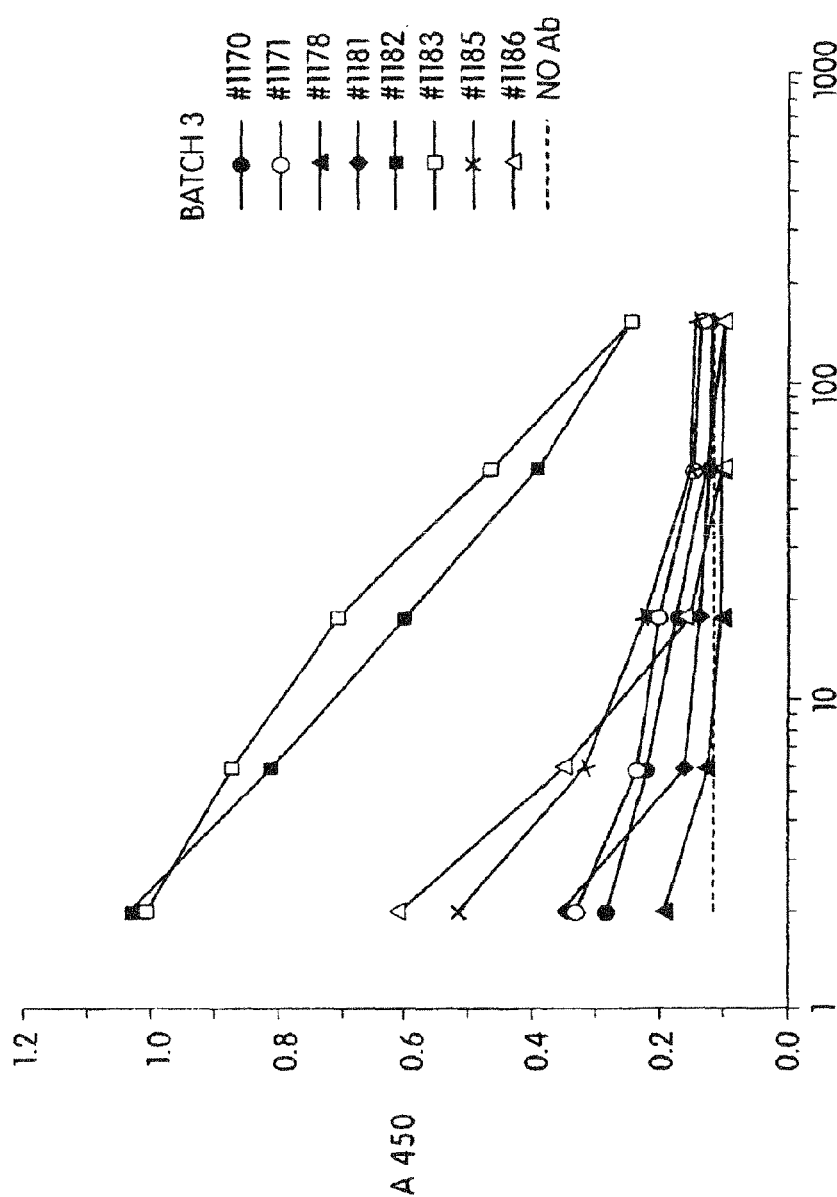
FIG. 38 is a graphic representation of a direct ELISA assay showing the binding response of eight patients' (Batch 3) plasma IgE to purified native Cry j II.
Figure 39:
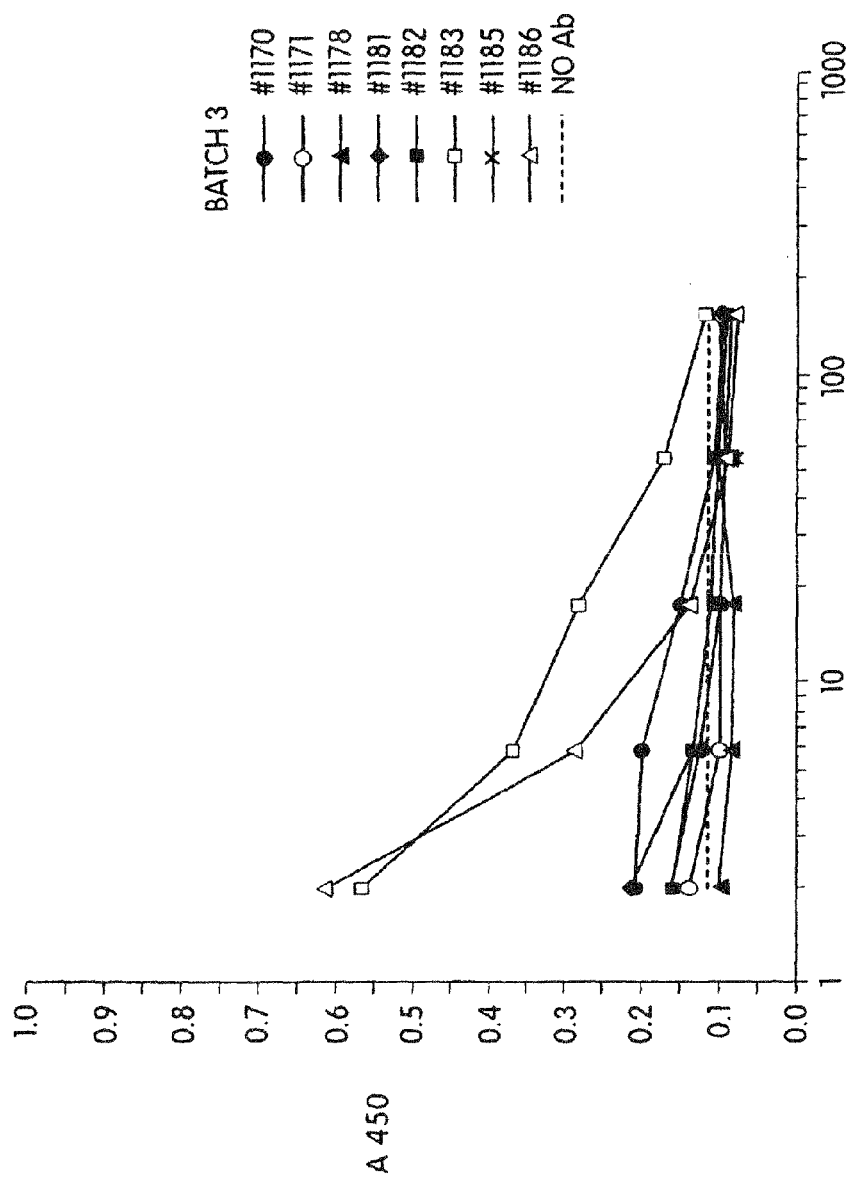
FIG. 39 is a graphic representation of a direct ELISA assay showing the binding response of eight patients' (Batch 3) plasma IgE to recombinant Cry j II.

In FIG. 31 the binding response of the monoclonal antibody, 4B11, and seven patients' (Batch 1) plasma IgE is shown to purified Cry j I as the coating antigen. The monoclonal antibody, raised against purified Cry j I shows a saturating level of binding for the whole dilution series. The individual patient samples show a variable response of IgE binding to the Cry j I preparation. One patient, #1034, has no detectable binding to this protein preparation. All the patient samples were obtained from individuals claiming to be symptomatic for Japanese cedar pollen allergy and the results of their MAST scores are shown in FIG. 40. FIG. 32 is a graph representing the binding of the same antibody set as in FIG. 31 to purified native Cry j II. The anti-Cry j I monoclonal antibody, 4B11, is negative on this preparation demonstrating lack of cross-reactivity between the two allergen antigens. In general, there is a lower overall response to this allergenic component of cedar pollen with more patient samples showing decreased binding. However, patient #1034, that was negative on Cry j I shows very strong reactivity to Cry j II. In the last antigen set, FIG. 33, using recombinant Cry j II (rCry j II), monoclonal antibody 4B11 reactivity is negative and there is further reduction in binding of the human IgE samples compared to biochemically purified Cry j II. Two of the patients, #1143 and #1146, are clearly positive for IgE binding to the recombinant form of Cry j II although the patient that reacted the strongest to biochemically purified form is negative here, 1034. FIGS. 34-39 represent the application of the same antigen sets for the direct binding analysis of the next sixteen patients designated patient Batch 2 and patient Batch 3 in FIGS. 34-39.

The table shown in FIG. 40 summarizes both the MAST scores, performed in Japan on the plasma samples before shipment using a commercially available kit, and the direct ELISA results outlined above. Two patients were negative by the MAST assay, however, one of these patients, #1143, was positive on all the ELISA antigens. The number of positive responses for each antigen is shown and this represents a measure relative allergenicity of the different allergen preparations. These results demonstrate that Cry j II is an allergen as defined by human allergic patient IgE reactivity and that there are some patients who are not reactive to Cry j I but are reactive to Cry j II. The frequency of response in this population of patients is less to Cry j II than to Cry j I.

EXAMPLE 19

Japanese Cedar Pollen Allergic Patient T Cell Studies with Cry j II and Cry j II Peptides.
Synthesis of Cry j II Peptides Japanese cedar pollen Cry j II peptides designated Cry j IIA (SEQ ID NO: 185), Cry j IIB (SEQ ID NO: 186), Cry j IIG (SEQ ID NO: 191), Cry j IIH (SEQ ID NO: 192) and Cry j IIQ (SEQ ID NO: 193) were synthesized using standard Fmoc/tBoc synthetic chemistry and purified by Reverse Phase HPLC. The amino acid sequence of peptide Cry j IIA is FTFKVDGIIAAYQ (SEQ ID NO: 185) which corresponds to amino acids 116-128 of SEQ ID NO: 134; FIGS. 28 and 41. The amino acid sequences of peptide Cry j IIB is NGYFS-GHVIPACKN (SEQ ID NO: 186) which corresponds to amino acids 416-429 of SEQ ID NO: 134; FIGS. 28 and 41. The amino acid sequence of Cry j IIG is shown in FIG. 41 and corresponds to amino acids 152-175 of SEQ IS NO: 134, FIG. 28. The amino acid sequence of Cry j IIH is shown in FIG. 41 and corresponds to amino acids 386-409 of SEQ ID NO: 134, FIG. 28. The amino acid sequence of Cry j IIQ is shown in FIG. 41, and corresponds to amino acids 269-292 of SEQ ID NO: 134, FIG. 28. The amino acid sequences of the peptide names are consistent throughout.

Japanese cedar pollen Cry j II peptides designated Cry j IIC (SEQ ID NO: 187), Cry j IID (SEQ ID NO: 188), Cry j IIE (SEQ ID NO: 189), and Cry j IIF (SEQ ID NO: 190) having amino acid sequences as shown in FIG. 41 were synthesized using recombinant techniques and expressed as discussed in Example 20. These peptides are modified peptides derived from the full length amino acid sequence Cry j II (SEQ ID NO: 134) shown in FIG. 28. Peptide Cry j IIC (SEQ ID NO: 187) corresponds to amino acids 46-163 of SEQ ID NO: 134 shown in FIG. 28; peptide Cry j IID (SEQ ID NO: 188) corresponds to amino acids 164-280 of SEQ ID NO: 134 shown in FIG. 28; peptide Cry j IIE (SEQ ID NO: 189) corresponds to amino acids 281-396 of SEQ ID NO: 134 shown in FIG. 28; and peptide Cry j IIF (SEQ ID NO: 190) corresponds to amino acids 397-514 of SEQ ID NO: 134 shown in FIG. 28.

T Cell Responses to Japanese Cedar Pollen Antigen Peptides

Figure 42:
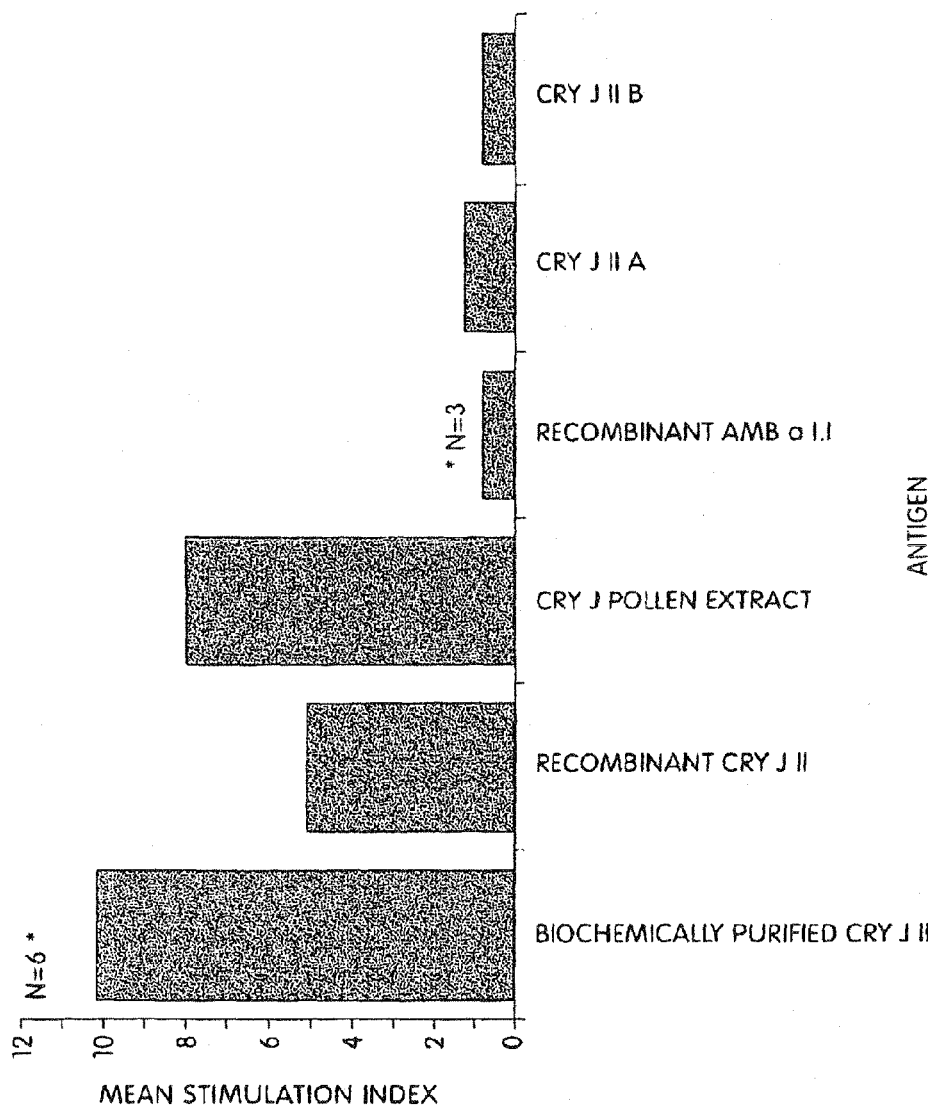
FIG. 42 is a graphic representation depicting T cell responses to Cry j II peptides Cry j IIA (SEQ ID NO: 185), and Cry j IIB (SEQ ID NO: 186); the mean S. I. is shown above each bar (in parentheses) as well as the percentage of responses, the positivity index (mean S.I. multiplied by percentage of responses) is the Y axis.

Peripheral blood mononuclear cells (PBMC) were purified by lymphocyte separation medium (LSM) centrifugation of 60 ml of heparinized blood from up to nine Japanese cedar pollen-allergic patients who exhibited clinical symptoms of seasonal rhinitis and was MAST and/or skin test positive for Japanese cedar pollen. Long term T cell lines were established by stimulation of $2\times10^6$ PBL/ml in bulk cultures of complete medium (RPMI-1640, 2 mM L-glutamine, 100 U/ml penicillin/streptomycin, $5\times10^{-5}$M 2-mercaptoethanol, and 10 mM HEPES supplemented with 5% heat inactivated human AB serum) with 10 µg/ml of partially purified native Cry j II for 7 days at 37° C. in a humidified 5% $CO_2$ incubator to select for Cry j II reactive T cells. This amount of priming antigen was determined to be optimal for the activation of T cells from most Japanese cedar pollen Cry j II allergic patients. Viable cells were purified by LSM centrifugation and cultured in complete medium supplemented with 5 units recombinant human IL-2/ml and 5 units recombinant human IL-4/ml for up to three weeks until the cells no longer responded to lymphokines and were considered "rested". The ability of the T cells to proliferate to peptides Cry j IIA (SEQ ID NO: 185) and Cry j IIB (SEQ ID NO: 186), recombinant Cry j II (rCry j II) (SEQ ID NO: 134), purified native Cry j II, was then assessed. For assay, $2\times10^4$ rested cells were restimulated in the presence of $2\times10^4$ autologous Epstein-Barr virus (EBV)-transformed B cells (prepared as described in Example 6) (gamma-irradiated with 25,000 RADS) with 2-50 'g/ml of rCry j II (SEQ ID NO: 134), purified native Cry j II, peptides Cry j IIA (SEQ ID NO: 185) and Cry j IIB (SEQ ID NO: 186), positive control (PHA), negative control (Amb a I.1), in a volume of 200 ml complete medium in duplicate or triplicate wells in 96-well round bottom plates for 2-4 days. The optimal incubation was found to be 3 days. Each well then received 1 µCi tritiated thymidine for 16-20 hours. The counts incorporated were collected onto glass fiber filter mats and processed for liquid scintillation counting. The maximum response in a titration of each peptide is expressed as the stimulation index (S.I.). The S.I. is the counts per minute (CPM) incorporated by cells in response to peptide, divided by the CPM incorporated by cells in medium only. A positivity index may be calculated by multiplying the mean S.I. (indicated above each bar in FIGS. 42 and 43) by the percentage of individuals responding to the peptide (indicated in parentheses above each bar in FIGS. 42 and 43). The results shown in FIG. 42 demonstrate that the Japanese cedar pollen allergic patients tested (n=6) respond well to recombinant Cry j II, and purified native Cry j II, as expected. There was minimal cross reaction with negative control Amb a I.1 whole protein as expected. The response to peptides Cry j IIA (SEQ ID NO: 185) and Cry j IIB (SEQ ID NO: 186) in a population of only six patients, indicates that it may be likely that epitopes exit within these peptides. Additional Japanese cedar pollen allergic patients will be tested in this assay system and it is believed that these studies will show that peptides Cry j IIA (SEQ ID NO: 185) and Cry j IIB (SEQ ID NO: 186) contain T cell epitopes.

Figure 43:
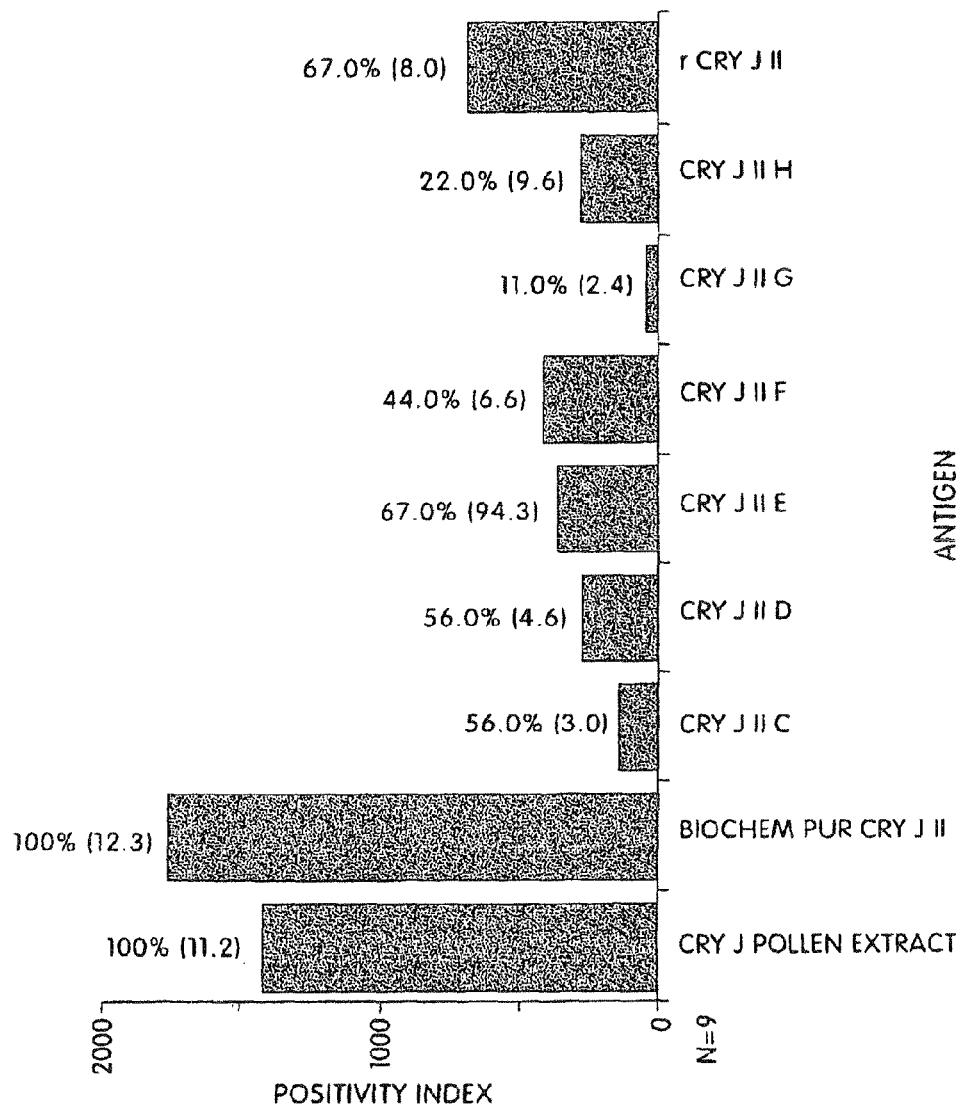
FIG. 43 is a graphic representation depicitng T cell responses to Cry j II peptides Cry j IIC (SEQ ID NO: 187), Cry j IID (SEQ ID NO: 188), Cry j IIE (SEQ ID NO: 189), Cry j IIF (SEQ ID NO: 190); Cry j IIG (SEQ ID NO: 191), Cry j IIH (SEQ ID NO. 192) the mean S.I. is shown above each bar (in parentheses) as well as the percentage of responses; the positivity index (mean S.I. multiplied by percentage of responses) is the Y axis.

FIG. 43 shows T cell proliferative assays performed substantially as described above with Cry j II reactive T cells from a total of 9 Japanese Cedar pollen allergic patients. As shown in FIG. 43, these T cell lines react not only to rCry j II, and purified native Cry j II as expected, but also to peptides Cry j IIC (SEQ ID NO: 187), Cry j IID (SEQ ID NO: 188), Cry j IIE (SEQ ID NO: 189), and Cry j IIF (SEQ ID NO: 190), Cry j IIG (SEQ ID NO: 191) and Cry j IIH (SEQ ID NO: 192). There was minimal cross reactivity with the negative control Amb a I.1 whole protein, as expected. The positive mean S.I. (indicated above each bar in parentheses) for each peptide tested indicates that each peptide contains at least one T cell epitope. Peptide fragments derived from each of peptides Cry j IIC (SEQ ID NO: 187), Cry j IID (SEQ ID NO: 188), Cry j IIE (SEQ ID NO: 189), and Cry j IIF (SEQ ID NO: 190) may be synthesized and used in the above-described T cell proliferation assay system to further analyze the location of each T cell epitope.

EXAMPLE 20

Recombinant Production of Peptide Subconstructs Designated Cry j IIC (SEQ ID NO: 187), Cry j IID (SEQ ID NO: 188), Cry j IIE (SEQ ID NO: 189), and Cry j IIF (SEQ ID NO: 190)

Four Cry j II peptide subconstructs designated construct #1(Cry j IIC (SEQ ID NO: 187)), construct #2 (Cry j IID (SEQ ID NO: 188)), construct #3 (Cry j IIE (SEQ ID NO: 189)), and construct #4 (Cry j IIF (SEQ ID NO: 190)), which cover amino acids 46 to 514 of the Cry j II protein sequence (SEQ ID NO: 133 and 134), were created by PCR using the clone pUC19JC140iiid as a template (See Example 16). All PCR reactions were carried out using Ultma™ DNA polymerase (Perkin Elmer Cetus, Norwalk Conn.) in a 100 µl reaction. Five µl 10× Ultma™ DNA Polymerase buffer, 6 µl MgCl$_2$ (1.5 mM final concentration), 3.2 µl 1.25 mM dNTPs (40 mM final concentration), and 100 pmol of each oligonucleotide in the pairs specified below were brought to 50 µl with dH$_2$O. The tubes containing these mixtures were covered with an Ampliwax Gem™ (Perkin Elmer Cetus, Norwalk Conn.) and sealed by heating to 80° C. for 5 min and then cooling to 25° C. for 1 min. Five µl 10× Ultma™ DNA Polymerase buffer, 1 µg (1 µg) of DNA from clone pUC19JC140iiid, 0.5 µl of Ultma™ DNA Polymerase, and 43.5 µl dH$_2$O were added to every sample tube. The samples were then subjected to 20 rounds of amplification with a Programmable Thermal Cycler™ (MJ Research Inc., Cambridge Mass.). Each round of amplification consisted of heating to 94° C. for 1 min, 55° C. for 1 min, and 72° C. for 1 min. The final round of amplification was followed by a 3 min incubation at 72° C.

Four sets of oligonucleotides were synthesized on an ABI 394 DNA/RNA synthesizer (Applied Biosystems, Foster City Calif.). For construct #1, the oligonucleotides CP-38 (See Example 3) and CP-73 were used, whereby CP-73 has the sequence 5'-GGCGGATCCTTACCATTGTTTTCCT-TGCCC-3' (SEQ ID NO:196), which is the noncoding strand sequence that corresponds to nucleotides 513-530 of FIG. 28. The nucleotides 5'-GGCGGATCC-3' (bases 1-9 of CP-73) represent a BamH I restriction site added for cloning purposes, followed by 5'-TTA-3' (bases 10-12 of CP-73) which encode a new stop codon. Construct #2 was generated using oligonucleotides CP-74 and CP-75. CP-74 has the sequence 5'-CGGGAATTCTGGGCTGGCCAATGTAAA-3' (SEQ ID NO: 197), which is the coding strand sequence that corresponds to nucleotides 531-548 of FIG. 28, and the nucleotides 5'-CGGGAATTC-3' (bases 1-9 of CP-74) represent an EcoR I restriction site added for cloning purposes. CP-75 has the sequence 5'-GGCGGATCCTTATATTCCATGGCCTG-GACC-3' (SEQ ID NO: 198), which is the noncoding strand sequence that corresponds to nucleotides 864-881 of FIG. 28. The nucleotides 5'-GGCGGATCC-3' (bases 1-9 of CP-75) represent a BamH I restriction site added for cloning purposes, followed by 5'-TTA-3' (bases 10-12 of CP-75) which encode a new stop codon. Construct #3, was generated using oligonucleotides CP-76 and CP-77. CP-76 has the sequence 5'-CGGGAATTCAGTATAGGAAGTCTTGGG-3' (SEQ ID NO: 199), which is the coding strand sequence that corresponds to nucleotides 882-899 of FIG. 28. The nucleotides 5'-CGGGAATTC-3' (bases 1-9 of CP-76) represent an EcoR I restriction site added for cloning purposes. CP-77 has the sequence 5'-GGCGGATCCTTAATCACTTAGCTT-TATATC-3' (SEQ ID NO: 200), which is the noncoding strand sequence that corresponds to nucleotides 1215-1232 of FIG. 28. Nucleotides 5'-GGCGGATCC-3' (bases 1-9 of CP-77) represent a BamH I restriction site added for cloning purposes, followed by 5'-TTA-3' (bases 10-12 of CP-77) which encode a new stop codon. Construct #4 was generated using oligonucleotides CP-78 and CP-53. CP-53 is described fully in Example 15, and CP-78 has the sequence 5'-CGGGAAT-TCATATCTTTGAAGCTTACC-3' (SEQ ID NO: 201), which is the coding strand sequence that corresponds to nucleotides 1233-1250 of FIG. 28. Nucleotides 5'-CGG-GAATTC-3' (bases 1-9 of CP-78) represent an EcoR I restriction site added for cloning purposes.

All 4 PCRs resulted in DNA fragments of approximately 370 nucleotides in length as visualized on ethidium bromide stained 2% agarose minigels, and all were cloned into pUC 19 as outlined in Example 16. Sequences from the resultant clones were verified using the Sequenase Kit™ as in Example 16, and a single clone for each construct was chosen for subcloning into the expression vector pET11dΔHRhis$_6$ (See Example 16). The clones chosen were named pUC19JC151iib, pUC19JC152iic, pUC19JC153iic, and pUC19JC154iin, for peptide constructs #1, #2, #3, and #4, respectively. DNA from each of these clones was digested simultaneously with EcoR I and BamH I to release the appropriate insert; these inserts were then ligated into EcoR I/BamH I digested pET11dΔHR, and the resultant clones again sequenced to verify cloning junctions.

A clone was chosen for each of the constructs #1, #2, #3, and #4, called pET11dΔHRhis$_6$JC151 iib.a, pET11dΔHRhis$_6$JC152iic.a, pET11dΔHRhis$_6$JC153iic.a, and pET11dΔHRhis$_6$JC154iin.c, respectively, for expression in *E. coli* strain BL21-DE3 as in Example 16. The four histidine-tagged recombinant proteins were then purified on NTA-Ni$^{2+}$ agarose, also as described in Example 16. One liter preps of Constructs#1, #3, and #4 gave 9.3 mg, 37.4 mg, and 18.8 mg of purified recombinant protein, respectively. Sequence analyses of these three recombinant proteins verified the NH$_2$-terminal protein sequence, and gave an estimated purity of 67%, 95%, and 95% for Constructs #1, #3, and #4, respectively. Construct #2 was expressed at very low levels: an initial prep of 6 L gave only about 1.5 mg of total purified protein with approximately 10% purity by sequence analysis. A subsequent 9 L prep gave I mg total purified protein of 23% purity, as determined by densitometry of a Coomassie Blue-stained SDS-PAGE gel. The isolated protein from these two preps was combined to give 2.5 mg protein of approximately 15% purity. This is referred to hereafter as #2A. A third large scale prep was prepared from a 9 L cell culture whereby the insoluble aggregates inside the *E. coli* were isolated (instead of the whole cell lysis and solubilization as above and in Example 16) by lysis of the *E. coli* pellet with 0.2 mg/ml lysozyme (Sigma, St. Louis Mo.) in 10 ml/L culture of lysis buffer (100 mM Na$_2$HPO$_4$, 50 mM NaCl, pH8.0) for 30 min on ice, followed by a rapid freeze (on dry ice/ethanol for 30 min), and thaw at 37° C. The cells were then subjected to bursts of sonication (5×20 sec) and the insoluble aggregates then collected by centrifugation (10,000×g, 20 min). The aggregates were then washed with 10 ml/L culture of the lysis buffer (without lysozyme), re-pelleted, and finally solubilized in 10 ml/L culture 6M guanidine hydrochloride, 0.1M Na$_2$HPO$_4$, 10 mM Tris-HCl, pH 8.0. This lysate was then applied to an NTA-Ni$^{2+}$ column and the recombinant protein purified as in Example 16. This final prep yielded 1 mg of total purified protein with a purity of 40% as determined by densitometry of a Coomassie Blue-stained SDS-PAGE gel; this Construct #2 protein is referred to as #2B.

EXAMPLE 21

Identification and Development of Unique Peptides Suitable as Peptide Candidates for Use in an Injectable Multipeptide Therapeutic Formulation.

As discussed in the specification, peptides CJI-24.5 (SEQ ID NO: 129), CJI-43.39 (SEQ ID NO: 128), and CJI-44.8 (SEQ ID NO: 132) were among a group of peptides which were "unique" as a result of modifications which resulted in each of these peptides possessing the characteristic of "superior" solubility (i.e. stability and solubility in an aqueous buffer of greater than 5 mg/ml over a pH range of pH6-pH8) and the characteristic of retaining similar T cell reactivity of the parent peptide from which it was derived. These peptides were then tested for T cell reactivity as discussed in Example 11 and shown in FIG. 21, which indicated that each of peptides CJ1-24.5 (SEQ ID NO: 129), CJ1-43.39 (SEQ ID NO: 128), and CJ1-44.8 (SEQ ID NO: 132) elicits T cell activity as did each of their "parent" peptides from which they were derived and thus are suitable as candidate peptides for formulating an injectable therapeutic.

These peptides among others described earlier are "unique" in that they were developed to fall within a very stringent set of parameters. Several different modifications of the parent peptides were attempted prior to identifying the peptide which met all of the stringent criteria for of a "unique" peptide which possesses "superior solubility".

For example, the amino acid sequence of CJI-44.8 (SEQ ID NO: 132) was derived from the protein sequence of Cry j I by first identifying those regions of the parent protein with high T cell reactivity using the set of overlapping peptides 20-mers as discussed in Example 6, and shown in FIG. 13, which covered the entire sequence. Two of these peptides, CJI-31 (SEQ ID NO: 54) and CJI-32 (SEQ ID NO: 56), individually exhibited high T-cell reactivity. Since these peptides were adjacent to each other in the native protein sequence and overlapped by 10 residues, peptide CJI-44 was synthesized to capture the total T cell reactivity of both peptides. CJI-44 (SEQ ID NO: 90) (FIG. 18) is a peptide 30-mer which contains all of the sequence present in the two 20-mers CJI-31 (SEQ ID NO: 54) and CJI-32 (SEQ ID NO: 56). However, although CJI-44 (SEQ ID NO: 90) posssessed T cell reactivity, when the solubility of this peptide was tested it had a solubility much lower than the 5 mg/ml solubility required for a "unique" peptide.

Thus, further attempts were made increase solubility by truncation at the N-terminus portion of CJI-44(SEQ ID NO: 90) which resulted in CJI-44.1 (SEQ ID NO: ). Additional truncation of two C-terminal residues yielded 44.2 (SEQ ID NO: ). However, although solubility was improved in these sequences it still did not reach the standard of "superior solubility". Thus, 44.2 (SEQ ID NO: ) was further modified by the addition of charged (hydrophilic residues) to the N-terminus and by replacement of the hydrophobic residue Val with the less hydrophobic residue Ala. Two of the resulting analogs, CJI-44.5 (SEQ ID NO: ) and CJI-44.6 (SEQ ID NO: ) (FIG. 20), showed increased solubility to using a "single pH point protocol procedure" (e.g. a protocol procedure wherein determinations of solubility were made at a single pH in 100 mM sodium phosphate buffer without mannitol under constant agitation) Two additional analogs were constructed in which the residue Asn was deleted. Of these two analogs, CJI-44.7 (SEQ ID NO: ) and CJI-44.8 (SEQ ID NO: 132) (FIG. 20 and FIG. 44), CJI-44.8 (SEQ ID NO: 132) was very soluble in the "single pH point protocol" and achieved "superior solubility" in the "pH range protocol procedure" (i.e. wherein solubility is measured as a function of pH in 50 mM sodium phosphate containing 5% mannitol with no agitation after initial mixing). CJI-44.8 (SEQ ID NO: 132) was stable and soluble at greater than 5 mg/ml over the pH range pH6-pH8 in an aqueous buffer.

Peptide CJI-44.8 (SEQ ID NO: 132) was classified as a "unique" peptide after confirmation that it retained a T-cell reactivity similar to its parent peptides, CJI-31 (SEQ ID NO: 54), CJI-32 (SEQ ID NO: 56) and CJI-44 (SEQ ID NO: 90) (FIGS. 13 and 20). As discussed earlier unique peptides are particularly suitable as candidate peptides for the formulation of injectable multipeptide therapeutic compositions and formulations. Development of other "unique" peptides (e.g. CJI-24.5 (SEQ ID NO: 129) and CJI-43.39 (SEQ ID NO: 128)) followed a process similar to that described above for CJI-44.8 (SEQ ID NO: 132).

The combination of candidate peptides CJI-24.5 (SEQ ID NO: 129), CJI-43.39 (SEQ ID NO: 128), and CJI-44.8 (SEQ ID NO: 1-32) was tested as described in earlier to determine if the combination of all three peptides covered a sufficient percentage of T cell epitopes suitable for formulation of the peptides in a multipeptide injectable therapeutic formulation. As discussed earlier, based on an analysis of 36 patients (FIG. 45), the frequency of response at 97% represents reactivity to at least one of the candidate peptides, indicating that this combination of peptides is suitable for preparation as a therapeutic composition of the invention as well as a multipeptide formulation of the invention.

Although the invention has been described with reference to its preferred embodiments, other embodiments, can achieve the same results. Variations and modifications to the present invention will be obvious to those skilled in the art and it is intended to cover in the appended claims all such modification and equivalents and follow in the true spirit and scope of this invention.

---

SEQUENCE LISTING

```
<160> NUMBER OF SEQ ID NOS: 283

<210> SEQ ID NO 1
<211> LENGTH: 1337
<212> TYPE: DNA
<213> ORGANISM: Cryptomeria japonica
<220> FEATURE:
<221> NAME/KEY: CDS
<222> LOCATION: (66)..(1187)
<220> FEATURE:
<221> NAME/KEY: mat_peptide
<222> LOCATION: (129)..(1187)

<400> SEQUENCE: 1
agtcaatctg ctcataatca tagcatagcc gtatagaaag aaattctaca ctctgctacc       60 aaaaa atg gat tcc cct tgc tta gta gca tta ctg gtt ttc tct ttt gta     110
      Met Asp Ser Pro Cys Leu Val Ala Leu Leu Val Phe Ser Phe Val
          -20              -15                  -10 att gga tct tgc ttt tct gat aat ccc ata gac agc tgc tgg aga gga       158
Ile Gly Ser Cys Phe Ser Asp Asn Pro Ile Asp Ser Cys Trp Arg Gly
     -5              -1  1               5                      10 gac tca aac tgg gcc caa aat aga atg aag ctc gca gat tgt gca gtg       206
Asp Ser Asn Trp Ala Gln Asn Arg Met Lys Leu Ala Asp Cys Ala Val
                15                  20                  25 ggc ttc gga agc tcc acc atg gga ggc aag gga gga gat ctt tat acg       254
Gly Phe Gly Ser Ser Thr Met Gly Gly Lys Gly Gly Asp Leu Tyr Thr
             30                  35                  40 gtc acg aac tca gat gac gac cct gtg aat cct gca cca gga act ctg       302
Val Thr Asn Ser Asp Asp Asp Pro Val Asn Pro Ala Pro Gly Thr Leu
         45                  50                  55 cgc tat gga gca acc cga gat agg ccc ctg tgg ata att ttc agt ggg       350
Arg Tyr Gly Ala Thr Arg Asp Arg Pro Leu Trp Ile Ile Phe Ser Gly
     60                  65                  70 aat atg aat ata aag ctc aaa atg cct atg tac att gct ggg tat aag       398
Asn Met Asn Ile Lys Leu Lys Met Pro Met Tyr Ile Ala Gly Tyr Lys
75                  80                  85                  90 act ttt gat ggc agg gga gca caa gtt tat att ggc aat ggc ggt ccc       446
Thr Phe Asp Gly Arg Gly Ala Gln Val Tyr Ile Gly Asn Gly Gly Pro
                 95                 100                 105
```

```
tgt gtg ttt atc aag aga gtt agc aat gtt atc ata cac ggt ttg tat      494
Cys Val Phe Ile Lys Arg Val Ser Asn Val Ile Ile His Gly Leu Tyr
            110                 115                 120 ctg tac ggc tgt agt act agt gtt ttg ggg aat gtt ttg ata aac gag      542
Leu Tyr Gly Cys Ser Thr Ser Val Leu Gly Asn Val Leu Ile Asn Glu
        125                 130                 135 agt ttt ggg gtg gag cct gtt cat cct cag gat ggc gat gct ctt act      590
Ser Phe Gly Val Glu Pro Val His Pro Gln Asp Gly Asp Ala Leu Thr
    140                 145                 150 ctg cgc act gct aca aat att tgg att gat cat aat tct ttc tcc aat      638
Leu Arg Thr Ala Thr Asn Ile Trp Ile Asp His Asn Ser Phe Ser Asn
155                 160                 165                 170 tct tct gat ggt ctg gtc gat gtc act ctt act tcg act gga gtt act      686
Ser Ser Asp Gly Leu Val Asp Val Thr Leu Thr Ser Thr Gly Val Thr
                175                 180                 185 att tca aac aat ctt ttt ttc aac cat cat aaa gtg atg ttg tta ggg      734
Ile Ser Asn Asn Leu Phe Phe Asn His His Lys Val Met Leu Leu Gly
            190                 195                 200 cat gat gat gca tat agt gat gac aaa tcc atg aag gtg aca gtg gcg      782
His Asp Asp Ala Tyr Ser Asp Asp Lys Ser Met Lys Val Thr Val Ala
        205                 210                 215 ttc aat caa ttt gga cct aac tgt gga caa aga atg ccc agg gca cga      830
Phe Asn Gln Phe Gly Pro Asn Cys Gly Gln Arg Met Pro Arg Ala Arg
    220                 225                 230 tat gga ctt gta cat gtt gca aac aat aat tat gac cca tgg act ata      878
Tyr Gly Leu Val His Val Ala Asn Asn Asn Tyr Asp Pro Trp Thr Ile
235                 240                 245                 250 tat gca att ggt ggg agt tca aat cca acc att cta agt gaa ggg aat      926
Tyr Ala Ile Gly Gly Ser Ser Asn Pro Thr Ile Leu Ser Glu Gly Asn
                255                 260                 265 agt ttc act gca cca aat gag agc tac aag aag caa gta acc ata cgt      974
Ser Phe Thr Ala Pro Asn Glu Ser Tyr Lys Lys Gln Val Thr Ile Arg
            270                 275                 280 att gga tgc aaa aca tca tca tct tgt tca aat tgg gtg tgg caa tct     1022
Ile Gly Cys Lys Thr Ser Ser Ser Cys Ser Asn Trp Val Trp Gln Ser
        285                 290                 295 aca caa gat gtt ttt tat aat gga gct tat ttt gta tca tca ggg aaa     1070
Thr Gln Asp Val Phe Tyr Asn Gly Ala Tyr Phe Val Ser Ser Gly Lys
    300                 305                 310 tat gaa ggg ggt aat ata tac aca aag aaa gaa gct ttc aat gtt gag     1118
Tyr Glu Gly Gly Asn Ile Tyr Thr Lys Lys Glu Ala Phe Asn Val Glu
315                 320                 325                 330 aat ggg aat gca act cct caa ttg aca aaa aat gct ggg gtt tta aca     1166
Asn Gly Asn Ala Thr Pro Gln Leu Thr Lys Asn Ala Gly Val Leu Thr
                335                 340                 345 tgc tct ctc tct aaa cgt tgt tgatgatgca tatattctag catgttgtac        1217
Cys Ser Leu Ser Lys Arg Cys
            350 tatctaaatt aacatcaaca agaaaatata tcatgatgta tattgttgta ttgatgtcaa   1277 aataaaaatg tatcttttac tattaaaaaa aaaaatgatc gatcggacgg tacctctaga   1337

<210> SEQ ID NO 2
<211> LENGTH: 374
<212> TYPE: PRT
<213> ORGANISM: Cryptomeria japonica

<400> SEQUENCE: 2

Met Asp Ser Pro Cys Leu Val Ala Leu Leu Val Phe Ser Phe Val Ile
1               5                   10                  15

Gly Ser Cys Phe Ser Asp Asn Pro Ile Asp Ser Cys Trp Arg Gly Asp
```

```
                    20                  25                  30
Ser Asn Trp Ala Gln Asn Arg Met Lys Leu Ala Asp Cys Ala Val Gly
            35                  40                  45
Phe Gly Ser Ser Thr Met Gly Gly Lys Gly Gly Asp Leu Tyr Thr Val
        50                  55                  60
Thr Asn Ser Asp Asp Pro Val Asn Pro Ala Pro Gly Thr Leu Arg
 65                  70                  75                  80
Tyr Gly Ala Thr Arg Asp Arg Pro Leu Trp Ile Ile Phe Ser Gly Asn
                85                  90                  95
Met Asn Ile Lys Leu Lys Met Pro Met Tyr Ile Ala Gly Tyr Lys Thr
            100                 105                 110
Phe Asp Gly Arg Gly Ala Gln Val Tyr Ile Gly Asn Gly Pro Cys
        115                 120                 125
Val Phe Ile Lys Arg Val Ser Asn Val Ile Ile His Gly Leu Tyr Leu
        130                 135                 140
Tyr Gly Cys Ser Thr Ser Val Leu Gly Asn Val Leu Ile Asn Glu Ser
145                 150                 155                 160
Phe Gly Val Glu Pro Val His Pro Gln Asp Gly Asp Ala Leu Thr Leu
                165                 170                 175
Arg Thr Ala Thr Asn Ile Trp Ile Asp His Asn Ser Phe Ser Asn Ser
            180                 185                 190
Ser Asp Gly Leu Val Asp Val Thr Leu Thr Ser Thr Gly Val Thr Ile
        195                 200                 205
Ser Asn Asn Leu Phe Phe Asn His His Lys Val Met Leu Leu Gly His
        210                 215                 220
Asp Asp Ala Tyr Ser Asp Lys Ser Met Lys Val Thr Val Ala Phe
225                 230                 235                 240
Asn Gln Phe Gly Pro Asn Cys Gly Gln Arg Met Pro Arg Ala Arg Tyr
                245                 250                 255
Gly Leu Val His Val Ala Asn Asn Asn Tyr Asp Pro Trp Thr Ile Tyr
            260                 265                 270
Ala Ile Gly Gly Ser Ser Asn Pro Thr Ile Leu Ser Glu Gly Asn Ser
        275                 280                 285
Phe Thr Ala Pro Asn Glu Ser Tyr Lys Lys Gln Val Thr Ile Arg Ile
        290                 295                 300
Gly Cys Lys Thr Ser Ser Ser Cys Ser Asn Trp Val Trp Gln Ser Thr
305                 310                 315                 320
Gln Asp Val Phe Tyr Asn Gly Ala Tyr Phe Val Ser Ser Gly Lys Tyr
                325                 330                 335
Glu Gly Gly Asn Ile Tyr Thr Lys Lys Glu Ala Phe Asn Val Glu Asn
            340                 345                 350
Gly Asn Ala Thr Pro Gln Leu Thr Lys Asn Ala Gly Val Leu Thr Cys
        355                 360                 365
Ser Leu Ser Lys Arg Cys
        370

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: a, c, t, g, unknown or other
```

<400> SEQUENCE: 3
gayaayccna thgayws                                          17

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: a, c, t, g, unknown or other

<400> SEQUENCE: 4
gggaattcaa ytgggcncar aaysg                                 25

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: a, c, t, g, unknown or other

<400> SEQUENCE: 5
ctgcagccrt tytcnacrtt raa                                   23

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: Inosine
<220> FEATURE:
<221> NAME/KEY: modified_base
<222> LOCATION: (15)..(15)
<223> OTHER INFORMATION: a, c, t, g, unknown or other

<400> SEQUENCE: 6
ttcatnckrt tytgngccca                                       20

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(16)
<223> OTHER INFORMATION: a, c, t, g, unknown or other

<400> SEQUENCE: 7
cctgcagckr ttytgngccc aartt                                 25

<210> SEQ ID NO 8
<211> LENGTH: 18

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atggattccc cttgctta                                                    18

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gggaattcga taatcccata gacagc                                           26

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atgcctatgt acattgc                                                     17

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcaatgtaca taggcat                                                     17

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tccaattctt ctgatggt                                                    18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttttgtcaat tgaggagt                                                    18

<210> SEQ ID NO 14
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 14
cctgcagaag cttcatcaac aacgtttaga                                        30

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tagcaactcc agtcgaagt                                                    19

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tagctctcat ttggtgc                                                      17

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tatgcaattg gtgggagt                                                     18

<210> SEQ ID NO 18
<211> LENGTH: 20
<212> TYPE: PRT
<213> ORGANISM: Cryptomeria japonica
<220> FEATURE:
<221> NAME/KEY: MOD_RES
<222> LOCATION: (7)..(7)
<223> OTHER INFORMATION: Ser, Cys, Thr or His

<400> SEQUENCE: 18

Asp Asn Pro Ile Asp Ser Xaa Trp Arg Gly Asp Ser Asn Trp Ala Gln
1               5                   10                  15

Asn Arg Met Lys
            20

<210> SEQ ID NO 19
<211> LENGTH: 16
<212> TYPE: PRT
<213> ORGANISM: Cryptomeria japonica

<400> SEQUENCE: 19

Glu Ala Phe Asn Val Glu Asn Gly Asn Ala Thr Pro Gln Leu Thr Lys
1               5                   10                  15

<210> SEQ ID NO 20
<211> LENGTH: 30
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 20
gggtctagag gtaccgtccg atcgatcatt                                           30

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gggtctagag gtaccgtccg                                                      20

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aatgatcgat gct                                                             13

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggaattctct agactgcagg t                                                    21

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggaattctct agactgcagg ttttttttttt ttttt                                    35

<210> SEQ ID NO 25
<211> LENGTH: 5
<212> TYPE: PRT
<213> ORGANISM: Juniperus sabinoides

<400> SEQUENCE: 25

Asp Asn Pro Ile Asp
1               5

<210> SEQ ID NO 26
<211> LENGTH: 20
<212> TYPE: PRT
<213> ORGANISM: Cryptomeria japonica

<400> SEQUENCE: 26
```

-continued

Asp Asn Pro Ile Asp Ser Cys Trp Arg Gly Asp Ser Asn Trp Ala Gln
1               5                   10                  15

Asn Arg Met Lys
            20

<210> SEQ ID NO 27
<211> LENGTH: 20
<212> TYPE: PRT
<213> ORGANISM: Cryptomeria japonica

<400> SEQUENCE: 27

Asp Ser Asn Trp Ala Gln Asn Arg Met Lys Leu Ala Asp Cys Ala Val
1               5                   10                  15

Gly Phe Gly Ser
            20

<210> SEQ ID NO 28
<211> LENGTH: 20
<212> TYPE: PRT
<213> ORGANISM: Cryptomeria japonica

<400> SEQUENCE: 28

Leu Ala Asp Cys Ala Val Gly Phe Gly Ser Ser Thr Met Gly Gly Lys
1               5                   10                  15

Gly Gly Asp Leu
            20

<210> SEQ ID NO 29
<211> LENGTH: 20
<212> TYPE: PRT
<213> ORGANISM: Cryptomeria japonica

<400> SEQUENCE: 29

Ser Thr Met Gly Gly Lys Gly Gly Asp Leu Tyr Thr Val Thr Asn Ser
1               5                   10                  15

Asp Asp Asp Pro
            20

<210> SEQ ID NO 30
<211> LENGTH: 20
<212> TYPE: PRT
<213> ORGANISM: Cryptomeria japonica

<400> SEQUENCE: 30

Tyr Thr Val Thr Asn Ser Asp Asp Asp Pro Val Asn Pro Ala Pro Gly
1               5                   10                  15

Thr Leu Arg Tyr
            20

<210> SEQ ID NO 31
<211> LENGTH: 20
<212> TYPE: PRT
<213> ORGANISM: Cryptomeria japonica

<400> SEQUENCE: 31

Val Asn Pro Ala Pro Gly Thr Leu Arg Tyr Gly Ala Thr Arg Asp Arg
1               5                   10                  15

Pro Leu Trp Ile
            20

<210> SEQ ID NO 32
<211> LENGTH: 20
<212> TYPE: PRT

<213> ORGANISM: Cryptomeria japonica

<400> SEQUENCE: 32

Gly Ala Thr Arg Asp Arg Pro Leu Trp Ile Ile Phe Ser Gly Asn Met
1               5                   10                  15

Asn Ile Lys Leu
            20

<210> SEQ ID NO 33
<211> LENGTH: 20
<212> TYPE: PRT
<213> ORGANISM: Cryptomeria japonica

<400> SEQUENCE: 33

Ile Phe Ser Gly Asn Met Asn Ile Lys Leu Lys Met Pro Met Tyr Ile
1               5                   10                  15

Ala Gly Tyr Lys
            20

<210> SEQ ID NO 34
<211> LENGTH: 20
<212> TYPE: PRT
<213> ORGANISM: Cryptomeria japonica

<400> SEQUENCE: 34

Lys Met Pro Met Tyr Ile Ala Gly Tyr Lys Thr Phe Asp Gly Arg Gly
1               5                   10                  15

Ala Gln Val Tyr
            20

<210> SEQ ID NO 35
<211> LENGTH: 20
<212> TYPE: PRT
<213> ORGANISM: Cryptomeria japonica

<400> SEQUENCE: 35

Thr Phe Asp Gly Arg Gly Ala Gln Val Tyr Ile Gly Asn Gly Gly Pro
1               5                   10                  15

Cys Val Phe Ile
            20

<210> SEQ ID NO 36
<211> LENGTH: 20
<212> TYPE: PRT
<213> ORGANISM: Cryptomeria japonica

<400> SEQUENCE: 36

Ile Gly Asn Gly Gly Pro Cys Val Phe Ile Lys Arg Val Ser Asn Val
1               5                   10                  15

Ile Ile His Gly
            20

<210> SEQ ID NO 37
<211> LENGTH: 20
<212> TYPE: PRT
<213> ORGANISM: Cryptomeria japonica

<400> SEQUENCE: 37

Lys Arg Val Ser Asn Val Ile Ile His Gly Leu Tyr Leu Tyr Gly Cys
1               5                   10                  15

Ser Thr Ser Val
            20

```
<210> SEQ ID NO 38
<211> LENGTH: 20
<212> TYPE: PRT
<213> ORGANISM: Cryptomeria japonica

<400> SEQUENCE: 38

Leu Tyr Leu Tyr Gly Cys Ser Thr Ser Val Leu Gly Asn Val Leu Ile
1               5                   10                  15

Asn Glu Ser Phe
            20

<210> SEQ ID NO 39
<211> LENGTH: 20
<212> TYPE: PRT
<213> ORGANISM: Cryptomeria japonica

<400> SEQUENCE: 39

Leu Gly Asn Val Leu Ile Asn Glu Ser Phe Gly Val Glu Pro Val His
1               5                   10                  15

Pro Gln Asp Gly
            20

<210> SEQ ID NO 40
<211> LENGTH: 20
<212> TYPE: PRT
<213> ORGANISM: Cryptomeria japonica

<400> SEQUENCE: 40

Gly Val Glu Pro Val His Pro Gln Asp Gly Asp Ala Leu Thr Leu Arg
1               5                   10                  15

Thr Ala Thr Asn
            20

<210> SEQ ID NO 41
<211> LENGTH: 20
<212> TYPE: PRT
<213> ORGANISM: Cryptomeria japonica

<400> SEQUENCE: 41

Asp Ala Leu Thr Leu Arg Thr Ala Thr Asn Ile Trp Ile Asp His Asn
1               5                   10                  15

Ser Phe Ser Asn
            20

<210> SEQ ID NO 42
<211> LENGTH: 20
<212> TYPE: PRT
<213> ORGANISM: Cryptomeria japonica

<400> SEQUENCE: 42

Ile Trp Ile Asp His Asn Ser Phe Ser Asn Ser Ser Asp Gly Leu Val
1               5                   10                  15

Asp Val Thr Leu
            20

<210> SEQ ID NO 43
<211> LENGTH: 20
<212> TYPE: PRT
<213> ORGANISM: Cryptomeria japonica

<400> SEQUENCE: 43

Ser Ser Asp Gly Leu Val Asp Val Thr Leu Thr Ser Thr Gly Val Thr
1               5                   10                  15
```

Ile Ser Asn Asn
            20

<210> SEQ ID NO 44
<211> LENGTH: 20
<212> TYPE: PRT
<213> ORGANISM: Cryptomeria japonica

<400> SEQUENCE: 44

Thr Ser Thr Gly Val Thr Ile Ser Asn Asn Leu Phe Phe Asn His His
1               5                   10                  15

Lys Val Met Leu
            20

<210> SEQ ID NO 45
<211> LENGTH: 20
<212> TYPE: PRT
<213> ORGANISM: Cryptomeria japonica

<400> SEQUENCE: 45

Leu Phe Phe Asn His His Lys Val Met Leu Leu Gly His Asp Asp Ala
1               5                   10                  15

Tyr Ser Asp Asp
            20

<210> SEQ ID NO 46
<211> LENGTH: 20
<212> TYPE: PRT
<213> ORGANISM: Cryptomeria japonica

<400> SEQUENCE: 46

Leu Gly His Asp Asp Ala Tyr Ser Asp Asp Lys Ser Met Lys Val Thr
1               5                   10                  15

Val Ala Phe Asn
            20

<210> SEQ ID NO 47
<211> LENGTH: 20
<212> TYPE: PRT
<213> ORGANISM: Cryptomeria japonica

<400> SEQUENCE: 47

Lys Ser Met Lys Val Thr Val Ala Phe Asn Gln Phe Gly Pro Asn Cys
1               5                   10                  15

Gly Gln Arg Met
            20

<210> SEQ ID NO 48
<211> LENGTH: 20
<212> TYPE: PRT
<213> ORGANISM: Cryptomeria japonica

<400> SEQUENCE: 48

Gln Phe Gly Pro Asn Cys Gly Gln Arg Met Pro Arg Ala Arg Tyr Gly
1               5                   10                  15

Leu Val His Val
            20

<210> SEQ ID NO 49
<211> LENGTH: 20
<212> TYPE: PRT
<213> ORGANISM: Cryptomeria japonica

```
<400> SEQUENCE: 49

Pro Arg Ala Arg Tyr Gly Leu Val His Val Ala Asn Asn Asn Tyr Asp
1               5                   10                  15

Pro Trp Thr Ile
            20

<210> SEQ ID NO 50
<211> LENGTH: 20
<212> TYPE: PRT
<213> ORGANISM: Cryptomeria japonica

<400> SEQUENCE: 50

Ala Asn Asn Asn Tyr Asp Pro Trp Thr Ile Tyr Ala Ile Gly Gly Ser
1               5                   10                  15

Ser Asn Pro Thr
            20

<210> SEQ ID NO 51
<211> LENGTH: 20
<212> TYPE: PRT
<213> ORGANISM: Cryptomeria japonica

<400> SEQUENCE: 51

Tyr Ala Ile Gly Gly Ser Ser Asn Pro Thr Ile Leu Ser Glu Gly Asn
1               5                   10                  15

Ser Phe Thr Ala
            20

<210> SEQ ID NO 52
<211> LENGTH: 20
<212> TYPE: PRT
<213> ORGANISM: Cryptomeria japonica

<400> SEQUENCE: 52

Ile Leu Ser Glu Gly Asn Ser Phe Thr Ala Pro Asn Glu Ser Tyr Lys
1               5                   10                  15

Lys Gln Val Thr
            20

<210> SEQ ID NO 53
<211> LENGTH: 20
<212> TYPE: PRT
<213> ORGANISM: Cryptomeria japonica

<400> SEQUENCE: 53

Pro Asn Glu Ser Tyr Lys Lys Gln Val Thr Ile Arg Ile Gly Cys Lys
1               5                   10                  15

Thr Ser Ser Ser
            20

<210> SEQ ID NO 54
<211> LENGTH: 20
<212> TYPE: PRT
<213> ORGANISM: Cryptomeria japonica

<400> SEQUENCE: 54

Ile Arg Ile Gly Cys Lys Thr Ser Ser Ser Cys Ser Asn Trp Val Trp
1               5                   10                  15

Gln Ser Thr Gln
            20

<210> SEQ ID NO 55
```

```
<211> LENGTH: 20
<212> TYPE: PRT
<213> ORGANISM: Cryptomeria japonica

<400> SEQUENCE: 55

Cys Ser Asn Trp Val Trp Gln Ser Thr Gln Asp Val Phe Tyr Asn Gly
1               5                   10                  15

Ala Tyr Phe Val
            20

<210> SEQ ID NO 56
<211> LENGTH: 20
<212> TYPE: PRT
<213> ORGANISM: Cryptomeria japonica

<400> SEQUENCE: 56

Asp Val Phe Tyr Asn Gly Ala Tyr Phe Val Ser Ser Gly Lys Tyr Glu
1               5                   10                  15

Gly Gly Asn Ile
            20

<210> SEQ ID NO 57
<211> LENGTH: 20
<212> TYPE: PRT
<213> ORGANISM: Cryptomeria japonica

<400> SEQUENCE: 57

Ser Ser Gly Lys Tyr Glu Gly Gly Asn Ile Tyr Thr Lys Lys Glu Ala
1               5                   10                  15

Phe Asn Val Glu
            20

<210> SEQ ID NO 58
<211> LENGTH: 20
<212> TYPE: PRT
<213> ORGANISM: Cryptomeria japonica

<400> SEQUENCE: 58

Tyr Thr Lys Lys Glu Ala Phe Asn Val Glu Asn Gly Asn Ala Thr Pro
1               5                   10                  15

Gln Leu Thr Lys
            20

<210> SEQ ID NO 59
<211> LENGTH: 20
<212> TYPE: PRT
<213> ORGANISM: Cryptomeria japonica

<400> SEQUENCE: 59

Asn Gly Asn Ala Thr Pro Gln Leu Thr Lys Asn Ala Gly Val Leu Thr
1               5                   10                  15

Cys Ser Leu Ser
            20

<210> SEQ ID NO 60
<211> LENGTH: 13
<212> TYPE: PRT
<213> ORGANISM: Cryptomeria japonica

<400> SEQUENCE: 60

Asn Ala Gly Val Leu Thr Cys Ser Leu Ser Lys Arg Cys
1               5                   10
```

-continued

<210> SEQ ID NO 61
<211> LENGTH: 60
<212> TYPE: PRT
<213> ORGANISM: Cryptomeria japonica

<400> SEQUENCE: 61

Asp Asn Pro Ile Asp Ser Cys Trp Arg Gly Asp Ser Asn Trp Ala Gln
1               5                   10                  15

Asn Arg Met Lys Asp Ser Asn Trp Ala Gln Asn Arg Met Lys Leu Ala
            20                  25                  30

Asp Cys Ala Val Gly Phe Gly Ser Ser Thr Met Gly Gly Lys Gly Gly
        35                  40                  45

Asp Leu Tyr Thr Val Thr Asn Ser Asp Asp Pro
    50                  55                  60

<210> SEQ ID NO 62
<211> LENGTH: 60
<212> TYPE: PRT
<213> ORGANISM: Cryptomeria japonica

<400> SEQUENCE: 62

Gly Ala Thr Arg Asp Arg Pro Leu Trp Ile Ile Phe Ser Gly Asn Met
1               5                   10                  15

Asn Ile Lys Leu Lys Met Pro Met Tyr Ile Ala Gly Tyr Lys Thr Phe
            20                  25                  30

Asp Gly Arg Gly Ala Gln Val Tyr Ile Gly Asn Gly Gly Pro Cys Val
        35                  40                  45

Phe Ile Lys Arg Val Ser Asn Val Ile Ile His Gly
    50                  55                  60

<210> SEQ ID NO 63
<211> LENGTH: 50
<212> TYPE: PRT
<213> ORGANISM: Cryptomeria japonica

<400> SEQUENCE: 63

Leu Gly Asn Val Leu Ile Asn Glu Ser Phe Gly Val Glu Pro Val His
1               5                   10                  15

Pro Gln Asp Gly Asp Ala Leu Thr Leu Arg Thr Ala Thr Asn Ile Trp
            20                  25                  30

Ile Asp His Asn Ser Phe Ser Asn Ser Ser Asp Gly Leu Val Asp Val
        35                  40                  45

Thr Leu
    50

<210> SEQ ID NO 64
<211> LENGTH: 90
<212> TYPE: PRT
<213> ORGANISM: Cryptomeria japonica

<400> SEQUENCE: 64

Leu Phe Phe Asn His His Lys Val Met Leu Leu Gly His Asp Asp Ala
1               5                   10                  15

Tyr Ser Asp Asp Lys Ser Met Lys Val Thr Val Ala Phe Asn Gln Phe
            20                  25                  30

Gly Pro Asn Cys Gly Gln Arg Met Pro Arg Ala Arg Tyr Gly Leu Val
        35                  40                  45

His Val Ala Asn Asn Tyr Asp Pro Trp Thr Ile Tyr Ala Ile Gly
    50                  55                  60

Gly Ser Ser Asn Pro Thr Ile Leu Ser Glu Gly Asn Ser Phe Thr Ala

```
                65                  70                  75                  80
Pro Asn Glu Ser Tyr Lys Lys Gln Val Thr
                85                  90

<210> SEQ ID NO 65
<211> LENGTH: 63
<212> TYPE: PRT
<213> ORGANISM: Cryptomeria japonica

<400> SEQUENCE: 65

Cys Ser Asn Trp Val Trp Gln Ser Thr Gln Asp Val Phe Tyr Asn Gly
1               5                   10                  15

Ala Tyr Phe Val Ser Ser Gly Lys Tyr Glu Gly Gly Asn Ile Tyr Thr
            20                  25                  30

Lys Lys Glu Ala Phe Asn Val Glu Asn Gly Asn Ala Thr Pro Gln Leu
        35                  40                  45

Thr Lys Asn Ala Gly Val Leu Thr Cys Ser Leu Ser Lys Arg Cys
    50                  55                  60

<210> SEQ ID NO 66
<211> LENGTH: 50
<212> TYPE: PRT
<213> ORGANISM: Cryptomeria japonica

<400> SEQUENCE: 66

Asp Asn Pro Ile Asp Ser Cys Trp Arg Gly Asp Ser Asn Trp Ala Gln
1               5                   10                  15

Asn Arg Met Lys Asp Ser Asn Trp Ala Gln Asn Arg Met Lys Leu Ala
            20                  25                  30

Asp Cys Ala Val Gly Phe Gly Ser Ser Thr Met Gly Gly Lys Gly Gly
        35                  40                  45

Asp Leu
    50

<210> SEQ ID NO 67
<211> LENGTH: 30
<212> TYPE: PRT
<213> ORGANISM: Cryptomeria japonica

<400> SEQUENCE: 67

Lys Met Pro Met Tyr Ile Ala Gly Tyr Lys Thr Phe Asp Gln Arg Gly
1               5                   10                  15

Ala Gln Val Tyr Ile Gly Asn Gly Gly Pro Cys Val Phe Ile
            20                  25                  30

<210> SEQ ID NO 68
<211> LENGTH: 30
<212> TYPE: PRT
<213> ORGANISM: Cryptomeria japonica

<400> SEQUENCE: 68

Asp Ala Leu Thr Leu Arg Thr Ala Thr Asn Ile Trp Ile Asp His Asn
1               5                   10                  15

Ser Phe Ser Asn Ser Ser Asp Gly Leu Val Asp Val Thr Leu
            20                  25                  30

<210> SEQ ID NO 69
<211> LENGTH: 50
<212> TYPE: PRT
<213> ORGANISM: Cryptomeria japonica

<400> SEQUENCE: 69
```

-continued

```
Leu Phe Phe Asn His His Lys Val Met Leu Gly His Asp Asp Ala
1               5                   10                  15

Tyr Ser Asp Asp Lys Ser Met Lys Val Thr Val Ala Phe Asn Gln Phe
                20                  25                  30

Gly Pro Asn Cys Gly Gln Arg Met Pro Arg Ala Arg Tyr Gly Leu Val
            35                  40                  45

His Val
    50
```

<210> SEQ ID NO 70
<211> LENGTH: 40
<212> TYPE: PRT
<213> ORGANISM: Cryptomeria japonica

<400> SEQUENCE: 70

```
Cys Ser Asn Trp Val Trp Gln Ser Thr Gln Asp Val Phe Tyr Asn Gly
1               5                   10                  15

Ala Tyr Phe Val Ser Ser Gly Lys Tyr Glu Gly Gly Asn Ile Tyr Thr
                20                  25                  30

Lys Lys Glu Ala Phe Asn Val Glu
            35                  40
```

<210> SEQ ID NO 71
<211> LENGTH: 30
<212> TYPE: PRT
<213> ORGANISM: Cryptomeria japonica

<400> SEQUENCE: 71

```
Lys Met Pro Met Tyr Ile Ala Gly Tyr Lys Thr Phe Asp Gly Arg Gly
1               5                   10                  15

Ala Gln Val Tyr Ile Gly Asn Gly Gly Pro Cys Val Phe Ile
                20                  25                  30
```

<210> SEQ ID NO 72
<211> LENGTH: 24
<212> TYPE: PRT
<213> ORGANISM: Cryptomeria japonica

<400> SEQUENCE: 72

```
Pro Met Tyr Ile Ala Gly Tyr Lys Thr Phe Asp Gly Arg Gly Ala Gln
1               5                   10                  15

Val Tyr Ile Gly Asn Gly Gly Pro
                20
```

<210> SEQ ID NO 73
<211> LENGTH: 22
<212> TYPE: PRT
<213> ORGANISM: Cryptomeria japonica

<400> SEQUENCE: 73

```
Tyr Ile Ala Gly Tyr Lys Thr Phe Asp Gly Arg Gly Ala Gln Val Tyr
1               5                   10                  15

Ile Gly Asn Gly Gly Pro
                20
```

<210> SEQ ID NO 74
<211> LENGTH: 24
<212> TYPE: PRT
<213> ORGANISM: Cryptomeria japonica

<400> SEQUENCE: 74

```
Lys Lys Tyr Ile Ala Gly Tyr Lys Thr Phe Asp Gly Arg Gly Ala Gln
1               5                   10                  15

Val Tyr Ile Gly Asn Gly Gly Pro
            20
```

<210> SEQ ID NO 75
<211> LENGTH: 30
<212> TYPE: PRT
<213> ORGANISM: Cryptomeria japonica

<400> SEQUENCE: 75

```
Asp Ala Leu Thr Leu Arg Thr Ala Thr Asn Ile Trp Ile Asp His Asn
1               5                   10                  15

Ser Phe Ser Asn Ser Ser Asp Gly Leu Val Asp Val Thr Leu
            20                  25                  30
```

<210> SEQ ID NO 76
<211> LENGTH: 22
<212> TYPE: PRT
<213> ORGANISM: Cryptomeria japonica

<400> SEQUENCE: 76

```
Arg Thr Ala Thr Asn Ile Trp Ile Asp His Asn Ser Phe Ser Asn Ser
1               5                   10                  15

Ser Asp Gly Leu Val Asp
            20
```

<210> SEQ ID NO 77
<211> LENGTH: 24
<212> TYPE: PRT
<213> ORGANISM: Cryptomeria japonica

<400> SEQUENCE: 77

```
Lys Arg Thr Ala Thr Asn Ile Trp Ile Asp His Asn Ser Phe Ser Asn
1               5                   10                  15

Ser Ser Asp Gly Leu Val Asp Lys
            20
```

<210> SEQ ID NO 78
<211> LENGTH: 36
<212> TYPE: PRT
<213> ORGANISM: Cryptomeria japonica

<400> SEQUENCE: 78

```
Lys Ser Met Lys Val Thr Val Ala Phe Asn Gln Phe Gly Pro Asn Cys
1               5                   10                  15

Gly Gln Arg Met Pro Arg Ala Arg Tyr Gly Leu Val His Val Ala Asn
            20                  25                  30

Asn Asn Tyr Asp
        35
```

<210> SEQ ID NO 79
<211> LENGTH: 30
<212> TYPE: PRT
<213> ORGANISM: Cryptomeria japonica

<400> SEQUENCE: 79

```
Lys Ser Met Lys Val Thr Val Ala Phe Asn Gln Phe Gly Pro Asn Cys
1               5                   10                  15

Gly Gln Arg Met Pro Arg Ala Arg Tyr Gly Leu Val His Val
            20                  25                  30
```

<210> SEQ ID NO 80
<211> LENGTH: 30
<212> TYPE: PRT
<213> ORGANISM: Cryptomeria japonica

<400> SEQUENCE: 80

Lys Ser Met Lys Val Thr Val Ala Phe Asn Gln Phe Gly Pro Asn Ser
1               5                   10                  15

Gly Gln Arg Met Pro Arg Ala Arg Tyr Gly Leu Val His Val
            20                  25                  30

<210> SEQ ID NO 81
<211> LENGTH: 28
<212> TYPE: PRT
<213> ORGANISM: Cryptomeria japonica

<400> SEQUENCE: 81

Lys Ser Met Lys Val Thr Val Ala Phe Asn Gln Phe Gly Pro Asn Cys
1               5                   10                  15

Gly Gln Arg Met Pro Arg Ala Arg Tyr Gly Leu Val
            20                  25

<210> SEQ ID NO 82
<211> LENGTH: 28
<212> TYPE: PRT
<213> ORGANISM: Cryptomeria japonica

<400> SEQUENCE: 82

Lys Ser Met Lys Val Thr Val Ala Phe Asn Gln Phe Gly Pro Asn Cys
1               5                   10                  15

Gly Gln Arg Met Pro Arg Ala Arg Tyr Gly Leu Val
            20                  25

<210> SEQ ID NO 83
<211> LENGTH: 26
<212> TYPE: PRT
<213> ORGANISM: Cryptomeria japonica

<400> SEQUENCE: 83

Lys Ser Met Lys Val Thr Val Ala Phe Asn Gln Phe Gly Pro Asn Cys
1               5                   10                  15

Gly Gln Arg Met Pro Arg Ala Arg Tyr Gly
            20                  25

<210> SEQ ID NO 84
<211> LENGTH: 26
<212> TYPE: PRT
<213> ORGANISM: Cryptomeria japonica

<400> SEQUENCE: 84

Lys Ser Met Lys Val Thr Val Ala Phe Asn Gln Phe Gly Pro Asn Ser
1               5                   10                  15

Gly Gln Arg Met Pro Arg Ala Arg Tyr Gly
            20                  25

<210> SEQ ID NO 85
<211> LENGTH: 28
<212> TYPE: PRT
<213> ORGANISM: Cryptomeria japonica

<400> SEQUENCE: 85

Lys Ser Met Lys Val Thr Val Ala Phe Asn Gln Phe Gly Pro Asn Ser
1               5                   10                  15

Gly Gln Arg Met Pro Arg Ala Arg Tyr Gly Lys Lys
            20                  25

<210> SEQ ID NO 86
<211> LENGTH: 26
<212> TYPE: PRT
<213> ORGANISM: Cryptomeria japonica

<400> SEQUENCE: 86

Lys Ser Met Lys Val Thr Val Ala Phe Asn Gln Phe Gly Pro Asn Cys
1               5                   10                  15

Gly Gln Arg Met Pro Arg Ala Arg Tyr Gly
            20                  25

<210> SEQ ID NO 87
<211> LENGTH: 30
<212> TYPE: PRT
<213> ORGANISM: Cryptomeria japonica

<400> SEQUENCE: 87

Pro Arg Ala Arg Tyr Gly Leu Val His Val Ala Asn Asn Asn Tyr Asp
1               5                   10                  15

Pro Trp Thr Ile Tyr Ala Ile Gly Gly Ser Ser Asn Pro Thr
            20                  25                  30

<210> SEQ ID NO 88
<211> LENGTH: 28
<212> TYPE: PRT
<213> ORGANISM: Cryptomeria japonica

<400> SEQUENCE: 88

Arg Ala Arg Tyr Gly Leu Val His Val Ala Asn Asn Asn Tyr Asp Pro
1               5                   10                  15

Trp Thr Ile Tyr Ala Ile Gly Gly Ser Ser Asn Pro
            20                  25

<210> SEQ ID NO 89
<211> LENGTH: 26
<212> TYPE: PRT
<213> ORGANISM: Cryptomeria japonica

<400> SEQUENCE: 89

Arg Ala Arg Tyr Gly Leu Val His Val Ala Asn Asn Asn Tyr Asp Pro
1               5                   10                  15

Trp Thr Ile Tyr Ala Ile Gly Gly Ser Ser
            20                  25

<210> SEQ ID NO 90
<211> LENGTH: 30
<212> TYPE: PRT
<213> ORGANISM: Cryptomeria japonica

<400> SEQUENCE: 90

Asp Val Phe Tyr Asn Gly Ala Tyr Phe Val Ser Ser Gly Lys Tyr Glu
1               5                   10                  15

Gly Gly Asn Ile Tyr Thr Lys Lys Glu Ala Phe Asn Val Glu
            20                  25                  30

<210> SEQ ID NO 91
<211> LENGTH: 26
<212> TYPE: PRT
<213> ORGANISM: Cryptomeria japonica

<400> SEQUENCE: 91

Asn Gly Ala Tyr Phe Val Ser Ser Gly Lys Tyr Glu Gly Gly Asn Ile
1               5                   10                  15

Tyr Thr Lys Lys Glu Ala Phe Asn Val Glu
            20                  25

<210> SEQ ID NO 92
<211> LENGTH: 24
<212> TYPE: PRT
<213> ORGANISM: Cryptomeria japonica

<400> SEQUENCE: 92

Asn Gly Ala Tyr Phe Val Ser Ser Gly Lys Tyr Glu Gly Gly Asn Ile
1               5                   10                  15

Tyr Thr Lys Lys Glu Ala Phe Asn
            20

<210> SEQ ID NO 93
<211> LENGTH: 26
<212> TYPE: PRT
<213> ORGANISM: Cryptomeria japonica

<400> SEQUENCE: 93

Lys Lys Asn Gly Ala Tyr Phe Val Ser Ser Gly Lys Tyr Glu Gly Gly
1               5                   10                  15

Asn Ile Tyr Thr Lys Lys Glu Ala Phe Asn
            20                  25

<210> SEQ ID NO 94
<211> LENGTH: 1170
<212> TYPE: DNA
<213> ORGANISM: Juniperus sabinoides
<220> FEATURE:
<221> NAME/KEY: CDS
<222> LOCATION: (26)..(1126)
<220> FEATURE:
<221> NAME/KEY: mat_peptide
<222> LOCATION: (89)..(1126)

<400> SEQUENCE: 94
aaattctata ttctgaaccc taaaa atg gct tcc cca tgc tta ata gca gtc        52
                            Met Ala Ser Pro Cys Leu Ile Ala Val
                                -20                 -15 ctt gtt ttc ctt tgt gca att gta tct tgt tac tct gat aat ccc atc     100
Leu Val Phe Leu Cys Ala Ile Val Ser Cys Tyr Ser Asp Asn Pro Ile
        -10                 -5                  -1  1 gac agc tgc tgg aga gga gat tcg aac tgg gat caa aac aga atg aag     148
Asp Ser Cys Trp Arg Gly Asp Ser Asn Trp Asp Gln Asn Arg Met Lys
5               10                  15                  20 ctc gca gac tgt gct gtg gga ttt gga agc tcc acc atg gga ggc aaa     196
Leu Ala Asp Cys Ala Val Gly Phe Gly Ser Ser Thr Met Gly Gly Lys
            25                  30                  35 gga gga gat ttt tac acc gtc aca agc aca gat gat aat cct gtg aat     244
Gly Gly Asp Phe Tyr Thr Val Thr Ser Thr Asp Asp Asn Pro Val Asn
            40                  45                  50 cct aca cca gga act ttg cgc tat gga gca aca aga gaa aaa gca ctt     292
Pro Thr Pro Gly Thr Leu Arg Tyr Gly Ala Thr Arg Glu Lys Ala Leu
        55                  60                  65 tgg atc att ttc tct cag aat atg aat ata aag ctc aag atg cct ttg     340
Trp Ile Ile Phe Ser Gln Asn Met Asn Ile Lys Leu Lys Met Pro Leu
70                  75                  80 tat gtt gct gga cat aag act att gac ggc agg gga gca gat gtt cat     388
Tyr Val Ala Gly His Lys Thr Ile Asp Gly Arg Gly Ala Asp Val His
85                  90                  95                  100

| | | | | | | | | | | | | | | | |
|---|---|---|---|---|---|---|---|---|---|---|---|---|---|---|---|
| ctt | ggc | aac | ggc | ggt | ccc | tgt | ctg | ttt | atg | agg | aaa | gtg | agc | cat | gtt | 436
| Leu | Gly | Asn | Gly | Gly | Pro | Cys | Leu | Phe | Met | Arg | Lys | Val | Ser | His | Val |
| | | | 105 | | | | 110 | | | | | 115 | | | | att ctc cat agt ttg cat ata cac ggt tgt aat acg agt gtt ttg ggg   484
Ile Leu His Ser Leu His Ile His Gly Cys Asn Thr Ser Val Leu Gly
            120                 125                 130 gat gtt ttg gta agt gag tct att ggg gtc gag cct gtt cat gct cag   532
Asp Val Leu Val Ser Glu Ser Ile Gly Val Glu Pro Val His Ala Gln
            135                 140                 145 gat ggg gac gcc att act atg cgc cat gtt aca aat gct tgg att gat   580
Asp Gly Asp Ala Ile Thr Met Arg His Val Thr Asn Ala Trp Ile Asp
        150                 155                 160 cat aat tct ctc tcc gat tgt tct gat ggt ctt atc gat gtt acg ctt   628
His Asn Ser Leu Ser Asp Cys Ser Asp Gly Leu Ile Asp Val Thr Leu
165                 170                 175                 180 ggc tcc act gga att act atc tcc aac aat cac ttc ttc aac cat cat   676
Gly Ser Thr Gly Ile Thr Ile Ser Asn Asn His Phe Phe Asn His His
                185                 190                 195 aaa gtg atg tta tta gga cat gat gat aca tat gac gat gac aaa tct   724
Lys Val Met Leu Leu Gly His Asp Asp Thr Tyr Asp Asp Asp Lys Ser
            200                 205                 210 atg aaa gtg aca gtg gcg ttc aat caa ttt gga cct aat gct ggg caa   772
Met Lys Val Thr Val Ala Phe Asn Gln Phe Gly Pro Asn Ala Gly Gln
            215                 220                 225 aga atg cca agg gca cga tat gga ctt gta cat gtt gca aac aat aat   820
Arg Met Pro Arg Ala Arg Tyr Gly Leu Val His Val Ala Asn Asn Asn
        230                 235                 240 tat gat cca tgg aat ata tat gct att ggt ggg agt tca aat cca acc   868
Tyr Asp Pro Trp Asn Ile Tyr Ala Ile Gly Gly Ser Ser Asn Pro Thr
245                 250                 255                 260 att ctg agt gaa ggg aat agt ttc act gcc cca agt gag agt tac aag   916
Ile Leu Ser Glu Gly Asn Ser Phe Thr Ala Pro Ser Glu Ser Tyr Lys
                265                 270                 275 aag caa gta aca aag cgt ata ggg tgt gaa tca cca tca gct tgt gcg   964
Lys Gln Val Thr Lys Arg Ile Gly Cys Glu Ser Pro Ser Ala Cys Ala
            280                 285                 290 aac tgg gtg tgg aga tct aca cga gat gct ttt att aat gga gct tat  1012
Asn Trp Val Trp Arg Ser Thr Arg Asp Ala Phe Ile Asn Gly Ala Tyr
            295                 300                 305 ttt gta tca tcg ggg aaa act gaa gag acc aat ata tac aat agt aat  1060
Phe Val Ser Ser Gly Lys Thr Glu Glu Thr Asn Ile Tyr Asn Ser Asn
        310                 315                 320 gaa gct ttc aaa gtt gag aat ggg aat gca gct cct caa tta acc aaa  1108
Glu Ala Phe Lys Val Glu Asn Gly Asn Ala Ala Pro Gln Leu Thr Lys
325                 330                 335                 340 aat gct gga gtt gta acc taagctctct ctaaatcttg cttatgaaac         1156
Asn Ala Gly Val Val Thr
                345 gaaaaaatat atag                                                  1170

<210> SEQ ID NO 95
<211> LENGTH: 367
<212> TYPE: PRT
<213> ORGANISM: Juniperus sabinoides

<400> SEQUENCE: 95

Met Ala Ser Pro Cys Leu Ile Ala Val Leu Val Phe Leu Cys Ala Ile
1               5                   10                  15

Val Ser Cys Tyr Ser Asp Asn Pro Ile Asp Ser Cys Trp Arg Gly Asp
            20                  25                  30

Ser Asn Trp Asp Gln Asn Arg Met Lys Leu Ala Asp Cys Ala Val Gly
                35                  40                  45

Phe Gly Ser Ser Thr Met Gly Lys Gly Gly Asp Phe Tyr Thr Val
 50                  55                  60

Thr Ser Thr Asp Asp Asn Pro Val Asn Pro Thr Pro Gly Thr Leu Arg
 65                  70                  75                  80

Tyr Gly Ala Thr Arg Glu Lys Ala Leu Trp Ile Ile Phe Ser Gln Asn
                 85                  90                  95

Met Asn Ile Lys Leu Lys Met Pro Leu Tyr Val Ala Gly His Lys Thr
                100                 105                 110

Ile Asp Gly Arg Gly Ala Asp Val His Leu Gly Asn Gly Pro Cys
                115                 120                 125

Leu Phe Met Arg Lys Val Ser His Val Ile Leu His Ser Leu His Ile
130                 135                 140

His Gly Cys Asn Thr Ser Val Leu Gly Asp Val Leu Val Ser Glu Ser
145                 150                 155                 160

Ile Gly Val Glu Pro Val His Ala Gln Asp Gly Asp Ala Ile Thr Met
                165                 170                 175

Arg His Val Thr Asn Ala Trp Ile Asp His Asn Ser Leu Ser Asp Cys
                180                 185                 190

Ser Asp Gly Leu Ile Asp Val Thr Leu Gly Ser Thr Gly Ile Thr Ile
                195                 200                 205

Ser Asn Asn His Phe Phe Asn His His Lys Val Met Leu Leu Gly His
                210                 215                 220

Asp Asp Thr Tyr Asp Asp Asp Lys Ser Met Lys Val Thr Val Ala Phe
225                 230                 235                 240

Asn Gln Phe Gly Pro Asn Ala Gly Gln Arg Met Pro Arg Ala Arg Tyr
                245                 250                 255

Gly Leu Val His Val Ala Asn Asn Tyr Asp Pro Trp Asn Ile Tyr
                260                 265                 270

Ala Ile Gly Gly Ser Ser Asn Pro Thr Ile Leu Ser Glu Gly Asn Ser
                275                 280                 285

Phe Thr Ala Pro Ser Glu Ser Tyr Lys Lys Gln Val Thr Lys Arg Ile
290                 295                 300

Gly Cys Glu Ser Pro Ser Ala Cys Ala Asn Trp Val Trp Arg Ser Thr
305                 310                 315                 320

Arg Asp Ala Phe Ile Asn Gly Ala Tyr Phe Val Ser Ser Gly Lys Thr
                325                 330                 335

Glu Glu Thr Asn Ile Tyr Asn Ser Asn Glu Ala Phe Lys Val Glu Asn
                340                 345                 350

Gly Asn Ala Ala Pro Gln Leu Thr Lys Asn Ala Gly Val Val Thr
                355                 360                 365

<210> SEQ ID NO 96
<211> LENGTH: 1278
<212> TYPE: DNA
<213> ORGANISM: Juniperus virginiana
<220> FEATURE:
<221> NAME/KEY: CDS
<222> LOCATION: (36)..(1145)
<220> FEATURE:
<221> NAME/KEY: mat_peptide
<222> LOCATION: (99)..(1145)

<400> SEQUENCE: 96
cggtatagat agattctata ttctgagccc taaaa atg gct tcc cca tgc tta      53
                                       Met Ala Ser Pro Cys Leu

```
                                -20
ata gca ttc ctt gtt ttc ctt tgt gca att gta tct tgt tgc tct gat    101
Ile Ala Phe Leu Val Phe Leu Cys Ala Ile Val Ser Cys Cys Ser Asp
-15             -10                  -5                  -1   1 aat ccc ata gac agc tgc tgg aga gga gat tcg aac tgg ggt caa aac    149
Asn Pro Ile Asp Ser Cys Trp Arg Gly Asp Ser Asn Trp Gly Gln Asn
            5                   10                  15 aga atg aag ctc gca gat tgc gct gtg gga ttt gga agc tcc acc atg    197
Arg Met Lys Leu Ala Asp Cys Ala Val Gly Phe Gly Ser Ser Thr Met
        20                  25                  30 gga gga aaa gga gga gat ttt tac acc gtc aca agc gca gat gat aat    245
Gly Gly Lys Gly Gly Asp Phe Tyr Thr Val Thr Ser Ala Asp Asp Asn
    35                  40                  45 cct gtg aat cct aca cca gga act ttg cgc tat gga gca aca aga gaa    293
Pro Val Asn Pro Thr Pro Gly Thr Leu Arg Tyr Gly Ala Thr Arg Glu
50              55                  60                  65 aaa gca ctt tgg atc att ttc tct cag aat atg aat ata aag ctc aag    341
Lys Ala Leu Trp Ile Ile Phe Ser Gln Asn Met Asn Ile Lys Leu Lys
                70                  75                  80 atg cct ttg tat gtt gct gga cat aag act att gac ggc agg gga gca    389
Met Pro Leu Tyr Val Ala Gly His Lys Thr Ile Asp Gly Arg Gly Ala
            85                  90                  95 gat gtt cat ctt ggc aac ggc ggt ccc tgt ctg ttt atg agg aaa gtg    437
Asp Val His Leu Gly Asn Gly Gly Pro Cys Leu Phe Met Arg Lys Val
        100                 105                 110 agc cat gtt att ctc cat ggt ttg cat ata cac ggt tgt aat act agt    485
Ser His Val Ile Leu His Gly Leu His Ile His Gly Cys Asn Thr Ser
    115                 120                 125 gtt ttg ggg gat gtt ttg gta agt gag tct att ggg gtg gtg cct gta    533
Val Leu Gly Asp Val Leu Val Ser Glu Ser Ile Gly Val Val Pro Val
130                 135                 140                 145 cac ccc cag gac gga gat gcg ttt act gtg agg acc tct gaa cat att    581
His Pro Gln Asp Gly Asp Ala Phe Thr Val Arg Thr Ser Glu His Ile
                150                 155                 160 tgg gtc gac cat aat act ctc tcc aat ggc acc gac ggc ctc gtc gac    629
Trp Val Asp His Asn Thr Leu Ser Asn Gly Thr Asp Gly Leu Val Asp
            165                 170                 175 gtt act ctt gct tcc act gct gtt act att tcc aat aac cac ttc ttc    677
Val Thr Leu Ala Ser Thr Ala Val Thr Ile Ser Asn Asn His Phe Phe
        180                 185                 190 gac cat gat gaa gtg atg ttg tta gga cat agt gat tca ttc tca gat    725
Asp His Asp Glu Val Met Leu Leu Gly His Ser Asp Ser Phe Ser Asp
    195                 200                 205 gat aaa gtg atg aaa gtc aca gtt gca ttt aac cac ttt gga cct aat    773
Asp Lys Val Met Lys Val Thr Val Ala Phe Asn His Phe Gly Pro Asn
210                 215                 220                 225 tgt gtg caa cga ttg cca agg gct aga tat gga cac ttt cat gtt gtt    821
Cys Val Gln Arg Leu Pro Arg Ala Arg Tyr Gly His Phe His Val Val
                230                 235                 240 aat aat aat tat gag cca tgg gga aaa tat gcc att gga gga agt tct    869
Asn Asn Asn Tyr Glu Pro Trp Gly Lys Tyr Ala Ile Gly Gly Ser Ser
            245                 250                 255 gat cca aca att ata agt gaa ggg aat aga ttt ctt gca cca aat gaa    917
Asp Pro Thr Ile Ile Ser Glu Gly Asn Arg Phe Leu Ala Pro Asn Glu
        260                 265                 270 tct tat aaa aag gag gtg aca ata cgt gta ggt tgt aaa tct aca agt    965
Ser Tyr Lys Lys Glu Val Thr Ile Arg Val Gly Cys Lys Ser Thr Ser
    275                 280                 285 tgt gat gca tgg gag tgg aga tca aaa gat gat gcc ttc ctt aat ggt    1013
Cys Asp Ala Trp Glu Trp Arg Ser Lys Asp Asp Ala Phe Leu Asn Gly
```

```
                290                 295                 300                 305
gcc tat ttt gta caa tca ggc aag ggg tat aat ggt gga gag gca ttc        1061
Ala Tyr Phe Val Gln Ser Gly Lys Gly Tyr Asn Gly Gly Glu Ala Phe
                310                 315                 320 aag gtt gaa agt gca aat gag gtg cca aca ttg act aaa cat gct gga        1109
Lys Val Glu Ser Ala Asn Glu Val Pro Thr Leu Thr Lys His Ala Gly
            325                 330                 335 gca tta aaa tgt ata cct acc aaa caa tgt gtg ata tgaaaagtca             1155
Ala Leu Lys Cys Ile Pro Thr Lys Gln Cys Val Ile
        340                 345 atcgatataa taatgtgtta tttgtaatat ttcagctttg aatatgtata gaaaagaat       1215 ttcaacaaaa tgacactatt atataaataa attcttagtt tattagttgg tattaaaaaa      1275
aaa                                                                    1278

<210> SEQ ID NO 97
<211> LENGTH: 370
<212> TYPE: PRT
<213> ORGANISM: Juniperus virginiana

<400> SEQUENCE: 97

Met Ala Ser Pro Cys Leu Ile Ala Phe Leu Val Phe Leu Cys Ala Ile
1               5                   10                  15

Val Ser Cys Cys Ser Asp Asn Pro Ile Asp Ser Cys Trp Arg Gly Asp
            20                  25                  30

Ser Asn Trp Gly Gln Asn Arg Met Lys Leu Ala Asp Cys Ala Val Gly
        35                  40                  45

Phe Gly Ser Ser Thr Met Gly Gly Lys Gly Gly Asp Phe Tyr Thr Val
    50                  55                  60

Thr Ser Ala Asp Asp Asn Pro Val Asn Pro Thr Pro Gly Thr Leu Arg
65                  70                  75                  80

Tyr Gly Ala Thr Arg Glu Lys Ala Leu Trp Ile Ile Phe Ser Gln Asn
                85                  90                  95

Met Asn Ile Lys Leu Lys Met Pro Leu Tyr Val Ala Gly His Lys Thr
            100                 105                 110

Ile Asp Gly Arg Gly Ala Asp Val His Leu Gly Asn Gly Gly Pro Cys
        115                 120                 125

Leu Phe Met Arg Lys Val Ser His Val Ile Leu His Gly Leu His Ile
    130                 135                 140

His Gly Cys Asn Thr Ser Val Leu Gly Asp Val Leu Val Ser Glu Ser
145                 150                 155                 160

Ile Gly Val Val Pro Val His Pro Gln Asp Gly Asp Ala Phe Thr Val
                165                 170                 175

Arg Thr Ser Glu His Ile Trp Val Asp His Asn Thr Leu Ser Asn Gly
            180                 185                 190

Thr Asp Gly Leu Val Asp Val Thr Leu Ala Ser Thr Ala Val Thr Ile
        195                 200                 205

Ser Asn Asn His Phe Phe Asp His Asp Glu Val Met Leu Leu Gly His
    210                 215                 220

Ser Asp Ser Phe Ser Asp Asp Lys Val Met Lys Val Thr Val Ala Phe
225                 230                 235                 240

Asn His Phe Gly Pro Asn Cys Val Gln Arg Leu Pro Arg Ala Arg Tyr
                245                 250                 255

Gly His Phe His Val Val Asn Asn Tyr Glu Pro Trp Gly Lys Tyr
            260                 265                 270

Ala Ile Gly Gly Ser Ser Asp Pro Thr Ile Ile Ser Glu Gly Asn Arg
```

```
                275                 280                 285
Phe Leu Ala Pro Asn Glu Ser Tyr Lys Lys Glu Val Thr Ile Arg Val
    290                 295                 300

Gly Cys Lys Ser Thr Ser Cys Asp Ala Trp Glu Trp Arg Ser Lys Asp
305                 310                 315                 320

Asp Ala Phe Leu Asn Gly Ala Tyr Phe Val Gln Ser Gly Lys Gly Tyr
                325                 330                 335

Asn Gly Gly Glu Ala Phe Lys Val Glu Ser Ala Asn Glu Val Pro Thr
            340                 345                 350

Leu Thr Lys His Ala Gly Ala Leu Lys Cys Ile Pro Thr Lys Gln Cys
        355                 360                 365

Val Ile
    370

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gggctcgagc tgcagttttt ttttttttt ttv                                33

<210> SEQ ID NO 99
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cataaaatgg cttcccca                                                18

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cgggaattct agatgtgcaa ttgtatcttg tta                               33

<210> SEQ ID NO 101
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cgggaattct agatgtgcaa tagtatcttg ttg                               33

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 102
ggaattctct agactgcagg t                                              21

<210> SEQ ID NO 103
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ggaattctct agactgcagg tttttttttt ttttt                               35

<210> SEQ ID NO 104
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (22)..(22)
<223> OTHER INFORMATION: a, c, t, g, unknown or other
<220> FEATURE:
<221> NAME/KEY: modified_base
<222> LOCATION: (25)..(25)
<223> OTHER INFORMATION: a, c, t, g, unknown or other
<220> FEATURE:
<221> NAME/KEY: modified_base
<222> LOCATION: (28)..(28)
<223> OTHER INFORMATION: a, c, t, g, unknown or other

<400> SEQUENCE: 104
ggcctgcagy yarcanckkt tnsmnarnsw rca                                 33

<210> SEQ ID NO 105
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
ccrctraada tdatcca                                                   17

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (15)..(15)
<223> OTHER INFORMATION: a, c, t, g, unknown or other

<400> SEQUENCE: 106
gcrtccccrt cytgnggrtg                                                20

<210> SEQ ID NO 107
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gtccayggrt crtarttrtt                                                    20

<210> SEQ ID NO 108
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other

<400> SEQUENCE: 108
gccctgcagt ccccrtcytg nggrtgnac                                          29

<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gctccaccat ggdaggca                                                      18

<210> SEQ ID NO 110
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: a, c, t, g, unknown or other

<400> SEQUENCE: 110
cayccncarg aygggaygc                                                     20

<210> SEQ ID NO 111
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (27)..(27)
<223> OTHER INFORMATION: a, c, t, g, unknown or other

<400> SEQUENCE: 111
cgggaattcc ctcargaygg ggaygcny                                           28

<210> SEQ ID NO 112
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
taggacatga tgatacat                                                  18

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gagatctaca cgagatgc                                                  18

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
raawctattc ccttcact                                                  18

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
taggacatag tgattcat                                                  18

<210> SEQ ID NO 116
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
ccgggatcct tacaaataac acattat                                        27

<210> SEQ ID NO 117
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
cccgaattca tggcttcccc atgctta                                        27

<210> SEQ ID NO 118
<211> LENGTH: 27
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 118
ccgggatccc gtttcataag caagatt                                          27

<210> SEQ ID NO 119
<211> LENGTH: 21
<212> TYPE: PRT
<213> ORGANISM: Cryptomeria japonica

<400> SEQUENCE: 119

Asp Glu Arg Thr Ala Thr Asn Ile Trp Ile Asp His Asn Ser Phe Ser
1               5                   10                  15

Asn Ser Ser Asp Asp
            20

<210> SEQ ID NO 120
<211> LENGTH: 24
<212> TYPE: PRT
<213> ORGANISM: Cryptomeria japonica

<400> SEQUENCE: 120

Asp Glu Arg Thr Ala Thr Asn Ile Trp Ile Asp His Asn Ser Phe Ser
1               5                   10                  15

Asn Ser Ser Asp Gly Leu Ala Asp
            20

<210> SEQ ID NO 121
<211> LENGTH: 19
<212> TYPE: PRT
<213> ORGANISM: Cryptomeria japonica

<400> SEQUENCE: 121

Asp Glu Lys Ser Met Lys Ala Thr Val Ala Phe Asn Gln Phe Gly Pro
1               5                   10                  15

Asn Asp Glu

<210> SEQ ID NO 122
<211> LENGTH: 19
<212> TYPE: PRT
<213> ORGANISM: Cryptomeria japonica

<400> SEQUENCE: 122

Asp Glu Lys Ser Met Lys Val Thr Ala Ala Phe Asn Gln Phe Gly Pro
1               5                   10                  15

Asn Asp Glu

<210> SEQ ID NO 123
<211> LENGTH: 21
<212> TYPE: PRT
<213> ORGANISM: Cryptomeria japonica

<400> SEQUENCE: 123

Asp Glu Glu Lys Ser Met Lys Ala Thr Val Ala Phe Asn Glu Phe Gly
1               5                   10                  15

Pro Asn Asp Glu Glu
            20

<210> SEQ ID NO 124
<211> LENGTH: 21

```
<212> TYPE: PRT
<213> ORGANISM: Cryptomeria japonica

<400> SEQUENCE: 124

Asp Glu Glu Lys Ser Met Lys Val Thr Val Ala Ala Asn Gln Phe Gly
1               5                   10                  15

Pro Asn Asp Glu Glu
            20

<210> SEQ ID NO 125
<211> LENGTH: 21
<212> TYPE: PRT
<213> ORGANISM: Cryptomeria japonica

<400> SEQUENCE: 125

Asp Glu Glu Lys Ser Met Lys Val Thr Val Ala Phe Asn Gln Ala Gly
1               5                   10                  15

Pro Asn Asp Glu Glu
            20

<210> SEQ ID NO 126
<211> LENGTH: 19
<212> TYPE: PRT
<213> ORGANISM: Cryptomeria japonica

<400> SEQUENCE: 126

Asp Glu Lys Ser Met Lys Ala Thr Ala Ala Phe Asn Gln Phe Gly Pro
1               5                   10                  15

Asn Asp Glu

<210> SEQ ID NO 127
<211> LENGTH: 21
<212> TYPE: PRT
<213> ORGANISM: Cryptomeria japonica

<400> SEQUENCE: 127

Asp Glu Glu Lys Ser Met Lys Ala Thr Ala Ala Phe Asn Gln Phe Gly
1               5                   10                  15

Pro Asn Asp Glu Glu
            20

<210> SEQ ID NO 128
<211> LENGTH: 22
<212> TYPE: PRT
<213> ORGANISM: Cryptomeria japonica

<400> SEQUENCE: 128

Asp Asp Ala Tyr Ser Asp Lys Ser Met Lys Val Thr Val Ala Phe
1               5                   10                  15

Asn Gln Phe Gly Asp Glu
            20

<210> SEQ ID NO 129
<211> LENGTH: 26
<212> TYPE: PRT
<213> ORGANISM: Cryptomeria japonica

<400> SEQUENCE: 129

Asp Lys Glu Pro Arg Ala Arg Tyr Gly Leu Val His Val Ala Asn Asn
1               5                   10                  15

Asn Tyr Asp Pro Trp Thr Ile Glu Glu Glu
            20                  25
```

<210> SEQ ID NO 130
<211> LENGTH: 28
<212> TYPE: PRT
<213> ORGANISM: Cryptomeria japonica

<400> SEQUENCE: 130

Asp Glu Asn Gly Ala Tyr Phe Val Ser Ser Gly Lys Tyr Glu Gly Gly
1               5                   10                  15

Asn Ile Tyr Thr Lys Lys Glu Ala Phe Asn Ala Glu
            20                  25

<210> SEQ ID NO 131
<211> LENGTH: 29
<212> TYPE: PRT
<213> ORGANISM: Cryptomeria japonica

<400> SEQUENCE: 131

Asp Glu Glu Asn Gly Ala Tyr Phe Val Ser Ser Gly Lys Tyr Glu Gly
1               5                   10                  15

Gly Asn Ile Tyr Thr Lys Lys Glu Ala Phe Asn Val Glu
            20                  25

<210> SEQ ID NO 132
<211> LENGTH: 28
<212> TYPE: PRT
<213> ORGANISM: Cryptomeria japonica

<400> SEQUENCE: 132

Asp Glu Glu Gly Ala Tyr Phe Val Ser Ser Gly Lys Tyr Glu Gly Gly
1               5                   10                  15

Asn Ile Tyr Thr Lys Lys Glu Ala Phe Asn Val Glu
            20                  25

<210> SEQ ID NO 133
<211> LENGTH: 1726
<212> TYPE: DNA
<213> ORGANISM: Cryptomeria japonica
<220> FEATURE:
<221> NAME/KEY: CDS
<222> LOCATION: (42)..(1586)

<400> SEQUENCE: 133

```
tgagttcgag acaagtatag aaagaatttt cttttattaa a atg gcc atg aaa tta         56
                                             Met Ala Met Lys Leu
                                             1               5 att gct cca atg gcc ttt ctg gcc atg caa ttg att ata atg gcg gca         104
Ile Ala Pro Met Ala Phe Leu Ala Met Gln Leu Ile Ile Met Ala Ala
            10                  15                  20 gca gaa gat caa tct gcc caa att atg ttg gac agt gtt gtc gaa aaa         152
Ala Glu Asp Gln Ser Ala Gln Ile Met Leu Asp Ser Val Val Glu Lys
        25                  30                  35 tat ctt aga tcg aat cgg agt tta aga aaa gtt gag cat tct cgt cat         200
Tyr Leu Arg Ser Asn Arg Ser Leu Arg Lys Val Glu His Ser Arg His
    40                  45                  50 gat gct atc aac atc ttc aat gtg gaa aag tat ggc gca gta ggc gat         248
Asp Ala Ile Asn Ile Phe Asn Val Glu Lys Tyr Gly Ala Val Gly Asp
55                  60                  65 gga aag cat gat tgc act gag gca ttt tca aca gca tgg caa gct gca         296
Gly Lys His Asp Cys Thr Glu Ala Phe Ser Thr Ala Trp Gln Ala Ala
70                  75                  80                  85 tgc aaa aac cca tca gca atg ttg ctt gtg cca ggc agc aag aaa ttt         344
Cys Lys Asn Pro Ser Ala Met Leu Leu Val Pro Gly Ser Lys Lys Phe
            90                  95                  100
```

|  |  |
|---|---|
| gtt gta aac aat ctg ttc ttc aat ggg cca tgt caa cct cac ttt act<br>Val Val Asn Asn Leu Phe Phe Asn Gly Pro Cys Gln Pro His Phe Thr<br>     105                   110                  115 | 392 |
| ttt aag gta gat ggg ata ata gct gcg tac caa aat cca gcg agc tgg<br>Phe Lys Val Asp Gly Ile Ile Ala Ala Tyr Gln Asn Pro Ala Ser Trp<br>120                  125                   130 | 440 |
| aag aat aat aga ata tgg ttg cag ttt gct aaa ctt aca ggt ttt act<br>Lys Asn Asn Arg Ile Trp Leu Gln Phe Ala Lys Leu Thr Gly Phe Thr<br>     135                   140                  145 | 488 |
| cta atg ggt aaa ggt gta att gat ggg caa gga aaa caa tgg tgg gct<br>Leu Met Gly Lys Gly Val Ile Asp Gly Gln Gly Lys Gln Trp Trp Ala<br>150                  155                   160                  165 | 536 |
| ggc caa tgt aaa tgg gtc aat gga cga gaa att tgc aac gat cgt gat<br>Gly Gln Cys Lys Trp Val Asn Gly Arg Glu Ile Cys Asn Asp Arg Asp<br>               170                  175                  180 | 584 |
| aga cca aca gcc att aaa ttc gat ttt tcc acg ggt ctg ata atc caa<br>Arg Pro Thr Ala Ile Lys Phe Asp Phe Ser Thr Gly Leu Ile Ile Gln<br>               185                  190                  195 | 632 |
| gga ctg aaa cta atg aac agt ccc gaa ttt cat tta gtt ttt ggg aat<br>Gly Leu Lys Leu Met Asn Ser Pro Glu Phe His Leu Val Phe Gly Asn<br>200                  205                   210 | 680 |
| tgt gag gga gta aaa atc atc ggc att agt att acg gca ccg aga gac<br>Cys Glu Gly Val Lys Ile Ile Gly Ile Ser Ile Thr Ala Pro Arg Asp<br>     215                   220                  225 | 728 |
| agt cct aac act gat gga att gat atc ttt gca tct aaa aac ttt cac<br>Ser Pro Asn Thr Asp Gly Ile Asp Ile Phe Ala Ser Lys Asn Phe His<br>230                  235                  240                  245 | 776 |
| tta caa aag aac acg ata gga aca ggg gat gac tgc gtc gct ata ggc<br>Leu Gln Lys Asn Thr Ile Gly Thr Gly Asp Asp Cys Val Ala Ile Gly<br>                   250                  255                  260 | 824 |
| aca ggg tct tct aat att gtg att gag gat ctg att tgc ggt cca ggc<br>Thr Gly Ser Ser Asn Ile Val Ile Glu Asp Leu Ile Cys Gly Pro Gly<br>               265                  270                  275 | 872 |
| cat gga ata agt ata gga agt ctt ggg agg gaa aac tct aga gca gag<br>His Gly Ile Ser Ile Gly Ser Leu Gly Arg Glu Asn Ser Arg Ala Glu<br>               280                  285                  290 | 920 |
| gtt tca tac gtg cac gta aat ggg gct aaa ttc ata gac aca caa aat<br>Val Ser Tyr Val His Val Asn Gly Ala Lys Phe Ile Asp Thr Gln Asn<br>295                  300                   305 | 968 |
| gga tta aga atc aaa aca tgg cag ggt ggt tca ggc atg gca agc cat<br>Gly Leu Arg Ile Lys Thr Trp Gln Gly Gly Ser Gly Met Ala Ser His<br>310                  315                  320                  325 | 1016 |
| ata att tat gag aat gtt gaa atg ata aat tcg gag aac ccc ata tta<br>Ile Ile Tyr Glu Asn Val Glu Met Ile Asn Ser Glu Asn Pro Ile Leu<br>               330                  335                  340 | 1064 |
| ata aat caa ttc tac tgc act tca gct tct gct tgc caa aac cag agg<br>Ile Asn Gln Phe Tyr Cys Thr Ser Ala Ser Ala Cys Gln Asn Gln Arg<br>               345                  350                  355 | 1112 |
| tct gcg gtt caa atc caa gat gtg aca tac aag aac ata cgt ggg aca<br>Ser Ala Val Gln Ile Gln Asp Val Thr Tyr Lys Asn Ile Arg Gly Thr<br>               360                  365                  370 | 1160 |
| tca gca aca gca gca gca att caa ctt aag tgc agt gac agt atg ccc<br>Ser Ala Thr Ala Ala Ala Ile Gln Leu Lys Cys Ser Asp Ser Met Pro<br>375                  380                   385 | 1208 |
| tgc aaa gat ata aag cta agt gat ata tct ttg aag ctt acc tca ggg<br>Cys Lys Asp Ile Lys Leu Ser Asp Ile Ser Leu Lys Leu Thr Ser Gly<br>390                  395                  400                  405 | 1256 |
| aaa att gct tcc tgc ctt aat gat aat gca aat gga tat ttc agt gga<br>Lys Ile Ala Ser Cys Leu Asn Asp Asn Ala Asn Gly Tyr Phe Ser Gly<br>               410                  415                  420 | 1304 |

```
cac gtc atc cct gca tgc aag aat tta agt cca agt gct aag cga aaa    1352
His Val Ile Pro Ala Cys Lys Asn Leu Ser Pro Ser Ala Lys Arg Lys
            425                 430                 435 gaa tct aaa tcc cat aaa cac cca aaa act gta atg gtt gaa aat atg    1400
Glu Ser Lys Ser His Lys His Pro Lys Thr Val Met Val Glu Asn Met
        440                 445                 450 cga gca tat gac aag ggt aac aga aca cgc ata ttg ttg ggg tcg agg    1448
Arg Ala Tyr Asp Lys Gly Asn Arg Thr Arg Ile Leu Leu Gly Ser Arg
    455                 460                 465 cct ccg aat tgt aca aac aaa tgt cat ggt tgc agt cca tgt aag gcc    1496
Pro Pro Asn Cys Thr Asn Lys Cys His Gly Cys Ser Pro Cys Lys Ala
470                 475                 480                 485 aag tta gtt att gtt cat cgt att atg ccg cag gag tat tat cct cag    1544
Lys Leu Val Ile Val His Arg Ile Met Pro Gln Glu Tyr Tyr Pro Gln
                490                 495                 500 agg tgg ata tgc agc tgt cat ggc aaa atc tac cat cca taa            1586
Arg Trp Ile Cys Ser Cys His Gly Lys Ile Tyr His Pro
            505                 510 tgagatacat tgaaactgta tgtgctagtg aatattcttg tggtacaata ttagaactga  1646
tattgaaaat aaatcatcaa tgtttctaag gcatttataa tagattatat taatggttca  1706
gcctggtgca aaaaaaaaa                                                1726

<210> SEQ ID NO 134
<211> LENGTH: 514
<212> TYPE: PRT
<213> ORGANISM: Cryptomeria japonica

<400> SEQUENCE: 134

Met Ala Met Lys Leu Ile Ala Pro Met Ala Phe Leu Ala Met Gln Leu
1               5                   10                  15

Ile Ile Met Ala Ala Ala Glu Asp Gln Ser Ala Gln Ile Met Leu Asp
            20                  25                  30

Ser Val Val Glu Lys Tyr Leu Arg Ser Asn Arg Ser Leu Arg Lys Val
        35                  40                  45

Glu His Ser Arg His Asp Ala Ile Asn Ile Phe Asn Val Glu Lys Tyr
    50                  55                  60

Gly Ala Val Gly Asp Gly Lys His Asp Cys Thr Glu Ala Phe Ser Thr
65                  70                  75                  80

Ala Trp Gln Ala Ala Cys Lys Asn Pro Ser Ala Met Leu Leu Val Pro
                85                  90                  95

Gly Ser Lys Lys Phe Val Val Asn Leu Phe Asn Gly Pro Cys
            100                 105                 110

Gln Pro His Phe Thr Phe Lys Val Asp Gly Ile Ile Ala Ala Tyr Gln
        115                 120                 125

Asn Pro Ala Ser Trp Lys Asn Asn Arg Ile Trp Leu Gln Phe Ala Lys
    130                 135                 140

Leu Thr Gly Phe Thr Leu Met Gly Lys Gly Val Ile Asp Gly Gln Gly
145                 150                 155                 160

Lys Gln Trp Trp Ala Gly Gln Cys Lys Trp Val Asn Gly Arg Glu Ile
                165                 170                 175

Cys Asn Asp Arg Asp Arg Pro Thr Ala Ile Lys Phe Asp Phe Ser Thr
            180                 185                 190

Gly Leu Ile Ile Gln Gly Leu Lys Leu Met Asn Ser Pro Glu Phe His
        195                 200                 205

Leu Val Phe Gly Asn Cys Glu Gly Val Lys Ile Ile Gly Ile Ser Ile
    210                 215                 220
```

```
Thr Ala Pro Arg Asp Ser Pro Asn Thr Asp Gly Ile Asp Ile Phe Ala
225                 230                 235                 240

Ser Lys Asn Phe His Leu Gln Lys Asn Thr Ile Gly Thr Gly Asp Asp
                245                 250                 255

Cys Val Ala Ile Gly Thr Gly Ser Ser Asn Ile Val Ile Glu Asp Leu
            260                 265                 270

Ile Cys Gly Pro Gly His Gly Ile Ser Ile Gly Ser Leu Gly Arg Glu
        275                 280                 285

Asn Ser Arg Ala Glu Val Ser Tyr Val His Val Asn Gly Ala Lys Phe
    290                 295                 300

Ile Asp Thr Gln Asn Gly Leu Arg Ile Lys Thr Trp Gln Gly Gly Ser
305                 310                 315                 320

Gly Met Ala Ser His Ile Ile Tyr Glu Asn Val Glu Met Ile Asn Ser
                325                 330                 335

Glu Asn Pro Ile Leu Ile Asn Gln Phe Tyr Cys Thr Ser Ala Ser Ala
            340                 345                 350

Cys Gln Asn Gln Arg Ser Ala Val Gln Ile Gln Asp Val Thr Tyr Lys
        355                 360                 365

Asn Ile Arg Gly Thr Ser Ala Thr Ala Ala Ile Gln Leu Lys Cys
    370                 375                 380

Ser Asp Ser Met Pro Cys Lys Asp Ile Lys Leu Ser Asp Ile Ser Leu
385                 390                 395                 400

Lys Leu Thr Ser Gly Lys Ile Ala Ser Cys Leu Asn Asp Asn Ala Asn
                405                 410                 415

Gly Tyr Phe Ser Gly His Val Ile Pro Ala Cys Lys Asn Leu Ser Pro
            420                 425                 430

Ser Ala Lys Arg Lys Glu Ser Lys Ser His Lys His Pro Lys Thr Val
        435                 440                 445

Met Val Glu Asn Met Arg Ala Tyr Asp Lys Gly Asn Arg Thr Arg Ile
    450                 455                 460

Leu Leu Gly Ser Arg Pro Pro Asn Cys Thr Asn Lys Cys His Gly Cys
465                 470                 475                 480

Ser Pro Cys Lys Ala Lys Leu Val Ile Val His Arg Ile Met Pro Gln
                485                 490                 495

Glu Tyr Tyr Pro Gln Arg Trp Ile Cys Ser Cys His Gly Lys Ile Tyr
            500                 505                 510

His Pro

<210> SEQ ID NO 135
<211> LENGTH: 45
<212> TYPE: PRT
<213> ORGANISM: Cryptomeria japonica

<400> SEQUENCE: 135

Arg Lys Val Glu His Ser Arg His Asp Ala Ile Asn Ile Phe Asn Val
1               5                   10                  15

Glu Lys Tyr Gly Ala Val Gly Asp Gly Lys His Asp Cys Thr Glu Ala
            20                  25                  30

Phe Ser Thr Ala Trp Gln Ala Ala Cys Lys Asn Pro Ser
        35                  40                  45

<210> SEQ ID NO 136
<211> LENGTH: 41
<212> TYPE: PRT
<213> ORGANISM: Cryptomeria japonica
```

<400> SEQUENCE: 136

Arg Lys Val Glu His Ser Arg His Asp Ala Ile Asn Ile Phe Asn Val
1               5                   10                  15

Glu Lys Tyr Gly Ala Val Gly Asp Gly Lys His Asp Cys Thr Glu Ala
            20                  25                  30

Phe Ser Thr Ala Trp Gln Lys Asn Pro
            35                  40

<210> SEQ ID NO 137
<211> LENGTH: 36
<212> TYPE: PRT
<213> ORGANISM: Cryptomeria japonica

<400> SEQUENCE: 137

Ser Arg His Asp Ala Ile Asn Ile Phe Asn Val Glu Lys Tyr Gly Ala
1               5                   10                  15

Val Gly Asp Gly Lys His Asp Cys Thr Glu Ala Phe Ser Thr Ala Trp
            20                  25                  30

Gln Lys Asn Pro
            35

<210> SEQ ID NO 138
<211> LENGTH: 10
<212> TYPE: PRT
<213> ORGANISM: Cryptomeria japonica

<400> SEQUENCE: 138

Ala Ile Asn Ile Phe Asn Val Glu Lys Tyr
1               5                   10

<210> SEQ ID NO 139
<211> LENGTH: 1410
<212> TYPE: DNA
<213> ORGANISM: Cryptomeria japonica

<400> SEQUENCE: 139

```
agaaaagttg agcattctcg tcatgatgct atcaacatct tcaatgtgga aaagtatggc      60
gcagtaggcg atggaaagca tgattgcact gaggcatttt caacagcatg gcaagctgca     120
tgcaaaaacc catcagcaat gttgcttgtg ccaggcagca agaaatttgt tgtaaacaat     180
ctgttcttca atgggccatg tcaacctcac tttactttta aggtagatgg gataatagct     240
gcgtaccaaa atccagcgag ctggaagaat aatagaatat ggttgcagtt tgctaaactt     300
acaggtttta ctctaatggg taaaggtgta attgatgggc aaggaaaaca atggtgggct     360
ggccaatgta aatgggtcaa tggacgagaa atttgcaacg atcgtgatag accaacagcc     420
attaaattcg attttttccac gggtctgata atccaaggac tgaaactaat gaacagtccc     480
gaatttcatt tagttttttgg gaattgtgag ggagtaaaaa tcatcggcat tagtattacg     540
gcaccgagag acagtcctaa cactgatgga attgatatct ttgcatctaa aaactttcac     600
ttacaaaaga cacgatagg aacagggggat gactgcgtcg ctataggcac agggtcttct     660
aatattgtga ttgaggatct gatttgcggt ccaggccatg gaataagtat aggaagtctt     720
ggagggaaa actctagagc agaggtttca tacgtgcacg taaatggggc taaattcata     780
gacacacaaa atggattaag aatcaaaaca tggcagggtg gttcaggcat ggcaagccat     840
ataatttatg agaatgttga aatgataaat tcggagaacc ccatattaat aaatcaattc     900
tactgcactt cagcttctgc ttgccaaaac cagaggtctg cggttcaaat ccaagatgtg     960
acatacaaga acatacgtgg gacatcagca acagcagcag caattcaact taagtgcagt    1020
```

| | |
|---|---|
| gacagtatgc cctgcaaaga tataaagcta agtgatatat cttttgaagct tacctcaggg | 1080 |
| aaaattgctt cctgccttaa tgataatgca aatggatatt tcagtggaca cgtcatccct | 1140 |
| gcatgcaaga atttaagtcc aagtgctaag cgaaaagaat ctaaatccca taaacaccca | 1200 |
| aaaactgtaa tggttgaaaa tatgcgagca tatgacaagg gtaacagaac acgcatattg | 1260 |
| ttggggtcga ggcctccgaa ttgtacaaac aaatgtcatg gttgcagtcc atgtaaggcc | 1320 |
| aagttagtta ttgttcatcg tattatgccg caggagtatt atcctcagag gtggatatgc | 1380 |
| agctgtcatg gcaaaatcta ccatccataa | 1410 |

<210> SEQ ID NO 140
<211> LENGTH: 1395
<212> TYPE: DNA
<213> ORGANISM: Cryptomeria japonica

<400> SEQUENCE: 140

| | |
|---|---|
| tctcgtcatg atgctatcaa catcttcaat gtggaaaagt atggcgcagt aggcgatgga | 60 |
| aagcatgatt gcactgaggc attttcaaca gcatggcaag ctgcatgcaa aaacccatca | 120 |
| gcaatgttgc ttgtgccagg cagcaagaaa tttgttgtaa acaatctgtt cttcaatggg | 180 |
| ccatgtcaac ctcactttac ttttaaggta gatgggataa tagctgcgta ccaaaatcca | 240 |
| gcgagctgga agaataatag aatatggttg cagtttgcta aacttacagg ttttactcta | 300 |
| atgggtaaag gtgtaattga tgggcaagga aaacaatggt gggctggcca atgtaaatgg | 360 |
| gtcaatggac gagaaatttg caacgatcgt gatagaccaa cagccattaa attcgatttt | 420 |
| tccacgggtc tgataatcca aggactgaaa ctaatgaaca gtcccgaatt tcatttagtt | 480 |
| tttgggaatt gtgagggagt aaaaatcatc ggcattagta ttacggcacc gagagacagt | 540 |
| cctaacactg atggaattga tatctttgca tctaaaaact ttcacttaca aaagaacacg | 600 |
| ataggaacag gggatgactg cgtcgctata ggcacagggt cttctaatat tgtgattgag | 660 |
| gatctgattt gcggtccagg ccatggaata agtataggaa gtcttgggag ggaaaactct | 720 |
| agagcagagg tttcatacgt gcacgtaaat ggggctaaat tcatagacac acaaaatgga | 780 |
| ttaagaatca aaacatggca gggtggttca ggcatggcaa gccatataat ttatgagaat | 840 |
| gttgaaatga taaattcgga gaaccccata ttaataaatc aattctactg cacttcagct | 900 |
| tctgcttgcc aaaaccagag gtctgcggtt caaatccaag atgtgacata caagaacata | 960 |
| cgtgggacat cagcaacagc agcagcaatt caacttaagt gcagtgacag tatgccctgc | 1020 |
| aaagatataa agctaagtga tatatctttg aagcttacct cagggaaaat tgcttcctgc | 1080 |
| cttaatgata tgcaaatgg atatttcagt ggacacgtca tccctgcatg caagaattta | 1140 |
| agtccaagtg ctaagcgaaa agaatctaaa tcccataaac acccaaaaac tgtaatggtt | 1200 |
| gaaaatatgc gagcatatga caagggtaac agaacacgca tattgttggg gtcgaggcct | 1260 |
| ccgaattgta caaacaaatg tcatggttgc agtccatgta aggccaagtt agttattgtt | 1320 |
| catcgtatta tgccgcagga gtattatcct cagaggtgga tatgcagctg tcatggcaaa | 1380 |
| atctaccatc cataa | 1395 |

<210> SEQ ID NO 141
<211> LENGTH: 1479
<212> TYPE: DNA
<213> ORGANISM: Cryptomeria japonica

<400> SEQUENCE: 141

| | |
|---|---|
| gaagatcaat ctgcccaaat tatgttggac agtgttgtcg aaaaatatct tagatcgaat | 60 |

```
cggagtttaa gaaaagttga gcattctcgt catgatgcta tcaacatctt caatgtggaa      120
aagtatggcg cagtaggcga tggaaagcat gattgcactg aggcattttc aacagcatgg      180
caagctgcat gcaaaaaccc atcagcaatg ttgcttgtgc caggcagcaa gaaatttgtt      240
gtaaacaatc tgttcttcaa tgggccatgt caacctcact ttacttttaa ggtagatggg      300
ataatagctg cgtaccaaaa tccagcgagc tggaagaata tagaatatg gttgcagttt       360 gctaaactta caggttttac tctaatgggt aaaggtgtaa ttgatgggca aggaaaacaa      420
tggtgggctg gccaatgtaa atgggtcaat ggacgagaaa tttgcaacga tcgtgataga      480
ccaacagcca ttaaattcga ttttttccacg ggtctgataa tccaaggact gaaactaatg     540
aacagtcccg aatttcattt agtttttggg aattgtgagg gagtaaaaat catcggcatt      600
agtattacgg caccgagaga cagtcctaac actgatggaa ttgatatctt tgcatctaaa     660
aactttcact acaaaagaa cacgatagga acagggatg actgcgtcgc tataggcaca       720
gggtcttcta atattgtgat tgaggatctg atttgcggtc caggccatgg aataagtata      780
ggaagtcttg ggagggaaaa ctctagagca gaggtttcat acgtgcacgt aaatggggct     840
aaattcatag acacacaaaa tggattaaga atcaaaacat ggcagggtgg ttcaggcatg      900
gcaagccata aatttatga gaatgttgaa atgataaatt cggagaaccc catattaata       960
aatcaattct actgcacttc agcttctgct tgccaaaacc agaggtctgc ggttcaaatc      1020
caagatgtga catacaagaa catacgtggg acatcagcaa cagcagcagc aattcaactt      1080
aagtgcagtg acagtatgcc ctgcaaagat ataaagctaa gtgatatatc tttgaagctt      1140
acctcaggga aaattgcttc ctgccttaat gataatgcaa atggatattt cagtggacac      1200
gtcatccctg catgcaagaa tttaagtcca agtgctaagc gaaaagaatc taaatcccat     1260
aaacacccaa aaactgtaat ggttgaaaat atgcgagcat atgacaaggg taacagaaca      1320
cgcatattgt tggggtcgag gcctccgaat tgtacaaaca aatgtcatgg ttgcagtcca      1380
tgtaaggcca agttagttat tgttcatcgt attatgccgc aggagtatta tcctcagagg      1440
tggatatgca gctgtcatgg caaaatctac catccataa                             1479
```

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(10)
<223> OTHER INFORMATION: a, c, t, g, unknown or other

<400> SEQUENCE: 142
rtayttytcn acrttraa                                                      18

<210> SEQ ID NO 143
<211> LENGTH: 6
<212> TYPE: PRT
<213> ORGANISM: Cryptomeria japonica

<400> SEQUENCE: 143

Phe Asn Val Glu Lys Tyr
1               5

<210> SEQ ID NO 144
<211> LENGTH: 27

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: a, c, t, g, unknown or other
<220> FEATURE:
<221> NAME/KEY: modified_base
<222> LOCATION: (25)..(25)
<223> OTHER INFORMATION: a, c, t, g, unknown or other

<400> SEQUENCE: 144
cctgcagtay ttytcnacrt traanat                                27

<210> SEQ ID NO 145
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145 cctgcag                                                      7

<210> SEQ ID NO 146
<211> LENGTH: 7
<212> TYPE: PRT
<213> ORGANISM: Cryptomeria japonica

<400> SEQUENCE: 146

Ile Phe Asn Val Glu Lys Tyr
1               5

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)..(16)
<223> OTHER INFORMATION: a, c, t, g, unknown or other

<400> SEQUENCE: 147
cctgcagtay ttytcnacrt traadat                                27

<210> SEQ ID NO 148
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: a, c, t, g, unknown or other

<400> SEQUENCE: 148
gcnathaaya thttyaa                                           17

<210> SEQ ID NO 149
<211> LENGTH: 6
<212> TYPE: PRT
```

<213> ORGANISM: Cryptomeria japonica

<400> SEQUENCE: 149

Ala Ile Asn Ile Phe Asn
1               5

<210> SEQ ID NO 150
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(11)
<223> OTHER INFORMATION: a, c, t, g, unknown or other

<400> SEQUENCE: 150
ggaattccgc nathaayath ttyaaygt                                    28

<210> SEQ ID NO 151
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151 ggaattcc                                                           8

<210> SEQ ID NO 152
<211> LENGTH: 7
<212> TYPE: PRT
<213> ORGANISM: Cryptomeria japonica

<400> SEQUENCE: 152

Ala Ile Asn Ile Phe Asn Val
1               5

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: a, c, t, g, unknown or other

<400> SEQUENCE: 153
gcytcngtrc artcrtgytt                                             20

<210> SEQ ID NO 154
<211> LENGTH: 7
<212> TYPE: PRT
<213> ORGANISM: Cryptomeria japonica

<400> SEQUENCE: 154

Lys His Asp Cys Thr Glu Ala
1               5

<210> SEQ ID NO 155
<211> LENGTH: 28
<212> TYPE: DNA

```
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(23)
<223> OTHER INFORMATION: a, c, t, g, unknown or other

<400> SEQUENCE: 155
ggctgcaggt rcartcrtgy ttnccrtc                                          28

<210> SEQ ID NO 156
<211> LENGTH: 8
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156 ggctgcag                                                                 8

<210> SEQ ID NO 157
<211> LENGTH: 7
<212> TYPE: PRT
<213> ORGANISM: Cryptomeria japonica

<400> SEQUENCE: 157

Asp Gly Lys His Asp Cys Thr
1               5

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
atgttggaca gtgttgtcga a                                                 21

<210> SEQ ID NO 159
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gggaattcag aaaagttgag cattctcgt                                         29

<210> SEQ ID NO 160
<211> LENGTH: 8
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160 gggaattc                                                                 8

<210> SEQ ID NO 161
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 161
gttcttcaat gggccatgt                                                  19

<210> SEQ ID NO 162
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gtgttaggac tgtctctcgg                                                 20

<210> SEQ ID NO 163
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
tgtccaggcc atggaataag                                                 20

<210> SEQ ID NO 164
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gccttacatg gactgcaacc                                                 20

<210> SEQ ID NO 165
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
tccacgggtc tgataatcca                                                 20

<210> SEQ ID NO 166
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
aggcaggaag caattttccc                                                 20

<210> SEQ ID NO 167
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 167
tactgcactt cagcttctgc                                               20

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gggggtctcc gaatttatca                                               20

<210> SEQ ID NO 169
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
ggatatttca gtggacacgt                                               20

<210> SEQ ID NO 170
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
tattagaaga ccctgcgcct                                               20

<210> SEQ ID NO 171
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
ccatgtaagg ccaagttagt                                               20

<210> SEQ ID NO 172
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
acacctttac ccattagagt                                               20

<210> SEQ ID NO 173
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 173
ctgtccaaca taatttgggc                                                  20

<210> SEQ ID NO 174
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
catggcaggg tggttcaggc                                                  20

<210> SEQ ID NO 175
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
tagccccatt tacgtgcacg                                                  20

<210> SEQ ID NO 176
<211> LENGTH: 20
<212> TYPE: DNA
<213> ORGANISM: Cryptomeria japonica

<400> SEQUENCE: 176
ttggggtcga ggcctccgaa                                                  20

<210> SEQ ID NO 177
<211> LENGTH: 9
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 177 taaaauggc                                                               9

<210> SEQ ID NO 178
<211> LENGTH: 9
<212> TYPE: RNA
<213> ORGANISM: Cryptomeria japonica

<400> SEQUENCE: 178 aacaauggc                                                               9

<210> SEQ ID NO 179
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
gccgaattca tggccatgaa attaatt                                          27
```

```
<210> SEQ ID NO 180
<211> LENGTH: 9
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180 gccgaattc                                                              9

<210> SEQ ID NO 181
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
cggggatcct cattatggat ggtagat                                          27

<210> SEQ ID NO 182
<211> LENGTH: 9
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182 cggggatcc                                                              9

<210> SEQ ID NO 183
<211> LENGTH: 13
<212> TYPE: PRT
<213> ORGANISM: Cryptomeria japonica

<400> SEQUENCE: 183

Phe Thr Phe Lys Val Asp Gly Ile Ile Ala Ala Tyr Gln
1               5                   10

<210> SEQ ID NO 184
<211> LENGTH: 14
<212> TYPE: PRT
<213> ORGANISM: Cryptomeria japonica

<400> SEQUENCE: 184

Asn Gly Tyr Phe Ser Gly His Val Ile Pro Ala Cys Lys Asn
1               5                   10

<210> SEQ ID NO 185
<211> LENGTH: 13
<212> TYPE: PRT
<213> ORGANISM: Cryptomeria japonica

<400> SEQUENCE: 185

Phe Thr Phe Lys Val Asp Gly Ile Ile Ala Ala Tyr Gln
1               5                   10

<210> SEQ ID NO 186
<211> LENGTH: 14
<212> TYPE: PRT
<213> ORGANISM: Cryptomeria japonica

<400> SEQUENCE: 186
```

```
Asn Gly Tyr Phe Ser Gly His Val Ile Pro Ala Cys Lys Asn
1               5                   10
```

```
<210> SEQ ID NO 187
<211> LENGTH: 128
<212> TYPE: PRT
<213> ORGANISM: Cryptomeria japonica

<400> SEQUENCE: 187

Met Gly His His His His His Glu Phe Arg Lys Val Glu His Ser
1               5                   10                  15

Arg His Asp Ala Ile Asn Ile Phe Asn Val Glu Lys Tyr Gly Ala Val
            20                  25                  30

Gly Asp Gly Lys His Asp Cys Thr Glu Ala Phe Ser Thr Ala Trp Gln
        35                  40                  45

Ala Ala Cys Lys Asn Pro Ser Ala Met Leu Leu Val Pro Gly Ser Lys
    50                  55                  60

Lys Phe Val Val Asn Asn Leu Phe Phe Asn Gly Pro Cys Gln Pro His
65                  70                  75                  80

Phe Thr Phe Lys Val Asp Gly Ile Ile Ala Ala Tyr Gln Asn Pro Ala
                85                  90                  95

Ser Trp Lys Asn Asn Arg Ile Trp Leu Gln Phe Ala Lys Leu Thr Gly
            100                 105                 110

Phe Thr Leu Met Gly Lys Gly Val Ile Asp Gly Gln Gly Lys Gln Trp
        115                 120                 125
```

```
<210> SEQ ID NO 188
<211> LENGTH: 127
<212> TYPE: PRT
<213> ORGANISM: Cryptomeria japonica

<400> SEQUENCE: 188

Met Gly His His His His His Glu Phe Trp Ala Gly Gln Cys Lys
1               5                   10                  15

Trp Val Asn Gly Arg Glu Ile Cys Asn Asp Arg Asp Arg Pro Thr Ala
            20                  25                  30

Ile Lys Phe Asp Phe Ser Thr Gly Leu Ile Ile Gln Gly Leu Lys Leu
        35                  40                  45

Met Asn Ser Pro Glu Phe His Leu Val Phe Gly Asn Cys Glu Gly Val
    50                  55                  60

Lys Ile Ile Gly Ile Ser Ile Thr Ala Pro Arg Asp Ser Pro Asn Thr
65                  70                  75                  80

Asp Gly Ile Asp Ile Phe Ala Ser Lys Asn Phe His Leu Gln Lys Asn
                85                  90                  95

Thr Ile Gly Thr Gly Asp Asp Cys Val Ala Ile Gly Thr Gly Ser Ser
            100                 105                 110

Asn Ile Val Ile Glu Asp Leu Ile Cys Gly Pro Gly His Gly Ile
        115                 120                 125
```

```
<210> SEQ ID NO 189
<211> LENGTH: 127
<212> TYPE: PRT
<213> ORGANISM: Cryptomeria japonica

<400> SEQUENCE: 189

Met Gly His His His His His Glu Phe Ser Ile Gly Ser Leu Gly
1               5                   10                  15

Arg Glu Asn Ser Arg Ala Glu Val Ser Tyr Val His Val Asn Gly Ala
            20                  25                  30
```

```
Lys Phe Ile Asp Thr Gln Asn Gly Leu Arg Ile Lys Thr Trp Gln Gly
            35                  40                  45

Gly Ser Gly Met Ala Ser His Ile Ile Tyr Glu Asn Val Glu Met Ile
        50                  55                  60

Asn Ser Glu Asn Pro Ile Leu Ile Asn Gln Phe Tyr Cys Thr Ser Ala
 65                  70                  75                  80

Ser Ala Cys Gln Asn Gln Arg Ser Ala Val Gln Ile Gln Asp Val Thr
                85                  90                  95

Tyr Lys Asn Ile Arg Gly Thr Ser Ala Thr Ala Ala Ile Gln Leu
                100                 105                 110

Lys Cys Ser Asp Ser Met Pro Cys Lys Asp Ile Lys Leu Ser Asp
                115                 120                 125
```

<210> SEQ ID NO 190
<211> LENGTH: 127
<212> TYPE: PRT
<213> ORGANISM: Cryptomeria japonica

<400> SEQUENCE: 190

```
Met Gly His His His His His Glu Phe Ile Ser Leu Lys Leu Thr
 1               5                  10                  15

Ser Gly Lys Ile Ala Ser Cys Leu Asn Asp Asn Ala Asn Gly Tyr Phe
                20                  25                  30

Ser Gly His Val Ile Pro Ala Cys Lys Asn Leu Ser Pro Ser Ala Lys
                35                  40                  45

Arg Lys Glu Ser Lys Ser His Lys His Pro Lys Thr Val Met Val Glu
 50                  55                  60

Asn Met Arg Ala Tyr Asp Lys Gly Asn Arg Thr Arg Ile Leu Leu Gly
 65                  70                  75                  80

Ser Arg Pro Pro Asn Cys Thr Asn Lys Cys His Gly Cys Ser Pro Cys
                85                  90                  95

Lys Ala Lys Leu Val Ile Val His Arg Ile Met Pro Gln Glu Tyr Tyr
                100                 105                 110

Pro Gln Arg Trp Ile Cys Ser Cys His Gly Lys Ile Tyr His Pro
                115                 120                 125
```

<210> SEQ ID NO 191
<211> LENGTH: 24
<212> TYPE: PRT
<213> ORGANISM: Cryptomeria japonica

<400> SEQUENCE: 191

```
Gly Lys Gly Val Ile Asp Gly Gln Gly Lys Gln Trp Trp Ala Gly Gln
 1               5                  10                  15

Cys Lys Trp Val Asn Gly Arg Glu
                20
```

<210> SEQ ID NO 192
<211> LENGTH: 24
<212> TYPE: PRT
<213> ORGANISM: Cryptomeria japonica

<400> SEQUENCE: 192

```
Asp Ser Met Pro Cys Lys Asp Ile Lys Leu Ser Asp Ile Ser Leu Lys
 1               5                  10                  15

Leu Thr Ser Gly Lys Ile Ala Ser
                20
```

```
<210> SEQ ID NO 193
<211> LENGTH: 24
<212> TYPE: PRT
<213> ORGANISM: Cryptomeria japonica

<400> SEQUENCE: 193

Ile Glu Asp Leu Ile Cys Gly Pro Gly His Gly Ile Ser Ile Gly Ser
1               5                   10                  15

Leu Gly Arg Glu Asn Ser Arg Ala
            20

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: Inosine
<220> FEATURE:
<221> NAME/KEY: modified_base
<222> LOCATION: (15)..(15)
<223> OTHER INFORMATION: Inosine

<400> SEQUENCE: 194
aayccnathg aywsncgytg g                                              21

<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (18)..(18)
<223> OTHER INFORMATION: Inosine

<400> SEQUENCE: 195
aaytgggcnc araayrgnat gaa                                            23

<210> SEQ ID NO 196
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
ggcggatcct taccattgtt ttccttgccc                                     30

<210> SEQ ID NO 197
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
cgggaattct gggctggcca atgtaaa                                        27
```

<210> SEQ ID NO 198
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
ggcggatcct tatattccat ggcctggacc                                    30

<210> SEQ ID NO 199
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
cgggaattca gtataggaag tcttggg                                       27

<210> SEQ ID NO 200
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
ggcggatcct taatcactta gctttatatc                                    30

<210> SEQ ID NO 201
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
cgggaattca tatctttgaa gcttacc                                       27

<210> SEQ ID NO 202
<211> LENGTH: 26
<212> TYPE: PRT
<213> ORGANISM: Cryptomeria japonica

<400> SEQUENCE: 202

Lys Asp Asp Arg Thr Ala Thr Asn Ile Trp Ile Asp His Asn Ser Phe
1               5                   10                  15

Ser Asn Ser Ser Asp Gly Leu Val Asp Lys
            20                  25

<210> SEQ ID NO 203
<211> LENGTH: 20
<212> TYPE: PRT
<213> ORGANISM: Cryptomeria japonica

<400> SEQUENCE: 203

Asp Arg Thr Ala Thr Asn Ile Trp Ile Asp His Asn Ser Phe Ser Asn
1               5                   10                  15

Ser Ser Asp Asp
            20

```
<210> SEQ ID NO 204
<211> LENGTH: 23
<212> TYPE: PRT
<213> ORGANISM: Cryptomeria japonica

<400> SEQUENCE: 204

Asp Lys Glu Arg Thr Ala Thr Asn Ile Trp Ile Asp His Asn Ser Phe
1               5                   10                  15

Ser Asn Ser Ser Asp Asp Glu
            20

<210> SEQ ID NO 205
<211> LENGTH: 25
<212> TYPE: PRT
<213> ORGANISM: Cryptomeria japonica

<400> SEQUENCE: 205

Asp Glu Arg Thr Ala Thr Asn Ile Trp Ile Asp His Asn Ser Phe Ser
1               5                   10                  15

Asn Ser Ser Asp Gly Leu Val Asp Asp
            20                  25

<210> SEQ ID NO 206
<211> LENGTH: 23
<212> TYPE: PRT
<213> ORGANISM: Cryptomeria japonica

<400> SEQUENCE: 206

Asp Glu Asp Arg Thr Ala Thr Asn Ile Trp Ile Asp His Asn Ser Phe
1               5                   10                  15

Ser Asn Ser Ser Asp Glu Asp
            20

<210> SEQ ID NO 207
<211> LENGTH: 23
<212> TYPE: PRT
<213> ORGANISM: Cryptomeria japonica

<400> SEQUENCE: 207

Asp Lys Glu Arg Thr Ala Thr Asn Ile Trp Ile Asp His Asn Ser Phe
1               5                   10                  15

Ser Asn Ser Ser Asp Lys Glu
            20

<210> SEQ ID NO 208
<211> LENGTH: 21
<212> TYPE: PRT
<213> ORGANISM: Cryptomeria japonica

<400> SEQUENCE: 208

Asp Glu Asp Arg Thr Ala Thr Asn Ile Trp Ile Asp His Asn Ser Phe
1               5                   10                  15

Ser Asn Asp Glu Asp
            20

<210> SEQ ID NO 209
<211> LENGTH: 21
<212> TYPE: PRT
<213> ORGANISM: Cryptomeria japonica

<400> SEQUENCE: 209

Asp Lys Glu Arg Thr Ala Thr Asn Ile Trp Ile Asp His Asn Ser Phe
```

```
                1               5                  10                  15

Ser Asn Asp Lys Glu
                20

<210> SEQ ID NO 210
<211> LENGTH: 18
<212> TYPE: PRT
<213> ORGANISM: Cryptomeria japonica

<400> SEQUENCE: 210

Asp Glu Asp Arg Thr Ala Thr Asn Ile Trp Ile Asp His Asn Ser Asp
1               5                   10                  15

Glu Asp

<210> SEQ ID NO 211
<211> LENGTH: 18
<212> TYPE: PRT
<213> ORGANISM: Cryptomeria japonica

<400> SEQUENCE: 211

Asp Lys Glu Arg Thr Ala Thr Asn Ile Trp Ile Asp His Asn Ser Asp
1               5                   10                  15

Lys Glu

<210> SEQ ID NO 212
<211> LENGTH: 16
<212> TYPE: PRT
<213> ORGANISM: Cryptomeria japonica

<400> SEQUENCE: 212

Lys Arg Thr Ala Thr Asn Ile Trp Ile Asp His Asn Ser Lys Arg Lys
1               5                   10                  15

<210> SEQ ID NO 213
<211> LENGTH: 33
<212> TYPE: PRT
<213> ORGANISM: Cryptomeria japonica

<400> SEQUENCE: 213

Lys Val Thr Val Ala Phe Asn Gln Phe Gly Pro Asn Cys Gly Gln Arg
1               5                   10                  15

Met Pro Arg Ala Arg Tyr Gly Leu Val His Val Ala Asn Asn Asn Tyr
                20                  25                  30

Asp

<210> SEQ ID NO 214
<211> LENGTH: 31
<212> TYPE: PRT
<213> ORGANISM: Cryptomeria japonica

<400> SEQUENCE: 214

Thr Val Ala Phe Asn Gln Phe Gly Pro Asn Cys Gly Gln Arg Met Pro
1               5                   10                  15

Arg Ala Arg Tyr Gly Leu Val His Val Ala Asn Asn Asn Tyr Asp
                20                  25                  30

<210> SEQ ID NO 215
<211> LENGTH: 31
<212> TYPE: PRT
<213> ORGANISM: Cryptomeria japonica

<400> SEQUENCE: 215
```

Lys Lys Ala Phe Asn Gln Phe Gly Pro Asn Cys Gly Gln Arg Met Pro
1               5                   10                  15

Arg Ala Arg Tyr Gly Leu Val His Val Ala Asn Asn Asn Tyr Asp
                20                  25                  30

<210> SEQ ID NO 216
<211> LENGTH: 29
<212> TYPE: PRT
<213> ORGANISM: Cryptomeria japonica

<400> SEQUENCE: 216

Ala Phe Asn Gln Phe Gly Pro Asn Cys Gly Gln Arg Met Pro Arg Ala
1               5                   10                  15

Arg Tyr Gly Leu Val His Val Ala Asn Asn Asn Tyr Asp
                20                  25

<210> SEQ ID NO 217
<211> LENGTH: 28
<212> TYPE: PRT
<213> ORGANISM: Cryptomeria japonica

<400> SEQUENCE: 217

Lys Ser Met Lys Val Thr Val Ala Phe Asn Gln Phe Gly Pro Asn Cys
1               5                   10                  15

Gly Gln Arg Met Pro Arg Ala Tyr Gly Asp Lys
                20                  25

<210> SEQ ID NO 218
<211> LENGTH: 28
<212> TYPE: PRT
<213> ORGANISM: Cryptomeria japonica

<400> SEQUENCE: 218

Asp Ser Met Lys Val Thr Val Ala Phe Asn Gln Phe Gly Pro Asn Ser
1               5                   10                  15

Gly Gln Arg Met Pro Arg Ala Arg Tyr Gly Asp Glu
                20                  25

<210> SEQ ID NO 219
<211> LENGTH: 28
<212> TYPE: PRT
<213> ORGANISM: Cryptomeria japonica

<400> SEQUENCE: 219

Lys Ser Met Lys Val Thr Val Ala Phe Asn Gln Phe Gly Pro Asn Ser
1               5                   10                  15

Gly Gln Arg Met Pro Arg Ala Arg Tyr Gly Asp Glu
                20                  25

<210> SEQ ID NO 220
<211> LENGTH: 29
<212> TYPE: PRT
<213> ORGANISM: Cryptomeria japonica

<400> SEQUENCE: 220

Asp Lys Ser Met Lys Val Thr Val Ala Phe Asn Gln Phe Gly Pro Asn
1               5                   10                  15

Ser Gly Gln Arg Met Pro Arg Ala Arg Tyr Gly Asp Glu
                20                  25

<210> SEQ ID NO 221
<211> LENGTH: 30
<212> TYPE: PRT

-continued

<213> ORGANISM: Cryptomeria japonica

<400> SEQUENCE: 221

Asp Glu Lys Ser Met Lys Val Thr Val Ala Phe Asn Gln Phe Gly Pro
1               5                   10                  15

Asn Ser Gly Gln Arg Met Pro Arg Ala Arg Tyr Gly Asp Glu
            20                  25                  30

<210> SEQ ID NO 222
<211> LENGTH: 29
<212> TYPE: PRT
<213> ORGANISM: Cryptomeria japonica

<400> SEQUENCE: 222

Lys Lys Ser Met Lys Val Thr Val Ala Phe Asn Gln Phe Gly Pro Asn
1               5                   10                  15

Ser Gly Gln Arg Met Pro Arg Ala Arg Tyr Gly Lys Lys
            20                  25

<210> SEQ ID NO 223
<211> LENGTH: 28
<212> TYPE: PRT
<213> ORGANISM: Cryptomeria japonica

<400> SEQUENCE: 223

Lys Ser Met Lys Val Thr Val Ala Phe Asn Gln Phe Gly Pro Asn Ser
1               5                   10                  15

Gly Gln Arg Met Pro Arg Ala Arg Tyr Gly Lys Lys
            20                  25

<210> SEQ ID NO 224
<211> LENGTH: 24
<212> TYPE: PRT
<213> ORGANISM: Cryptomeria japonica

<400> SEQUENCE: 224

Asp Glu Lys Ser Met Lys Val Thr Val Ala Phe Asn Gln Phe Gly Pro
1               5                   10                  15

Asn Ser Gly Gln Arg Met Asp Glu
            20

<210> SEQ ID NO 225
<211> LENGTH: 23
<212> TYPE: PRT
<213> ORGANISM: Cryptomeria japonica

<400> SEQUENCE: 225

Asp Glu Ser Met Lys Val Thr Val Ala Phe Asn Gln Phe Gly Pro Asn
1               5                   10                  15

Ser Gly Gln Arg Met Asp Glu
            20

<210> SEQ ID NO 226
<211> LENGTH: 23
<212> TYPE: PRT
<213> ORGANISM: Cryptomeria japonica

<400> SEQUENCE: 226

Asp Glu Lys Ser Met Lys Val Thr Val Ala Phe Asn Gln Phe Gly Pro
1               5                   10                  15

Asn Ser Gly Gln Arg Asp Glu
            20

<210> SEQ ID NO 227
<211> LENGTH: 19
<212> TYPE: PRT
<213> ORGANISM: Cryptomeria japonica

<400> SEQUENCE: 227

Asp Glu Lys Ser Met Lys Val Thr Val Ala Phe Asn Gln Phe Gly Pro
1               5                   10                  15

Asn Asp Glu

<210> SEQ ID NO 228
<211> LENGTH: 26
<212> TYPE: PRT
<213> ORGANISM: Cryptomeria japonica

<400> SEQUENCE: 228

Arg Ser Met Lys Val Thr Val Ala Phe Asn Gln Phe Gly Pro Asn Ser
1               5                   10                  15

Gly Gln Arg Met Pro Arg Ala Arg Tyr Gly
            20                  25

<210> SEQ ID NO 229
<211> LENGTH: 26
<212> TYPE: PRT
<213> ORGANISM: Cryptomeria japonica

<400> SEQUENCE: 229

Arg Ser Met Lys Val Thr Val Ala Phe Asn Gln Phe Gly Pro Asn Ser
1               5                   10                  15

Gly Gln Arg Met Pro Arg Ala Arg Ala Gly
            20                  25

<210> SEQ ID NO 230
<211> LENGTH: 20
<212> TYPE: PRT
<213> ORGANISM: Cryptomeria japonica

<400> SEQUENCE: 230

Asp Glu Glu Lys Ser Met Lys Val Thr Val Ala Phe Asn Gln Phe Gly
1               5                   10                  15

Pro Asn Asp Glu
            20

<210> SEQ ID NO 231
<211> LENGTH: 21
<212> TYPE: PRT
<213> ORGANISM: Cryptomeria japonica

<400> SEQUENCE: 231

Asp Glu Glu Lys Ser Met Lys Val Thr Val Ala Phe Asn Gln Phe Gly
1               5                   10                  15

Pro Asn Asp Glu Glu
            20

<210> SEQ ID NO 232
<211> LENGTH: 26
<212> TYPE: PRT
<213> ORGANISM: Cryptomeria japonica

<400> SEQUENCE: 232

Lys Ser Met Lys Val Thr Val Ala Phe Asn Gln Phe Gly Pro Asn Ser
1               5                   10                  15

```
Gly Glu Arg Ala Pro Arg Ala Arg Ala Gly
        20                  25

<210> SEQ ID NO 233
<211> LENGTH: 23
<212> TYPE: PRT
<213> ORGANISM: Cryptomeria japonica

<400> SEQUENCE: 233

Asp Glu Glu Lys Ser Met Lys Val Thr Val Ala Phe Asn Gln Phe Gly
1               5                   10                  15

Pro Asn Ser Gly Asp Lys Glu
            20

<210> SEQ ID NO 234
<211> LENGTH: 20
<212> TYPE: PRT
<213> ORGANISM: Cryptomeria japonica

<400> SEQUENCE: 234

Asp Asp Ala Tyr Ser Asp Asp Lys Ser Met Lys Val Thr Val Ala Phe
1               5                   10                  15

Asn Gln Phe Gly
            20

<210> SEQ ID NO 235
<211> LENGTH: 13
<212> TYPE: PRT
<213> ORGANISM: Cryptomeria japonica

<400> SEQUENCE: 235

Lys Ser Met Lys Val Thr Val Ala Phe Asn Gln Phe Gly
1               5                   10

<210> SEQ ID NO 236
<211> LENGTH: 19
<212> TYPE: PRT
<213> ORGANISM: Cryptomeria japonica

<400> SEQUENCE: 236

Lys Lys Lys Ser Met Lys Val Thr Val Ala Phe Asn Gln Phe Gly Pro
1               5                   10                  15

Asn Lys Lys

<210> SEQ ID NO 237
<211> LENGTH: 23
<212> TYPE: PRT
<213> ORGANISM: Cryptomeria japonica

<400> SEQUENCE: 237

Asp Asp Ala Tyr Ser Asp Asp Lys Ser Met Lys Val Thr Val Ala Phe
1               5                   10                  15

Asn Gln Phe Gly Asp Lys Glu
            20

<210> SEQ ID NO 238
<211> LENGTH: 24
<212> TYPE: PRT
<213> ORGANISM: Cryptomeria japonica

<400> SEQUENCE: 238

Asp Lys Asp Ala Tyr Ser Asp Asp Lys Ser Met Lys Val Thr Val Ala
1               5                   10                  15
```

Phe Asn Gln Phe Gly Asp Lys Glu
            20

<210> SEQ ID NO 239
<211> LENGTH: 19
<212> TYPE: PRT
<213> ORGANISM: Cryptomeria japonica

<400> SEQUENCE: 239

Asp Asp Asp Lys Ser Met Lys Val Thr Val Ala Phe Asn Gln Phe Gly
1               5                   10                  15

Asp Glu Asp

<210> SEQ ID NO 240
<211> LENGTH: 17
<212> TYPE: PRT
<213> ORGANISM: Cryptomeria japonica

<400> SEQUENCE: 240

Asp Asp Asp Lys Ser Met Lys Val Thr Val Ala Phe Asn Gln Asp Glu
1               5                   10                  15

Asp

<210> SEQ ID NO 241
<211> LENGTH: 17
<212> TYPE: PRT
<213> ORGANISM: Cryptomeria japonica

<400> SEQUENCE: 241

Asp Glu Asp Lys Ser Met Lys Val Thr Val Ala Phe Asn Gln Asp Glu
1               5                   10                  15

Asp

<210> SEQ ID NO 242
<211> LENGTH: 17
<212> TYPE: PRT
<213> ORGANISM: Cryptomeria japonica

<400> SEQUENCE: 242

Asp Glu Asp Lys Ser Met Lys Val Thr Val Ala Phe Asn Gln Ala Glu
1               5                   10                  15

Asp

<210> SEQ ID NO 243
<211> LENGTH: 16
<212> TYPE: PRT
<213> ORGANISM: Cryptomeria japonica

<400> SEQUENCE: 243

Lys Arg Lys Ser Met Lys Val Thr Val Ala Phe Asn Gln Lys Arg Lys
1               5                   10                  15

<210> SEQ ID NO 244
<211> LENGTH: 16
<212> TYPE: PRT
<213> ORGANISM: Cryptomeria japonica

<400> SEQUENCE: 244

Lys Arg Lys Ser Met Lys Val Thr Val Ala Phe Asn Gln Ala Arg Lys
1               5                   10                  15

<210> SEQ ID NO 245
<211> LENGTH: 15

```
<212> TYPE: PRT
<213> ORGANISM: Cryptomeria japonica

<400> SEQUENCE: 245

Lys Arg Lys Ser Met Lys Val Thr Val Ala Phe Asn Gln Arg Lys
1               5                   10                  15

<210> SEQ ID NO 246
<211> LENGTH: 16
<212> TYPE: PRT
<213> ORGANISM: Cryptomeria japonica

<400> SEQUENCE: 246

Asp Glu Asp Glu Asp Lys Ser Met Lys Val Thr Val Ala Phe Asn Gln
1               5                   10                  15

<210> SEQ ID NO 247
<211> LENGTH: 14
<212> TYPE: PRT
<213> ORGANISM: Cryptomeria japonica

<400> SEQUENCE: 247

Lys Ser Met Lys Val Thr Val Ala Phe Asn Gln Ala Arg Lys
1               5                   10

<210> SEQ ID NO 248
<211> LENGTH: 16
<212> TYPE: PRT
<213> ORGANISM: Cryptomeria japonica

<400> SEQUENCE: 248

Lys Ser Met Lys Val Thr Val Ala Phe Asn Gln Phe Gly Lys Arg Lys
1               5                   10                  15

<210> SEQ ID NO 249
<211> LENGTH: 16
<212> TYPE: PRT
<213> ORGANISM: Cryptomeria japonica

<400> SEQUENCE: 249

Asp Ser Met Lys Val Thr Val Ala Phe Asn Gln Phe Gly Glu Asp Glu
1               5                   10                  15

<210> SEQ ID NO 250
<211> LENGTH: 16
<212> TYPE: PRT
<213> ORGANISM: Cryptomeria japonica

<400> SEQUENCE: 250

Lys Ser Met Lys Val Thr Val Ala Phe Asn Gln Phe Gly Arg Lys Arg
1               5                   10                  15

<210> SEQ ID NO 251
<211> LENGTH: 17
<212> TYPE: PRT
<213> ORGANISM: Cryptomeria japonica

<400> SEQUENCE: 251

Lys Ser Met Lys Val Thr Val Ala Phe Asn Gln Phe Gly Asp Glu Asp
1               5                   10                  15

Glu

<210> SEQ ID NO 252
<211> LENGTH: 18
<212> TYPE: PRT
```

<213> ORGANISM: Cryptomeria japonica

<400> SEQUENCE: 252

Lys Arg Lys Ser Met Lys Val Thr Val Ala Phe Asn Gln Phe Gly Lys
1               5                   10                  15

Arg Lys

<210> SEQ ID NO 253
<211> LENGTH: 18
<212> TYPE: PRT
<213> ORGANISM: Cryptomeria japonica

<400> SEQUENCE: 253

Asp Glu Lys Ser Met Lys Val Thr Val Ala Phe Asn Gln Phe Gly Asp
1               5                   10                  15

Glu Asp

<210> SEQ ID NO 254
<211> LENGTH: 16
<212> TYPE: PRT
<213> ORGANISM: Cryptomeria japonica

<400> SEQUENCE: 254

Lys Ser Met Lys Val Thr Val Ala Phe Asn Gln Ala Gly Lys Arg Lys
1               5                   10                  15

<210> SEQ ID NO 255
<211> LENGTH: 15
<212> TYPE: PRT
<213> ORGANISM: Cryptomeria japonica

<400> SEQUENCE: 255

His Lys Ser Met Lys Val Thr Val Ala Phe Asn Gln Phe Gly His
1               5                   10                  15

<210> SEQ ID NO 256
<211> LENGTH: 15
<212> TYPE: PRT
<213> ORGANISM: Cryptomeria japonica

<400> SEQUENCE: 256

Asn Lys Ser Met Lys Val Thr Val Ala Phe Asn Gln Phe Gly Asn
1               5                   10                  15

<210> SEQ ID NO 257
<211> LENGTH: 17
<212> TYPE: PRT
<213> ORGANISM: Cryptomeria japonica

<400> SEQUENCE: 257

Asn Asn Lys Ser Met Lys Val Thr Val Ala Phe Asn Gln Phe Gly Asn
1               5                   10                  15

Asn

<210> SEQ ID NO 258
<211> LENGTH: 19
<212> TYPE: PRT
<213> ORGANISM: Cryptomeria japonica

<400> SEQUENCE: 258

Arg Ala Arg Tyr Gly Leu Val His Val Ala Asn Asn Asn Tyr Asp Pro
1               5                   10                  15

Trp Thr Ile

<210> SEQ ID NO 259
<211> LENGTH: 27
<212> TYPE: PRT
<213> ORGANISM: Cryptomeria japonica

<400> SEQUENCE: 259

Asp Glu Gly Ala Tyr Phe Val Ser Ser Gly Lys Tyr Glu Gly Gly Asn
1               5                   10                  15

Ile Tyr Thr Lys Lys Glu Ala Phe Asn Ala Glu
            20                  25

<210> SEQ ID NO 260
<211> LENGTH: 30
<212> TYPE: PRT
<213> ORGANISM: Cryptomeria japonica

<400> SEQUENCE: 260

Asp Glu Glu Gly Ala Tyr Phe Val Ser Ser Gly Lys Tyr Glu Gly Gly
1               5                   10                  15

Asn Ile Tyr Thr Lys Lys Glu Ala Phe Asn Val Glu Asp Glu
            20                  25                  30

<210> SEQ ID NO 261
<211> LENGTH: 30
<212> TYPE: PRT
<213> ORGANISM: Cryptomeria japonica

<400> SEQUENCE: 261

Asp Lys Glu Gly Ala Tyr Phe Val Ser Ser Gly Lys Tyr Glu Gly Gly
1               5                   10                  15

Asn Ile Tyr Thr Lys Lys Glu Ala Phe Asn Val Glu Lys Asp
            20                  25                  30

<210> SEQ ID NO 262
<211> LENGTH: 21
<212> TYPE: PRT
<213> ORGANISM: Cryptomeria japonica

<400> SEQUENCE: 262

Arg Lys Val Glu His Ser Arg His Asp Ala Ile Asn Ile Phe Asn Val
1               5                   10                  15

Glu Lys Tyr Gly Ala
            20

<210> SEQ ID NO 263
<211> LENGTH: 16
<212> TYPE: PRT
<213> ORGANISM: Cryptomeria japonica

<400> SEQUENCE: 263

Ser Arg His Asp Ala Ile Asn Ile Phe Asn Val Glu Lys Tyr Gly Ala
1               5                   10                  15

<210> SEQ ID NO 264
<211> LENGTH: 24
<212> TYPE: PRT
<213> ORGANISM: Cryptomeria japonica

<400> SEQUENCE: 264

Val Gly Asp Gly Lys His Asp Cys Thr Glu Ala Phe Ser Thr Ala Trp
1               5                   10                  15

Gln Ala Ala Cys Lys Asn Pro Ser

```
                    20

<210> SEQ ID NO 265
<211> LENGTH: 20
<212> TYPE: PRT
<213> ORGANISM: Cryptomeria japonica

<400> SEQUENCE: 265

Val Gly Asp Gly Lys His Asp Cys Thr Glu Ala Phe Ser Thr Ala Trp
1               5                   10                  15

Gln Lys Asn Pro
            20

<210> SEQ ID NO 266
<211> LENGTH: 6
<212> TYPE: PRT
<213> ORGANISM: Cryptomeria japonica

<400> SEQUENCE: 266

Asp Asn Pro Ile Asp Ser
1               5

<210> SEQ ID NO 267
<211> LENGTH: 6
<212> TYPE: PRT
<213> ORGANISM: Cryptomeria japonica

<400> SEQUENCE: 267

Asn Trp Ala Gln Asn Arg
1               5

<210> SEQ ID NO 268
<211> LENGTH: 6
<212> TYPE: PRT
<213> ORGANISM: Cryptomeria japonica

<400> SEQUENCE: 268

Phe Asn Val Glu Asn Gly
1               5

<210> SEQ ID NO 269
<211> LENGTH: 7
<212> TYPE: PRT
<213> ORGANISM: Cryptomeria japonica

<400> SEQUENCE: 269

Trp Ala Gln Asn Arg Met Lys
1               5

<210> SEQ ID NO 270
<211> LENGTH: 6
<212> TYPE: PRT
<213> ORGANISM: Cryptomeria japonica

<400> SEQUENCE: 270

Met Asp Ser Pro Cys Leu
1               5

<210> SEQ ID NO 271
<211> LENGTH: 6
<212> TYPE: PRT
<213> ORGANISM: Cryptomeria japonica

<400> SEQUENCE: 271

Met Pro Met Tyr Ile Ala
```

```
1               5

<210> SEQ ID NO 272
<211> LENGTH: 6
<212> TYPE: PRT
<213> ORGANISM: Cryptomeria japonica

<400> SEQUENCE: 272

Ser Asn Ser Ser Asp Gly
1               5

<210> SEQ ID NO 273
<211> LENGTH: 6
<212> TYPE: PRT
<213> ORGANISM: Cryptomeria japonica

<400> SEQUENCE: 273

Thr Pro Gln Leu Thr Lys
1               5

<210> SEQ ID NO 274
<211> LENGTH: 6
<212> TYPE: PRT
<213> ORGANISM: Cryptomeria japonica

<400> SEQUENCE: 274

Thr Ser Thr Gly Val Thr
1               5

<210> SEQ ID NO 275
<211> LENGTH: 6
<212> TYPE: PRT
<213> ORGANISM: Cryptomeria japonica

<400> SEQUENCE: 275

Ala Pro Asn Glu Ser Tyr
1               5

<210> SEQ ID NO 276
<211> LENGTH: 6
<212> TYPE: PRT
<213> ORGANISM: Cryptomeria japonica

<400> SEQUENCE: 276

Tyr Ala Ile Gly Gly Ser
1               5

<210> SEQ ID NO 277
<211> LENGTH: 4
<212> TYPE: PRT
<213> ORGANISM: Cryptomeria japonica

<400> SEQUENCE: 277

Ser Lys Arg Cys
1

<210> SEQ ID NO 278
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
cctgacagaa gctt                                                       14
```

```
<210> SEQ ID NO 279
<211> LENGTH: 6
<212> TYPE: PRT
<213> ORGANISM: Juniperus sabinoides

<400> SEQUENCE: 279

Ser Glu Gly Asn Ser Phe
1               5

<210> SEQ ID NO 280
<211> LENGTH: 6
<212> TYPE: PRT
<213> ORGANISM: Juniperus virginiana

<400> SEQUENCE: 280

Leu Gly His Ser Asp Ser
1               5

<210> SEQ ID NO 281
<211> LENGTH: 6
<212> TYPE: PRT
<213> ORGANISM: Juniperus sabinoides

<400> SEQUENCE: 281

Met Ala Ser Pro Cys Leu
1               5

<210> SEQ ID NO 282
<211> LENGTH: 6
<212> TYPE: PRT
<213> ORGANISM: Juniperus sabinoides

<400> SEQUENCE: 282

Leu Gly His Asp Asp Thr
1               5

<210> SEQ ID NO 283
<211> LENGTH: 6
<212> TYPE: PRT
<213> ORGANISM: Juniperus sabinoides

<400> SEQUENCE: 283

Arg Ser Thr Arg Asp Ala
1               5
```

What is claimed is:

1. An isolated Japanese cedar pollen allergen produced in a host cell transformed with a nucleic acid comprising the nucleotide sequence of SEQ ID NO:1, or the coding region thereof, wherein the allergen is recombinantly produced is free of other cedar pollen allergens and is non-glycosyl.

2. An isolated Japanese cedar pollen allergen, comprising the amino acid sequence of SEQ ID NO:2, or the mature portion thereof, wherein the allergen is recombinantly produced is free of other cedar pollen allergens and is non-glycosylated.

* * * * *